(12) United States Patent
Barnes et al.

(10) Patent No.: US 8,324,239 B2
(45) Date of Patent: Dec. 4, 2012

(54) FUROPYRIDINE COMPOUNDS AND USES THEREOF

(75) Inventors: David Barnes, Waban, MA (US); Rajiv Chopra, Andover, MA (US); Scott Louis Cohen, Peabody, MA (US); Jiping Fu, Lafayette, CA (US); Mitsunori Kato, Cambridge, MA (US); Peichao Lu, Malden, MA (US); Mohindra Seepersaud, Acton, MA (US); Wei Zhang, Somerville, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/089,764

(22) Filed: Apr. 19, 2011

(65) Prior Publication Data

US 2012/0015907 A1 Jan. 19, 2012

Related U.S. Application Data

(60) Provisional application No. 61/326,491, filed on Apr. 21, 2010.

(51) Int. Cl.
*A61K 31/4355* (2006.01)
*C07D 491/048* (2006.01)
(52) U.S. Cl. .................................. 514/302; 546/115
(58) Field of Classification Search .................. 514/302; 436/115, 116; 546/115
See application file for complete search history.

(56) References Cited

U.S. PATENT DOCUMENTS

| 5,703,116 A | 12/1997 | Gaeta et al. |
|---|---|---|
| 2003/0220365 A1 | 11/2003 | Stewart et al. |
| 2004/0235888 A1 | 11/2004 | Yamamori et al. |
| 2008/0021026 A1 | 1/2008 | Kahraman et al. |
| 2010/0063058 A1 | 3/2010 | Macdonald et al. |

FOREIGN PATENT DOCUMENTS

| WO | WO 02/051849 | 7/2002 |
|---|---|---|
| WO | WO 02/072549 | 9/2002 |
| WO | WO 03/010140 | 2/2003 |
| WO | WO 2004/012671 | 2/2004 |
| WO | WO 2004/032874 | 4/2004 |
| WO | WO 2004/041201 | 5/2004 |
| WO | WO 2004/096813 | 11/2004 |
| WO | WO 2005/009389 | 2/2005 |
| WO | WO 2005/030213 | 4/2005 |
| WO | WO 2005/067900 | 7/2005 |
| WO | WO 2005/072412 | 8/2005 |
| WO | WO 2005/080377 | 9/2005 |
| WO | WO 2005/082905 | 9/2005 |
| WO | WO 2005/112932 | 12/2005 |
| WO | WO 2006/010008 | 1/2006 |
| WO | WO 2006/013095 | 2/2006 |
| WO | WO 2006/030031 | 3/2006 |
| WO | WO 2006/043145 | 4/2006 |
| WO | WO 2007/059422 | 5/2007 |
| WO | WO 2007/084667 | 7/2007 |
| WO | WO 2008/057856 | 5/2008 |
| WO | WO 2008/057857 | 5/2008 |
| WO | WO 2008/100867 | 8/2008 |
| WO | WO 2008/108309 | 9/2008 |
| WO | WO 2008/125874 | 10/2008 |
| WO | WO 2008/127585 | 10/2008 |
| WO | WO 2009/005676 | 1/2009 |
| WO | WO 2009/027732 | 3/2009 |
| WO | WO 2009/041591 | 4/2009 |
| WO | WO 2009/101022 | 8/2009 |
| WO | WO 2009/137492 | 11/2009 |
| WO | WO 2009/137500 | 11/2009 |
| WO | WO 2010/030538 | 3/2010 |
| WO | WO 2010/030592 | 3/2010 |

OTHER PUBLICATIONS

Norman M. Kneteman et al., "HCV796: A Selective Nonstructural Protein 5B Polymers Inhibitor with Potent Anti-Hepatitis C Virus Activity In Vitro, in Mice with Chimeric Human Livers, and in Humans Infected with Hepatitis C Virus" *Hepatology* 49:745-752, Mar. 2009.

Ariel Feldstein et al., "Severe Hepatocellular Injury with Apoptosis Induced by a Hepatitis C Polymerase Inhibitor" *J. Clin. Gastroenterol* 43(4): 374-381, Apr. 2009.

Priyamvad Chandra et al., "Antiviral Activity of the Non-Nucleoside Polymerase Inhibitor, HCV-796, in Pateint With Chronic Hepatitis C Virus: Preliminary Results from a Randomized, Double-Blind, Placebo-Controlled Ascending Multiple Dose Study" Presented at Digestive Disease Week, May 20-25, 2006; Los Angeles, California.

Stephen Villano et al., "Antiviral Activity of the Non-Nucleoside Polymerase Inhibitor, HCV-796, in Combination with Pegylated Interferon Alfa-2b in Treatment-Naive Patients With Chronic Hepatitis C Virus" Presented at the 42$^{nd}$ Annual Meeting of the European Association for the Study of the Liver (EASL), Apr. 13, 2007, Barcelona, Spain.

*Primary Examiner* — Charanjit Aulakh
(74) *Attorney, Agent, or Firm* — Mark W. Milstead

(57) ABSTRACT

The present invention provides a compound of formula I;

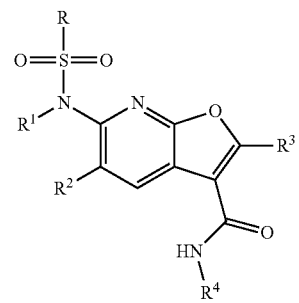

a method for manufacturing the compounds of the invention, and its therapeutic uses. The present invention further provides a combination of pharmacologically active agents and a pharmaceutical composition.

10 Claims, No Drawings

FUROPYRIDINE COMPOUNDS AND USES THEREOF

This application claims priority to U.S. Provisional Application Ser. No. 61/326,491 filed 21 Apr. 2010, the contents of which are incorporated herein by reference in their entirety.

FIELD OF THE INVENTION

Compounds and compositions, methods for their preparation, and methods for their use in treating viral infections in patients mediated, at least in part, by a virus in the Flaviviridae family of viruses are disclosed.

STATE OF THE ART

Chronic infection with HCV is a major health problem associated with liver cirrhosis, hepatocellular carcinoma, and liver failure. An estimated 170 million chronic carriers worldwide are at risk of developing liver disease (Szabo, E. et al., *Pathol. Oncol. Res.* 2003, 9:215-221; Hoofnagle J. H., *Hepatology* 1997, 26:15 S-20S). In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured.

At present, the standard treatment for chronic HCV is pegylated interferon alpha (IFN-alpha) in combination with ribavirin and this requires at least six (6) months of treatment. IFN-alpha belongs to a family of naturally occurring small proteins with characteristic biological effects such as antiviral, immunoregulatory, and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load and there is a clear need for more effective antiviral therapy of HCV infection (Fried, M. W., et al. *N. Engl. J. Med* 2002, 347:975-982).

A number of approaches are being pursued to combat the virus. These include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4a protease and the NS5b RNA-dependent RNA polymerase are considered the most promising viral targets for new drugs (see Ni, Z. J. and Wagman, A. S. *Curr. Opin. Drug Discov. Devel.* 2004, 7, 446-459; Beaulieu, P. L. and Tsantrizos, Y. S. *Curr. Opin. Investig. Drugs* 2004, 5, 838-850; and Griffith, R. C. et al., *Ann. Rep. Med. Chem.* 39, 223-237, 2004). However, none of these compounds have progressed beyond clinical trials.

In view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

In a first embodiment, the invention provides compounds of Formula (I), compositions thereof and methods of using same to treat viral infection. In particular, the compounds of the invention as defined by Formula (I) are useful for the treatment or prevention of hepatitis C virus infection and diseases associated with or caused by HCV infection. The structure of compounds of Formula (I) is as follows:

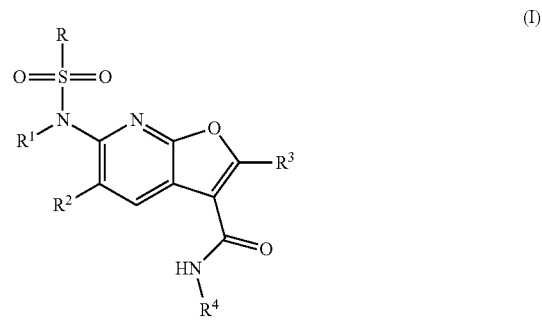

Compounds of Formula (I) includes salts thereof. Definitions for variables present in Formula (I) are defined infra.

Unless specified otherwise, the term "compounds of the present invention" refers to compounds of Formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

In one embodiment provided is a pharmaceutical composition comprising a pharmaceutically acceptable carrier and a therapeutically effective amount of a compound of Formula (I).

In other embodiments provided are methods for preparing the compounds of Formula (I) and compositions thereof and for their therapeutic uses. In one embodiment provided is a method for treating a viral infection in a patient mediated at least in part by a virus in the Flaviviridae family of viruses, comprising administering to said patient a composition comprising a compound or a salt of Formula (I). In some aspects, the viral infection is mediated by hepatitis C virus.

These and other embodiments of the invention are further described in the text that follows.

DETAILED DESCRIPTION OF THE INVENTION

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Phenyl may be unsubstituted or substituted by 1-5 substituents independently selected at each occurrence from the group consisting of hydroxy, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, where each of the aforementioned hydrocarbon groups (e.g., alkyl, alkenyl, alkynyl, alkoxy substituents) may be further substituted by one or more substituents independently selected at each occurrence from halogen, hydroxy or $C_1$-$C_4$-alkoxy groups.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 6-, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, and thiomorpholine.

The term "heterocyclyl" further refers to heterocyclic groups as defined herein substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) amido or carboxamido;
(m) cyano;
(n) sulfamoyl, sulfamido or sulfonamido;
(o) aryl;
(p) alkyl-C(O)—O—;

(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.
(y) alkyl substituted with cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, sulfamido, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 10 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) amido or carboxamido
(m) cyano;
(n) sulfamoyl, sulfamido or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.
(y) alkyl substituted with cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
(a) alkyl;
(b) hydroxy (or protected hydroxy);
(c) halo;
(d) oxo, i.e., =O;
(e) amino, alkylamino or dialkylamino;
(f) alkoxy;

(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) amido or carboxamido
(m) cyano;
(n) sulfamoyl, sulfamido or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.
(y) alkyl substituted with cycloalkyl, alkoxy, hydroxy, amino, alkyl-C(O)—NH—, alkylamino, dialkylamino or halogen.

In one aspect, compounds of Formula (I) are provided:

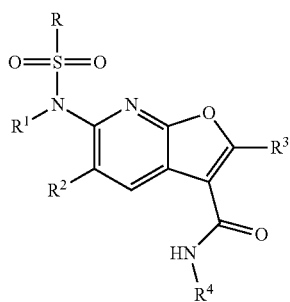

(I)

or a salt thereof, wherein

R is $C_1$-$C_6$alkyl, halo$C_1$-$C_4$alkyl, or phenyl;

$R^1$ is $C_1$-$C_{12}$alkyl, $C_2$-$C_{12}$alkenyl, $C_2$-$C_{12}$alkynyl or $C_1$-$C_8$alkoxy$C_1$-$C_{12}$alkyl, each of which is unsubstituted or substituted with 1, 2, or 3 substituents independently selected from the group consisting of hydroxy, halogen, cyano, $CO_2H$, $C(O)N(R^{1D})_2$, $N(R^{1A})S(O)_2R^{1B}$, $N(R^{1A})C(O)R^{1B}$, $S(O)_2R^{1C}$, $S(O)R^{1C}$, $N(R^{1A})S(O)_2N(R^{1D})_2$, $N(R^{1A})C(O)N(R^{1D})_2$, $OC(O)N(R^{1D})_2$, $N(R^{1A})C(O)_2R^{1B}$, $C(O)R^{1B}$, $P(O)(R^{1E})_2$, $C(O)R^{1F}$, $C_1$-$C_6$alkoxy, amino, mono- and di-$C_1$-$C_4$alkylamino, $C_3$-$C_6$cycloalkyl, phenyl, phenoxy, heteroaryl, heteroaryloxy, and heterocycle, which heterocycle is saturated or partially unsaturated, has one or two rings and 1 or 2 ring heteroatoms selected from N, O or S, and wherein each phenyl, phenoxy, heteroaryl and heteroaryloxy is unsubstituted or substituted with one to four groups independently selected from the group consisting of $C_1$-$C_4$alkyl, $CO_2H$, $C(O)C_1$-$C_4$alkyl, $C(O)_2C_1$-$C_4$alkyl and halogen, and wherein the heterocycle and cycloalkyl substitutents are unsubstituted or substituted with one to four groups independently selected from the group consisting of $C_1$-$C_4$alkyl, $CO_2H$, $C(O)C_1$-$C_4$alkyl, $C(O)_2C_1$-$C_4$alkyl, oxo and halogen;

$R^{1A}$ is independently selected at each occurrence from the group consisting of hydrogen, $C_1$-$C_6$alkyl and $C_2$-$C_6$alkenyl;

$R^{1B}$ is independently selected at each occurrence from $C_1$-$C_6$alkyl, $CF_3$ or phenyl, which phenyl is unsubstituted or substituted with one, two or three groups independently selected from $C_1$-$C_4$alkyl, halogen, $C_1$-$C_4$alkoxy, halo$C_1$-$C_4$alkyl or halo$C_1$-$C_4$alkoxy, wherein $R^{1A}$ and $R^{1B}$ may be taken together to form a cycle;

$R^{1C}$ is independently selected at each occurrence from the group consisting of $C_1$-$C_6$alkyl, hydroxy$C_1$-$C_6$alkyl, halo$C_1$-$C_4$alkyl, mono- and di-$C_1$-$C_4$alkylamino, or phenyl, which phenyl is unsubstituted or substituted with 1 or 2 $C_1$-$C_4$alkyl, $C_1$-$C_4$alkoxy, halo$C_1$-$C_4$alkyl, cyano, halogen morpholino, piperadino, piperazino, and pyrrolidino wherein each morpholino, piperadino, piperazino and pyrrolidino residue is unsubstituted or substituted with 1 or 2 groups independently selected from $C_1$-$C_4$alkyl, $C_1$-$C_4$alkoxy, halo$C_1$-$C_4$alkyl, hydroxy, or halogen;

$R^{1D}$ is independently selected at each occurrence from hydrogen or $C_1$-$C_6$alkyl, wherein each alkyl is substituted with 0, 1 or 2 substituents independently selected from the group consisting hydroxy, phenyl, $CO_2H$ or $C(O)_2C_1$-$C_4$alkyl; or $N(R^{1D})_2$, taken in combination, forms a five or six member heterocycle having 0, 1, or 2 additional ring heteroatoms selected from N or O and which is unsubstituted or substituted with one or two groups independently selected form $C_1$-$C_4$alkyl, benzyl, oxo or hydroxy;

$R^{1E}$ is independently selected at each occurrence from the group consisting of hydroxy, $C_1$-$C_4$alkyl, $C_1$-$C_4$alkoxy and benzyl wherein at least one occurrence of $R^{1E}$ is not $C_1$-$C_4$alkyl;

$R^{1F}$ is selected at each occurrence from the group consisting of $C_1$-$C_6$alkyl and $C_1$-$C_6$alkoxy each of which is optionally substituted with $OP(O)(R^{1E})_2$;

$R^2$ is halogen, or $R^2$ is hydrogen, $C_3$-$C_6$cycloalkyl, $C_1$-$C_{10}$alkyl, $C_2$-$C_{10}$alkanoyl, $C_2$-$C_{10}$alkenyl, or $C_2$-$C_{10}$alkynyl each of which is unsubstituted or substituted with 1, 2, or 3 groups independently selected from the group consisting of hydroxy, halogen, cyano, $C(O)NH_2$, $C(O)N(H)SO_2R^{2C}$, $S(O)_2R^{2C}$, $CO_2H$, $C(O)_2C_1$-$C_6$alkyl, $C(O)$heterocycle, which heterocycle is a saturated azacycle having 5 or 6 ring atoms and 0 or 1 additional ring heteroatom selected from N, O or S, which heterocycle is unsubstituted or substituted with $C(O)_2C_1$-$C_6$alkyl or $C(O)NH_2$; or $R^1$ and $R^2$, taken in combination, form a heterocyclic ring having between 6 and 12 ring atoms, 0, 1, or 2 additional ring heteroatoms which are independently selected from N, O or S, and which heterocycle is further substituted with 0, 1, 2, or 3 groups independently selected from the group consisting of hydroxy, oxo, $OC(O)N(R^{2D})_2$, $C(O)N(R^{2D})_2$, $C_1$-$C_6$alkyl, $=CH_2$, $C(O)_2H$, $C(O)_2C_1$-$C_6$alkyl, $C(O)R^{2B}$, $N(R^{2A})C(O)R^{2B}$, $N(R^{2A})S(O)_2R^{2B}$, $S(O)_2R^{2C}$ and $S(O)R^{2C}$;

$R^{2A}$ is independently selected at each occurrence from $C_1$-$C_6$alkyl and phenyl, which phenyl is unsubstituted or substituted with methyl, methoxy, fluoro, or chloro;

$R^{2B}$ is independently selected at each occurrence from $C_1$-$C_6$alkyl or phenyl, which phenyl is unsubstituted or substituted with one, two or three groups independently selected from $C_1$-$C_4$alkyl, halogen, $C_1$-$C_4$alkoxy, halo$C_1$-$C_4$alkyl or halo$C_1$-$C_4$alkoxy, wherein $R^{2A}$ and $R^{2B}$ may be taken together to form a cycle;

$R^{2C}$ is independently selected at each occurrence from the group consisting of $C_1$-$C_6$alkyl, $C_1$-$C_6$alkyl substituted with $CO_2H$, halo$C_1$-$C_4$alkyl, mono- and di-$C_1$-$C_4$alkylamino, or phenyl, which phenyl is unsubstituted or substituted with 1 or 2 $C_1$-$C_4$alkyl, $C_1$-$C_4$alkoxy, halo$C_1$-$C_4$alkyl, cyano, halogen, morpholino, piperadino, piperazino, and pyrrolidino wherein each morpholino, piperadino, piperazino and pyrrolidino residue is unsubstituted or substituted with 1 or 2 groups independently selected from $C_1$-$C_4$alkyl, $C_1$-$C_4$alkoxy, halo$C_1$-$C_4$alkyl, hydroxy, or halogen;

$NR^{2D}$ is independently selected at each occurrence from hydrogen or $C_1$-$C_6$alkyl or $N(R^{2D})_2$, taken in combination, forms a five or six member heterocycle having 0, 1, or 2 additional ring heteroatoms selected from N or O and which is unsubstituted or substituted with one or two groups independently selected form $C_1$-$C_4$alkyl, oxo or hydroxy;

$R^3$ is phenyl or pyridyl, which is substituted with 0, 1, 2 or 3 groups independently selected from the group consisting of $C_1$-$C_6$alkyl, halogen, $C_1$-$C_6$alkoxy, halo$C_1$-$C_6$alkyl, and halo$C_1$-$C_6$alkoxy, and the phenyl or pyridyl is further substituted with 0 or 1 groups selected from $C_3$-$C_6$cycloalkyl, benzyl, phenoxy, pyridyloxy, phenylamino, and pyridylamino, wherein each benzyl, phenoxy, pyridyloxy, phenylamino and pyridylamino is para to the point of attachment of the $R^3$ group to the furyl ring and each benzyl, phenoxy, pyridyloxy, phenylamino and pyridylamino is unsubstituted or substituted with one to three groups independently selected from $C_1$-$C_4$alkyl, halo$C_1$-$C_4$alkyl, $C_1$-$C_4$alkoxy, cyano, fluoro, or chloro; and $R^4$ is H or $C_1$-$C_4$alkyl.

In one aspect, compounds of Formula (Ia) are provided:

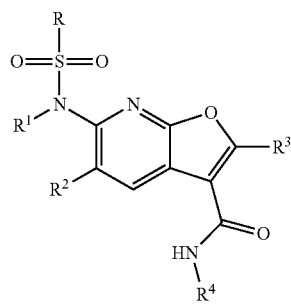

(Ia)

or a salt thereof, wherein

Rf is $C_1$-$C_6$alkyl, halo$C_1$-$C_4$alkyl, or phenyl;

$R^1$ is $C_1$-$C_{10}$alkyl, $C_2$-$C_{10}$alkenyl, $C_2$-$C_{10}$alkynyl, or $C_1C_6$alkoxy$C_1$-$C_6$alkyl, each of which is unsubstituted or substituted with 1, 2, or 3 substituents selected from the group consisting of hydroxy, halogen, cyano, $CO_2H$, $C(O)N(R^{1D})_2$, $C(O)_2C_1$-$C_6$alkyl, $N(R^{1A})S(O)_2R^{1B}$, $N(R^{1A})C(O)R^{1B}$, $S(O)_2R^{1C}$, $S(O)R^{1C}$, $N(R^{1A})S(O)_2N(R^{1D})_2$, $N(R^{1A})C(O)N(R^{1D})_2$, $OC(O)N(R^{1D})_2$, $N(R^{1A})C(O)_2R^{1B}$, $C(O)R^{1B}$, amino, mono- and di-$C_1$-$C_4$alkylamino, $C_3$-$C_6$cycloalkyl, phenyl, phenoxy, heteroaryl, heteroaryloxy, and heterocycle, which heterocycle is saturated or partially unsaturated, has one or two rings and 1 or 2 ring heteroatoms selected from N, O or S, and wherein each phenyl, phenoxy, heteroaryl, heteroaryloxy and heterocycle is unsubstituted or substituted with one to four groups independently selected from the group consisting of $C_1$-$C_4$alkyl, $CO_2H$, $C(O)_2C_1$-$C_4$alkyl, oxo and halogen, and wherein the cycloalkyl substituent is optionally substituted with a $CO_2H$ substituent;

$R^{1A}$ is independently selected at each occurrence from the group consisting of hydrogen, $C_1$-$C_6$alkyl and $C_2$-$C_6$alkenyl;

$R^{1B}$ is independently selected at each occurrence from $C_1$-$C_6$alkyl or phenyl, which phenyl is unsubstituted or substituted with one, two or three groups independently selected from $C_1$-$C_4$alkyl, halogen, $C_1$-$C_4$alkoxy, halo$C_1$-$C_4$alkyl or halo$C_1$-$C_4$alkoxy, wherein $R^{1A}$ and $R^{1B}$ may be taken together to form a cycle;

$R^{1C}$ is independently selected at each occurrence from the group consisting of $C_1$-$C_6$alkyl, hydroxy$C_1$-$C_6$alkyl, halo$C_1$-$C_4$alkyl, mono- and di-$C_1$-$C_4$alkylamino, or phenyl, which phenyl is unsubstituted or substituted with 1 or 2 $C_1$-$C_4$alkyl, $C_1$-$C_4$alkoxy, halo$C_1$-$C_4$alkyl, cyano, halogen morpholino, piperadino, piperazino, and pyrrolidino wherein each morpholino, piperadino, piperazino and pyrrolidino residue is unsubstituted or substituted with 1 or 2 groups independently selected from $C_1$-$C_4$alkyl, $C_1$-$C_4$alkoxy, halo$C_1$-$C_4$alkyl, hydroxy, or halogen;

$R^{1D}$ is independently selected at each occurrence from hydrogen or $C_1$-$C_6$alkyl or $N(R^{1D})_2$, taken in combination, forms a five or six member heterocycle having 0, 1, or 2 additional ring heteroatoms selected from N or O and which is unsubstituted or substituted with one or two groups independently selected form $C_1$-$C_4$alkyl, oxo or hydroxy;

$R^2$ is halogen, or $R^2$ is hydrogen, $C_3$-$C_6$cycloalkyl, $C_1$-$C_{10}$alkyl, $C_1$-$C_{10}$alkanoyl, $C_2$-$C_{10}$alkenyl, or $C_2$-$C_{10}$alkynyl each of which is unsubstituted or substituted with 1, 2, or 3 groups independently selected from the group consisting of hydroxy, halogen, cyano, $C(O)NH_2$, $C(O)N(H)SO_2R^{2C}$, $S(O)_2R^{2C}$, $CO_2H$, $C(O)_2C_1$-$C_6$alkyl, C(O)heterocycle, which heterocycle is a saturated azacycle having 5 or 6 ring atoms and 0 or 1 additional ring heteroatom selected from N, O or S, which heterocycle is unsubstituted or substituted with $C(O)_2C_1$-$C_6$alkyl or $C(O)NH_2$; or $R^1$ and $R^2$, taken in combination, form a heterocyclic ring having between 6 and 12 ring atoms, 0, 1, or 2 additional ring heteroatoms which are independently selected from N, O or S, and which heterocycle is further substituted with 0, 1, 2, or 3 groups independently selected from the group consisting of hydroxy, oxo, $OC(O)N(R^{2D})_2$, $C(O)N(R^{2D})_2$, $C_1$-$C_6$alkyl, =$CH_2$, $C(O)_2H$, $C(O)_2C_1$-$C_6$alkyl, $C(O)R^{2B}$, $N(R^{2A})C(O)R^{2B}$, $N(R^{2A})S(O)_2R^{2B}$, $S(O)_2R^{2C}$ and $S(O)R^{2C}$;

$R^{2A}$ is independently selected at each occurrence from $C_1$-$C_6$alkyl and phenyl, which phenyl is unsubstituted or substituted with methyl, methoxy, fluoro, or chloro;

$R^{2B}$ is independently selected at each occurrence from $C_1$-$C_6$alkyl or phenyl, which phenyl is unsubstituted or substituted with one, two or three groups independently selected from $C_1$-$C_4$alkyl, halogen, $C_1$-$C_4$alkoxy, halo$C_1$-$C_4$alkyl or halo$C_1$-$C_4$alkoxy, wherein $R^{2A}$ and $R^{2B}$ may be taken together to form a cycle;

$R^{2C}$ is independently selected at each occurrence from the group consisting of $C_1$-$C_6$alkyl, $C_1$-$C_6$alkyl substituted with $CO_2H$, halo$C_1$-$C_4$alkyl, mono- and di-$C_1$-alkylamino, or phenyl, which phenyl is unsubstituted or substituted with 1 or 2 $C_1$-$C_4$alkyl, $C_1$-$C_4$alkoxy, halo$C_1$-$C_4$alkyl, cyano, halogen, morpholino, piperadino, piperazino, and pyrrolidino wherein each morpholino, piperadino, piperazino and pyrrolidino residue is unsubstituted or substituted with 1 or 2 groups independently selected from $C_1$-$C_4$alkyl, $C_1$-$C_4$alkoxy, halo$C_1$-$C_4$alkyl, hydroxy, or halogen;

$NR^{2D}$ is independently selected at each occurrence from hydrogen or $C_1$-$C_6$alkyl or $N(R^{2D})_2$, taken in combination, forms a five or six member heterocycle having 0, 1, or 2 additional ring heteroatoms selected from N or O and which is unsubstituted or substituted with one or two groups independently selected form $C_1$-$C_4$alkyl, oxo or hydroxy;

$R^3$ is phenyl or pyridyl, which is substituted with 0, 1, 2 or 3 groups independently selected from the group consisting of $C_1$-$C_6$alkyl, halogen, $C_1$-$C_6$alkoxy, halo$C_1$-$C_6$alkyl, and halo$C_1$-$C_6$alkoxy, and the phenyl or pyridyl is further substituted with 0 or 1 groups selected from $C_3$-$C_6$cycloalkyl, benzyl, phenoxy, pyridyloxy, phenylamino, and pyridylamino, wherein each benzyl, phenoxy, pyridyloxy, phenylamino and pyridylamino is para to the point of attachment of the $R^3$ group to the furyl ring and each benzyl, phenoxy, pyridyloxy, phenylamino and pyridylamino is unsubstituted or substituted with one to three groups independently selected from $C_1$-$C_4$alkyl, halo$C_1$-$C_4$alkyl, $C_1$-$C_4$alkoxy, cyano, fluoro, or chloro; and $R^4$ is H or $C_1$-$C_4$alkyl.

Certain compounds of Formula (I) include those compounds or salts thereof in which R is methyl, $CF_3$ or ethyl.

Certain other compounds of Formula (I) include those compounds or salts thereof in which $R^1$ is $C_1$-$C_6$alkyl which is unsubstituted or substituted with 1 or 2 substituents selected from the group consisting of hydroxy, halogen, cyano, $CO_2H$, $C(O)_2C_1$-$C_6$alkyl, $N(R^{1A})S(O)_2R^{1B}$, $S(O)_2R^{1C}$;

$R^{1A}$ is independently selected at each occurrence from the group consisting of hydrogen $C_1$-$C_6$alkyl and $C_2$-$C_6$alkenyl;

$R^{1B}$ is independently selected at each occurrence from $C_1$-$C_6$alkyl or phenyl, which phenyl is unsubstituted or substituted with one or two groups independently selected from $C_1$-$C_4$alkyl, halogen, or $C_1$-$C_4$alkoxy; wherein $R^{1A}$ and $R^{1B}$ may be taken together to form a cycle; and $R^{1C}$ is independently selected at each occurrence from $C_1$-$C_6$alkyl and phenyl, which phenyl is unsubstituted or substituted with methyl, methoxy, fluoro, or chloro.

In certain other compounds of Formula (I), $R^1$ is selected from $C_2$-$C_5$alkyl substituted with hydroxy, $CO_2H$, $CO_2CH_3$, $CO_2C_2H_5$, $SO_2CH_3$, $SO_2Et$, $SO_2{}^iC_3H_7$, S,S-dioxo-tetrahydrothienyl, S,S,4-trioxo-tetrahydrothienyl, S,S-dioxo-isothiazolidinyl, and cyclopropyl substituted with carboxylic acid. Certain exemplary examples of $R^1$ substituents include, but are not limited to the substituents selected from the group consisting of:

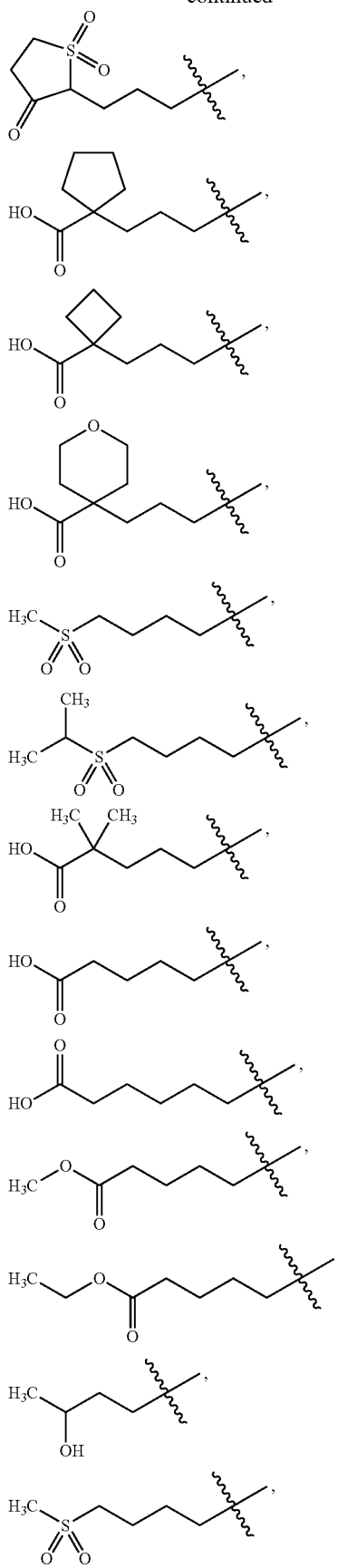

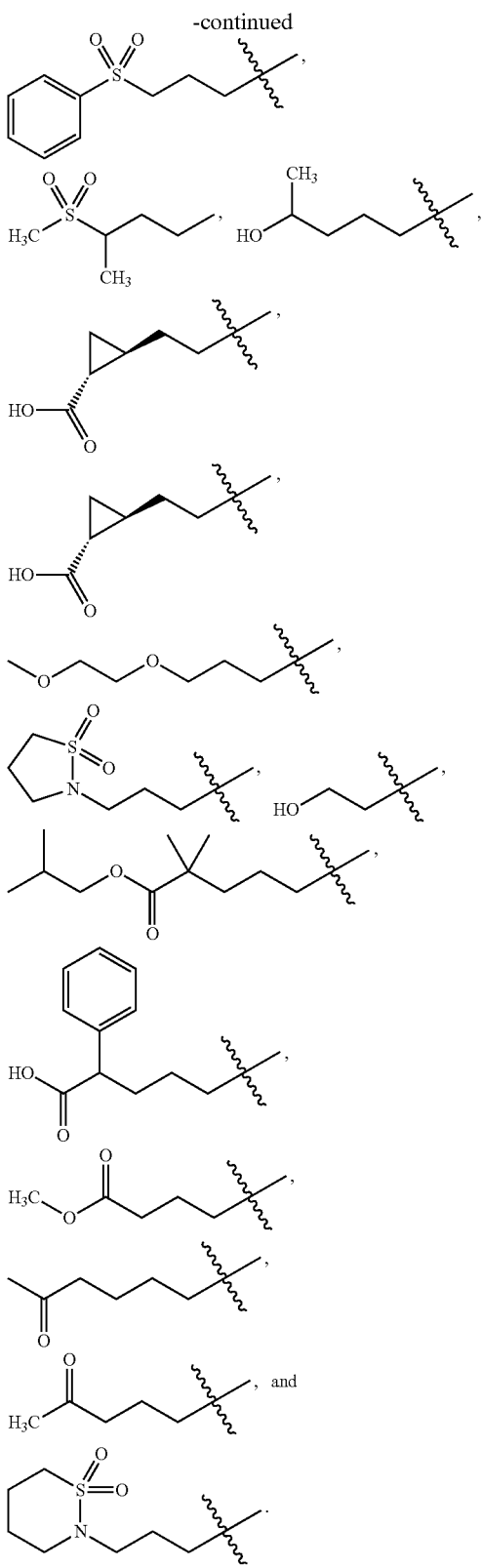

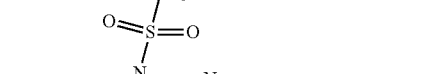

Still other compounds of Formula (I) include compounds and salts thereof in which $R^2$ is cyclopropyl, $C_1$-$C_4$alkyl, halo$C_1$-$C_4$alkyl, $C_2$-$C_4$alkenyl, or $R^2$ is (a) $C_2$-$C_{10}$alkyl substituted with $CO_2H$, cyclopropyl substituted with $CO_2H$, $S(O)_2C_1$-$C_4$alkyl or S,S-dioxo-tetrahydrothienyl; (b) $R^2$ is $C_2$-$C_{10}$alkyl substituted with C(O)-pyrrolidinyl optionally substituted with $C(O)_2C_1$-$C_4$alkyl; or (c) $R^2$ is $C_2$-$C_{10}$alkyl substituted with one or two hydroxy groups. Certain exemplary examples of $R^2$ substituents include, but are not limited to the group consisting of: iodo, ethyl, vinyl, cyclopropyl, and 5,6-dihydroxy-5,6-dimethyl-heptyl.

Certain other compounds of Formula (I) include those compounds or salts thereof in which $R^3$ is phenyl substituted with 1 or 2 groups independently selected from fluoro, chloro, methyl, or ethyl or phenyl is para-substituted with cyclopropyl, benzyl or phenoxy. Certain exemplary $R^3$ groups include para-fluorophenyl, para-chlorophenyl, para-methylphenyl, para-ethylphenyl, para-cyclopropylphenyl, para-benzylphenyl and para-phenoxyphenyl.

Certain compounds of Formula (I), herein referred to as compounds of Formula (II), including salts thereof, comprise those compounds of Formula (I) in which:

R is methyl, $CF_3$ or ethyl;

$R^1$ is $C_1$-$C_6$alkyl which is unsubstituted or substituted with 1 or 2 substituents selected from the group consisting of hydroxy, halogen, cyano, $CO_2H$, $C(O)_2C_1$-$C_6$alkyl, $N(R^{1A})S(O)_2R^{1B}$, $S(O)_2R^{1C}$;

$R^{1A}$ is independently selected at each occurrence from the group consisting of hydrogen and $C_1$-$C_6$alkyl;

$R^{1B}$ is independently selected at each occurrence from $C_1$-$C_6$alkyl or phenyl, which phenyl is unsubstituted or substituted with one or two groups independently selected from $C_1$-$C_4$alkyl, halogen, or $C_1$-$C_4$alkoxy;

$R^{1C}$ is independently selected at each occurrence from $C_1$-$C_6$alkyl and phenyl, which phenyl is unsubstituted or substituted with methyl, methoxy, fluoro, or chloro;

$R^2$ is cyclopropyl, $C_1$-$C_4$alkyl, halo$C_1$-$C_4$alkyl, $C_2$-$C_4$alkenyl, or $R^2$ is $C_2$-$C_{10}$alkyl substituted with $S(O)_2C_1$-$C_4$alkyl, C(O)-pyrrolidinyl optionally substituted with $C(O)_2C_1$-$C_4$alkyl, or $C_2$-$C_{10}$alkyl substituted with one or two hydroxy groups; and $R^3$ is phenyl substituted with 1 or 2 groups independently selected from fluoro, chloro, methyl, or phenoxy.

Certain compounds of Formula (I), herein referred to as compounds of Formula (III) include those compounds of Formula (I) and salts thereof in which $R^1$ and $R^2$, taken in combination form a heterocyclic ring having between 6 and 12 ring atoms, 0 or 1 additional ring heteroatoms selected from N and O, and which heterocycle is further substituted with 0, 1, 2, or 3 groups independently selected from the group consisting of hydroxy, methyl, $=CH_2$, $C(O)_2C_1$-$C_4$alkyl, $S(O)R^{2A}$ and $S(O)_2R^{2A}$; and $R^{2A}$ is independently selected at each occurrence from $C_1$-$C_4$alkyl and phenyl, which phenyl is unsubstituted or substituted with methyl, methoxy, fluoro, or chloro.

Certain exemplary compounds of Formula (III) include those compounds of the formulae:

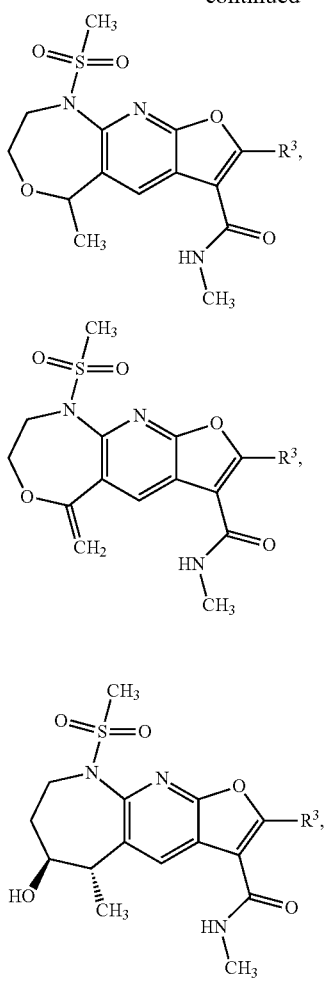

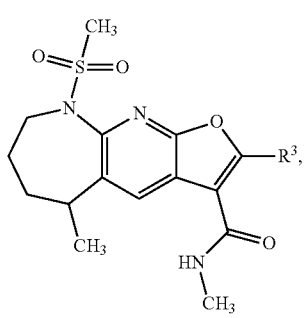

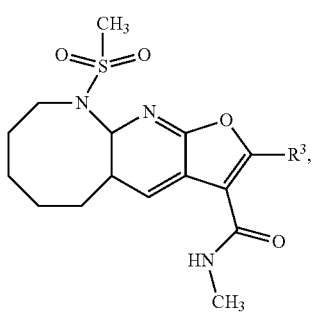

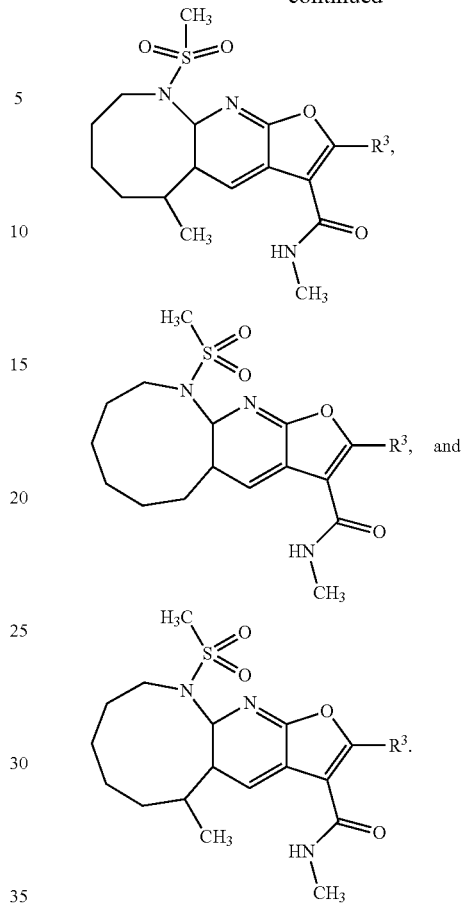

Still other compounds of the invention include those compounds of Formula (IV) and salts thereof:

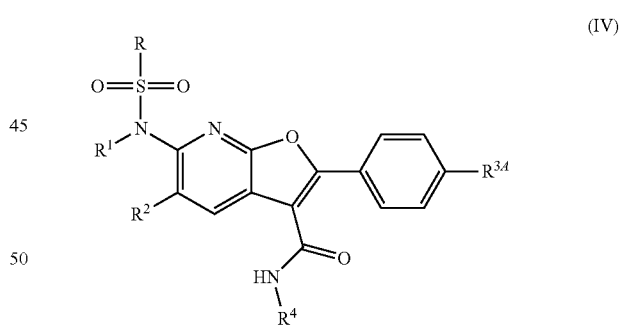

(IV)

R is methyl, $CF_3$ or ethyl;

$R^1$ is $C_1$-$C_6$alkyl which is unsubstituted or substituted with 1 or 2 substituents selected from the group consisting of hydroxy, halogen, cyano, $CO_2H$, $C(O)_2C_1$-$C_6$alkyl, $N(R^{1A})S(O)_2R^{1B}$, $S(O)_2R^{1C}$;

$R^{1A}$ is independently selected at each occurrence from the group consisting of hydrogen and $C_1$-$C_6$alkyl;

$R^{1B}$ is independently selected at each occurrence from $C_1$-$C_6$alkyl or phenyl, which phenyl is unsubstituted or substituted with one or two groups independently selected from $C_1$-$C_4$alkyl, halogen, or $C_1$-$C_4$alkoxy;

$R^{1C}$ is independently selected at each occurrence from $C_1$-$C_6$alkyl and phenyl, which phenyl is unsubstituted or substituted with methyl, methoxy, fluoro, or chloro;

$R^2$ is cyclopropyl, $C_1$-$C_4$alkyl, halo$C_1$-$C_4$alkyl, $C_2$-$C_4$alkenyl, or $R^2$ is $C_2$-$C_{10}$alkyl substituted with $S(O)_2C_1$-$C_4$alkyl, $C(O)$-pyrrolidinyl optionally substituted with $C(O)_2C_1$-$C_4$alkyl, or $C_2$-$C_{10}$alkyl substituted with one or two hydroxy groups; or $R^1$ and $R^2$, taken in combination, form a heterocyclic ring having between 6 and 12 ring atoms, 0 or 1 additional ring heteroatoms selected from N and O, and which heterocycle is further substituted with 0, 1, 2, or 3 groups independently selected from the group consisting of hydroxy, methyl, =$CH_2$, $C(O)_2C_1$-$C_4$alkyl, $S(O)R^{2A}$ and $S(O)_2R^{2A}$; and $R^{2A}$ is independently selected at each occurrence from $C_1$-$C_4$alkyl and phenyl, which phenyl is unsubstituted or substituted with methyl, methoxy, fluoro, or chloro;

$R^{3A}$ is fluoro, chloro, methyl, or phenoxy; and $R^4$ is methyl or ethyl.

Certain preferred compounds of Formula I and Ia include compounds of Formula (V):

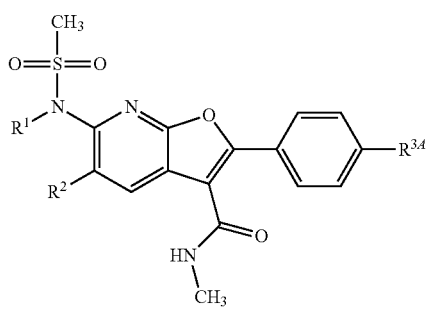

(V)

$R^1$ is $C_3$-$C_{10}$alkyl, $C_2$-$C_8$alkoxy$C_2$-$C_4$alkyl or heterocycle$C_1$-$C_6$alkyl, each of which is substituted with $CO_2H$ and 0, 1 or 2 additional $C_1$-$C_4$alkoxy substituents, wherein the heterocycle is a 4 to 6 member ring having 1 ring oxygen atom;

$R^2$ is cyclopropyl or ethyl, and $R^{3A}$ is fluoro, chloro, $C_1$-$C_3$alkyl, benzyl or phenoxy.

In another aspect, synthetic intermediates are provided which are suitable for use in the preparation of compounds of formula I, Ia, II, III, IV and/or V. The synthetic intermediates are selected from the group consisting of

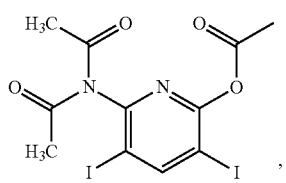

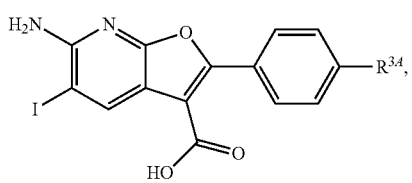

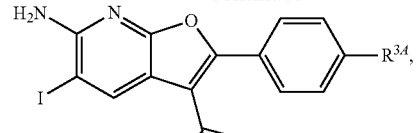

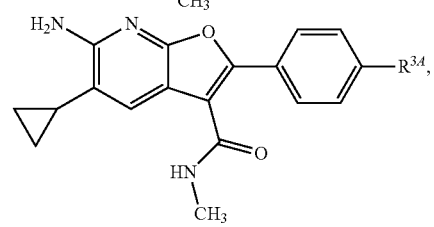

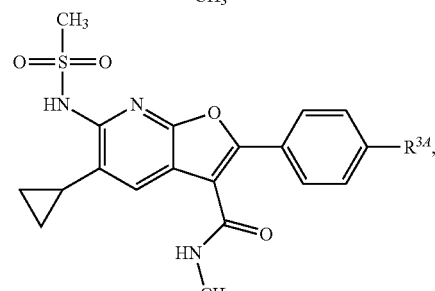

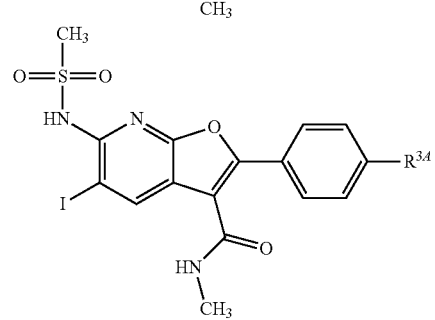

and salts thereof, wherein $R^{3A}$ is fluoro, chloro, methyl or ethyl.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, arginine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by HCV infection, or (ii) associated with HCV infection; or (2) reducing or inhibiting the viral replication or viral load of HCV. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of NS5b; or at least partially reducing or inhibiting the replication of HCV.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, microemulsions, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl disterarate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Emulsion or microemulsion formulations for oral use are also suitable for administration of compounds of Formula I, Ia, II, III, IV, and/or V.

Emulsions or microemulsions can offer greater ease of preparation due to spontaneous formation and thermodynamic stability. They improve the delivery of the drug because they can increase drug loading, enhance penetration, increase dissolution rate, increase bioavailability and reduce inter- and intra-individual variability in drug pharmacokinetics as compared to traditional approaches. As used herein, the term "bioavailable", with reference to a composition, means that composition provides a maximum concentration of the drug in that composition in a use environment that is at least 1.5-fold that of a control comprising an equivalent quantity of the undispersed drug.

As used herein, the term "self-emulsifying emulsion or self-emulsifying microemulsion preconcentrate" or "SEE or SEME preconcentrate" means a composition, or preconcentrate, which spontaneously forms an emulsion or microemulsion, e.g., an o/w emulsion or microemulsion, in an aqueous medium, in water, e.g., on dilution of 1:1 to 1:300, or from 1:1 to 1:70, or from 1:1 to 1:10 or in the gastrointestinal fluids after oral application.

A emulsion or microemulsion preconcentrate comprises a lipophilic component, a hydrophilic component and a surfactant. The hydrophilic component and the surfactant together in the drug delivery system can comprise up to 95% by weight of the composition of the carrier, e.g., 80%.

Within the SEE or SEME preconcentrate, the relative proportions of the lipophilic component, the hydrophilic component and the surfactant lie within the "emulsion or microemulsion" region on a standard three-way plot graph. Such graphs, or phase diagrams, can be generated in a conventional manner by one of ordinary skill in the art. For example, as described in Great Britain U.S. Pat. No. 2,222,770.

As used herein, the term "suspension" or "suspended" means a colloidal dispersion (mixture) in which a finely divided species is combined with another species, with the former being so finely divided and mixed that it doesn't rapidly settle out.

As used herein, the term "solidify" means to make solid or semisolid. "Semisolid" means having the qualities and/or attributes both of the solid and liquid states of matter.

As used herein, the term "lipophilic component" refers to a substance, material or ingredient that is more compatible with oil than with water. A material with lipophilic properties is insoluble or almost insoluble in water but is easily soluble in oil or other nonpolar solvents. The term "lipophilic component" can comprise one or more lipophilic substances that may be natural, synthetic or partially synthetic. Multiple lipophilic components constitute the lipophilic phase of the microemulsion preconcentrate and form the oil aspect, e.g., in an o/w microemulsion. At room temperature (approximately 25-27° C.), the lipophilic component and lipophilic phase of the microemulsion preconcentrate can be solid, semisolid or liquid. For example, a solid lipophilic component can exist as a paste, granular form, powder or flake.

Examples of solid lipophilic components, i.e., solid or semisolid at room temperature, include, but are not limited to, the following:
1. mixtures of mono-, di- and triglycerides, such as hydrogenated coco-glycerides [melting point (m.p.) of about 33.5° C. to about 37° C.], commercially-available as WITEPSOL H15 from Sasol Germany (Witten, Germany);
2. esters, such as propylene glycol (PG) stearate, commercially-available as MONOSTEOL (m.p. of about 33° C. to about 36° C.) from Gattefossé Corp. (Paramus, N.J.); propylene glycol (PG) laurate, commercially available as LAUROGLYCOL FCC from Gattefossé Corp. (Paramus, N.J.); propylene glycol (PG) monolaurate, commercially available as LAUROGLYCOL 90 from Gattefossé Corp. (Paramus, N.J.); propylene glycol dicaprylate/dicaprate, commercially available as CAPTEX 200 from Abitec Corp.; PEG-2 stearate, commercially-available as HYDRINE (m.p. of about 44.5° C. to about 48.5° C.) from Gattefossé Corp.; cetyl palmitate (m.p. of about 50° C.), commercially-available as CUTINA CP from Cognis Corp. (Hoboken, N.J.);
3. glyceryl fatty acid esters, such as hydrogenated palm/palm kernel oil PEG-6 esters (m.p. of about 30.5° to about 38° C.), commercially-available as LABRAFIL M2130 CS from Gattefossé Corp.;
4. fatty alcohols, such as myristyl alcohol (m.p. of about 39° C.), commercially-available as LANETTE 14 from Cognis Corp.;
5. polyglycosylated saturated glycerides, such as lauroyl macrogol-32 glycerides (m.p. of about 42-46° C.), commercially available as GELUCIRE 44/14 from Gattefossé Corp. Although GELUCIRE 44/14 is dispersible in water, for the present invention, GELUCIRE 44/14 is a solid lipophilic compound; and
6. α-tocopheryl polyethylene glycol succinate (m.p. of about 36° C.), commericially available as Vitamin E TPGS from Eastman Chemical Co. (Kingsport, Tenn.).

Examples of liquid lipophilic components, i.e., liquid at room temperature include, but are not limited to, the following:
1. mixtures of mono-, di- and triglycerides, such as medium chain mono- and di-glycerides glyceryl caprylate/caparate, commercially-available as CAPMUL MCM from Abitec Corp. (Columbus, Ohio);
2. esters, such as PG monocaprylate, commercially-available as CAPMUL PG-8 from Abitec Corp.;
3. oils, such as safflower oil, sesame oil, corn oil, castor oil, coconut oil, cotton seed oil, soybean oil, olive oil and mineral oil;
4. essential oils, or any of a class of volatile oils that give plants their characteristic odors, such as spearmint oil, clove oil, lemon oil and peppermint oil;
5. fractions or constituents of essential oils, such as menthol, carvacrol and thymol; and
6. synthetic oils, such as triacetin, tributryin, ethyl butyrate, ethyl caprylateoleic acid, ethyl oleate, isopropyl myristate and ethyl caprylate.

The lipophilic component may comprise from about 5% to about 85% by weight of the composition of the carrier, e.g., from about 10% to about 85%, e.g., from about 15% to about 60%, e.g., from about 20% to about 40%.

As used herein, the "hydrophilic component" comprises a hydrophilic component and/or water. A solid hydrophilic component is added in the microemulsion preconcentrate in order to render or help render the microemulsion preconcentrate a solid or semisolid at room temperature. Examples of hydrophilic components that may be used in the present invention include, but not limited to, polyethylene glycol (PEG), PEG derivatives, polyethylene oxide (PEO), and silicon dioxide ($SiO_2$).

One example of a hydrophilic component that may be used in the present invention is polyethylene glycol (PEG). Polyethylene glycol (PEG) is the polymer of ethylene oxide that conforms generally to the formula $H(OCH_2CH_2)_nOH$ in which n represents the average molecular weight of the polymer. The types of PEG useful in the present invention can be categorized by its state of matter, i.e., whether the substance exists in a solid or liquid form at room temperature and pressure. As used herein, "solid PEG" refers to PEG having a molecular weight such that the substance is in a solid state at room temperature and pressure. For example, PEG having a molecular weight ranging between 1,000 and 10,000 is a solid PEG. Particularly useful solid PEGs are those having a molecular weight between 1,450 and 8,000. Especially useful as a solid PEG are PEG 1450, PEG 3350, PEG 4000, PEG 8000, derivatives thereof and mixtures thereof. PEGs of various molecular weights are commercially-available as the CARBOWAX SENTRY series from Dow Chemicals (Danbury, Conn.). Moreover, solid PEGs have a crystalline structure, or polymeric matrix, which is a particularly useful attribute in the present invention.

Another hydrophilic component that may be used in the present invention is a PEG derivative. PEG derivatives useful as a hydrophilic component in the present invention include, but are not limited to, block co-polymers, such as different poloxamers commercially-available from BASF Corp. (Mt. Olive, N.J.) and Vitamin E TPGS.

In one exemplary embodiment of the present invention, up to 80% of the carrier (when liquefied), for example, comprising the salt form of the drug, the lipophilic component and the surfactant, can be incorporated into the hydrophilic component without disturbing the crystalline structure of the hydrophilic component.

In another exemplary embodiment, the hydrophilic component of the carrier consists of a single hydrophilic component, e.g., a solid PEG, e.g., PEG 1450, PEG 3350, PEG 4000 and PEG 8000. In this exemplary embodiment, the hydrophilic phase of the microemulsion component consists of a single hydrophilic substance. For example, if the carrier comprised PEG 3350, the carrier would contain no other hydrophilic substances, e.g., lower alkanols (lower alkyl being $C_1$-$C_4$), such as ethanol; or water. Substances that have affinity for both the lipophilic phase and the hydrophilic phase, such as surfactants would not be considered a hydrophilic substance for this exemplary embodiment. Thus, the carrier could contain a surfactant in addition to the single hydrophilic component.

In yet another alternative exemplary embodiment, the hydrophilic component of the carrier consists of a mixture of solid PEGs. For example, the hydrophilic component comprises PEG 1450, PEG 3350, PEG 4000, PEG 8000, derivatives thereof and any combinations and mixtures thereof.

Yet another hydrophilic component that may be used in the present invention is polyethylene oxide (PEO). Polyethylene oxide (PEO) which is a nonionic homopolymer of ethylene oxide, represented by the formula $(CH_2Ch_2O)_n$, in which n represents the average number of oxyethylene groups. The various grades of PEO are commercially-available as POLYOX from Dow Chemicals. At room temperature and pressure, PEO exists in a solid state. PEO, for example, has a molecular weight ranging from about 100,000 to 7,000,000.

Yet another hydrophilic component that may be used in the present invention is silicon dioxide ($SiO_2$), which is commercially available as AEROSIL from Evonik Industries. The hydrophilic component in the present invention can comprise PEG, PEO, $SiO_2$ and any combinations of the foregoing.

The hydrophilic component may comprise from about 15% to about 90% by weight of the carrier, e.g., from about 20% to about 70%, e.g., from about 30% to about 50%.

In the present invention, the carrier also comprises one or more surfactants, i.e., a mixture of surfactants; or surface active agents, which reduce interfacial tension. The surfactant can be added to either the hydrophilic or lipophilic phase of the carrier. The surfactant is, e.g., nonionic, ionic or amphoteric. Surfactants can be complex mixtures containing side products or unreacted starting products involved in the preparation thereof, e.g., surfactants made by polyoxyethylation may contain another side product, e.g., PEG. The surfactant or surfactants can have any HLB that is useful in the pharmaceutical arts. For example, the surfactant has a hydrophilic-lipophilic balance (HLB) having a mean HLB value of 8-17, e.g., 10-17. Examples of surfactant types include, but are not limited to, fatty acids; alkyl sulfonates; polyoxyethylene fatty acids; sorbitan derivatives; polyoxyethylene sorbitan fatty acid esters; lecithin; phospholipids; mono-, di- and triglycerides; and mixtures thereof.

Examples of such surfactants include, but are not limited to, 1. reaction products of a natural or hydrogenated castor oil and ethylene oxide. The natural or hydrogenated castor oil may be reacted with ethylene oxide in a molar ratio of from about 1:35 to about 1:60, with optional removal of the PEG component from the products. Various such surfactants are commercially-available, e.g., the CREMOPHOR series from BASF Corp. (Mt. Olive, N.J.), such as CREMOPHOR RH 40 which is PEG-40 hydrogenated castor oil which has a saponification value of about 50- to 60, an acid value less than about one, a water content, i.e., Fischer, less than about 2%, an $n_D^{60}$ of about 1.453-1.457, and an HLB of about 14-16;
2. polyoxyethylene fatty acid esters that include polyoxyethylene stearic acid esters, such as the MYRJ series from Uniqema (New Castle, Del.), e.g., MYRJ 53 having a m.p. of about 47° C. Particular compounds in the MYRJ series are, e.g., MYRJ 53 having a m.p. of about 47° C. and PEG-40-stearate available as MYRJ 52;
3. sorbitan derivatives that include the TWEEN series from Uniqema (New Castle, Del.), e.g., TWEEN 20, TWEEN 40, TWEEN 60 and TWEEN 80;
4. polyoxyethylene-polyoxypropylene co-polymers and block co-polymers or poloxamers, e.g., SYNPERONIC PE/F 87/108/127L44 from Uniqema and PLURONIC (Lutrol F127) from BASF;
5. polyoxyethylene alkyl ethers, e.g., such as polyoxyethylene glycol ethers of $C_{12}$-$C_{18}$ alcohols, e.g., polyoxyl 2-, 10- or 20-cetyl ether or polyoxyl 23-lauryl ether, or polyoxyl 20-oleyl ether, or polyoxyl 2-, 10-, 20- or 100-stearyl ether, as known and commercially-available as the BRIJ series from Uniqema. Particularly useful products from the BRIJ series are BRIJ 58; BRIJ 76; BRIJ 78; BRIJ 35, i.e., polyoxyl 23 lauryl ether; BRIJ 96; and BRIJ 98, i.e., polyoxyl 20 oleyl ether. These products have a m.p. between about 32° C. to about 43° C.;
6. water-soluble tocopheryl PEG succinic acid esters available from Eastman Chemical Co. (Kingsport, Tenn.) with a m.p. of about 36° C.;
7. PEG sterol ethers having, e.g., from 5-35 [$CH_2$—$CH_2$—O] units, e.g., 20-30 units, e.g., SOLULAN C24 (Choleth-24 and Cetheth-24) from Chemron (Paso Robles, Calif.);

8. polyglycerol fatty acid esters, e.g., having a range of glycerol units from 4-10, or 4, 6 or 10 glycerol units. For example, particularly suitable are deca-/hexa-/tetraglyceryl monostearate, e.g., DECAGLYN, HEXAGLYN and TETRAGLYN from Nikko Chemicals (Tokyo, Japan); and
9. alkylene polyol ether or ester, e.g., lauroyl macrogol-32 glycerides and/or stearoyl macrogol-32 glycerides which are GELUCIRE 44/14 and GELUCIRE 50/13 respectively.

The surfactant or mixture of surfactants may comprise from about 1-90% by weight of the carrier, e.g., from 5-85% by weight of the carrier, e.g., from 10-80% by weight of the carrier, e.g., from 20-60% by weight of the carrier, e.g., from 35-55% by weight of the carrier.

In certain embodiments of the present invention, the pharmaceutical composition may include optional additional excipients commonly found in pharmaceutical compositions. Examples of such excipients include, but are not limited to, cosurfactants, antioxidants, antimicrobial agents, fillers, acidifiers, enzyme inhibitors, stabilizers, disintegrants, binders, preservatives, flavors, sweeteners and other components as described in *Handbook of Pharmaceutical Excipients*, Rowe et al., Eds., $4^{th}$ Edition, Pharmaceutical Press (2003), which is hereby incorporated by reference.

A "cosurfactant", as used herein, is a surface-active agent that acts in addition to the surfactant by further lowering the interfacial energy but that cannot form micellar aggregates by itself. Cosurfactants can be, for example, hydrophilic or lipophilic. Examples of a cosurfactant include, but are not limited to, cetyl alcohol and stearyl alcohol.

Examples of antioxidants include, but are not limited to, ascorbic acid and its derivatives, tocopherol and its derivatives, butyl hydroxyl anisole and butyl hydroxyl toluene. Vitamin E as α-tocopherol is particularly useful.

Examples of fillers include, but are not limited to, microcrystalline cellulose, silicon dioxide, starch and its derivatives, lactose, dicalcium phosphate, mannitol.

Examples of acidifiers include, but are not limited to, citric acid, succinic acid, fumaric acid, ascorbic acid, phosphric acid, capric acid, oleic acid and glutamic acid.

Examples of disintegrants include, but are not limited to, alginic acid, carboxymethylcellulose calcium, carboxymethylcellulose sodium, colloidal silicon dioxide, croscarmellose sodium, crospovidone, guar gum, magnesium aluminum silicate, methyl cellulose, microcrystalline cellulose, polacrilin potassium, powdered cellulose, pregelatinized starch, sodium alginate, sodium starch glycolate and starch.

Examples of binders include, but are not limited to, polyvinylpyrrolidone, hydroxypropylmethylcellulose (HPMC), hydroxypropylcellulose (HPC), sucrose, gelatin and acacia.

These optional additional excipients may comprise from about 0.05-50% by weight of the total pharmaceutical composition. Antioxidants, anti-microbial agents, enzyme inhibitors, stabilizers or preservatives typically provide up to about 0.05-1% by weight of the total pharmaceutical composition. Sweetening or flavoring agents typically provide up to about 2.5% or 5% by weight of the total pharmaceutical composition.

In a further aspect of the present invention, a process for preparing a self-emulsifying pharmaceutical composition containing the free acid, free base or salt form of a drug substance, comprising the steps of bringing said drug substance and an emulsion or microemulsion preconcentrate comprising a lipophilic component, a surfactant and a hydrophilic component into suspended mixtures.

The self-emulsifying emulsion or microemulsion preconcentrate can be prepared separately before mixing with the drug. Alternatively, two or more of the components of the carrier can be mixed together with the drug substance.

The emulsion or microemulsion preconcentrate preferably spontaneously or substantially spontaneously forms an o/w emulsion, e.g., microemulsion, when diluted with an aqueous medium, such as water, to a dilution of 1:1 to 1:300, e.g., 1:1 to 1:70, especially 1:10 to 1:70, more especially, e.g., 1:10, or in the gastrointestinal fluids of a patient after oral administration.

In a further aspect of the present invention, the invention provides a process for the preparing a self-emulsifying emulsion or microemulsion containing the free acid, free base or salt form of a drug substance, which process comprises the following steps:
(a) mixing the free acid, free base or salt form of a drug substance and a SEE or SEME preconcentrate comprising a lipophilic component, a surfactant and a hydrophilic component to form a self-emulsifying pharmaceutical composition; and
(b) diluting the self-emulsifying pharmaceutical composition in an aqueous medium to form a microemulsion.

In a further aspect of the present invention, the invention provides a process for making a self-emulsifying emulsion or microemulsion drug delivery system containing the free acid, free base or salt form of a drug substance. The process comprises the steps of blending a drug substance in the free acid, free base or salt form with an oil, surfactant, polymer and optional additional excipients in a suitable container; melt granulating or extruding this mixture at a suitable temperature; milling this mixture and placing it in a capsule or tablet or other oral delivery dosage form.

The relative proportion of the lipophilic component(s), the surfactant(s) and the hydrophilic component(s) should lie within the "emulsion or microemulsion" region on a standard three-way plot graph. The compositions will therefore be of high stability that are capable, on addition to an aqueous medium, of providing emulsions or microemulsions, e.g., having a mean particle size less than 300 nm, especially less than 200 nm. The drug substance may either be dissolved or suspended in the emulsion or microemulsion. The emulsion or microemulsion formed may be administered enterally, e.g., orally, e.g., in the form of a drinkable solution. When the composition of the invention is an emulsion or microemulsion preconcentrate, a unit dosage of the emulsion or microemulsion preconcentrate can be used to fill orally administrable capsule shells. The capsule shells may be soft or hard capsule shells, e.g., made of gelatine or hydroxylpropylmethyl cellulose. When the capsule shells contact or immersed into an aqueous medium the shells dissolve or disintegrate release the their contents into the aqueous medium allowing the microemulsion to form.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (a g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. NS5b inhibitory properties, e.g. as indicated in in vitro and in vivo tests as provided in the next sections and are therefore indicated for therapy.

In one embodiment, the invention provides a method of treating an HCV-associated disorder comprising administering to a subject in need thereof a pharmaceutically acceptable amount of a compound of the invention, such that the HCV-associated disorder is treated.

In another embodiment, the invention provides a method of treating an HIV infection comprising administering to a subject in need thereof a pharmaceutically acceptable amount of a compound of the invention.

In still another embodiment, the invention provides a method of treating, inhibiting or preventing the activity of HCV in a subject in need thereof, comprising administering to the subject a pharmaceutically acceptable amount of a compound of the invention. In one embodiment, the compounds of the invention inhibit the activity of the NS2 protease, the NS3 protease, the NS3 helicase, the NS5a protein, and/or the NS5b polymerase. In another embodiment, the interaction between the NS3 protease and NS4A cofactor is disrupted. In yet another embodiment, the compounds of the invention prevent or alter the severing of one or more of the NS4A-NS4B, NS4B-NS5A and NS5A-NS5B junctions of the HCV. In another embodiment, the invention provides a method of inhibiting the activity of a serine protease, comprising the step of contacting said serine protease with a compound of the invention. In another embodiment, the invention provides a method of treating, inhibiting or preventing the activity of HCV in a subject in need thereof, comprising administering to the subject a pharmaceutically acceptable amount of a compound of the invention, wherein the compound interacts with any target in the HCV life cycle. In one embodiment, the target of the HCV life cycle is selected from the group consisting of NS2 protease, NS3 protease, NS3 helicase, NS5a protein and NS5b polymerase.

In another embodiment, the invention provides a method of decreasing the HCV RNA load in a subject in need thereof comprising administering to the subject a pharmaceutically acceptable amount of a compound of the invention.

In another embodiment, the compounds of the invention exhibit HCV protease activity. In one embodiment, the compounds are an HCV NS3-4A protease inhibitor.

In another embodiment, the invention provides a method of treating an HCV-associated disorder in a subject, comprising administering to a subject in need thereof a pharmaceutically acceptable amount of a compound of the invention, and a pharmaceutically acceptable carrier, such that the HCV-associated disorder is treated.

In still another embodiment, the invention provides a method of treating an HCV-associated disorder comprising administering to a subject in need thereof a pharmaceutically effective amount of a compound of the invention, in combination with a pharmaceutically effective amount of an additional HCV-modulating compound, such as interferon or derivatized interferon, or a cytochrome P450 monooxygenase inhibitor, such that the HCV-associated disorder is treated. In one embodiment, the additional HCV-modulating compound is selected from the group consisting of NIM811, ITMN191, MK-7009, TMC 435350, Sch 503034 and VX-950.

In another embodiment, the invention provides a method of inhibiting hepatitis C virus replication in a cell, comprising contacting said cell with a compound of the invention.

In yet another embodiment, the invention provides a packaged HCV-associated disorder treatment, comprising an HCV-modulating compound of the invention, packaged with instructions for using an effective amount of the HCV-modulating compound to treat an HCV-associated disorder.

In certain embodiments, the HCV-associated disorder is selected from the group consisting of HCV infection, liver cirrhosis, chronic liver disease, hepatocellular carcinoma, cryoglobulinaemia, non-Hodgkin's lymphoma, liver fibrosis and a suppressed innate intracellular immune response.

In another embodiment, the invention provides a method of treating HCV infection, liver cirrhosis, chronic liver disease, hepatocellular carcinoma, cryoglobulinaemia, non-Hodgkin's lymphoma, liver fibrosis and/or a suppressed innate intracellular immune response in subject in need thereof comprising administering to the subject a pharmaceutically acceptable amount of a compound of the invention.

In one embodiment, the HCV to be treated is selected of any HCV genotype. In another embodiment, the HCV is selected from HCV genotype 1, 2 and/or 3.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the in vitro & in vivo methods provided infra.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a viral infection or disease associated with viral infection or condition mediated by hepatitis C virus. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I).

In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition caused by or associated with HCV infection, wherein the medicament is prepared for administration with another therapeutic agent. The invention also provides the use of another therapeutic agent for treating a disease or condition caused by or associated with HCV infection, wherein the medicament is administered with a compound of formula (I).

The invention also provides a compound of formula (I) for use in a method of treating a disease or condition caused by or associated with HCV infection, wherein the compound of formula (I) is prepared for administration with another therapeutic agent. The invention also provides another therapeutic agent for use in a method of treating a disease or condition caused by or associated with HCV infection, wherein the other therapeutic agent is prepared for administration with a compound of formula (I). The invention also provides a compound of formula (I) for use in a method of treating a disease or condition caused by or associated with HCV infection, wherein the compound of formula (I) is administered with another therapeutic agent. The invention also provides another therapeutic agent for use in a method of treating a disease or condition caused by or associated with HCV infection, wherein the other therapeutic agent is administered with a compound of formula (I).

The invention also provides the use of a compound of formula (I) for treating a disease or condition caused by or associated with HCV infection, wherein the patient has previously (e.g. within 24 hours) been treated with another therapeutic agent. The invention also provides the use of another therapeutic agent for treating a disease or condition caused by or associated with HCV infection, wherein the patient has previously (e.g. within 24 hours) been treated with a compound of formula (I).

In one embodiment, the other therapeutic agent is selected from second therapeutic agents which are active against viruses and, in particular, against HCV. The compound and agent may be administered in a single or separate formulations. Agents active against HCV include, but are not limited to, interferon-α, pegylated interferon-α (peginterferon-α), albinterferon-α2b (albIFN, Novartis/Human Genome Science), PEG-Interferon lambda (BMS/ZymoGenetics), ribavirin, levovirin, viramidine, a combination of interferon-α and ribavirin, a combination of peginterferon-α and ribavirin, a combination of albIFN and ribavirin, a combination of interferon-α and levovirin, a combination of peginterferon-α and levovirin, and a combination of albIFN and levovirin. Interferon-α includes, but is not limited to, recombinant interferon-α2a (such as ROFERON interferon available from Hoffman-LaRoche, Nutley, N.J.), interferon-α2b (such as Intron-A interferon available from Schering Corp., Kenilworth, N.J., USA), a consensus interferon, and a purified interferon-α product. Pegylated interferon-α includes, but is not limited to, PEG IFN-α2a (such as Pegsys available from Hoffman-LaRoche, Nutley, N.J.), PEG IFN-α2b (such as PegIntron available from Schering Corp., Kenilworth, N.J., USA), For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

The agents active against hepatitis C virus also include agents that inhibit HCV NS2 or NS3 proteases, HCV NS5B polymerase, HCV NS5A protein, HCV NS3 helicase, HCV NS4B protein, HCV p7 protein, HCV NS4A protein, HCV IRES and protein translation, HCV entry, HCV assembly, HCV egress, and inosine 5'-monophosphate dehydrogenase, cyclophilins or other host factors that are required for HCV replication. Still other compounds include those disclosed in WO 2004/014313 and WO 2004/014852 and in the references cited therein.

Specific antiviral agents include BI-201335 (Boehringer Ingelheim), telaprevir (Vertex), VX-813 (Vertex), VX-500 (Vertex), boceprevir (Schering-Plough), Sch 900518 (Schering-Plough), ITMN-191/R7227 (Intermune/Roche), ITMN-5489 (Intermune), MK-7009 (Merck), TMC435 (Tibotec), BMS-650032 (Bristol-Myers-Squibb), PHX1766 (Phenomix), GS-9256 (Gilead), VCH-916 (Vertex), VCH-759 (Vertex), VCH-222/VX-222 (Vertex), ABT-333 (Abbott), ANA-598 (Anadys), PF-868,554 (Pfizer), MK-3281 (Merck), PSI-7851 (Pharmasset), R7128 (Pharmasset/Roche), R1626 (Roche), GS9190 (Gilead), BI-207127 (Boehringer Ingelheim), JTK-652 (Japan Tobacco Inc.), IDX375 (Idenix), Valopicitabine/NM283 (Idenix), IDX-184 (Idenix), AZD2836/A-831 (Arrow/AstraZeneca), AZD7295/A-689 (Arrow/AstraZeneca), BMS-790052 (Bristol-Myers-Squibb), PPI-461 (Presidio), EDP-239 (Enanta), Ceplene (Maxim Pharmaceuticals), Civacir (Nabi Biopharmaceuticals Inc, VX-497 (Vertex Pharmaceuticals Inc.), XTL-002 (XTL Biopharmaceuticals), isatoribine and its prodrugs ANA971, ANA975 and ANA773 (Anadys), NIM811 (Novartis), DEBIO-025 (DebioPharm/Novartis), SCY-635 (Scynexis), and nitazoxanide (Romark), IDN-6556 (Idun Pharmaceuticals), IP-501 (Indevus Pharmaceuticals), ISIS14803 (ISIS Pharmaceuticals Inc.), In some embodiments, the compositions and methods of the present invention contain a compound of the invention and interferon. In some aspects, the interferon is selected from the group consisting of interferon alpha 2B, pegylated interferon alpha, consensus interferon, interferon alpha 2A, and lymphoblastoid interferon tau.

In other embodiments the compositions and methods of the present invention contain a compound of the invention and a compound having anti-HCV activity is selected from the group consisting of interleukin 2, interleukin 6, interleukin 12, a compound that enhances the development of a type 1 helper T cell response, interfering RNA, anti-sense RNA, Imiquimod, ribavirin, an inosine 5'-monophospate dehydrogenase inhibitor, amantadine, and rimantadine.

In still other embodiments, the compound having anti-HCV activity is Ribavirin, levovirin, viramidine, thymosin alpha-1, an inhibitor of NS3 serine protease, and inhibitor of inosine monophosphate dehydrogenase, interferon-alpha, or pegylated interferon-alpha alone or in combination with Ribavirin or viramidine.

In another embodiments, the compound having anti-HCV activity is said agent active against HCV is interferon-alpha or pegylated interferon-alpha alone or in combination with Ribavirin or viramidine.

General Synthetic Methods

The compounds disclosed herein can be prepared by following the general procedures and examples set forth below.

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Typically, the compounds of formula (I) can be prepared according to the Schemes provided infra

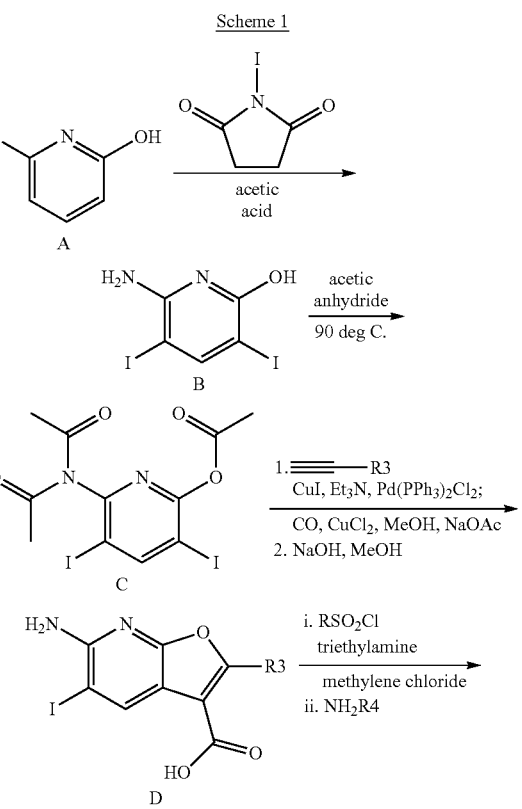

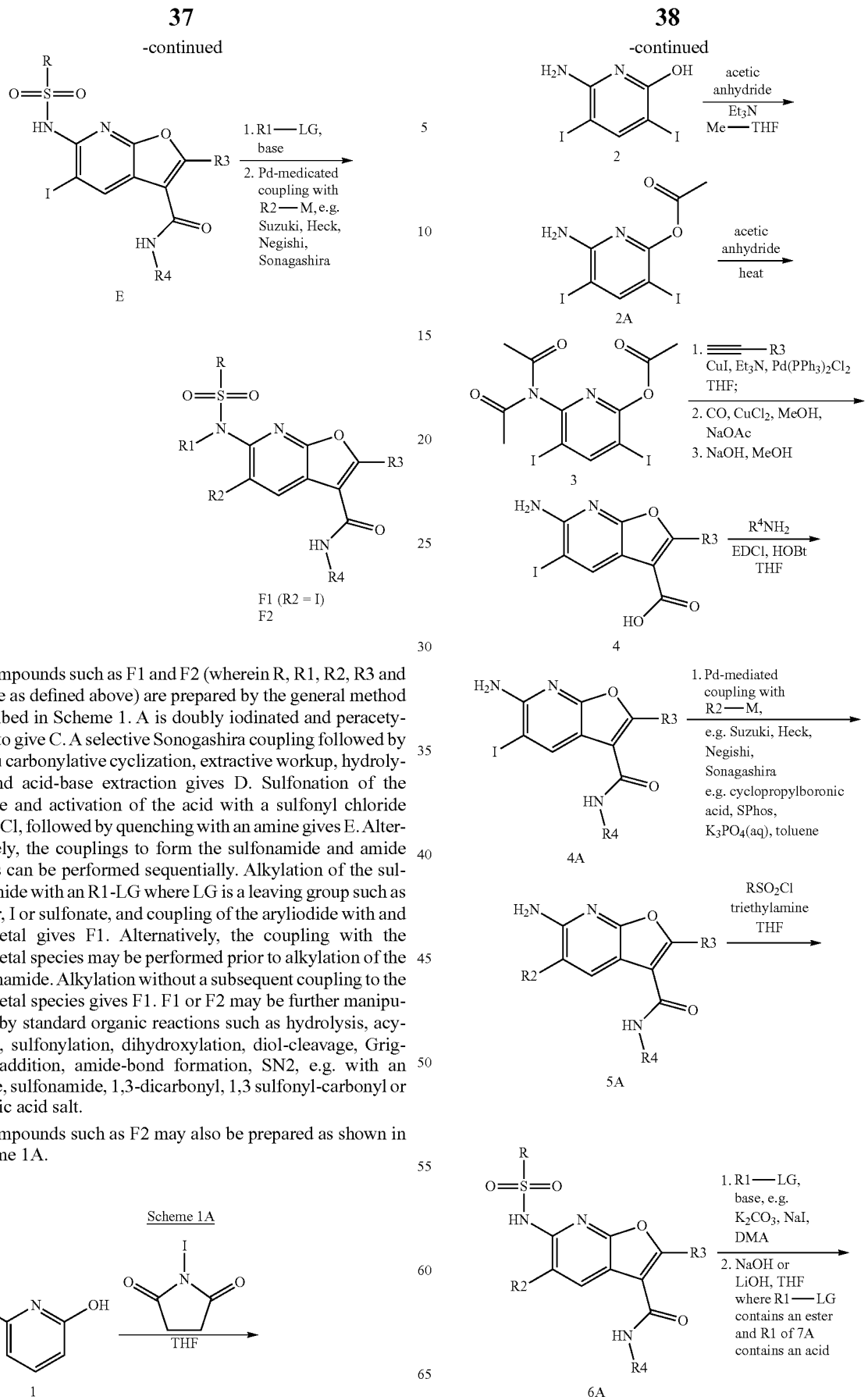

Compounds such as F1 and F2 (wherein R, R1, R2, R3 and R4 are as defined above) are prepared by the general method described in Scheme 1. A is doubly iodinated and peracetylated to give C. A selective Sonogashira coupling followed by in situ carbonylative cyclization, extractive workup, hydrolysis and acid-base extraction gives D. Sulfonation of the aniline and activation of the acid with a sulfonyl chloride $RSO_2Cl$, followed by quenching with an amine gives E. Alternatively, the couplings to form the sulfonamide and amide bonds can be performed sequentially. Alkylation of the sulfonamide with an R1-LG where LG is a leaving group such as Cl, Br, I or sulfonate, and coupling of the aryliodide with and R2-metal gives F1. Alternatively, the coupling with the R2-metal species may be performed prior to alkylation of the sulfonamide. Alkylation without a subsequent coupling to the R2-metal species gives F1. F1 or F2 may be further manipulated by standard organic reactions such as hydrolysis, acylation, sulfonylation, dihydroxylation, diol-cleavage, Grignard addition, amide-bond formation, SN2, e.g. with an amine, sulfonamide, 1,3-dicarbonyl, 1,3 sulfonyl-carbonyl or sulfinic acid salt.

Compounds such as F2 may also be prepared as shown in Scheme 1A.

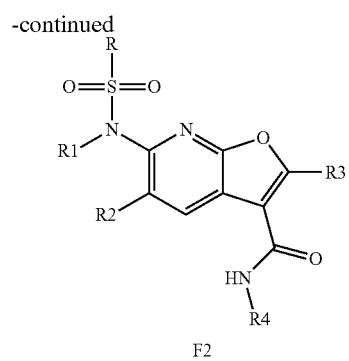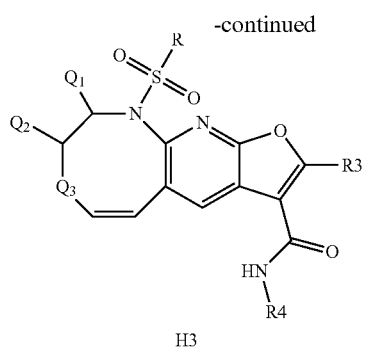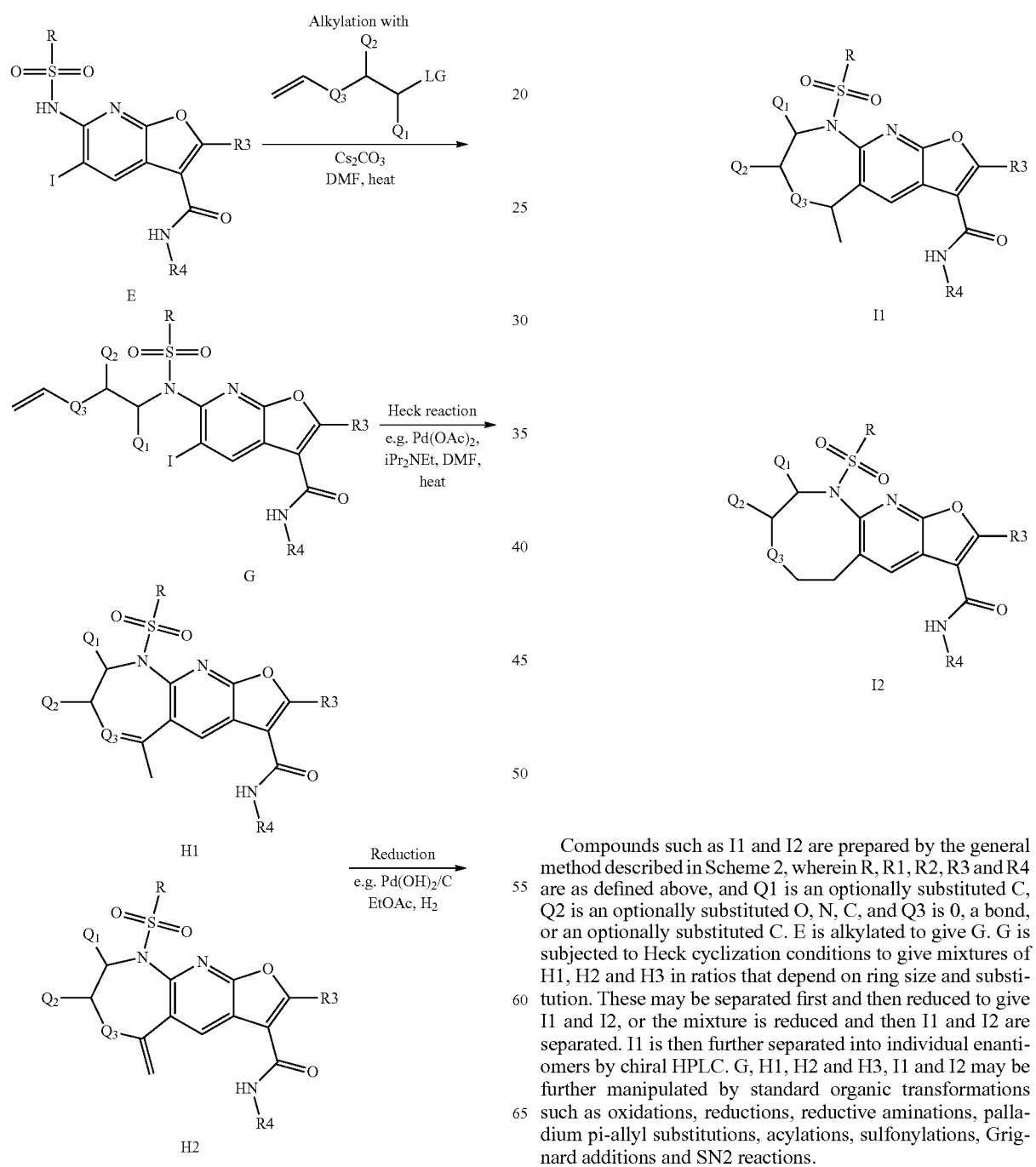

Compounds such as I1 and I2 are prepared by the general method described in Scheme 2, wherein R, R1, R2, R3 and R4 are as defined above, and Q1 is an optionally substituted C, Q2 is an optionally substituted O, N, C, and Q3 is 0, a bond, or an optionally substituted C. E is alkylated to give G. G is subjected to Heck cyclization conditions to give mixtures of H1, H2 and H3 in ratios that depend on ring size and substitution. These may be separated first and then reduced to give I1 and I2, or the mixture is reduced and then I1 and I2 are separated. I1 is then further separated into individual enantiomers by chiral HPLC. G, H1, H2 and H3, I1 and I2 may be further manipulated by standard organic transformations such as oxidations, reductions, reductive aminations, palladium pi-allyl substitutions, acylations, sulfonylations, Grignard additions and SN2 reactions.

Scheme 3

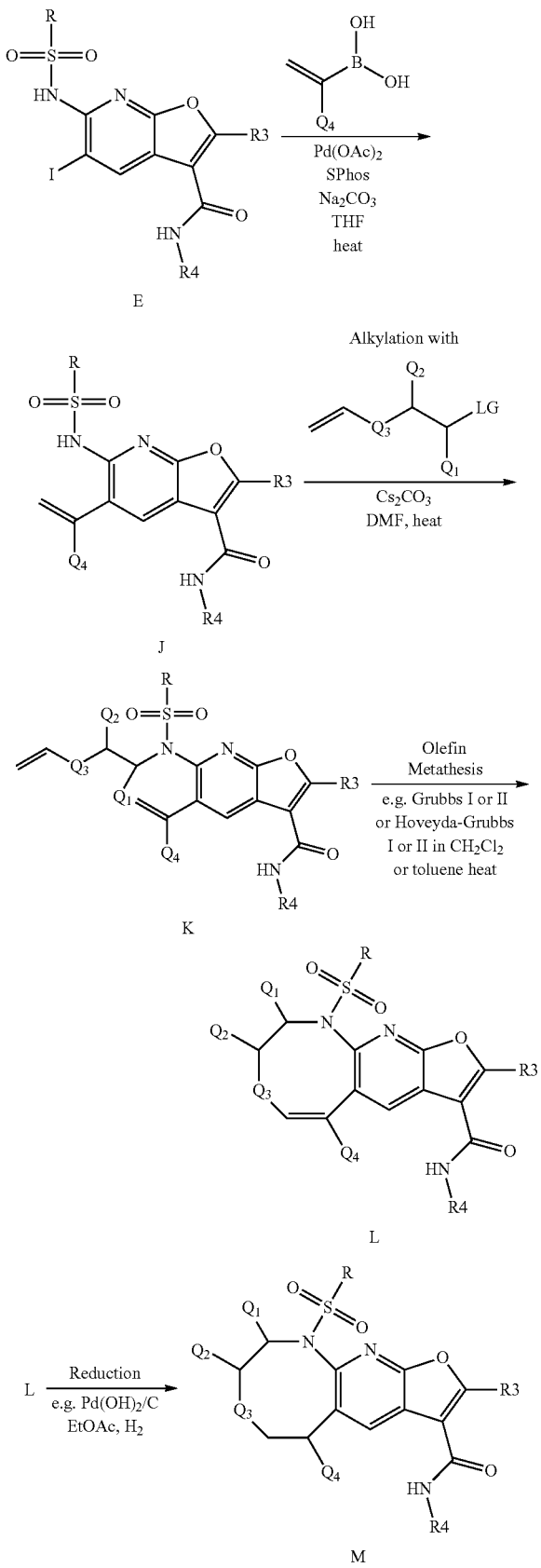

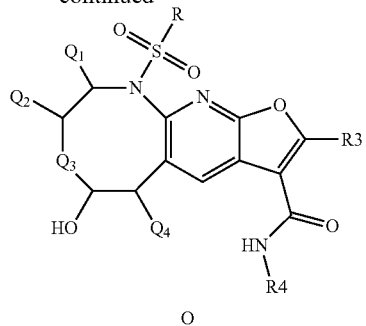

Compounds such as M and O (wherein R, R1, R2, R3 and R4, Q1, Q2, Q3 are as defined above and Q4 is $C_{1-3}$ alkyl) are prepared as described in Scheme 3. J is prepared by a palladium-catalyzed Suzuki coupling of E with a vinylboronic acid. This vinylboronic acid may prepared in situ by reaction of a vinylmagnesium halide and a trialkyl borate followed by treatment with water. A vinyltrifluoroborate salt may be substituted for the vinylboronic acid. J is alkylated to give K, which is then cyclized under olefin metathesis conditions to give L. L is reduced to give M or hydroborated and oxidized to give O. M and O are either prepared enantioselectively and/or resolved on chiral HPLC. L, M and O may be further manipulated by standard organic transformations such as oxidations, reductions, reductive aminations, palladium pi-allyl substitutions, acylations, sulfonylations, Grignard additions and SN2 reactions.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

In one embodiment, the invention provides a method of modulating viral activity in a subject, wherein the method comprises administering to the subject a therapeutically effective amount of the compound according to the definition of formula (I). Methods of inhibiting viral replication or inhibiting viral load in a subject are provided, wherein the virus is a member of the Flaviviridae family of viruses such as hepatitis C virus.

In one embodiment, the invention provides a method of treating a disorder or a disease in a subject caused by or associated with HCV infection, wherein the method comprises administering to the subject a therapeutically effective amount of the compound according to the definition of formula (I).

In one embodiment, the invention provides a method of treating a disorder or a disease in a subject caused by or associated with HCV infection, wherein the disorder or the disease is selected from of HCV infection, liver cirrhosis, chronic liver disease, hepatocellular carcinoma, cryoglobulinaemia, non-Hodgkin's lymphoma, liver fibrosis and a suppressed innate intracellular immune response.

In one embodiment, the invention provides a compound according to the definition of formula (I), for use as a medicament.

In one embodiment, the invention provides the use of a compound according to the definition of formula (I), for the treatment of a disorder or disease in a subject caused by or associated with HCV infection.

In one embodiment, the invention provides the use of a compound according to the definition of formula (I), in the manufacture of a medicament for the treatment of a disorder or disease in a subject caused by or associated with HCV infection, wherein said disorder or disease is in particular selected from HCV infection, liver cirrhosis, chronic liver disease, hepatocellular carcinoma, cryoglobulinaemia, non-Hodgkin's lymphoma, liver fibrosis and a suppressed innate intracellular immune response.

In one embodiment, the invention provides the use of a compound according to the definition of formula (I), for the treatment of a disorder or disease in a subject caused by or associated with HCV infection, wherein the disorder or disease is selected from HCV infection, liver cirrhosis, chronic liver disease, hepatocellular carcinoma, cryoglobulinaemia, non-Hodgkin's lymphoma, liver fibrosis and a suppressed innate intracellular immune response.

In another embodiment, the invention provides compounds according to the definition of formula (I), which compounds include the exemplified compounds provided infra. Certain compounds of Formula (I) provided by the invention include compounds selected from the group consisting of:

2-(4-Fluoro-phenyl)-5-iodo-6-(methanesulfonyl-methyl-amino)-furo[2,3-b]pyridine-3-carboxylic acid methylamide;
5-Cyclopropyl-2-(4-fluoro-phenyl)-6-(methanesulfonyl-methyl-amino)-furo[2,3-b]pyridine-3-carboxylic acid methylamide;
ethyl 5-(2-(4-fluorophenyl)-3-(methylcarbamoyl)-6-(N-methylmethylsulfonamido)furo[2,3-b]pyridin-5-yl)pentanoate;
5-(2-(4-fluorophenyl)-3-(methylcarbamoyl)-6-(N-methylmethylsulfonamido)furo[2,3-b]pyridin-5-yl)pentanoic acid;
(S)-methyl 1-(4-(2-(4-fluorophenyl)-3-(methylcarbamoyl)-6-(N-methylmethylsulfonamido)furo[2,3-b]pyridin-5-yl)butanoyl)pyrrolidine-2-carboxylate;
5-allyl-2-(4-fluorophenyl)-N-methyl-6-(N-methylmethylsulfonamido)furo[2,3-b]pyridine-3-carboxamide;
4-(2-(4-fluorophenyl)-3-(methylcarbamoyl)-6-(N-methylmethylsulfonamido)furo[2,3-b]pyridin-5-yl)butanoic acid;
5-(2-(4-fluorophenyl)-3-(methylcarbamoyl)-6-(N-methylmethylsulfonamido)furo[2,3-b]pyridin-5-yl)pent-4-ynoic acid;
5-Ethyl-2-(4-fluoro-phenyl)-6-(methanesulfonyl-methyl-amino)-furo[2,3-b]pyridine-3-carboxylic acid methylamide;
5-ethynyl-2-(4-fluorophenyl)-N-methyl-6-(N-methylmethylsulfonamido)furo[2,3-b]pyridine-3-carboxamide;
5-(1,1-difluoroethyl)-2-(4-fluorophenyl)-N-methyl-6-(N-methylmethylsulfonamido)furo[2,3-b]pyridine-3-carboxamide;
5-(1,2-dihydroxypropan-2-yl)-2-(4-fluorophenyl)-N-methyl-6-(N-methylmethylsulfonamido)furo[2,3-b]pyridine-3-carboxamide;
5-acetyl-2-(4-fluorophenyl)-N-methyl-6-(N-methylmethylsulfonamido)furo[2,3-b]pyridine-3-carboxamide;
2-(4-fluorophenyl)-5-(1-hydroxyethyl)-N-methyl-6-(N-methylmethylsulfonamido)furo[2,3-b]pyridine-3-carboxamide;
2-(4-fluorophenyl)-N-methyl-6-(N-methylmethylsulfonamido)-5-(oxiran-2-ylmethyl)furo[2,3-b]pyridine-3-carboxamide;
(E)-5-(2-cyanovinyl)-2-(4-fluorophenyl)-N-methyl-6-(N-methylmethylsulfonamido)furo[2,3-b]pyridine-3-carboxamide;
5-(2-cyanoethyl)-2-(4-fluorophenyl)-N-methyl-6-(N-methylmethylsulfonamido)furo[2,3-b]pyridine-3-carboxamide;
5-(3-aminopropyl)-2-(4-fluorophenyl)-N-methyl-6-(N-methylmethylsulfonamido)furo[2,3-b]pyridine-3-carboxamide;
5-cyclopropyl-N-methyl-6-(N-methylmethylsulfonamido)-2-(4-phenoxyphenyl)furo[2,3-b]pyridine-3-carboxamide;
5-ethyl-N-methyl-6-(N-methylmethylsulfonamido)-2-(4-phenoxyphenyl)furo[2,3-b]pyridine-3-carboxamide;
5-{[2-(4-Fluoro-phenyl)-5-iodo-3-methylcarbamoyl-furo[2,3-b]pyridin-6-yl]-methanesulfonyl-amino}-pentanoic acid methyl ester;
5-{[2-(4-Fluoro-phenyl)-5-iodo-3-methylcarbamoyl-furo[2,3-b]pyridin-6-yl]-methanesulfonyl-amino}-pentanoic acid;
6-[(4-Amino-butyl)methanesulfonyl-amino]-2-(4-fluoro-phenyl)-5-iodo-furo[2,3-b]pyridine-3-carboxylic acid methylamide;
5-Ethyl-2-(4-fluoro-phenyl)-6-[methanesulfonyl-(4-methanesulfonyl-butyl)-amino]-furo[2,3-b]pyridine-3-carboxylic acid methylamide;
5-Ethyl-2-(4-fluoro-phenyl)-6-[methanesulfonyl-(4-methanesulfonyl-butyl)-amino]-furo[2,3-b]pyridine-3-carboxylic acid methylamide;
5-[(5-Cyclopropyl-3-methylcarbamoyl-2-p-tolyl-furo[2,3-b]pyridin-6-yl)-methanesulfonyl-amino]-2,2-dimethyl-pentanoic acid;
2-(4-Fluoro-phenyl)-6-[methanesulfonyl-(3-methanesulfonyl-propyl)-amino]-furo[2,3-b]pyridine-3-carboxylic acid methylamide;
2-(4-Fluoro-phenyl)-5-iodo-6-[methanesulfonyl-(3-methanesulfonyl-propyl)-amino]-furo[2,3-b]pyridine-3-carboxylic acid methylamide;
5-[(5-Cyclopropyl-3-methylcarbamoyl-2-p-tolyl-furo[2,3-b]pyridin-6-yl)-methanesulfonyl-amino]-2,2-dimethyl-pentanoic acid;
2-(4-Fluoro-phenyl)-6-[methanesulfonyl-(3-methanesulfonyl-propyl)-amino]-furo[2,3-b]pyridine-3-carboxylic acid methylamide;
2-(4-Fluoro-phenyl)-9-methanesulfonyl-5-methyl-6,7,8,9-tetrahydro-5H-1-oxa-9,10-diaza-cyclohepta[f]indene-3-carboxylic acid methylamide;
2-(4-Fluoro-phenyl)-6-hydroxy-9-methanesulfonyl-5-methyl-6,7,8,9-tetrahydro-5H-1-oxa-9,10-diaza-cyclohepta[f]indene-3-carboxylic acid methylamide;
2-(4-Fluoro-phenyl)-5-hydroxy-9-methanesulfonyl-5-methyl-6,7,8,9-tetrahydro-5H-1-oxa-9,10-diaza-cyclohepta[f]indene-3-carboxylic acid methylamide;
2-(4-Fluoro-phenyl)-6-hydroxy-9-methanesulfonyl-5-methyl-6,7,8,9-tetrahydro-5H-1-oxa-9,10-diaza-cyclohepta[f]indene-3-carboxylic acid methylamide;
2-(4-Fluoro-phenyl)-5-hydroxy-9-methanesulfonyl-5-methyl-6,7,8,9-tetrahydro-5H-1-oxa-9,10-diaza-cyclohepta[f]indene-3-carboxylic acid methylamide;
(5R,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide;
(5S,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide;
(S)-6-(N-(2-(benzyloxy)but-3-enyl)methylsulfonamido)-2-(4-fluorophenyl)-N-methyl-5-(prop-1-en-2-yl)furo[2,3-b]pyridine-3-carboxamide;

2-(4-Fluorophenyl)-N-methyl-6-(methylsulfonamido)-5-vinylfuro[2,3-b]pyridine-3-carboxamide;

2-(4-Fluoro-phenyl)-10-methanesulfonyl-5,6,7,8,9,10-hexahydro-1-oxa-10,11-diaza-cycloocta[f]indene-3-carboxylic acid methylamide;

2-(4-Fluoro-phenyl)-11-methanesulfonyl-5-methyl-6,7,8,9,10,11-hexahydro-5H-1-oxa-11,12-diaza-cyclonona[f]indene-3-carboxylic acid methylamide;

2-(4-Fluoro-phenyl)-6-hydroxy-11-methanesulfonyl-5-methyl-6,7,8,9,10,11-hexahydro-5H-1-oxa-11,12-diaza-cyclonona[f]indene-3-carboxylic acid methylamide;

2-(4-Fluoro-phenyl)-9-methanesulfonyl-6,7,8,9-tetrahydro-5H-1-oxa-9,10-diaza-cyclohepta[f]indene-3-carboxylic acid methylamide; and 2-(4-Fluoro-phenyl)-7,10-bis-methanesulfonyl-5-methyl-5,6,7,8,9,10-hexahydro-1-oxa-7,10,11-triaza-cycloocta[f]indene-3-carboxylic acid methylamide.

The following examples are intended to illustrate the invention and are not to be construed as being limitations thereon. Temperatures are given in degrees centrigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LIST OF ABBREVIATIONS

| | |
|---|---|
| Ac | acetyl |
| ACN | Acetonitrile |
| AcOEt/EtOAc | Ethyl acetate |
| AcOH | acetic acid |
| aq | aqueous |
| Ar | aryl |
| Bn | benzyl |
| Bu | butyl (nBu = n-butyl, tBu = tert-butyl) |
| CDI | Carbonyldiimidazole |
| $CH_3CN$ | Acetonitrile |
| DBU | 1,8-Diazabicyclo[5.4.0]-undec-7-ene |
| DCE | 1,2-Dichloroethane |
| DCM | Dichloromethane |
| DIPEA | N-Ethyldiisopropylamine |
| DMAP | Dimethylaminopyridine |
| DMF | N,N'-Dimethylformamide |
| DMSO | Dimethylsulfoxide |
| EI | Electrospray ionisation |
| $Et_2O$ | Diethylether |
| $Et_3N$ | Triethylamine |
| Ether | Diethylether |
| EtOH | Ethanol |
| FC | Flash Chromatography |
| h | hour(s) |
| HATU | O-(7-Azabenzotriazole-1-yl)-N,N,N'N'-tetramethyluronium hexafluorophosphate |
| HBTU | O-(Benzotriazol-1-yl)-N,N,N',N'-tetramethyluronium hexafluorophosphate |
| HCl | Hydrochloric acid |
| HOBt | 1-Hydroxybenzotriazole |

LIST OF ABBREVIATIONS (continued)

| | |
|---|---|
| HPLC | High Performance Liquid Chromatography |
| $H_2O$ | Water |
| L | liter(s) |
| LC-MS | Liquid Chromatography Mass Spectrometry |
| Me | methyl |
| MeI | Iodomethane |
| MeOH | Methanol |
| mg | milligram |
| min | minute(s) |
| mL | milliliter |
| MS | Mass Spectrometry |
| Pd/C | palladium on charcoal |
| PG | protecting group |
| Ph | phenyl |
| Prep | Preparative |
| Rf | ratio of fronts |
| RP | reverse phase |
| Rt | Retention time |
| rt | Room temperature |
| $SiO_2$ | Silica gel |
| TBAF | Tetrabutylammonium fluoride |
| TEA | Triethylamine |
| TFA | Trifluoroacetic acid |
| THF | Tetrahydrofurane |
| TLC | Thin Layer Chromatography |

HPLC Methods:

Method A:

3 mm×33 mm Inersil C8-3 reverse phase, 3.0 um particle size running a gradient of 5-95% MeCN/water (5 mM ammonium formate) over a period of 2 min at a flow rate of 4 mL/min at 40° C. DAD-UV detection, 220-600 nm.

Method B:

3 mm×33 mm Inersil $C_{8-3}$ reverse phase, 3.0 um particle size running a gradient of 40-90% MeCN/water (5 mM ammonium formate) over a period of 2 min at a flow rate of 4 mL/min at 40° C. DAD-UV detection, 220-600 nm.

Method C:

3 mm×33 mm Inersil ODS3 reverse phase, 3.0 um particle size running a gradient of 20-80% MeCN/water (5 mM ammonium formate) over a period of 2 min at a flow rate of 4 mL/min at 40° C. DAD-UV detection, 220-600 nm.

Example 1

A. 6-Amino-3,5-diiodo-pyridin-2-ol

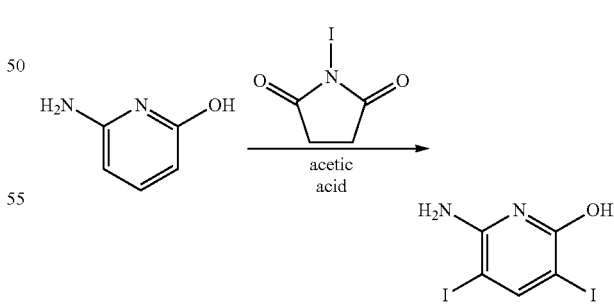

To a stirred solution of 6-Amino-pyridin-2-ol (1 g, 9.08 mmol) in acetic acid (10 ml) is added a solution of N-iodosuccinimide (4.09 g, 18.16 mmol) in acetic acid (90 ml). The reaction mixture is stirred for 1 h. LCMS of the reaction mixture indicates 100% desired product. The resulting precipitate is collected by filtration, washed with acetic acid and dried under vacuum to afford 6-Amino-3,5-diiodo-pyridin-2- ol (3.15 g, 8.70 mmol, 96% yield). $^1$H NMR (400 MHz, DMSO-d6) δ ppm 11.2 (br s, 1H), 7.88 (s, 1H), 6.05 (br s, 2H).

B. Acetic acid 6-diacetylamino-3,5-diiodo-pyridin-2-yl ester

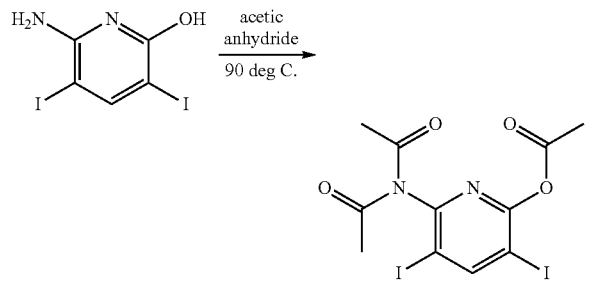

A stirred heterogeneous mixture of 6-Amino-3,5-diiodo-pyridin-2-ol U-11551-EXP072 (3 g, 8.29 mmol) in acetic anhydride (15 ml) is heated to 110° C. After 1 h, LCMS of the now homogeneous reaction mixture indicates 100% desired product. The acetic anhydride is mostly removed by distillation and the reaction mixture is then cooled and extracted between saturated aqueous sodium bicarbonate and methylene chloride. The organic layer is dried over sodium sulfate, filtered and concentrated in vacuo to afford Acetic acid 6-diacetylamino-3,5-diiodo-pyridin-2-yl ester, (3.7 g, 7.58 mmol, 91% yield). $^1$H NMR (400 MHz, CDCl3 δ ppm 8.68 (s, 1H), 2.38 (s, 3H), 2.31 (s, 3H)

C. 6-Amino-2-(4-fluoro-phenyl)-5-iodo-furo[2,3-b]pyridine-3-carboxylic acid

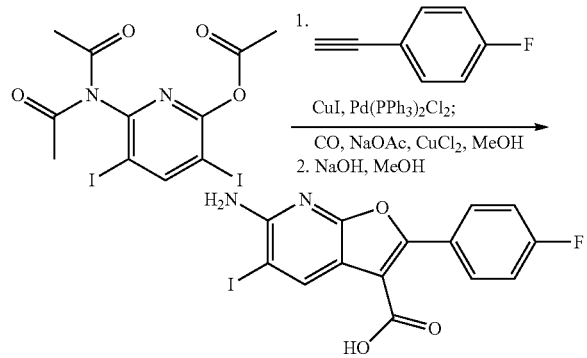

A 2000 mL 3-neck RBF is fitted with a magnetic stir bar, N2 inlet, thermocouple, and addition funnel. The flask is placed in a stainless steel bath/secondary container. Acetic acid 6-diacetylamino-3,5-diiodo-pyridin-2-yl ester (23 g, 47.1 mmol), THF (200 ml) and triethylamine (TEA) (10.01 g, 99 mmol) are charged to the flask. The bath is filled with ice-water and the mixture is cooled to 2 C. Copper Iodide (0.180 g, 0.943 mmol), and dichloropalladium bistriphenylphosphine (1.323 g, 1.885 mmol) are charged to the flask. The flask is evacuated and backfilled thrice with nitrogen. 4-Fluorophenylacetylene (5.77 g, 48.1 mmol) is added dropwise as a solution in THF (160 ml) over a period of 2 hrs. After 5 hrs, LC-MS indicates some starting material remaining. The mixture is allowed to stir overnight at room temperature. In the morning, LC-MS shows very clean conversion to the desired product with no starting material remaining and very minimal homocoupling of acetylene. Copper Chloride (19.01 g, 141 mmol), Sodium Acetate (15.46 g, 189 mmol), and Methanol (360 ml) are added. The flask is evacuated and a balloon of CO inserted. The balloon is refilled throughout the day. The mixture is allowed to stir at room temperature for 7 hrs and then checked by LC-MS. This indicates about 5 or 6 to 1 desired products to the 3-unsubstituted furopyridine compound. The mixture is transferred to a single neck round bottom flask and the solvent is removed in vaccuo. The residue is diluted with 1 L of methylene chloride (DCM) and 500 mL of 1N HCl. This is stirred vigorously for about 30 minutes and then filtered through celite. The filter cake is then washed with 100 mL of 2-MeTHF. The filtrate is transferred to a sep funnel and the layers separated. Solids are crashing out of the organic layer due to the cold temperature from the filtration. The organic layer is covered and stirred gently overnight. In the morning, the solids are not back into solution. An additional 100 mL 2-MeTHF is added to try and get a clear solution, but this is unsuccessful. The mixture is filtered. 2 g of an off-white solid is revealed to be highly pure title compound (by LC-MS). The DCM layer is then dried over sodium sulfate, filtered, and concentrated in vacuo. The solid and solid of m/z 455 are combined in a 2 L 3-neck flask and then treated with 450 mL MeOH and 400 mL 1N NaOH. The flask is equipped with a thermocouple and placed in a heating mantle. The internal temperature is set to 55 C and the mixture is allowed to stir at this temperature for an hour. At the time, heating is ceased and the mixture is allowed to stir at RT. LC-MS of an aliquot indicates complete consumption of starting material. The mixture is cooled to room temperature and then the methanol is removed in vacuo. The resulting slurry is diluted further with an additional liter of dil water. The aqueous mixture is washed with 200 mL of MTBE. The entire mixture is filtered through a medium porosity funnel, leaving behind a black residue. The MTBE layer is put aside and the aqueous layer is then neutralized and made slightly acidic (pH=5) with 6N HCl. The very cloudy aqueous layer is then extracted with 2×600 mL 2-MeTHF. The organic layer is allowed to sit over the weekend and then dried over sodium sulfate on Monday morning. The sample is filtered, concentrated in vacuo, and placed on the hi-vac for a couple hours. NMR in DMSO of the 11.5 g sample is consistent with the desired structure. This material is dried down to 11 g on the hi-vac over the weekend. $^1$H NMR (400 MHz, DMSO-d6) δ ppm 13.3 (br s, 1H), 8.40 (s, 1H), 8.12-8.04 (m, 2H), 7.38-7.32 (m, 2H), 6.50 (br s, 2H)

D. 2-(4-Fluoro-phenyl)-5-iodo-6-methanesulfonylamino-furo[2,3-b]pyridine-3-carboxylic acid methylamide

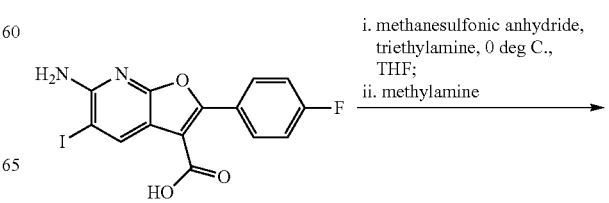

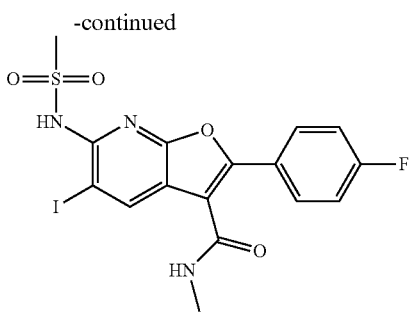

To a solution of 6-amino-2-(4-fluoro-phenyl)-5-iodo-furo[2,3-b]pyridine-3-carboxylic acid (5.0 g), triethylamine (12 ml, 7 eq.) and dry THF (200 ml) at 0° C. is slowly added methanesulfonic anhydride (13 g, 6 eq.) in portions. After stirring at 5° C. for 16 h, the reaction mixture is slowly poured into a methylamine solution (2 M in THF, 57 ml, 9 eq.) at 0° C. The resulting mixture is concentrated and diluted with water. Concentrated citric acid is added until pH 3.5, and the mixture is extracted with 3×EtOAc. The organic layers are concentrated to dryness. The residue is dissolved in MeOH (150 ml), and LiOH (1 M aqueous solution, 25 ml) was added. The mixture is stirred at rt for 1 h and concentrated. Water is added, and the mixture is washed with ether. The aqueous layer is adjusted to pH 6 using concentrated citric acid. A precipitate formed, which is filtered, washed with water and dried using a lyophilizer to yield the title compound as a beige solid (4.1 g, 66%). MS (ESI) m/z 490.0 (M+1). Retention time 1.13 min (Method A).

E. Example 2

2-(4-Fluoro-phenyl)-5-iodo-6-(methanesulfonyl-methyl-amino)-furo[2,3-b]pyridine-3-carboxylic acid methylamide

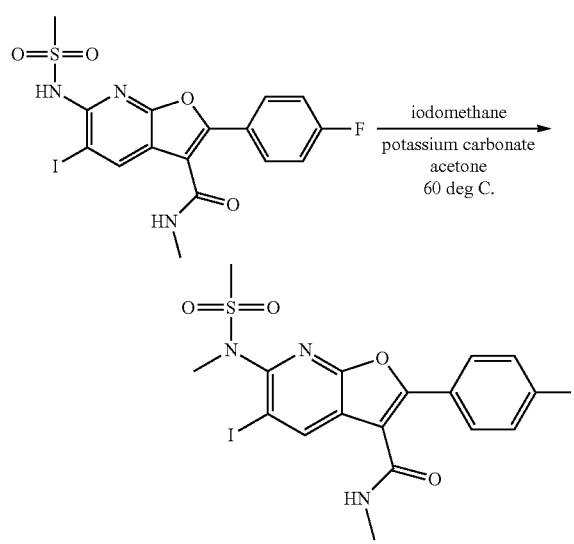

To 2-(4-Fluoro-phenyl)-5-iodo-6-methanesulfonylamino-furo[2,3-b]pyridine-3-carboxylic acid methylamide (9 mg, 0.018 mmol) and potassium carbonate (25.4 mg, 0.184 mmol) in acetone (0.1 ml) is added iodomethane (0.115 ml, 1.840 mmol). After heating at 60° C. for 1 day, the reaction mixture is filtered and concentrated to dryness to afford 2-(4-Fluoro-phenyl)-5-iodo-6-(methanesulfonyl-methyl-amino)-furo[2,3-b]pyridine-3-carboxylic acid methylamide (9.3 mg, 0.018 mmol, 100% yield). MS (ESI) m/z 503.9 (M+1). $^1$H NMR (400 MHz, CD$_3$CN) δ ppm 8.60 (s, 1H), 7.95 (m, 2H), 7.23-7.18 (m, 2H), 6.79 (br s, 1H), 3.14 (s, 3H), 2.80-2.79 (d, 3H).

F. 5-Cyclopropyl-2-(4-fluoro-phenyl)-6-(methanesulfonyl-methyl-amino)-furo[2,3-b]pyridine-3-carboxylic acid methylamide

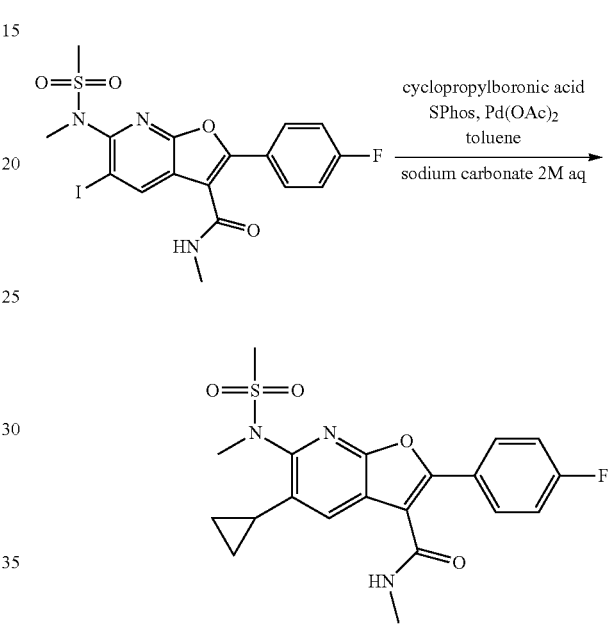

To 2-(4-Fluoro-phenyl)-5-iodo-6-(methanesulfonyl-methyl-amino)-furo[2,3-b]pyridine-3-carboxylic acid methylamide (7 mg, 0.014 mmol), is added a premixed solution of SPhos (0.571 mg, 1.391 μmol), palladium acetate (0.125 mg, 0.556 μmol) in toluene (0.5 ml) and cyclopropylboronic acid (5.97 mg, 0.070 mmol) premixed with sodium carbonate (0.035 ml, 0.070 mmol). The reaction mixture is heated under microwave irradiation at 120° C. for 10 min. LCMS indicates predominant conversion to product. The toluene layer is transferred to a vial, and the aqueous layer is extracted with toluene and added to the vial. The toluene is removed in vacuo, and the residue is dissolved in DMF, filtered and purified by HPLC to afford 5-Cyclopropyl-2-(4-fluoro-phenyl)-6-(methanesulfonyl-methyl-amino)-furo[2,3-b]pyridine-3-carboxylic acid methylamide (3 mg, 7.19 μmol, 51.7% yield). MS (ESI) m/z 503.9 (M+1). $^1$H NMR (400 MHz, CD$_3$CN) δ ppm 8.05-8.01 (m, 2H), 7.73 (s, 1H), 7.32-7.27 (m, 2H), 6.82 (br s, 1H), 3.30 (s, 3H), 3.23 (s, 3H), 2.92-2.90 (d, 3H), 2.43-2.38 (m, 1H), 1.12-1.07 (m, 2H), 0.84-0.80 (m, 2H)

Alternatively, for preparation of analogous compounds, the order of steps may be changed, for example the product of step C can be subjected to methylamide formation, then a Suzuki reaction with cyclopropyl boronic acid as in step F, then methanesulfonamide formation as in step D, with methanesulfonyl chloride or methanesulfonic anhydride, then a final step alkylation of the sulfonamide.

The compounds in Table 1 are prepared in analogy to examples 1 and 2.

TABLE 1

| Example | Structure | Name |
|---|---|---|
| 2.1 | 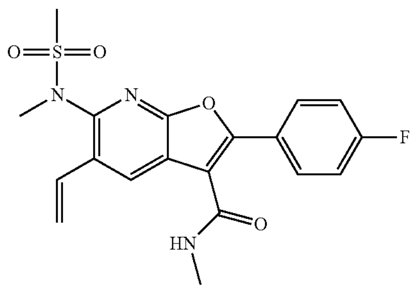 | 2-(4-fluorophenyl)-N-methyl-6-(N-methylmethylsulfonamido)-5-vinylfuro[2,3-b]pyridine-3-carboxamide |
| 2.2 | 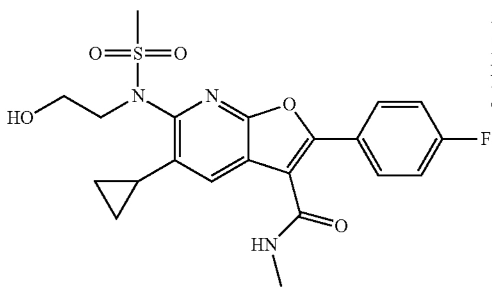 | 5-cyclopropyl-2-(4-fluorophenyl)-6-(N-(2-hydroxyethyl)methylsulfonamido)-N-methylfuro[2,3-b]pyridine-3-carboxamide |
| 2.3 | 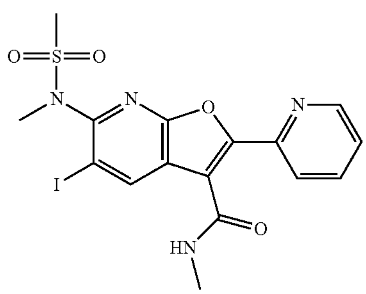 | 5-iodo-N-methyl-6-(N-methylmethylsulfonamido)-2-(pyridin-2-yl)furo[2,3-b]pyridine-3-carboxamide |
| 2.4 | 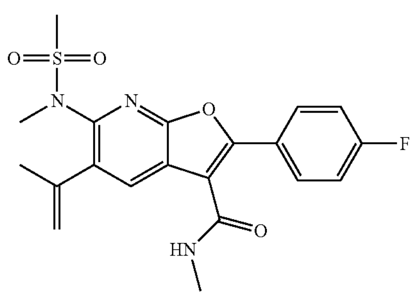 | 2-(4-fluorophenyl)-N-methyl-6-(N-methylmethylsulfonamido)-5-(prop-1-en-2-yl)furo[2,3-b]pyridine-3-carboxamide |
| 2.5 | 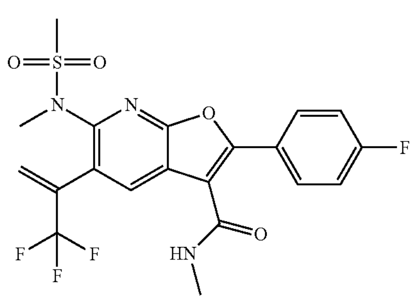 | 2-(4-fluorophenyl)-N-methyl-6-(N-methylmethylsulfonamido)-5-(3,3,3-trifluoroprop-1-en-2-yl)furo[2,3-b]pyridine-3-carboxamide |

TABLE 1-continued

| Example | Structure | Name |
|---|---|---|
| 2.6 | 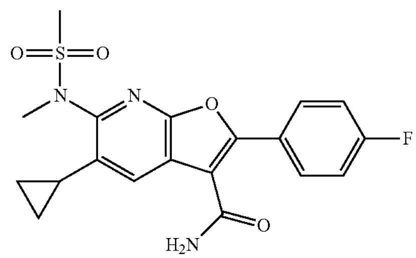 | 5-cyclopropyl-2-(4-fluorophenyl)-6-(N-methylmethylsulfonamido)furo[2,3-b]pyridine-3-carboxamide |
| 2.7 | 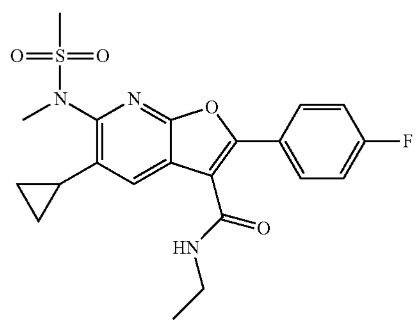 | 5-cyclopropyl-N-ethyl-2-(4-fluorophenyl)-6-(N-methylmethylsulfonamido)furo[2,3-b]pyridine-3-carboxamide |
| 2.8 | 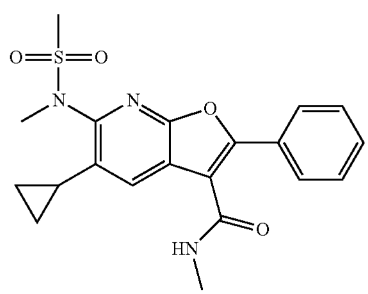 | 5-cyclopropyl-N-methyl-6-(N-methylmethylsulfonamido)-2-phenylfuro[2,3-b]pyridine-3-carboxamide |
| 2.9 | 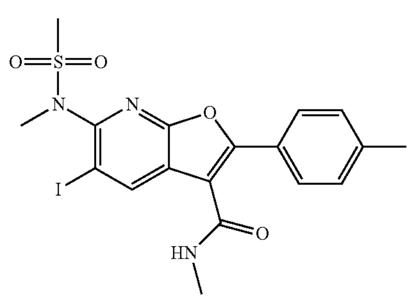 | 5-iodo-N-methyl-6-(N-methylmethylsulfonamido)-2-p-tolylfuro[2,3-b]pyridine-3-carboxamide |
| 2.91 | 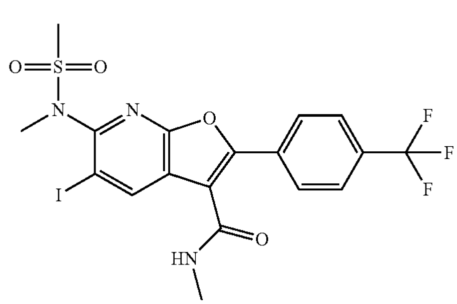 | 5-iodo-N-methyl-6-(N-methylmethylsulfonamide)-2-(4-(trifluoromethyl)phenyl)furo[2,3-b]pyridine-3-carboxamide |

TABLE 1-continued

| Example | Structure | Name |
|---|---|---|
| 2.92 | 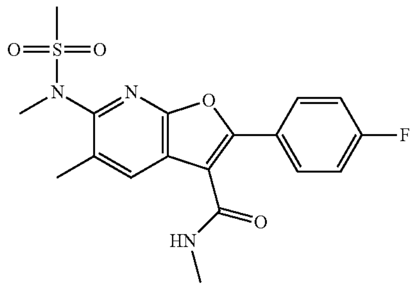 | 2-(4-fluorophenyl)-N,5-dimethyl-6-(N-methylmethylsulfonamido)furo[2,3-b]pyridine-3-carboxamide |
| 2.93 | 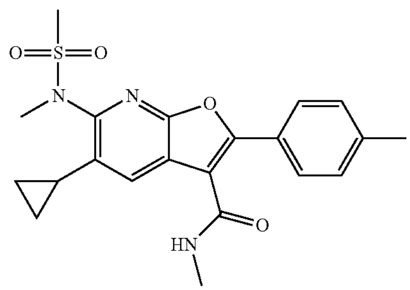 | 5-cyclopropyl-N-methyl-6-(N-methylmethylsulfonamido)-2-p-tolylfuro[2,3-b]pyridine-3-carboxamide |
| 2.94 | 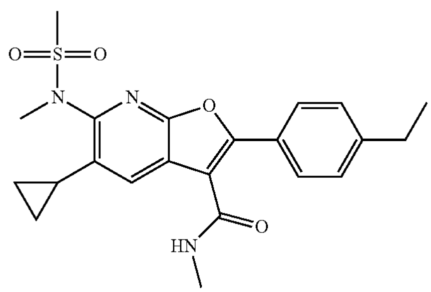 | 5-cyclopropyl-2-(4-ethylphenyl)-N-methyl-6-(N-methylmethylsulfonamido)furo[2,3-b]pyridine-3-carboxamide |
| 2.95 | 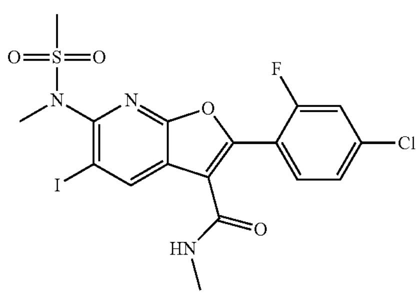 | 2-(4-chloro-2-fluorophenyl)-5-iodo-N-methyl-6-(N-methylmethylsulfonamido)furo[2,3-b]pyridine-3-carboxamide |
| 2.96 | 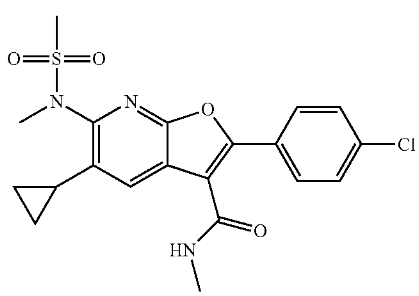 | 2-(4-chlorophenyl)-5-cyclopropyl-N-methyl-6-(N-methylmethylsulfonamido(furo[2,3-b]pyridine-3-carboxamide |

TABLE 1-continued

| Example | Structure | Name |
|---|---|---|
| 2.97 | 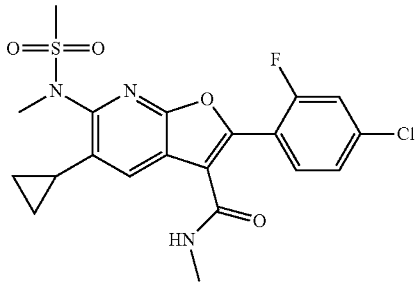 | 2-(4-chloro-2-fluorophenyl)-5-cyclopropyl-N-methyl-6-(N-methyl-6-(N-methylmethylsulfonamido)furo[2,3-b]pyridine-3-carboxamide |
| 2.98 | 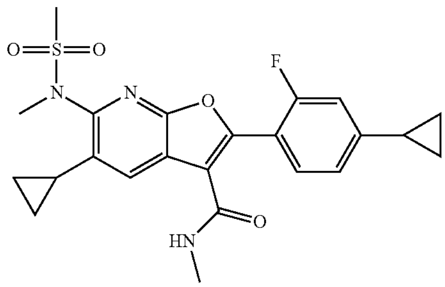 | 5-cyclopropyl-2-(4-cyclopropyl-2-fluorophenyl)-N-methyl-6-(N-methylmethylsulfonamido)furo[2,3-b]pyridine-3-carboxamide |
| 2.99 | 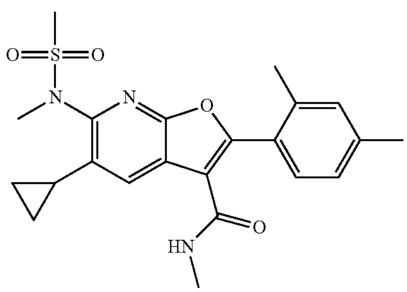 | 5-cyclopropyl-2-(2,4-dimethylphenyl)-N-methyl-6-(N-methylmethylsulfonamido)furo[2,3-b]pyridine-3-carboxamide |

Example 2.3 is obtained in analogy to example 2. Examples 2.96 and 2.97 are prepared using Pd(PPh3)4 in place of SPhos.

Example 3

Ethyl 5-(2-(4-fluorophenyl)-3-(methylcarbamoyl)-6-(N-methylmethylsulfonamido)furo[2,3-b]pyridin-5-yl)pentanoate

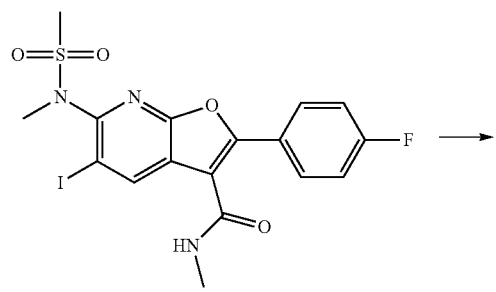
→
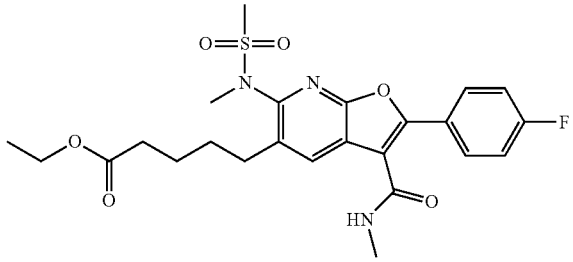

A solution of 5.1 mg ethyl pent-4-enoate and 79 µl 9-BBN (2 M solution in THF) is stirred at rt for 1 h. 10 µl of water is added and stirred at rt for 10 min. 30 µl of 2 M $K_2CO_3$ solution is added and stirred at rt for 30 min. 10 mg of 2-(4-fluorophenyl)-5-iodo-N-methyl-6-(N-methylmethylsulfonamido)furo[2,3-b]pyridine-3-carboxamide and 1.1 mg of Pd(PPh$_3$)$_4$ are added, bubbled with $N_2$, and microwaved at 120 C for 20 min. The crude reaction mixture is purified with preparative HPLC to afford the title compound (M+H)$^+$=506.3; Retention time=1.28 min, Method A.

Example 4

5-(2-(4-fluorophenyl)-3-(methylcarbamoyl)-6-(N-methylmethylsulfonamido)furo[2,3-b]pyridin-5-yl)pentanoic acid

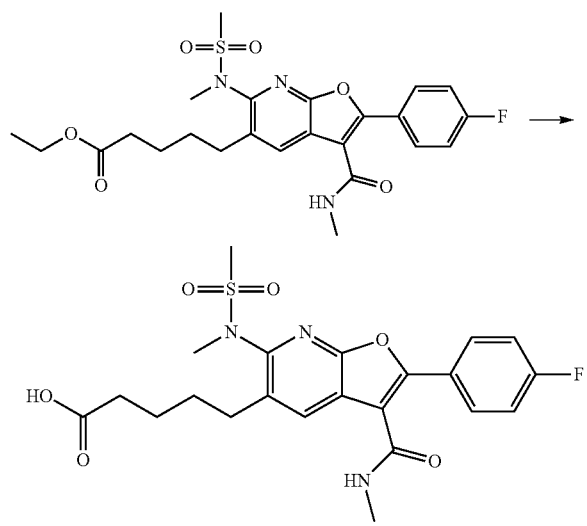

To a solution of 5-[2-(4-Fluoro-phenyl)-6-(methanesulfonyl-methyl-amino)-3-ethylcarbamoyl-furo[2,3-b]pyridin-5-yl]-pentanoic acid ethyl ester (3.0 mg) in MeOH (0.5 ml) is added LiOH (1 M in water, 0.25 ml) and the mixture is refluxed for 1 h, cooled to rt and purified by preparative HPLC to afford the title compound (M+H)$^+$=478.1; Retention time=1.03 min, Method A.

Example 4.1

(S)-methyl 1-(4-(2-(4-fluorophenyl)-3-(methylcarbamoyl)-6-(N-methylmethylsulfonamido)furo[2,3-b]pyridin-5-yl)butanoyl)pyrrolidine-2-carboxylate A. Example 4.2

5-allyl-2-(4-fluorophenyl)-N-methyl-6-(N-methylmethylsulfonamido)furo[2,3-b]pyridine-3-carboxamide

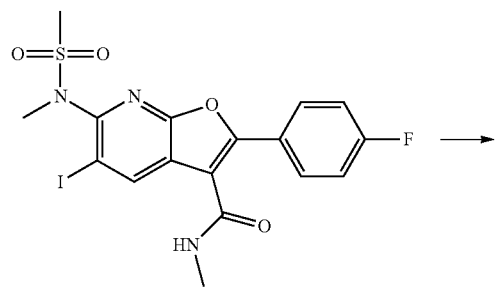

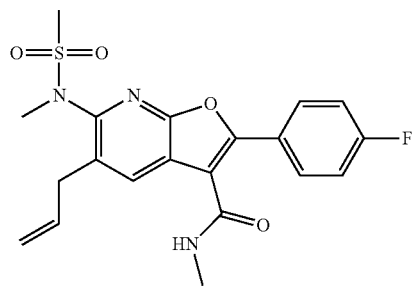

The title compound was prepared in analogy to Example 1 using allylboronic acid pinacol ester, CsF and Pd(PPh3)4 at 120 C. (M+H)$^+$=418.0; Retention time=1.36 min, Method A. $^1$H NMR (400 MHz, CDCl$_3$) d ppm 8.15 (s, 1H), 7.95-7.92 (m, 2H), 7.23-7.19 (m, 2H), 6.04-5.94 (m, 1H), 5.86 (br s, 1H), 5.17-5.12 (m, 2H), 3.72-3.70 (m, 2H), 3.28 (s, 3H), 3.15 (s, 3H)

B. 4-(2-(4-fluorophenyl)-3-(methylcarbamoyl)-6-(N-methylmethylsulfonamido)furo[2,3-b]pyridin-5-yl)butanoic acid

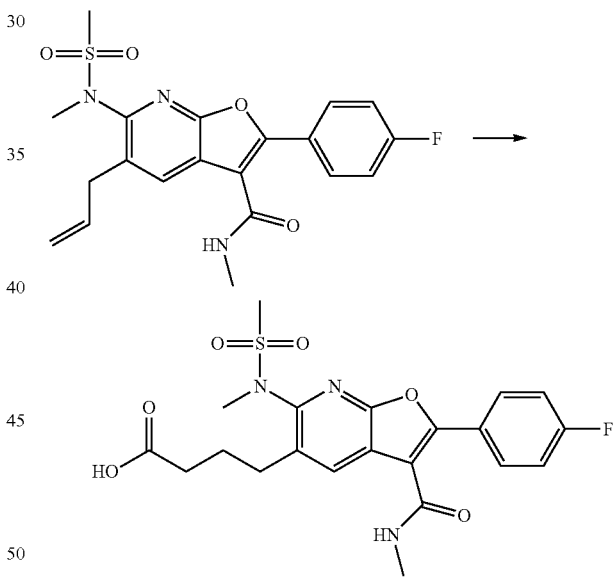

i) A mixture of 5-allyl-2-(4-fluorophenyl)-N-methyl-6-(N-methylmethylsulfonamido)furo[2,3-b]pyridine-3-carboxamide (43 mg), ethyl acrylate (52 mg), Hoveyda-Grubbs catalyst 2nd Generation (6.5 mg) and DCM (1.4 ml) was bubbled with nitrogen. Microwaved at 100 C for 15 min. Cooled to rt. Concentrated to dryness. ii) To the crude from last stage was added MeOH (4 ml), EtOAc (1 ml) and Pd(OH)$_2$/C (10%, wet, 38 mg). Stirred under hydrogen for 30 min. Filtered and concentrated to dryness. iii) To the crude from last stage was added MeOH (4 ml) and 1N LiOH (1 ml). Refluxed for 1 h. Cooled to rt and purified by preparative HPLC to afford the title compound. (M+H)$^+$=464.1; Retention time=0.98 min, Method A. $^1$H NMR (400 MHz, DMSO) d ppm 8.81-8.74 (m, 1H), 8.11 (m, 1H), 8.10-8.04 (m, 2H), 7.43-7.36 (m, 2H), 3.20

(s, 3H), 3.18 (s, 3H), 2.86 (d, 3H), 2.82-2.74 (m, 2H), 1.86-1.80 (m, 2H), 1.80-1.71 (m, 2H)

C. (S)-methyl 1-(4-(2-(4-fluorophenyl)-3-(methylcarbamoyl)-6-(N-methylmethylsulfonamido)furo[2,3-b]pyridin-5-yl)butanoyl)pyrrolidine-2-carboxylate

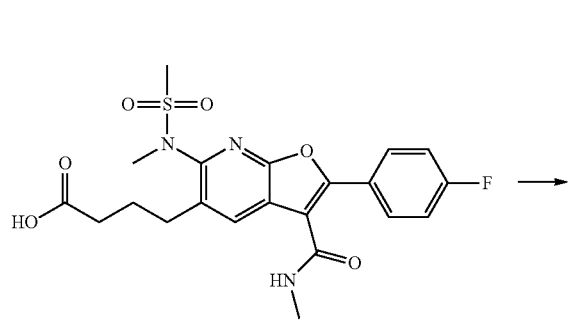

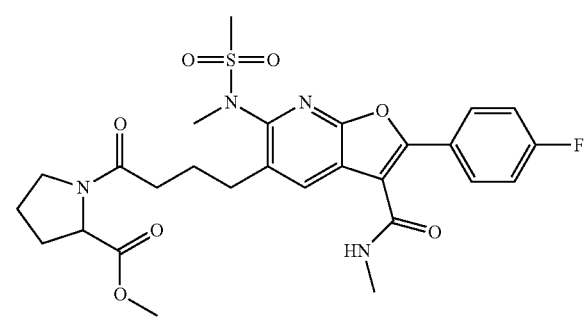

To a solution of 4-(2-(4-fluorophenyl)-3-(methylcarbamoyl)-6-(N-ethylmethylsulfonamido)furo[2,3-b]pyridin-5-yl)butanoic acid (15 mg) in DMF (1 ml) is added (S)-methylpyrrolidine-2-carboxylate (4.2 mg), HATU (18.5 mg) and DIPEA (17 μl), and the mixture is stirred at rt for 30 min, and purified by preparative HPLC to afford the title compound. (M+H)$^+$=575.2; Retention time=1.26 min, Method A. $^1$H NMR (400 MHz, CD$_3$CN) δ ppm 8.18 (m, 1H), 8.06-8.01 (m, 2H), 7.33-7.26 (m, 2H), 6.91 (br s, 1H), 4.33-4.29 (m, 1H), 3.67 (s, 3H), 3.61-3.50 (m, 2H), 3.27 (s, 3H), 3.16 (s, 3H), 2.98-2.90 (m, 2H), 2.92 (d, 3H), 2.51-2.36 (m, 2H), 2.32-1.78 (m, 6H)

Example 4.3

5-(4-amino-4-oxobutyl)-2-(4-fluorophenyl)-N-methyl-6-(N-methylmethylsulfonamido)furo[2,3-b]pyridine-3-carboxamide

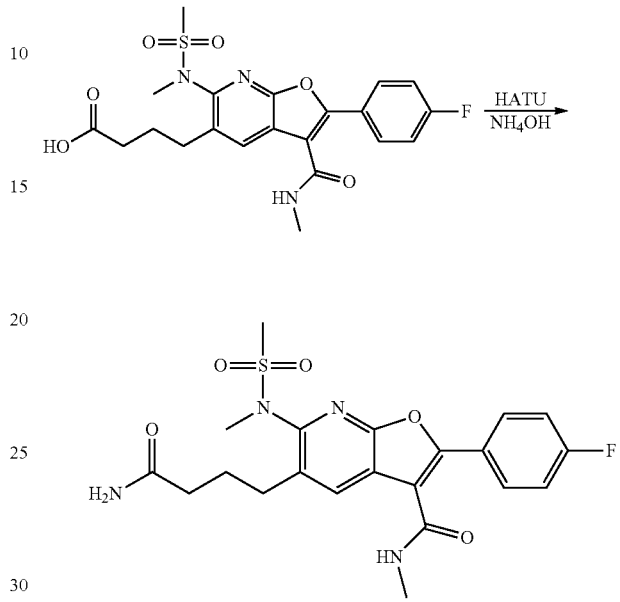

To a solution of 4-(2-(4-fluorophenyl)-3-(methylcarbamoyl)-6-(N-methylmethylsulfonamido) furo[2,3-b]pyridin-5-yl)butanoic acid (2.0 mg) in DMF (0.25 ml) is added HATU (3.3 mg). Stirred at rt for 10 min. Ammonium hydroxide (28% in water, 0.018 ml) is added and the mixture is stirred at rt for 30 min and purified by preparative HPLC to afford the title compound (M+H)$^+$=463.1; Retention time=1.10 min, Method A. $^1$H NMR (400 MHz, DMSO) δ ppm 8.54 (br s, 1H), 8.09 (m, 1H), 8.06-7.97 (m, 2H), 7.53-7.47 (m, 2H), 7.27 (br s, 1H), 6.76 (br s, 1H), 3.21 (s, 3H), 3.19 (s, 3H), 2.86 (s, 3H), 2.84-2.77 (m, 2H), 2.13-2.08 (m, 2H), 1.91-1.81 (m, 2H)

The compounds in Table 2 are made in analogy to 4.3, using the methods of olefin metathesis with 5-allyl-2-(4-fluorophenyl)-N-methyl-6-(N-methylmethylsulfonamido)furo[2,3-b]pyridine-3-carboxamide followed by hydrogenation, optionally followed by hydrolysis, amide-bond formation, hydrolysis and amide bond formation.

TABLE 2

| Ex. # | Structure | Name |
|---|---|---|
| 4.4 | 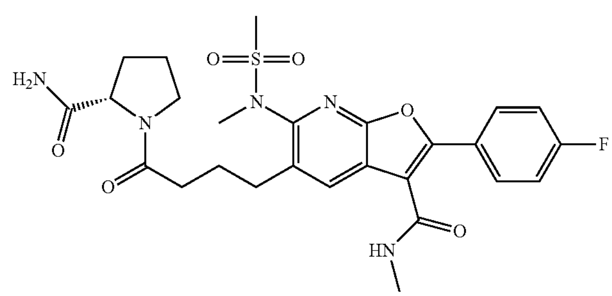 | (S)-5-(4-(2-carbamoylpyrrolidin-1-yl)-4-oxobutyl)-2-(4-fluorophenyl)-N-methyl-6-(N-methylmethylsulfonamido)furo[2,3-b]pyridine-3-carboxamide |

TABLE 2-continued

| Ex. # | Structure | Name |
|---|---|---|
| 4.5 | 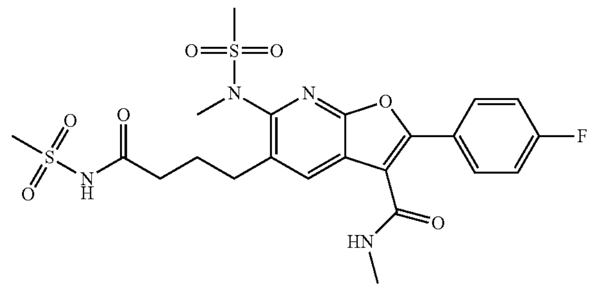 | 2-(4-fluorophenyl)-N-methyl-6-(N-methylmethylsulfonamido)-5-(4-(methylsulfonamido)-4-oxobutyl)furo[2,3-b]pyridine-3-carboxamide |
| 4.6 | 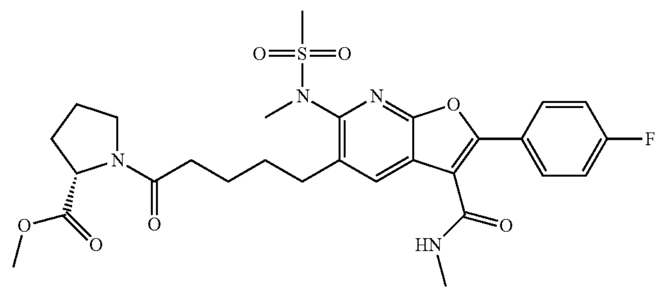 | (S)-methyl 1-(5-(2-(4-fluorophenyl)-3-(methylcarbamoyl)-6-(N-methylmethylsulfonamido)furo[2,3-b]pyridin-5-yl)pentanoyl)pyrrolidine-2-carboxylate |
| 4.7 | 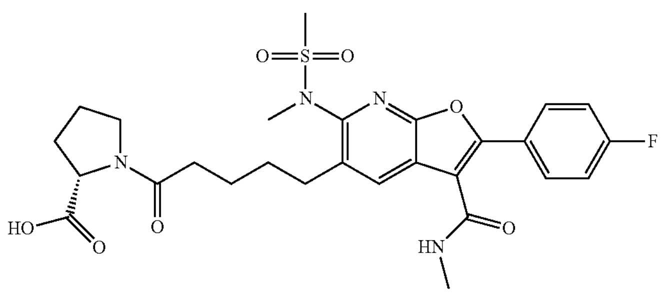 | (S)-1-(5-(2-(4-fluorophenyl)-3-(methylcarbamoyl)-6-(N-methylmethylsulfonamido)furo[2,3-b]pyridin-5-yl)pentanoyl)pyrrolidine-2-carboxylic acid |
| 4.8 | 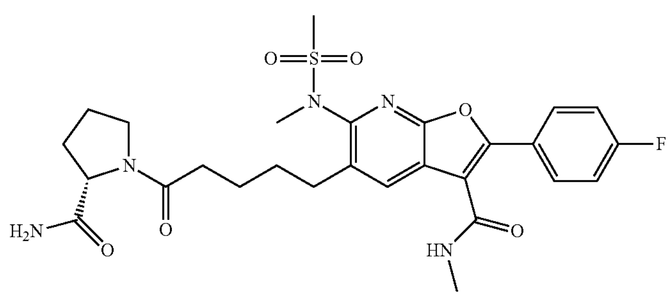 | (S)-5-(5-(2-carbamoylpyrrolidin-1-yl)-5-oxopentyl)-2-(4-fluorophenyl)-N-methyl-6-(N-methylmethylsulfonamido)furo[2,3-b]pyridine-3-carboxamide |
| 4.9 | 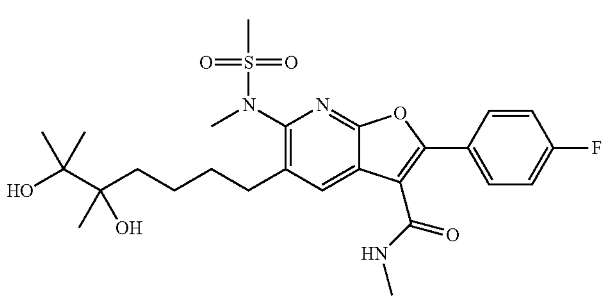 | 5-(5,6-dihydroxy-5,6-dimethylheptyl)-2-(4-fluorophenyl)-N-methyl-6-(N-methylmethylsulfonamido)furo[2,3-b]pyridine-3-carboxamide |

TABLE 2-continued

| Ex. # | Structure | Name |
|---|---|---|
| 4.91 | 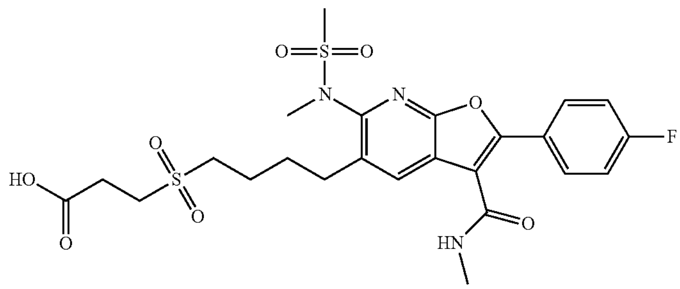 | 3-(4-(2-(4-fluorophenyl)-3-(methylcarbamoyl)-6-(N-methylmethylsulfonamido)furo[2,3-b]pyridin-5-yl)butylsulfonyl)propanoic acid |
| 4.92 | 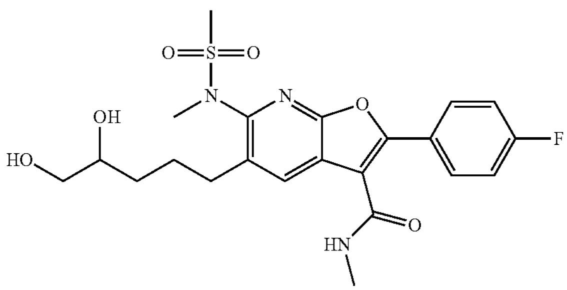 | 5-(4,5-dihydroxypentyl)-2-(4-fluorophenyl)-N-methyl-6-(N-methylmethylsulfonamido)furo[2,3-b]pyridine-3-carboxamide |
| 4.93 | 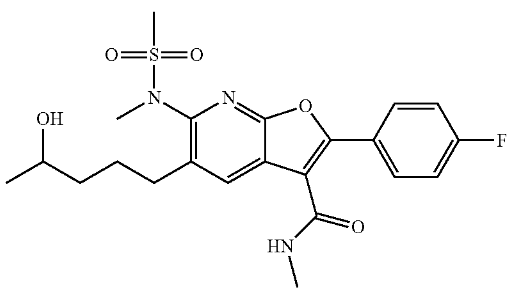 | 2-(4-fluorophenyl)-5-(4-hydroxypentyl)-N-methyl-6-(N-methylmethylsulfonamido)furo[2,3-b]pyridine-3-carboxamide |
| 4.94 | 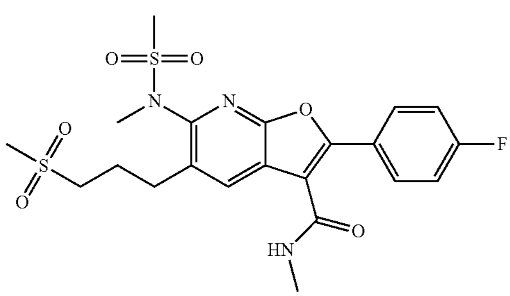 | 2-(4-fluorophenyl)-N-methyl-6-(N-methylmethylsulfonamido)-5-(3-(methylsulfonyl)propyl)furo[2,3-b]pyridine-3-carboxamide |
| 4.95 | 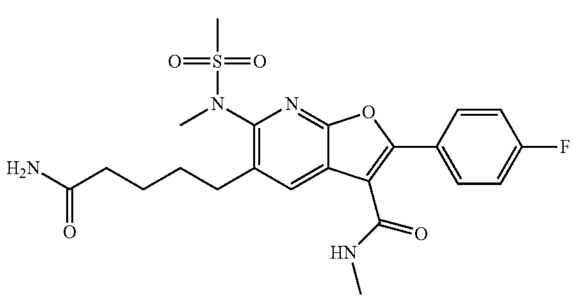 | 5-(5-amino-5-oxopentyl)-2-(4-fluorophenyl)-N-methyl-6-(N-methylmethylsulfonamido)furo[2,3-b]pyridine-3-carboxamide |

TABLE 2-continued

| Ex. # | Structure | Name |
|---|---|---|
| 4.96 | 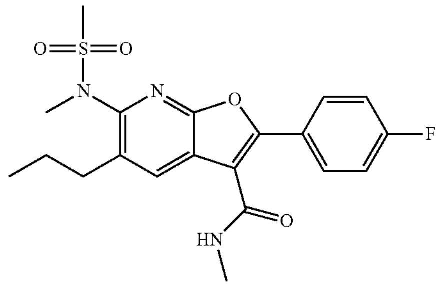 | 2-(4-fluorophenyl)-N-methyl-6-(N-methylmethylsulfonamido)-5-propylfuro[2,3-b]pyridine-3-carboxamide |

The material for the penultimate carboxylic acid intermediate to example 4.95 may also come from example 4. In example 4.96, the terminal olefin 5-allyl-2-(4-fluorophenyl)-N-methyl-6-(N-methylmethylsulfonamido)furo[2,3-b]pyridine-3-carboxamide was directly reduced without olefin cross metathesis first.

Example 5

5-(2-(4-fluorophenyl)-3-(methylcarbamoyl)-6-(N-methylmethylsulfonamido)furo[2,3-b]pyridin-5-yl)pent-4-ynoic acid

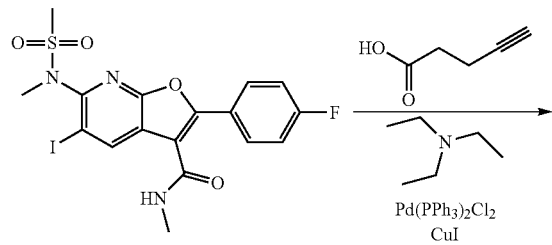

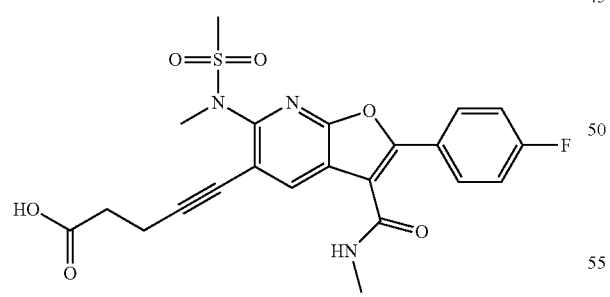

A mixture of 2-(4-fluorophenyl)-5-iodo-N-methyl-6-(N-methylmethylsulfonamido)furo[2,3-b]pyridine-3-carboxamide (52 mg), pent-4-ynoic acid (51 mg), triethylamine (0.43 ml), copper(I) iodide (0.79 mg), Pd(PPh$_3$)Cl$_2$ (5.8 mg) and THF (1.4 ml) was bubbled with nitrogen. Heated at 80° C. for 16 h. Cooled to rt and purified by preparative HPLC. (M+H)$^+$=474.1; Retention time=1.22 min, Method A.

Example 6

5-Ethyl-2-(4-fluoro-phenyl)-6-(methanesulfonyl-methyl-amino)-furo[2,3-b]pyridine-3-carboxylic acid methylamide

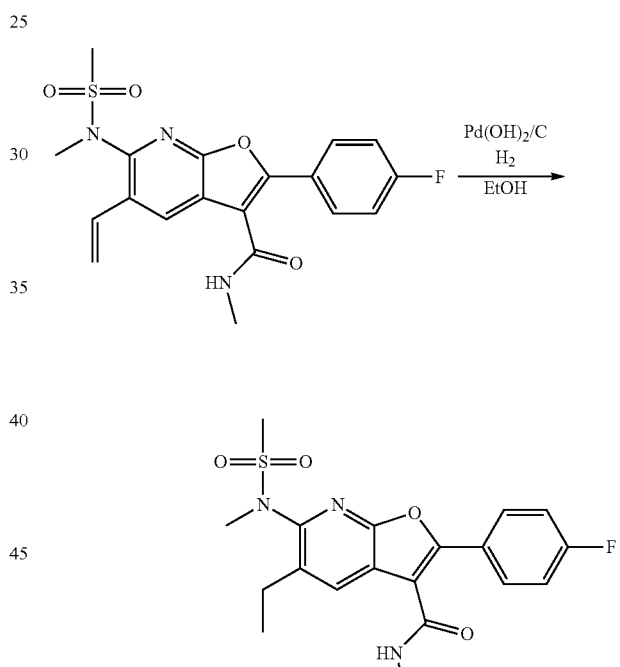

To 2-(4-Fluoro-phenyl)-6-(methanesulfonyl-methyl-amino)-5-vinyl-furo[2,3-b]pyridine-3-carboxylic acid methylamide (11 mg, 0.027 mmol) was added 8 mg of 20% Pd(OH)$_2$/C and ethyl acetate/methanol 5/1 (5 ml). The reaction flask was evacuated and filled with hydrogen gas from a balloon. After LCMS indicated conversion to product, the reaction mixture was filtered, evaporated to dryness and purified by HPLC to afford 5-Ethyl-2-(4-fluoro-phenyl)-6-(methanesulfonyl-methyl-amino)-furo[2,3-b]pyridine-3-carboxylic acid methylamide. MS (ESI) m/z 406.3 (M+1). $^1$H NMR (400 MHz, CDCl$_3$) δ ppm 8.18 (s, 1H), 7.96-7.92 (m, 2H), 7.25-7.20 (m, 2H), 5.79 (br s, 1H), 3.32 (s, 3H), 3.19 (s, 3H), 2.99-2.98 (d, 3H), 2.96-2.91 (q, 2H), 1.33-1.29 (t, 3H).

The compounds in Table 2 are prepared in analogy to Example 6.

TABLE 3

| Cmpd. # | Structure | Name |
|---|---|---|
| 6.1 | 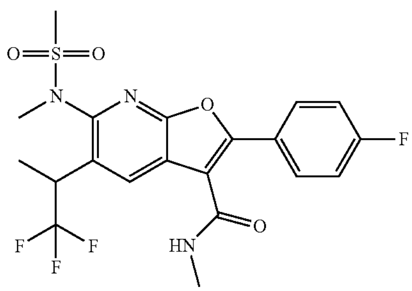 | 2-(4-fluorophenyl)-N-methyl-6-(N-methylmethylsulfonamido)-5-(1,1,1-trifluoropropan-2-yl)furo[2,3-b]pyridine-3-carboxamide |
| 6.2 | 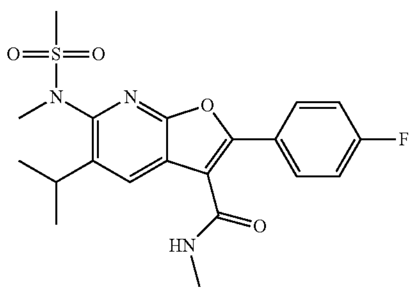 | 2-(4-fluorophenyl)-5-isopropyl-N-methyl-6-(N-methylmethylsulfonamido)furo[2,3-b]pyridine-3-carboxamide |

Example 7

5-(2-(4-fluorophenyl)-3-(methylcarbamoyl)-6-(N-methylmethylsulfonamido)furo[2,3-b]pyridin-5-yl)pent-4-ynoic acid 5-Ethyl-2-(4-fluoro-phenyl)-6-(methanesulfonyl-methyl-amino)-furo[2,3-b]pyridine-3-carboxylic acid methylamide 5-ethynyl-2-(4-fluorophenyl)-N-methyl-6-(N-methylmethylsulfonamido)furo[2,3-b]pyridine-3-carboxamide

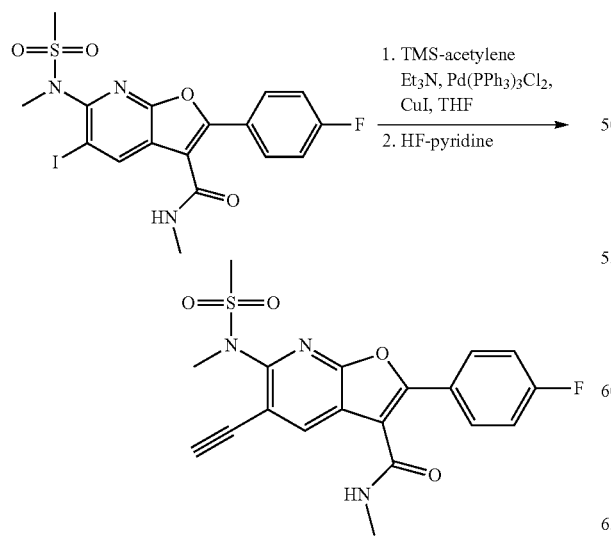

The coupling with trimethylsilylacetylene was conducted in analogy to example 5 and yielded a crude residue with a portion of the material having the TMS on and a portion with the final product lacking the TMS. The crude residue was taken up in acetonitrile in a polyethylene tube and treated with HF-pyridine (3 eq), until LCMS indicated the TMS-containing material had been converted to product, and which time the reaction mixture was evaporated to dryness and purified by HPLC to afford 5-ethynyl-2-(4-fluorophenyl)-N-methyl-6-(N-methylmethylsulfonamido)furo[2,3-b]pyridine-3-carboxamide. MS (ESI) m/z 402.1 (M+1). $^1$H NMR (400 MHz, CD$_3$CN) δ ppm 8.38 (s, 1H), 8.07-8.04 (m, 2H), 7.33-7.29 (m, 2H), 6.82 (br s, 1H), 3.77 (s, 1H), 3.35 (s, 3H), 3.27 (s, 3H), 2.91-2.90 (d, 3H)

Example 8

5-(1,1-difluoroethyl)-2-(4-fluorophenyl)-N-methyl-6-(N-methylmethylsulfonamido)furo[2,3-b]pyridine-3-carboxamide

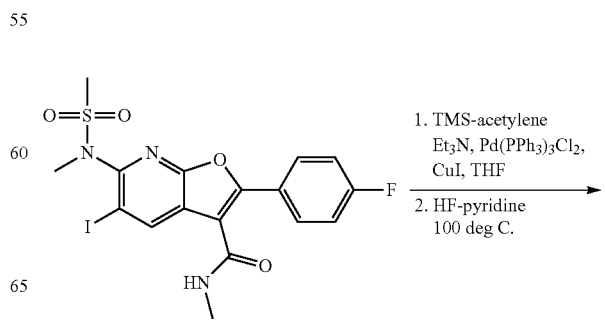

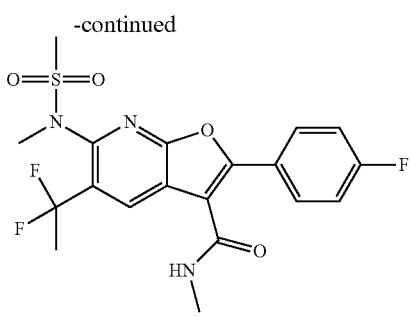

The coupling with trimethylsilylacetylene was conducted in analogy to example 5 and yielded a crude residue with a portion of the material having the TMS on and a portion with the final product lacking the TMS. The crude residue was transferred to a polyethylene tube and treated with neat HF-pyridine (0.1 mL) at 100° C. until LCMS indicated predominant conversion to product, and which time the reaction mixture was evaporated to dryness and purified by HPLC to afford 5-(1,1-difluoroethyl)-2-(4-fluorophenyl)-N-methyl-6-(N-methylmethylsulfonamido)furo[2,3-b]pyridine-3-carboxamide MS (ESI) m/z 442.1 (M+1). $^1$H NMR (400 MHz, CD$_3$CN) δ ppm 8.46 (s, 1H), 8.04-8.02 (m, 2H), 7.35-7.29 (m, 2H), 6.88 (br s, 1H), 3.34 (s, 3H), 3.25 (s, 3H), 2.91-2.92 (d, 3H), 2.17 (t, 3H, J=19 Hz)

Example 9

5-(1,2-dihydroxypropan-2-yl)-2-(4-fluorophenyl)-N-methyl-6-(N-methylmethylsulfonamido)furo[2,3-b]pyridine-3-carboxamide

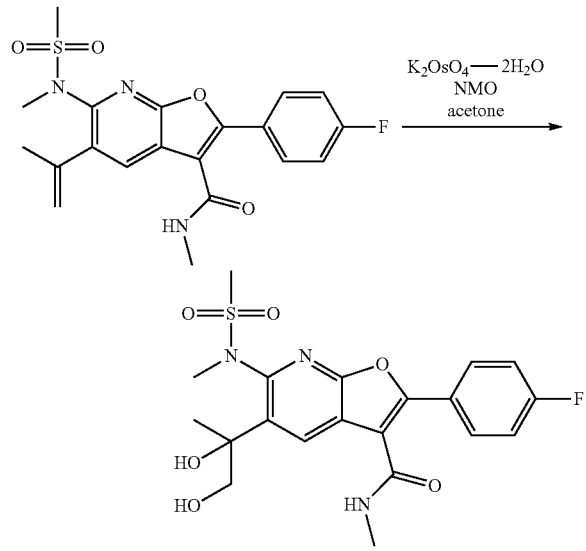

To 2-(4-fluorophenyl)-N-methyl-6-(N-methylmethylsulfonamido)-5-(prop-1-en-2-yl)furo[2,3-b]pyridine-3-carboxamide (11 mg, 0.026 mmol) in acetone (1 ml) was added NMO (9.26 mg, 0.079 mmol) and potassium osmate dihydrate (0.971 mg, 2.64 μmol). After LCMS indicated predominant conversion of starting material to product, the reaction mixture was purified by HPLC to afford the title compound. MS (ESI) m/z 452.0 (M+1). 2 rotamers confirmed by 2D NMR: $^1$H NMR (400 MHz, CD$_3$CN) δ ppm 8.66, 8.64 (s, 1H), 8.04-8.02 (m, 2H), 7.34-7.29 (m, 2H), 6.88 (br s, 1H), 4.16-4.13, 4.06-4.03 (m, 1H), 3.92, 3.88 (br s, 1H), 3.82-3.79 (m, 1H), 3.33, 3.32 (s, 3H), 3.29 (s, 3H), 3.15-3.02 (br s, 1H), 2.93-2.92 (d, 3H)

Example 9.1

5-(2,3-dihydroxypropyl)-N-methyl-6-(N-methylmethylsulfonamido)-2-p-tolylfuro[2,3-b]pyridine-3-carboxamide

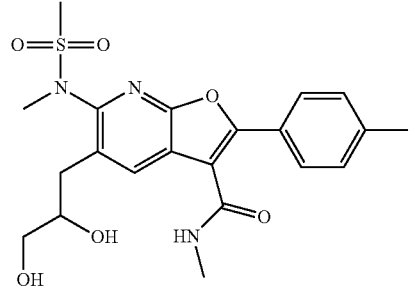

Example 9.1 was prepared by analogy to Examples 9 and 4.1

Example 9.2

5-(3-hydroxypropyl)-N-methyl-6-(N-methylmethylsulfonamido)-2-p-tolylfuro[2,3-b]pyridine-3-carboxamide

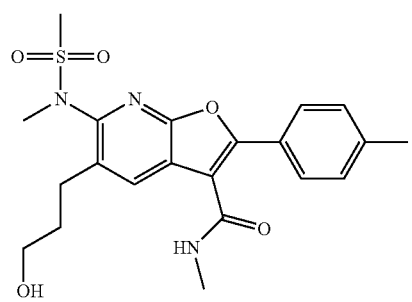

The title compound was prepared by analogy to Examples 4.1 and 42 B.

Example 10

5-acetyl-2-(4-fluorophenyl)-N-methyl-6-(N-methylmethylsulfonamido)furo[2,3-b]pyridine-3-carboxamide

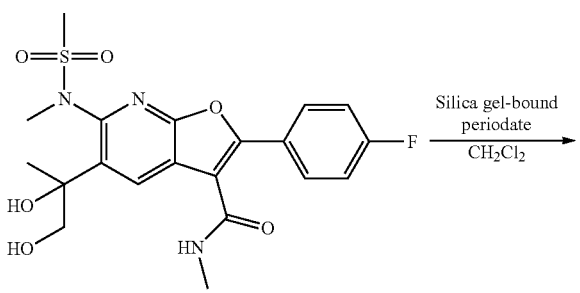

-continued

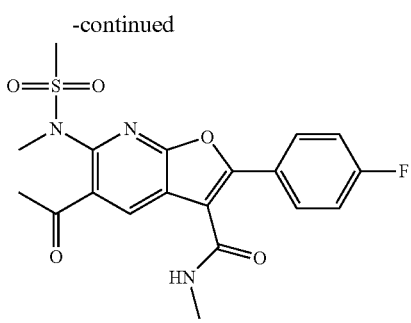

To 5-(1,2-dihydroxypropan-2-yl)-2-(4-fluorophenyl)-N-methyl-6-(N-methylmethylsulfonamido)furo[2,3-b]pyridine-3-carboxamide (10 mg, 0.022 mmol) was added silica-gel-bound-sodium periodate (0.667 mmol/g, 0.044 mmol, 66 mg, J. Org. Chem. 1997, 62, p. 2622-2624). After LCMS indicated complete conversion to product, the reaction mixture was filtered and concentrated to afford the title compound. MS (ESI) m/z 420.1 (M+1). NMR (400 MHz, CDCl$_3$) δ 8.45 (s, 1H), 7.96-7.93 (m, 2H), 7.19-7.14 (m, 2H), 5.80 (br s, 1H), 3.40 (s, 3H), 2.97 (s, 3H), 2.97-2.96 (d, 3H), 2.67 (s, 3H)

Example 11

2-(4-fluorophenyl)-5-(1-hydroxyethyl)-N-methyl-6-(N-methylmethylsulfonamido)furo[2,3-b]pyridine-3-carboxamide

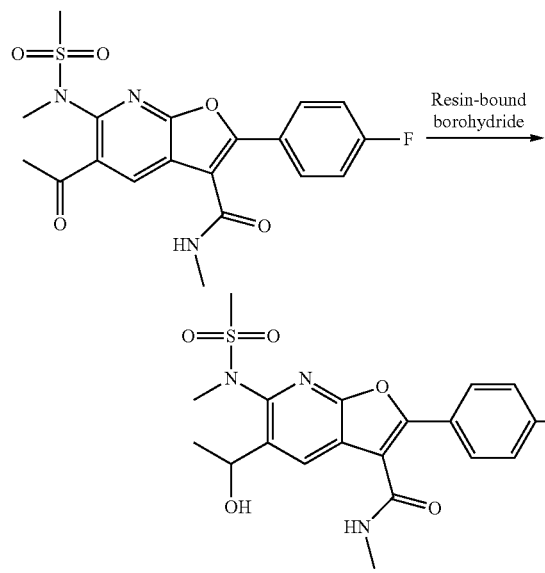

To 5-acetyl-2-(4-fluorophenyl)-N-methyl-6-(N-methylethylsulfonamido)furo[2,3-b]pyridine-3-carboxamide (3 mg, 7.15 μmol) in tetrahydrofuran (0.1 ml) was added 10 mg of resin-bound borohydride (Aldrich cat#328642, 2.5 mmol BH4/g). After LCMS indicated complete conversion to product, the reaction mixture was filtered and purified by HPLC to afford the title compound (1.5 mg, 50%). MS (ESI) m/z 422.3 (M+1). NMR (400 MHz, CDCl$_3$) δ 8.50 (s, 1H), 8.03-7.99 (m, 2H), 7.26-7.22 (m, 2H), 5.88 (br s, 1H), 5.55-5.53 (m, 1H), 3.37 (s, 3H), 3.13 (s, 3H), 3.06-3.05 (d, 3H), 1.61-1.60 (d, 3H)

Example 12

2-(4-fluorophenyl)-N-methyl-6-(N-methylmethylsulfonamido)-5-(oxiran-2-ylmethyl)furo[2,3-b]pyridine-3-carboxamide

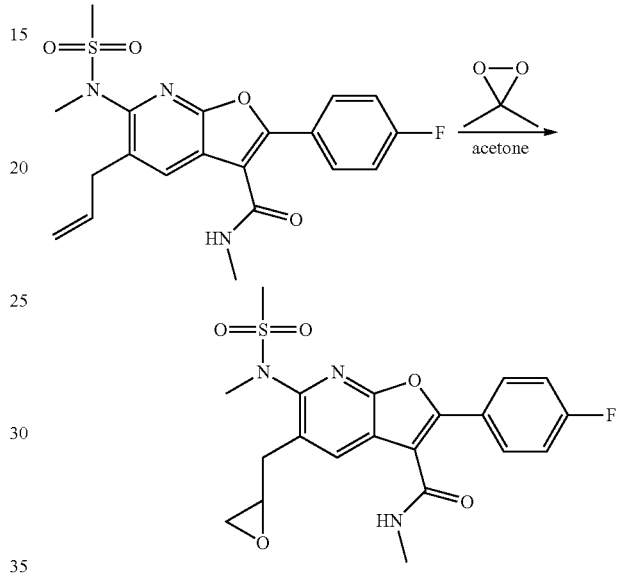

5-allyl-2-(4-fluorophenyl)-N-methyl-6-(N-methylmethylsulfonamido)furo[2,3-b]pyridine-3-carboxamide was stirred with a solution of dimethyldioxirane in acetone until LCMS indicated complete conversion to product. The solution was evaporated to dryness to afford the title compound. MS (ESI) m/z 434.1 (M+1). NMR (400 MHz, CD$_3$CN) δ 8.23 (s, 1H), 8.04-8.00 (m, 2H), 7.33-7.29 (m, 2H), 6.83 (br s, 1H), 3.28 (s, 3H), 3.26-3.24 (m, 2H), 3.16 (s, 3H), 3.05-2.99 (m, 1H), 2.92-2.90 (d, 3H), 2.82-2.79 (m, 1H), 2.63-2.61 (m, 1H)

Example 13

(E)-5-(2-cyanovinyl)-2-(4-fluorophenyl)-N-methyl-6-(N-methylmethylsulfonamido)furo[2,3-b]pyridine-3-carboxamide

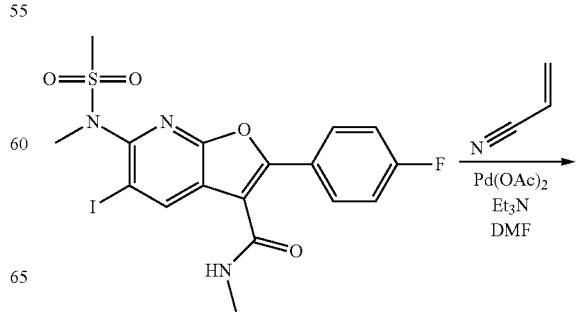

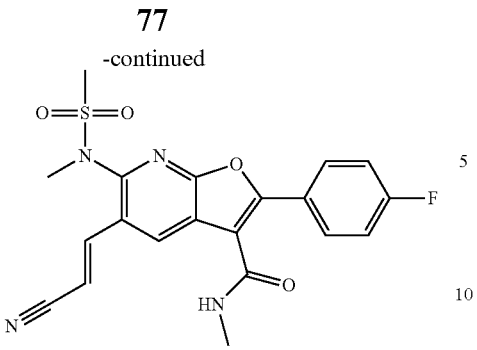

2-(4-Fluoro-phenyl)-5-iodo-6-(methanesulfonyl-methyl-amino)-furo[2,3-b]pyridine-3-carboxylic acid methylamide (10 mg, 0.020 mmol), acrylonitrile (1.371 mg, 0.026 mmol), palladium(II) acetate (0.446 mg, 1.987 μmol) and triethylamine (2.77 μl, 0.020 mmol) in DMF (1 ml) were heated under microwave irradiation at 120° C. for 40 min. After LCMS showed predominant conversion to product, the reaction mixture was concentrated to dryness, taken up in DMF, filtered and purified by HPLC to afford the title compound (6 mg, 0.014 mmol, 70.5% yield). MS (ESI) m/z 429.3 (M+1). NMR (400 MHz, CD$_3$CN) δ 8.51 (s, 1H), 8.06-8.03 (m, 2H), 7.94-7.89 (d, 1H, J=17 Hz), 7.34-7.30 (m, 2H), 6.91 (br s, 1H), 6.30-6.26 (d, 1H, J=17 Hz) (s, 1H), 3.31 (s, 3H), 3.12 (s, 3H), 2.91-2.89 (d, 3H).

Example 14 and 15

5-(2-cyanoethyl)-2-(4-fluorophenyl)-N-methyl-6-(N-methylmethylsulfonamido)furo[2,3-b]pyridine-3-carboxamide and 5-(3-aminopropyl)-2-(4-fluorophenyl)-N-methyl-6-(N-methylmethylsulfonamido)furo[2,3-b]pyridine-3-carboxamide

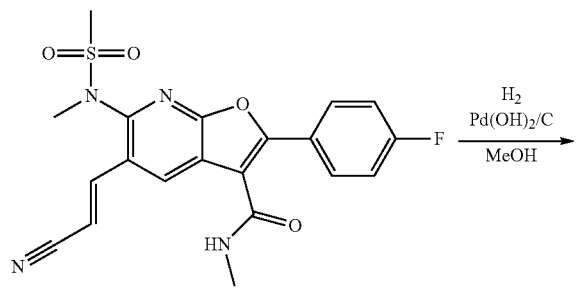

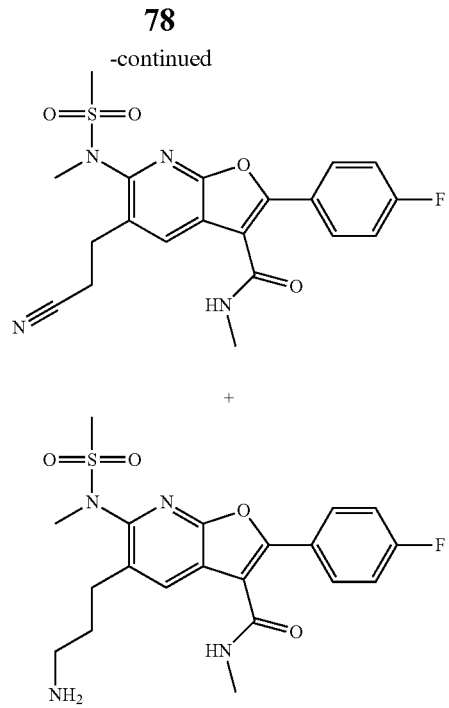

(E)-5-(2-cyanovinyl)-2-(4-fluorophenyl)-N-methyl-6-(N-methylmethylsulfonamido)furo[2,3-b]pyridine-3-carboxamide (6 mg, 0.014 mmol) was stirred under a balloon atmosphere of hydrogen gas with 40 mg of 10% Pd(OH)$_2$/C in methanol (30 ml) and THF (5 ml). After starting material was consumed and a substantial amount of materials were present by LCMS with ES+ consistent with the olefin reduced with either the nitrile intact or reduced to amine, the reaction mixture was filtered, concentrated to dryness and purified by HPLC to afford the title compounds. 5-(2-cyanoethyl)-2-(4-fluorophenyl)-N-methyl-6-(N-methylmethylsulfonamido)furo[2,3-b]pyridine-3-carboxamide (1 mg, 16%): MS (ESI) m/z 431.1 (M+1). NMR (400 MHz, CD$_3$CN) δ 8.24 (s, 1H), 8.04-7.99 (m, 2H), 7.34-7.28 (m, 2H), 6.81 (br s, 1H), 3.32 (s, 3H), 3.27-3.15 (m, 2H), 3.12 (s, 3H), 2.92-2.90 (d, 3H), 2.87-2.82 (m, 2H) 5-(3-aminopropyl)-2-(4-fluorophenyl)-N-methyl-6-(N-methylmethylsulfonamido)furo[2,3-b]pyridine-3-carboxamide (0.32 mg, 5%): MS (ESI) m/z 435.1 (M+1). $^1$H NMR (400 MHz, CD$_3$CN) δ 8.16 (s, 1H), 8.05-8.01 (m, 2H), 7.33-7.28 (m, 2H), 6.88 (br s, 1H), 3.26 (s, 3H), 3.17 (s, 3H), 2.95-2.93 (m, 2H), 2.92-2.91 (d, 3H), 2.73-2.70 (m, 2H), 1.82-1.78 (m, 2H)

The compounds in Table 4 are prepared in analogy to Example 14.

TABLE 4

| Ex. # | Structure | Name |
|---|---|---|
| 14.1 | 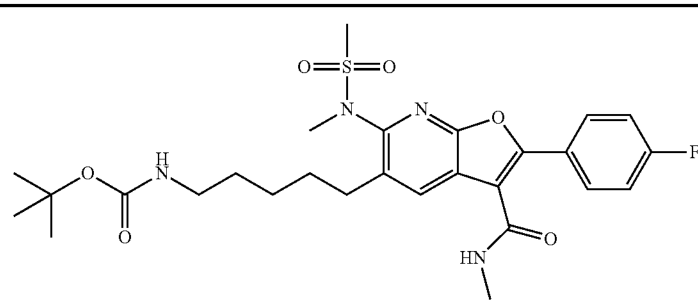 | tert-butyl 5-(2-(4-fluorophenyl)-3-(methylcarbamoyl)-6-(N-methylmethylsulfonamido)furo[2,3-b]pyridin-5-yl)pentylcarbamate |

TABLE 4-continued

| Ex. # | Structure | Name |
|---|---|---|
| 14.2 | 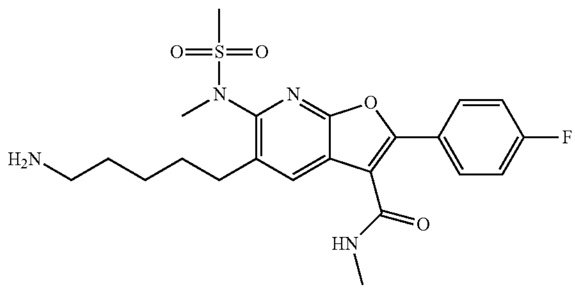 | 5-(5-aminopentyl)-2-(4-fluorophenyl)-N-methyl-6-(N-methylmethylsulfonamido)furo[2,3-b]pyridine-3-carboxamide |
| 14.3 | 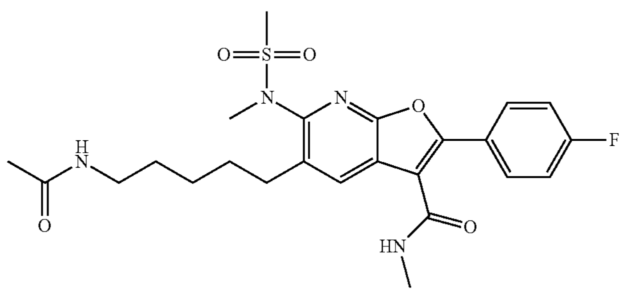 | 5-(5-Acetylamino-pentyl)-2-(4-fluoro-phenyl)-6-(methanesulfonyl-methyl-amino)-furo[2,3-b]pyridine-3-carboxylic acid methylamide |

In the preparation of Example 14.1, the butyloxycarbonyl (Boc) group is partially removed during the Heck reaction. The compounds with and without the Boc group by HPLC and reduced to give 14.1 and 14.2. Example 14.3 is prepared by reaction of example 14.2 with acetic anhydride.

Example 16

5-cyclopropyl-N-methyl-6-(N-methylmethylsulfonamido)-2-(4-phenoxyphenyl)furo[2,3-b]pyridine-3-carboxamide

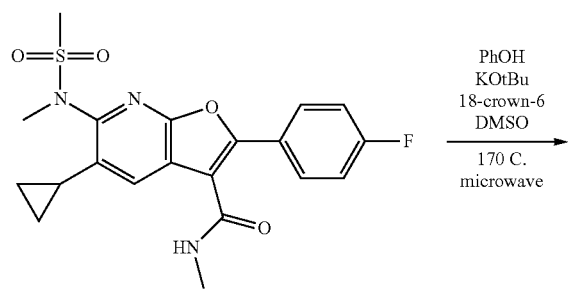

Example 16 is prepared in analogy to the procedure described in *Tetrahedron Letters*, 46 (2005), 7823-7826. The compound of example 1,5-Cyclopropyl-2-(4-fluoro-phenyl)-6-(methanesulfonyl-methyl-amino)-furo[2,3-b]pyridine-3-carboxylic acid methylamide (4 mg, 0.0096 mmol), is heated at 170 degrees C. under microwave irradiation for 10 min with phenol (3.6 mg, 0.038 mmol), potassium tert-butoxide (4.3 mg, 0.038 mmol), 18-crown-6 (10.1 mg, 0.038 mmol) in DMSO (0.2 mL). HPLC purification affords 5-cyclopropyl-N-methyl-6-(N-methylmethylsulfonamido)-2-(4-phenoxyphenyl)furo[2,3-b]pyridine-3-carboxamide (1 mg, 15%) MS (ESI) m/z 492.3 (M+1). Retention time=1.59 min, Method A.

Example 17

5-ethyl-N-methyl-6-(N-methylmethylsulfonamido)-2-(4-phenoxyphenyl)furo[2,3-b]pyridine-3-carboxamide

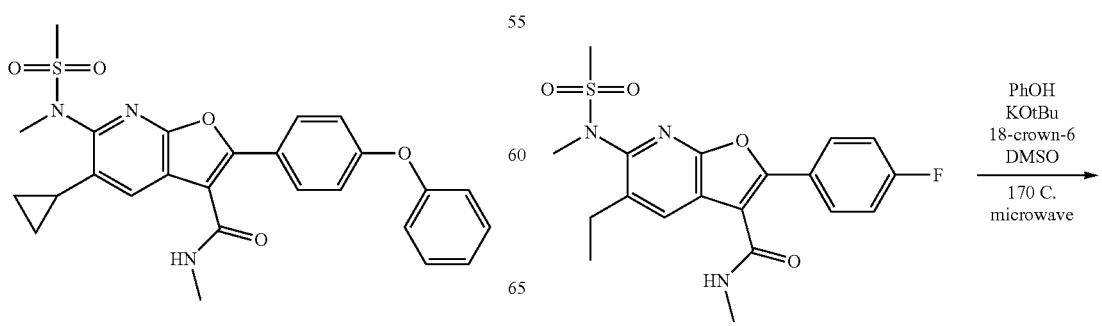

-continued

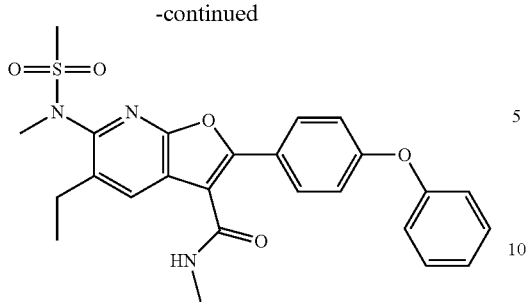

Example 17 is prepared from example 6, 5-ethyl-2-(4-fluorophenyl)-N-methyl-6-(N-methylmethylsulfonamido)furo[2,3-b]pyridine-3-carboxamide, in analogy to example 16. MS (ESI) m/z 480.2 (M+1). Retention time=1.59 min, Method A.

Example 18

5-{[2-(4-Fluoro-phenyl)-5-iodo-3-methylcarbamoyl-furo[2,3-b]pyridin-6-yl]-methanesulfonyl-amino}-pentanoic acid methyl ester

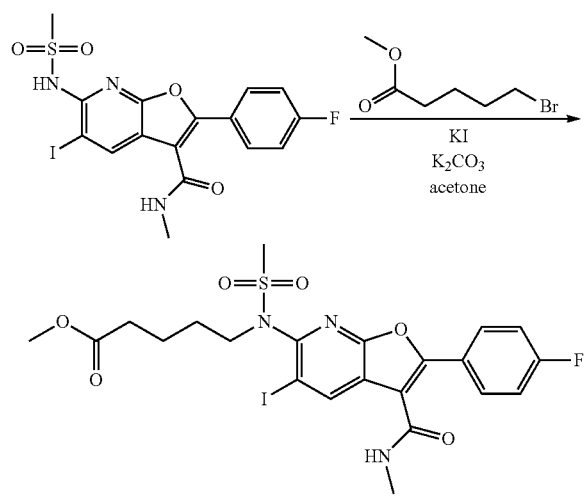

To 2-(4-Fluoro-phenyl)-5-iodo-6-methanesulfonylamino-furo[2,3-b]pyridine-3-carboxylic acid methylamide (300 mg, 0.613 mmol), K$_2$CO$_3$ (169 mg, 1.226 mmol), KI (1018 mg, 6.13 mmol), and methyl 5-bromopentanoate (250 µl, 1.747 mmol) is added acetone (3066 µl) and the reaction mixture is stirred at 60° C. overnight. The acetone is removed under N$_2$ and the mixture is taken up in 2 mL 1:1:1 DMF/H$_2$O/ACN and filtered with a 0.45µ PTFE filter. Purification is achieved by reverse phase HPLC with a C8 column with 40-80% MeOH (0.1% TFA)/H$_2$O (0.1% TFA). MS (ESI) m/z 604.0 (M+1). Retention time=1.48 min, Method A. $^1$H NMR (400 MHz, CDCl3 d ppm 8.77 (s, 1H), 7.96 (t, 2H), 7.19-7.36 (m, 2H), 5.80 (br s, 1H), 3.68 (t, 2H), 3.54 (s, 3H), 3.14 (s, 3H), 2.97 (d, 3H), 2.29 (t, 2H), 1.69-1.79 (m, 2H), 1.42 (s, 2H)

Example 19

5-{[2-(4-Fluoro-phenyl)-5-iodo-3-methylcarbamoyl-furo[2,3-b]pyridin-6-yl]-methanesulfonyl-amino}-pentanoic acid

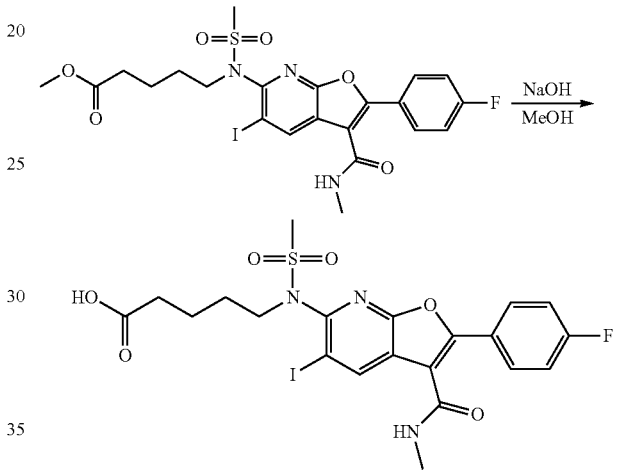

To 5-{[2-(4-Fluoro-phenyl)-5-iodo-3-methylcarbamoyl-furo[2,3-b]pyridin-6-yl]-methanesulfonyl-amino}-pentanoic acid methyl ester (14 mg, 0.023 mmol) in 1 mL MeOH is added NaOH (1N) (0.070 ml, 0.070 mmol) and the mixture is stirred at room temperature overnight. The mixture is concentrated under N$_2$ and extracted from 1N HCl with EtOAc. Purification is achieved by reverse phase HPLC with a C18 column and 2-20% ACN/water with 5 mM NH$_4$OH over 20 minutes. 13 mg (100%) MS (ESI) m/z 590.3 (M+1). Retention time=1.03 min, Method A. $^1$H NMR (400 MHz, MeOD) δ ppm 8.62 (s, 1H), 8.00 (t, 2H), 7.27-7.35 (m, 2H), 3.77 (t, 2H), 3.19 (s, 3H), 2.96 (s, 3H), 2.14 (t, 2H), 1.47-1.73 (m, 4H)

The compounds in Table 5 are made in analogy to Example 18.

TABLE 5

| Ex. # | Structure | Name |
| --- | --- | --- |
| 18.1 | 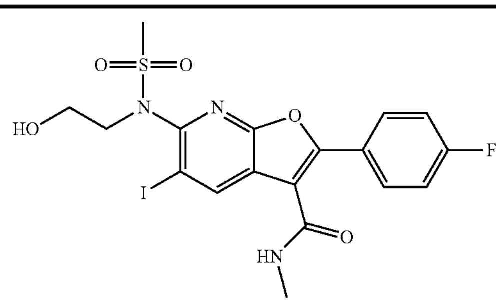 | 2-(4-fluorophenyl)-6-(N-(2-hydroxyethyl)methylsulfonamido)-5-iodo-N-methylfuro[2,3-b]pyridine-3-carboxamide |

TABLE 5-continued

| Ex. # | Structure | Name |
|---|---|---|
| 18.2 | 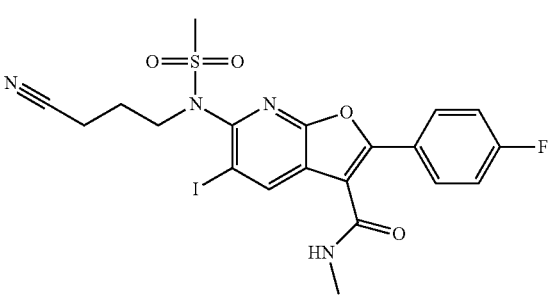 | 6-(N-(3-cyanopropyl)methylsulfonamido)-2-(4-fluorophenyl)-5-iodo-N-methylfuro[2,3-b]pyridine-3-carboxamide |
| 18.3 | 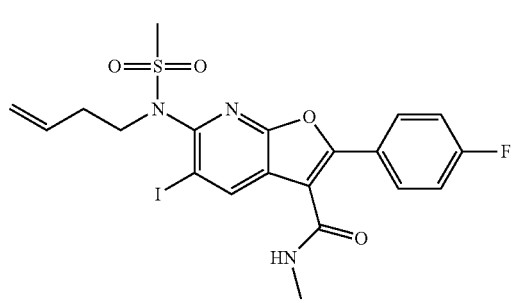 | 6-(N-(but-3-enyl)methylsulfonamido)-2-(4-fluorophenyl)-5-iodo-N-methylfuro[2,3-b]pyridine-3-carboxamide |
| 18.4 | 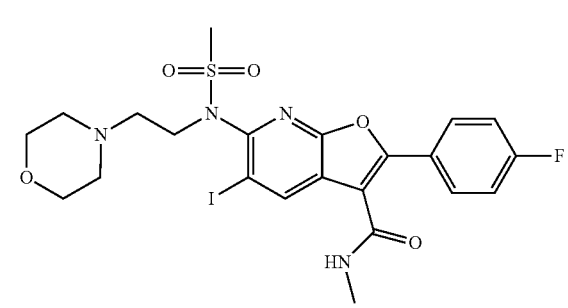 | 2-(4-fluorophenyl)-5-iodo-N-methyl-6-(N-(2-morpholinoethyl)methylsulfonamido)furo[2,3-b]pyridine-3-carboxamide |
| 18.5 | 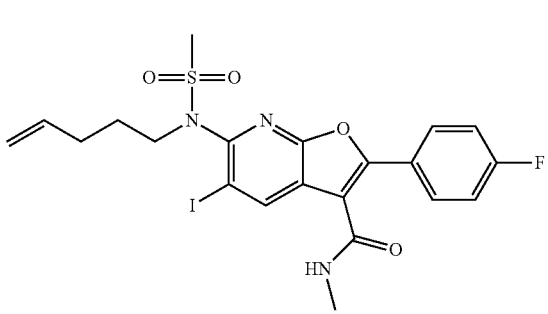 | 2-(4-fluorophenyl)-5-iodo-N-methyl-6-(N-(pent-4-enyl)methylsulfonamido)furo[2,3-b]pyridine-3-carboxamide |
| 18.6 | 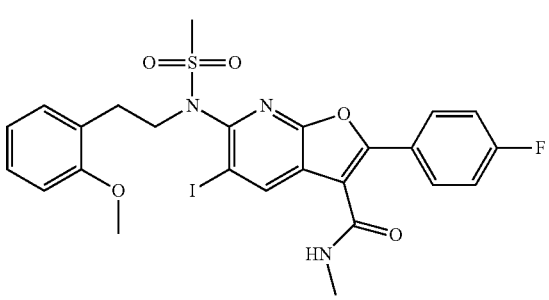 | 2-(4-fluorophenyl)-5-iodo-6-(N-(2-methoxyphenethyl)methylsulfonamido)-N-methylfuro[2,3-b]pyridine-3-carboxamide |

TABLE 5-continued

| Ex. # | Structure | Name |
|---|---|---|
| 18.7 | 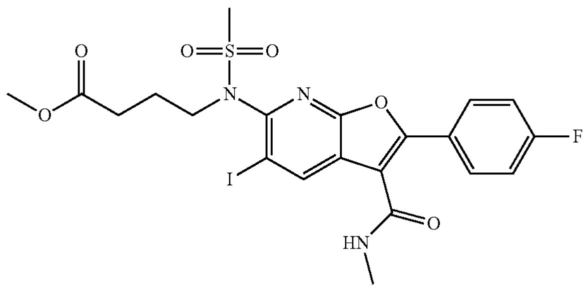 | methyl 4-(N-(2-(4-fluorophenyl)-5-iodo-3-(methylcarbamoyl)furo[2,3-b]pyridin-6-yl)methylsulfonamido)butanoate |
| 18.8 | 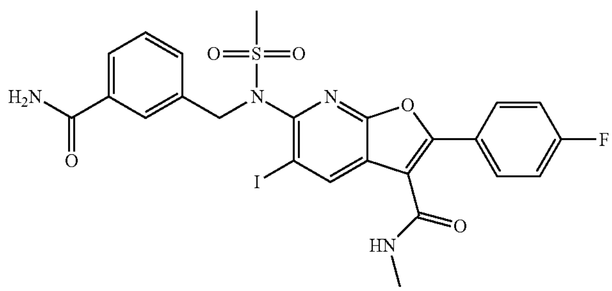 | 6-(N-(3-carbamoylbenzyl)methylsulfonamido)-2-(4-fluorophenyl)-5-iodo-N-methylfuro[2,3-b]pyridine-3-carboxamide |
| 18.9 | 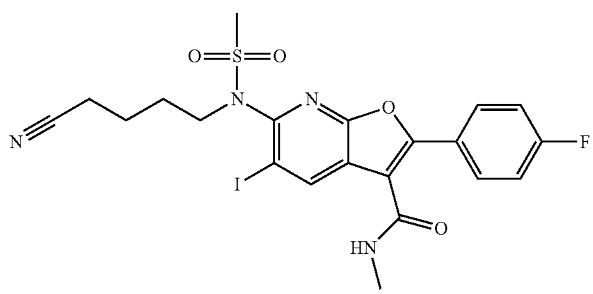 | 6-(N-(4-cyanobutyl)methylsulfonamido)-2-(4-fluorophenyl)-5-iodo-N-methylfuro[2,3-b]pyridine-3-carboxamide |
| 18.91 | 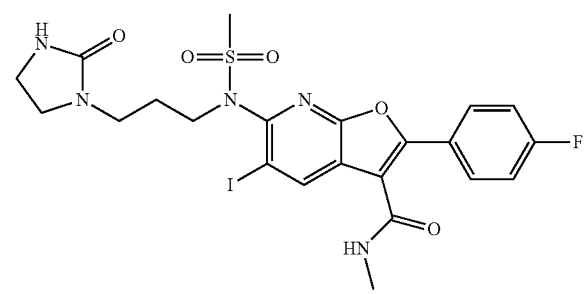 | 2-(4-fluorophenyl)-5-iodo-N-methyl-6-(N-(3-(2-oxoimidazolidin-1-yl)propyl)methylsulfonamido)furo[2,3-b]pyridine-3-carboxamide |
| 18.92 | 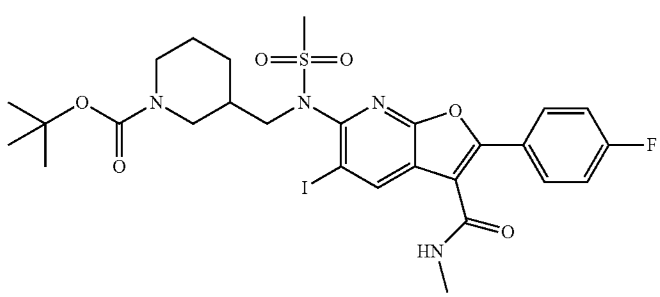 | tert-butyl 3-((N-(2-(4-fluorophenyl)-5-iodo-3-(methylcarbamoyl)furo[2,3-b]pyridin-6-yl)methylsulfonamido)methyl)piperidine-1-carboxylate |

TABLE 5-continued

| Ex. # | Structure | Name |
|---|---|---|
| 18.93 | 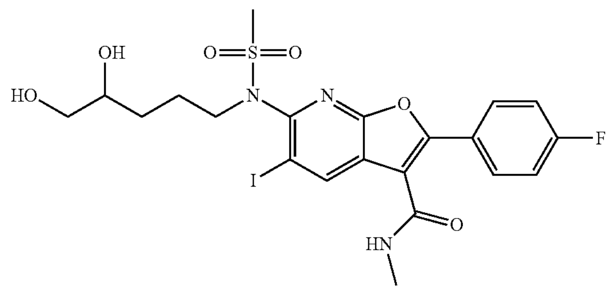 | 6-(N-(4,5-dihydroxypentyl)methylsulfonamido)-2-(4-fluorophenyl)-5-iodo-N-methylfuro[2,3-b]pyridine-3-carboxamide |
| 18.94 | 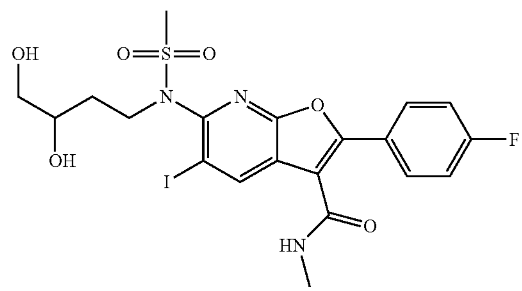 | 6-(N-(3,4-dihyroxybutyl)methylsulfonamido)-2-(4-fluorophenyl)-5-iodo-N-methylfuro[2,3-b]pyridine-3-carboxamide |
| 18.95 | 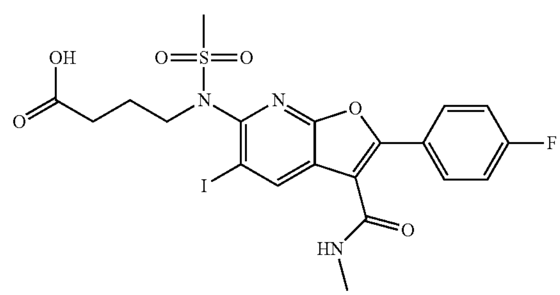 | 4-(N-(2-(4-fluorophenyl)-5-iodo-3-(methylcarbamoyl)furo[2,3-b]pyridin-6-yl)methylsulfonamido)butanoic acid |
| 18.96 | 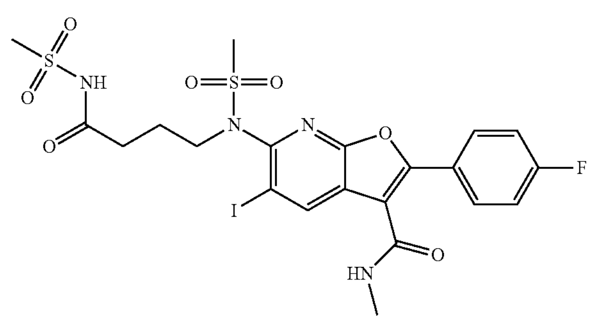 | 2-(4-fluorophenyl)-5-iodo-N-methyl-6-(N-(4-(methylsulfonamido)-4-oxobutyl)methylsulfonamido)furo[2,3-b]pyridine-3-carboxamide |
| 18.97 | 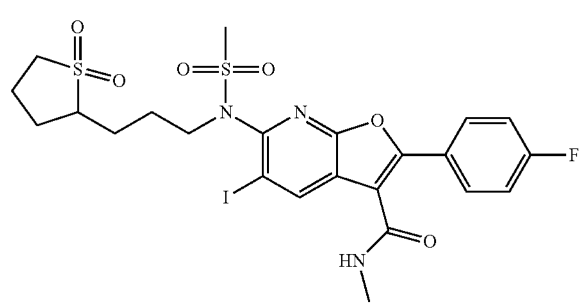 | 6-{[3-(1,1-Dioxo-tetrahydrothiophen-2-yl)-propyl]-methanesulfonyl-amino}-2-(4-fluoro-phenyl)-5-iodo-furo[2,3-b]pyridine-3-carboxylic acid methylamide |

TABLE 5-continued

| Ex. # | Structure | Name |
|---|---|---|
| 18.98 | 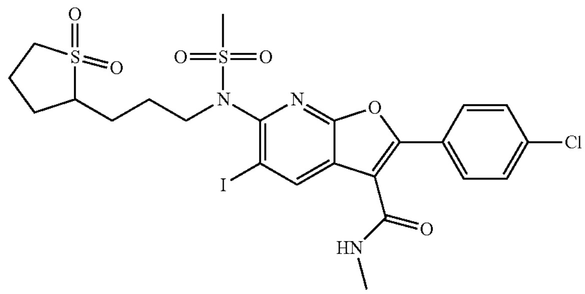 | 2-(4-Chloro-phenyl)-6-{[3-(1,1-dioxo-tetrahydrothiophen-2-yl)-propyl]-methanesulfonyl-amino}-5-iodo-furo[2,3-b]pyridine-3-carobxylic acid methylamide |
| 18.99 | 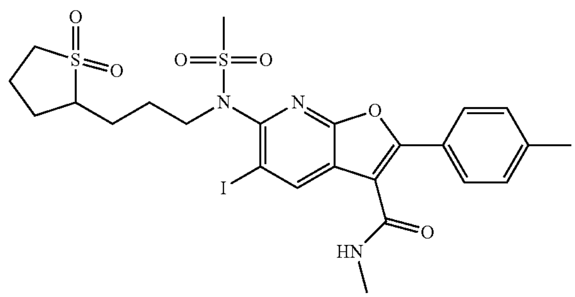 | 6-{[3-(1,1-Dioxo-tetrahydrothiophen-2-yl)-propyl]-methanesulfonyl-amino}-5-iodo-2-p-totyl-furo[2,3-b]pyridine-3-carboxylic acid methylamide |
| 18.991 | 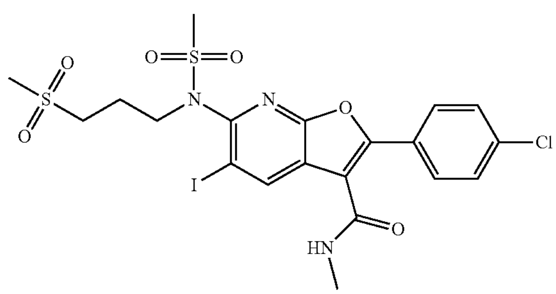 | 2-(4-chlorophenyl)-5-iodo-N-methyl-6-(N-(3-(methylsulfonyl)propyl)methylsulfonamido)furo[2,3-b]pyridine-3-carboxamide |
| 18.992 | 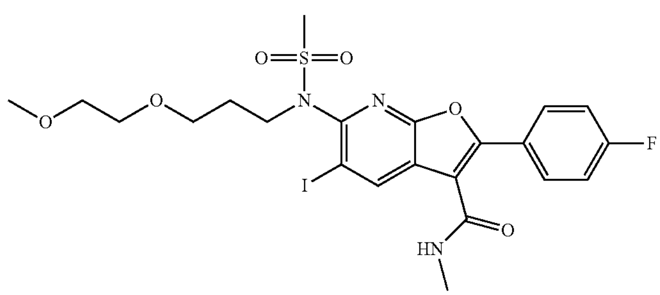 | 2-(4-fluorophenyl)-5-iodo-6-(N-(3-(2-methoxyethoxy)propyl)methylsulfonamido)-N-methylfuro[2,3-b]pyridine-3-carboxamide |
| 18.993 | 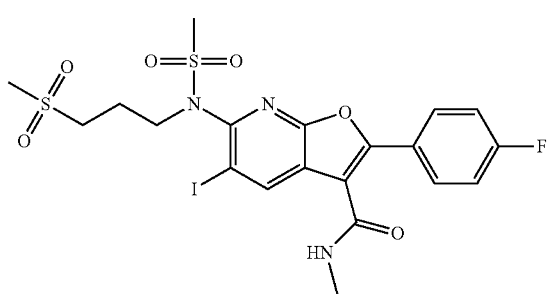 | 2-(4-fluorophenyl)-5-iodo-N-methyl-6-(N-(3-(methylsulfonyl)propyl)methylsulfonamido)furo[2,3-b]pyridine-3-carboxamide |

TABLE 5-continued

| Ex. # | Structure | Name |
|---|---|---|
| 18.994 | 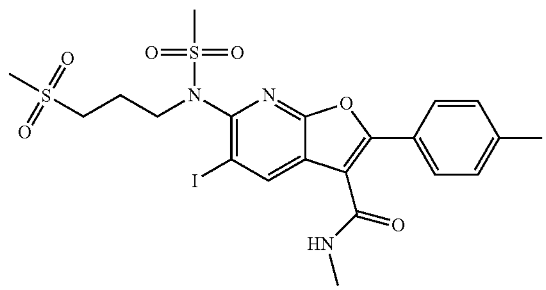 | 5-iodo-N-methyl-6-(N-(3-(methylsulfonyl)propyl)methylsulfonamido)-2-p-tolylfuro[2,3-b]pyridine-3-carboxamide |
| 18.995 | 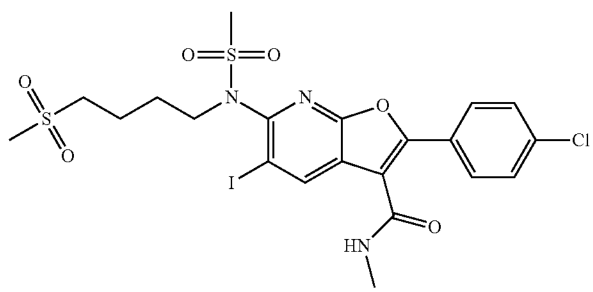 | 2-(4-chlorophenyl)-5-iodo-N-methyl-6-(N-(4-(methylsulfonyl)butyl)methylsulfonamido)furo[2,3-b]pyridine-3-carboxamide |
| 18.996 | 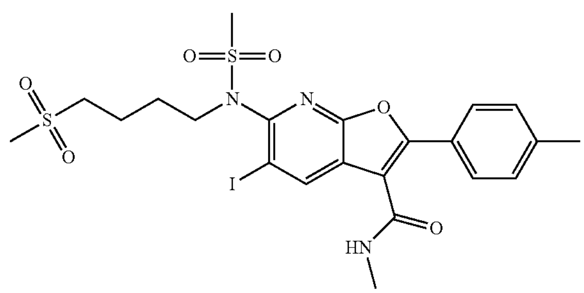 | 5-iodo-N-methyl-6-(N-(4-(methylsulfonyl)butyl)methylsulfonamido)-2-p-tolylfuro[2,3-b]pyridine-3-carboxamide |
| 18.997 | 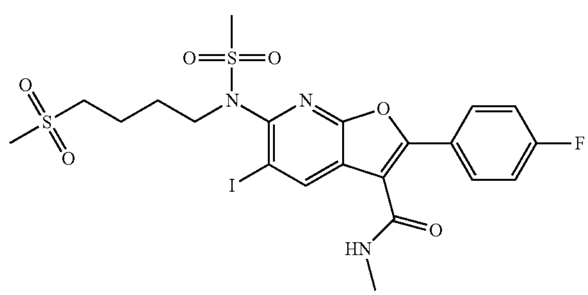 | 2-(4-fluorophenyl)-5-iodo-N-methyl-6-(N-(4-(methylsulfonyl)butyl)methylsulfonamido)furo[2,3-b]pyridine-3-carboxamide |
| 18.998 | 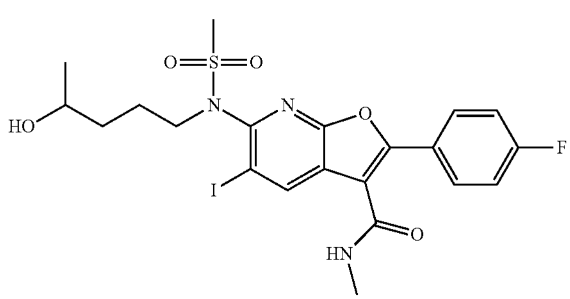 | 2-(4-fluorophenyl)-6-(N-(4-hydroxypentyl)methylsulfonamido)-5-iodo-N-methylfuro[2,3-b]pyridine-3-carboxamide |

TABLE 5-continued

| Ex. # | Structure | Name |
|---|---|---|
| 18.999 | 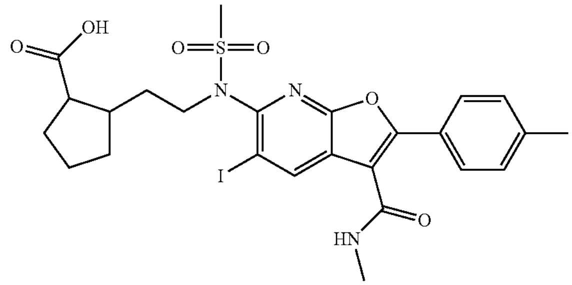 | 2-(2-(N-(5-iodo-3-(methylcarbamoyl)-2-p-tolylfuro[2,3-b]pyridin-6-yl)methylsulfonamido)ethyl)cyclopentanecarboxylic acid |
| 18.9991 | 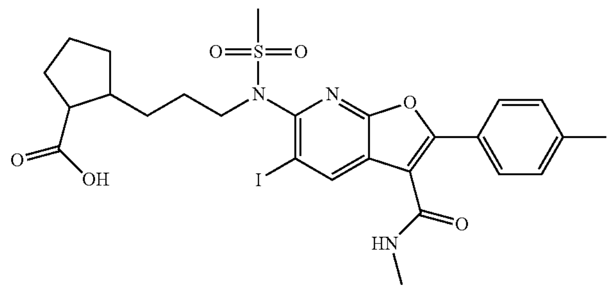 | 2-(3-(N-(5-iodo-3-(methylcarbamoyl)-2-p-tolylfuro[2,3-b]pyridin-6-yl)methylsulfonamido)propyl)cyclopentanecarboxylic acid |

In Examples 18.93 and 18.94, a dihydroxylation is performed in the last step in analogy to Example 9. For Example 18.95, a hydrolysis is performed in the last step in analogy to Example 19. Example 18.96 is derived from an HATU coupling of methanesulfonamide and Example 18.95 in analogy to 4.3. In Example 18.998, the alkylation step is performed with the tert-butyl-dimethylsilyl (TBS) ether of the secondary alcohol, and the TBS ether is removed by treatment with tetrabutylammonium fluoride to give 18.998. Examples 18.999 and 18.9991 were prepared by analogy to Examples 29.3 and 29.4.

Example 20

6-[(4-Amino-butyl)-methanesulfonyl-amino]-2-(4-fluoro-phenyl)-5-iodo-furo[2,3-b]pyridine-3-carboxylic acid methylamide

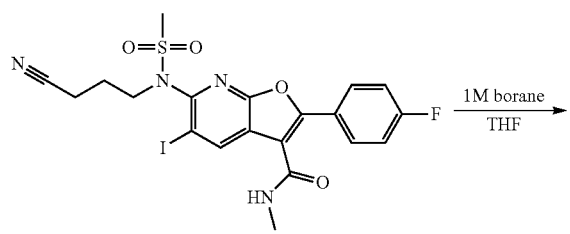

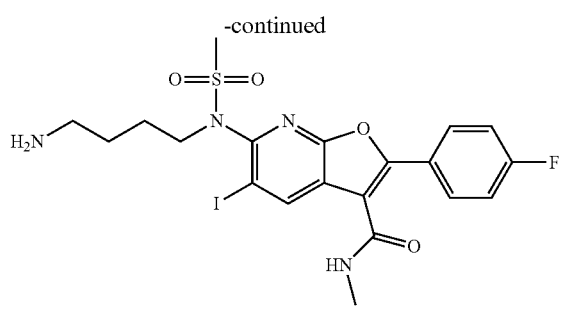

To the 6-[(3-Cyano-propyl)-methanesulfonyl-amino]-2-(4-fluoro-phenyl)-5-iodo-furo[2,3-b]pyridine-3-carboxylic acid methylamide (11 mg, 0.020 mmol) at 0° C. is added 0.5 mL 1N Borane in THF and stirred at 0° C. 5 min then stirred at room temperature overnight. The mixture is quenched with 1N HCl and THF is removed with a stream of $N_2$. Purification is achieved by reverse phase HPLC with a C8 column with 10-50% ACN/$H_2O$ (0.1% $NH_4OH$) to give 5 mg title compound. MS (ESI) m/z 561.0 (M+1). Retention time=1.00 min, Method A. $^1$H NMR (400 MHz, CD3CN) δ ppm 8.71 (s, 1H), 8.02-8.07 (m, 2H), 7.95 (t, 2H) 3.74 (t, 3H), 3.15 (s, 3H), 2.91 (d, 3H), 2.13-2.54 (m, 6H)

The examples in Table 6 are prepared in analogy to Example 18, with the exception that the sulfonamide that is alkylated is first converted from aryliodide to aryl-ethyl by benzylbromide alkylation in analogy to the procedure to make 18 and hydrogenation/hydrogenolysis in analogy to the procedure used to make Example 6.

TABLE 6

| Ex. # | Structure | Name |
|---|---|---|
| 21 | 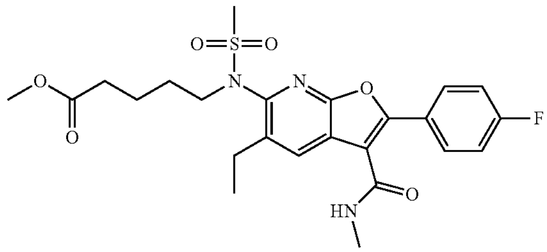 | methyl 5-(N-(5-ethyl-2-(4-fluorophenyl)-3-(methylcarbamoyl)furo[2,3-b]pyridin-6-yl)methylsulfonamido)pentanoate |
| 21.1 | 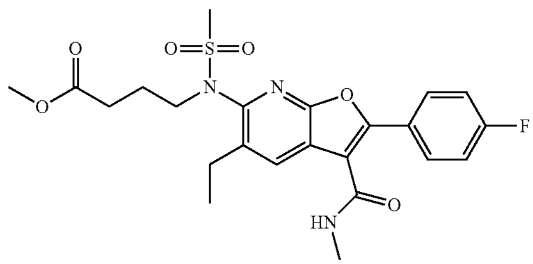 | methyl 4-(N-(5-ethyl-2-(4-fluorophenyl)-3-(methylcarbamoyl)furo[2,3-b]pyridin-6-yl)methylsulfonamido)butanoate |
| 21.2 | 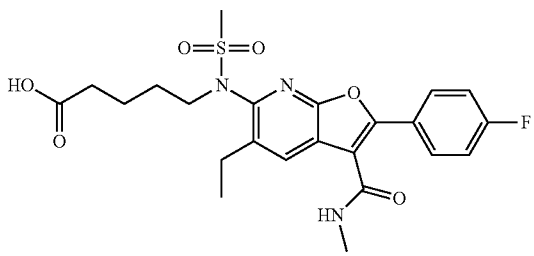 | 5-(N-(5-ethyl-2-(4-fluorophenyl)-3-(methylcarbamoyl)furo[2,3-b]pyridin-6-yl)methylsulfonamido)pentanoic acid |
| 21.3 | 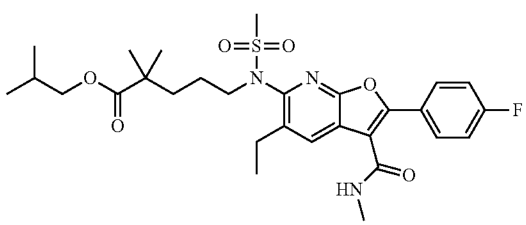 | isobutyl 5-(N-(5-ethyl-2-(4-fluorophenyl)-3-(methylcarbamoyl)furo[2,3-b]pyridin-6-yl)methylsulfonamido)-2,2-dimethylpentanoate |
| 21.4 | 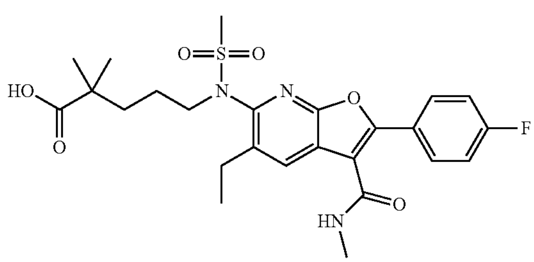 | 5-(N-(5-ethyl-2-(4-fluorophenyl)-3-(methylcarbamoyl)furo[2,3-b]pyridin-6-yl)methylsulfonamido)-2,2-dimethylpentanoic acid |
| 21.5 | 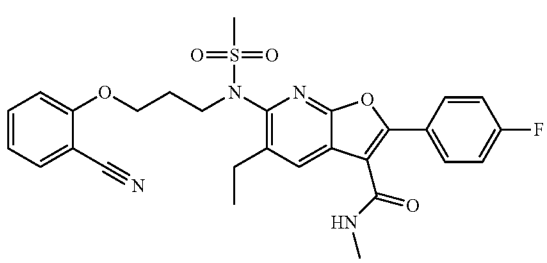 | 6-(N-(3-(2-cyanophenoxy)propyl)methylsulfonamido)-5-ethyl-2-(4-fluorophenyl)-N-methylfuro[2,3-b]pyridine-3-carboxamide |

TABLE 6-continued

| Ex. # | Structure | Name |
|---|---|---|
| 21.6 | 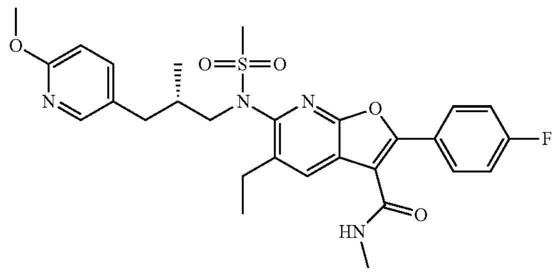 | (S)-5-ethyl-2-(4-fluorophenyl)-6-(N-(3-(6-methoxypyridin-3-yl)-2-methylpropyl)methylsulfonamido)-N-methylfuro[2,3-b]pyridine-3-carboxamide |
| 21.7 | 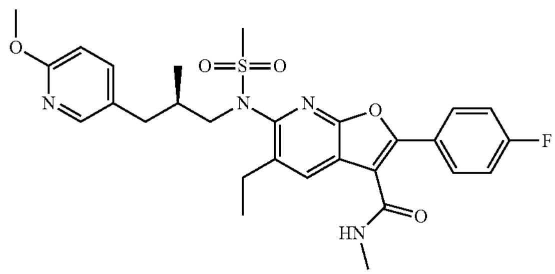 | (R)-5-ethyl-2-(4-fluorophenyl)-6-(N-(3-(6-methoxypyridin-3-yl)-2-methylpropyl)methylsulfonamido)-N-methylfuro[2,3-b]pyridine-3-carboxamide |
| 21.8 | 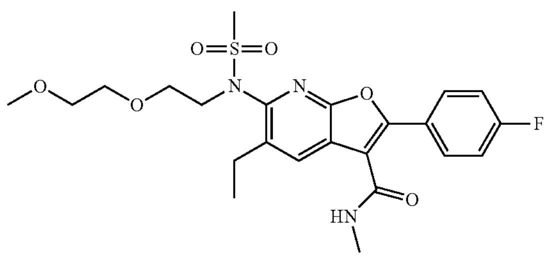 | 5-ethyl-2-(4-fluorophenyl)-6-(N-(2-(2-methoxyethoxy)ethyl)methylsulfonamido)-N-methylfuro[2,3-b]pyridine-3-carboxamide |
| 21.9 | 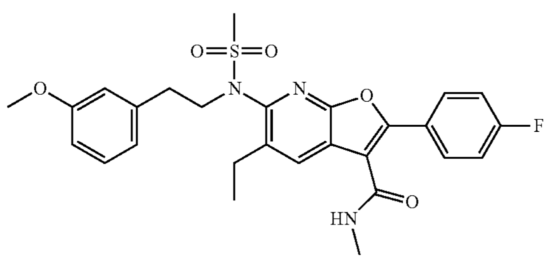 | 5-ethyl-2-(4-fluorophenyl)-6-(N-(3-methoxyphenethyl)methylsulfonamido)-N-methylfuro[2,3-b]pyridine-3-carboxamide |
| 21.91 | 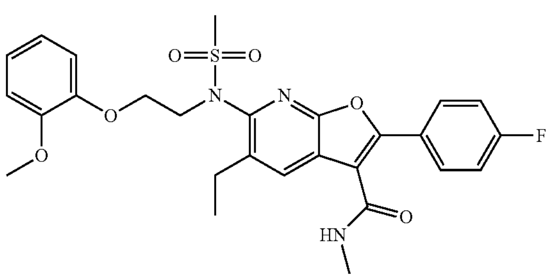 | 5-ethyl-2-(4-fluorophenyl)-6-(N-(2-(2-methoxyphenoxy)ethyl)methylsulfonamido)-N-methylfuro[2,3-b]pyridine-3-carboxamide |
| 21.92 | 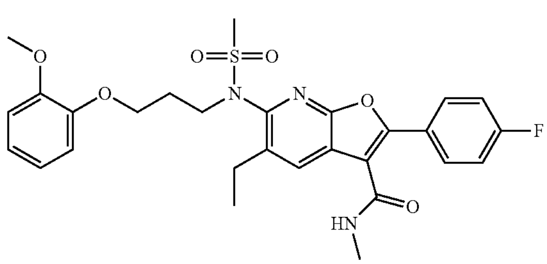 | 5-ethyl-2-(4-fluorophenyl)-6-(N-(3-(2-methoxyphenoxy)propyl)methylsulfonamido)-N-methylfuro[2,3-b]pyridine-3-carboxamide |

TABLE 6-continued

| Ex. # | Structure | Name |
|---|---|---|
| 21.93 | 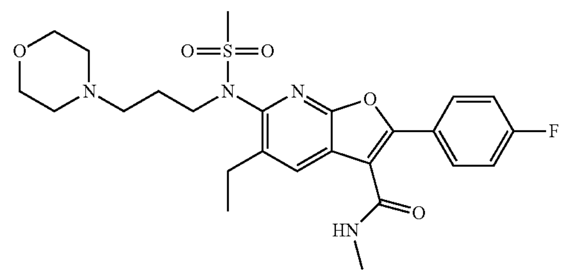 | 5-ethyl-2-(4-fluorophenyl)-N-methyl-6-(N-(3-morpholinopropyl)methylsulfonamido)furo[2,3-b]pyridine-3-carboxamide |
| 21.94 | 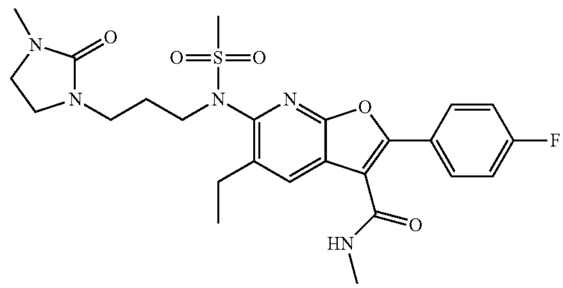 | 5-ethyl-2-(4-fluorophenyl)-N-methyl-6-(N-(3-(3-methyl-2-oxoimidazolidin-1-yl)propyl)methylsulfonamido)furo[2,3-b]pyridine-3-carboxamide |
| 21.95 | 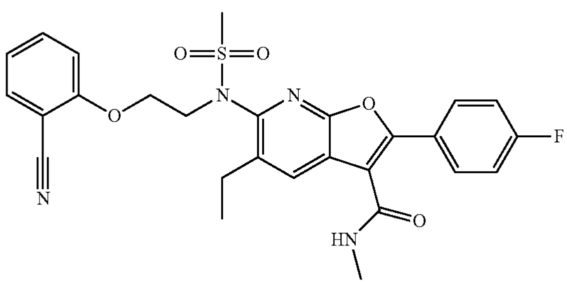 | 6-(N-(2-(2-cyanophenoxy)ethyl)methylsulfonamido)-5-ethyl-2-(4-fluorophenyl)-N-methylfuro[2,3-b]pyridine-3-carboxamide |
| 21.96 | 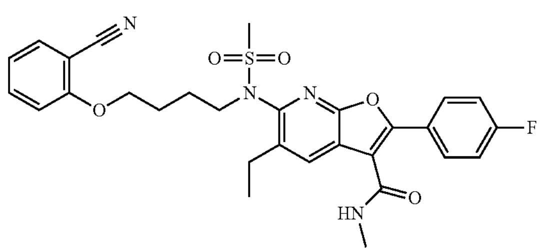 | 6-(N-(4-(2-cyanophenoxy)butyl)methylsulfonamido)-5-ethyl-2-(4-fluorophenyl)-N-methylfuro[2,3-b]pyridine-3-carboxamide |
| 21.97 | 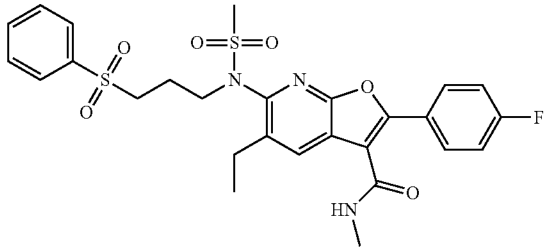 | 5-ethyl-2-(4-fluorophenyl)-N-methyl-6-(N-(3-(phenylsulfonyl)propyl)methylsulfonamido)furo[2,3-b]pyridine-3-carboxamide |

TABLE 6-continued

| Ex. # | Structure | Name |
| --- | --- | --- |
| 21.98 | 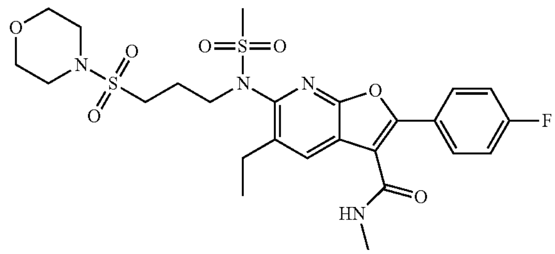 | 5-ethyl-2-(4-fluorophenyl)-N-methyl-6-(N-(3-(morpholinosulfonyl)propyl)methylsulfonamido)furo[2,3-b]pyridine-3-carboxamide |
| 21.99 | 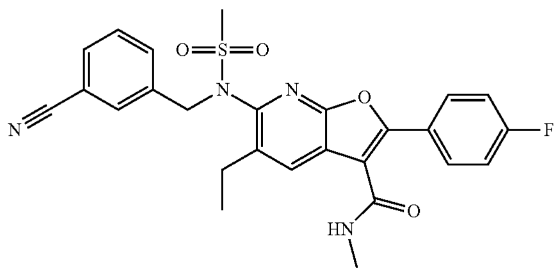 | 6-(N-(3-cyanobenzyl)methylsulfonamido)-5-ethyl-2-(4-fluorophenyl)-N-methylfuro[2,3-b]pyridine-3-carboxamide |
| 21.991 | 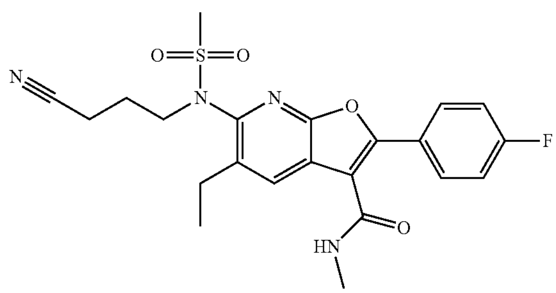 | 6-(N-(3-cyanopropyl)methylsulfonamido)-5-ethyl-2-(4-fluorophenyl)-N-methylfuro[2,3-b]pyridine-3-carboxamide |
| 21.992 | 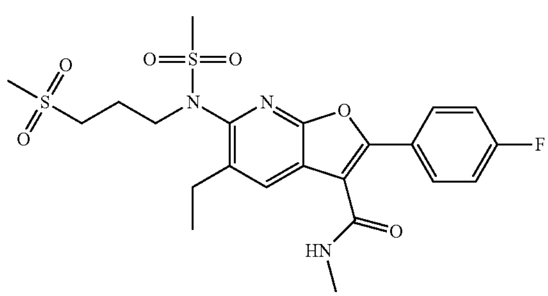 | 5-ethyl-2-(4-fluorophenyl)-N-methyl-6-(N-(3-(methylsulfonyl)propyl)methylsulfonamido)furo[2,3-b]pyridine-3-carboxamide |
| 21.993 | 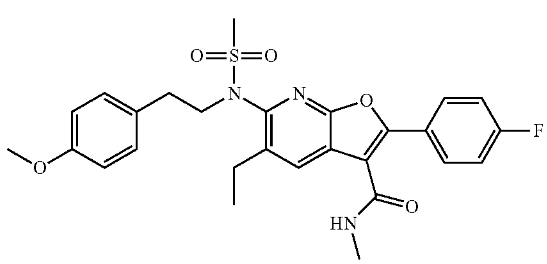 | 5-ethyl-2-(4-fluorophenyl)-6-(N-(4-methoxyphenethyl)methylsulfonamido)-N-methylfuro[2,3-b]pyridine-3-carboxamide |

TABLE 6-continued

| Ex. # | Structure | Name |
|---|---|---|
| 21.994 | 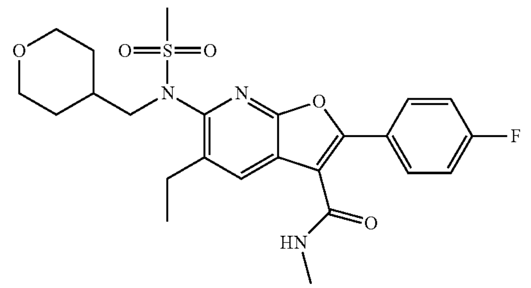 | 5-ethyl-2-(4-fluorophenyl)-N-methyl-6-(N-((tetrahydro-2H-pyran-4-yl)methyl)methylsulfonamido)furo[2,3-b]pyridine-3-carboxamide |
| 21.995 | 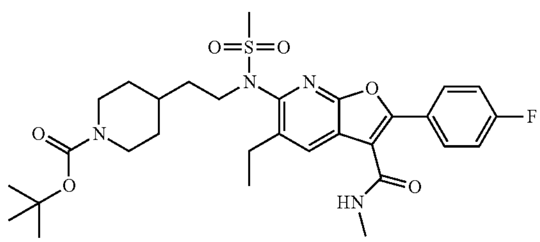 | tert-butyl 4-(2-(N-(5-ethyl-2-(4-fluorophenyl)-3-(methylcarbamoyl)furo[2,3-b]pyridin-6-yl)methylsulfonamido)ethyl)piperidine-1-carboxylate |
| 21.996 | 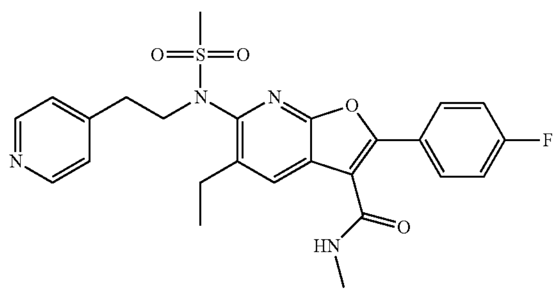 | 5-ethyl-2-(4-fluorophenyl)-N-methyl-6-(N-(2-(pyridin-4-yl)ethyl)methylsulfonamido)furo[2,3-b]pyridine-3-carboxamide |
| 21.997 | 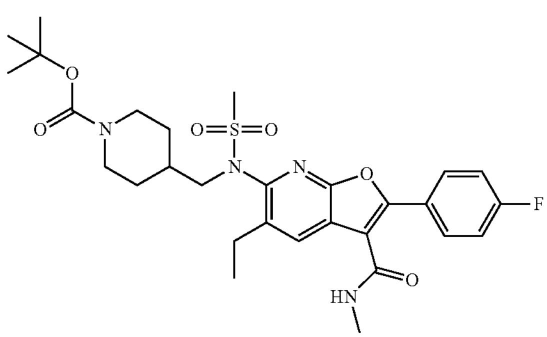 | tert-butyl 4-((N-(5-ethyl-2-(4-fluorophenyl)-3-(methylcarbamoyl)furo[2,3-b]pyridin-6-yl)methylsulfonamido)methyl)piperidine-1-carboxylate |
| 21.998 | 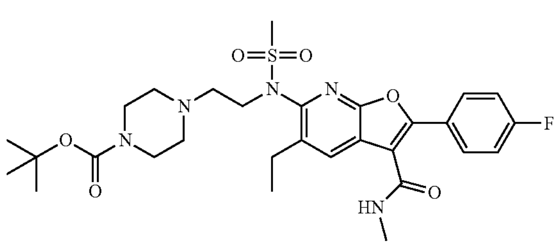 | tert-butyl 4-(2-(N-(5-ethyl-2-(4-fluorophenyl)-3-(methylcarbamoyl)furo[2,3-b]pyridin-6-yl)methylsulfonamido)ethyl)piperazine-1-carboxylate |

TABLE 6-continued

| Ex. # | Structure | Name |
|---|---|---|
| 21.999 | 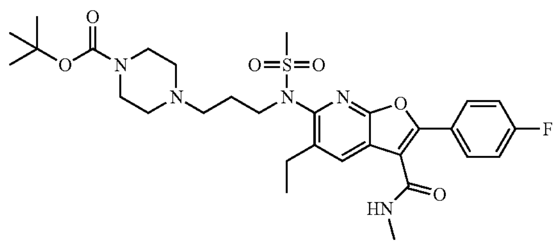 | tert-butyl 4-(3-(N-(5-ethyl-2-(4-fluorophenyl)-3-(methylcarbamoyl)furo[2,3-b]pyridin-6-yl)methylsulfonamido)propyl)piperazine-1-carboxylate |
| 22 | 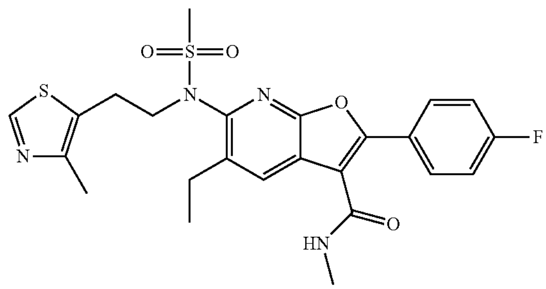 | 5-ethyl-2-(4-fluorophenyl)-N-methyl-6-(N-(2-(4-methylthiazol-5-yl)ethyl)methylsulfonamido)furo[2,3-b]pyridine-3-carboxamide |
| 22.1 | 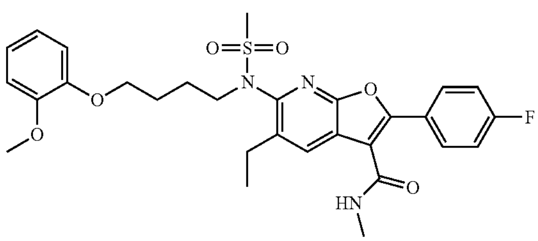 | 5-ethyl-2-(4-fluorophenyl)-6-(N-(4-(2-methoxyphenoxy)butyl)methylsulfonamido)-N-methylfuro[2,3-b]pyridine-3-carboxamide |
| 22.2 | 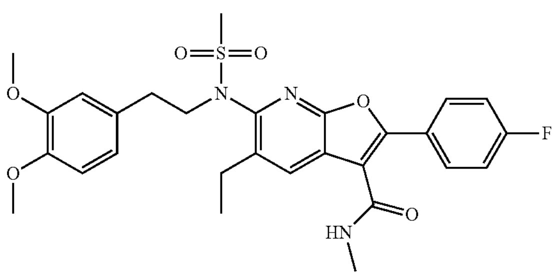 | 6-(N-(3,4-dimethoxyphenethyl)methylsulfonamido)-5-ethyl-2-(4-fluorophenyl)-N-methylfuro[2,3-b]pyridine-3-carboxamide |
| 22.3 | 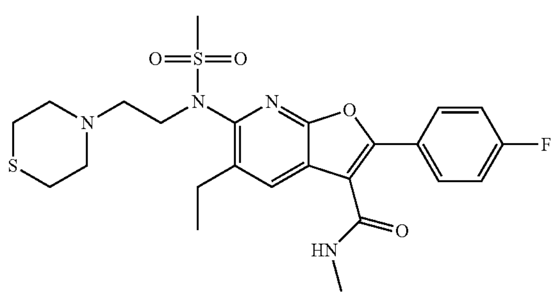 | 5-ethyl-2-(4-fluorophenyl)-N-methyl-6-(N-(2-thiomorpholinoethyl)methylsulfonamido)furo[2,3-b]pyridine-3-carboxamide |
| 22.4 | 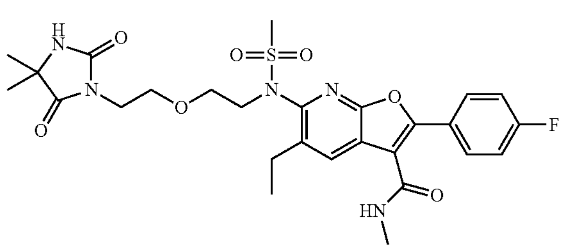 | 6-(N-(2-(2-(4,4-dimethyl-2,5-dioxoimidazolidin-1-yl)ethoxy)ethyl)methylsulfonamido)-5-ethyl-2-(4-fluorophenyl)-N-methylfuro[2,3-b]pyridine-3-carboxamide |

TABLE 6-continued

| Ex. # | Structure | Name |
|---|---|---|
| 22.5 | 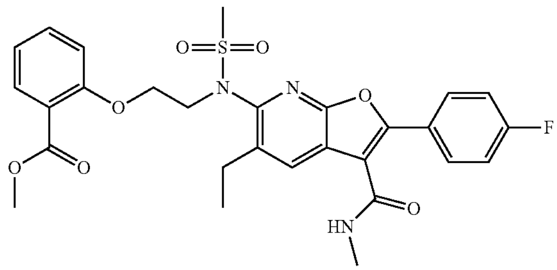 | methyl 2-(2-(N-(5-ethyl-2-(4-fluorophenyl)-3-(methylcarbamoyl)furo[2,3-b]pyridin-6-yl)methylsulfonamido)ethoxy)benzoate |
| 22.6 | 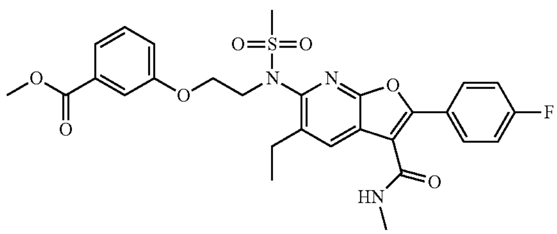 | methyl 3-(2-(N-(5-ethyl-2-(4-fluorophenyl)-3-(methylcarbamoyl)furo[2,3-b]pyridin-6-yl)methylsulfonamido)ethoxy)benzoate |
| 22.7 | 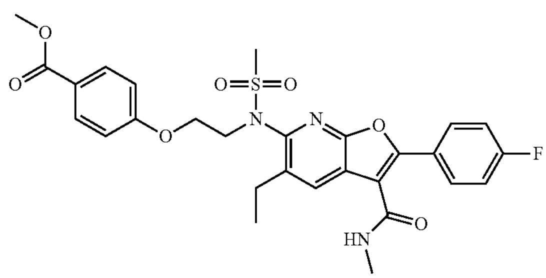 | methyl 4-(2-(N-(5-ethyl-2-(4-fluorophenyl)-3-(methylcarbamoyl)furo[2,3-b]pyridin-6-yl)methylsulfonamido)ethoxy)benzoate |
| 22.8 | 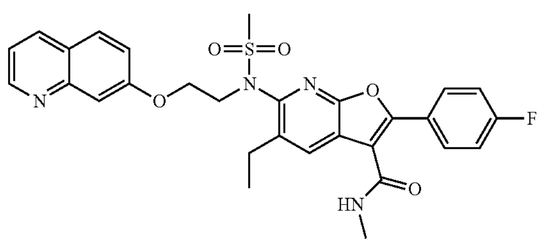 | 5-ethyl-2-(4-fluorophenyl)-N-methyl-6-(N-(2-(quinolin-7-yloxy)ethyl)methylsulfonamido)furo[2,3-b]pyridine-3-carboxamide |
| 22.9 | 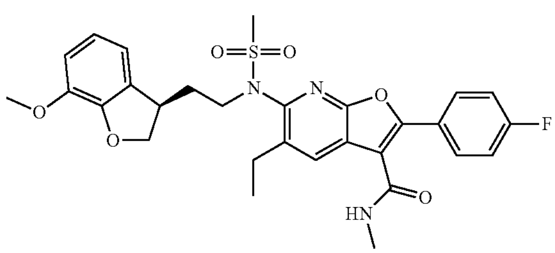 | (R)-5-ethyl-2-(4-fluorophenyl)-6-(N-(2-(7-methoxy-2,3-dihydrobenzofuran-3-yl)ethyl)methylsulfonamido)-N-methylfuro[2,3-b]pyridine-3-carboxamide |
| 22.91 | 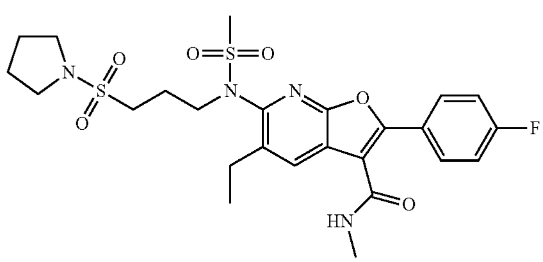 | 5-ethyl-2-(4-fluorophenyl)-N-methyl-6-(N-(3-(pyrrolidin-1-ylsulfonyl)propyl)methylsulfonamido)furo[2,3-b]pyridine-3-carboxamide |

TABLE 6-continued

| Ex. # | Structure | Name |
|---|---|---|
| 22.92 | 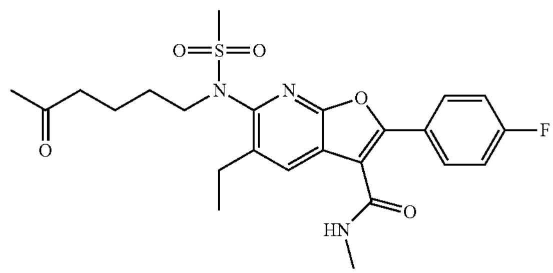 | 5-ethyl-2-(4-fluorophenyl)-N-methyl-6-(N-(5-oxohexyl)methylsulfonamido)furo[2,3-b]pyridine-3-carboxamide |
| 22.93 | 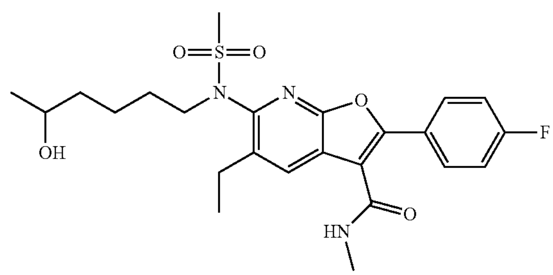 | 5-ethyl-2-(4-fluorophenyl)-6-(N-(5-hydroxyhexyl)methylsulfonamido)-N-methylfuro[2,3-b]pyridine-3-carboxamide |
| 22.94 | 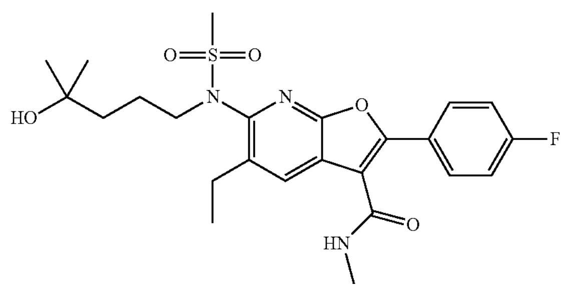 | 5-ethyl-2-(4-fluorophenyl)-6-(N-(4-hydroxy-4-methylpentyl)methylsulfonamido)-N-methylfuro[2,3-b]pyridine-3-carboxamide |
| 22.95 | 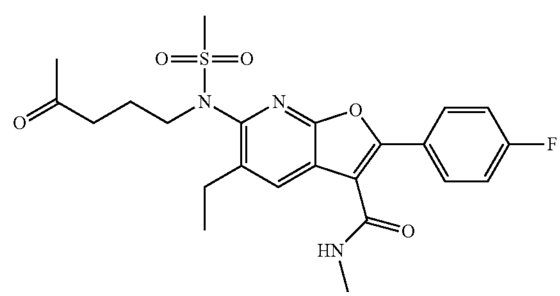 | 5-ethyl-2-(4-fluorophenyl)-N-methyl-6-(N-(4-oxopentyl)methylsulfonamido)furo[2,3-b]pyridine-3-carboxamide |
| 22.96 | 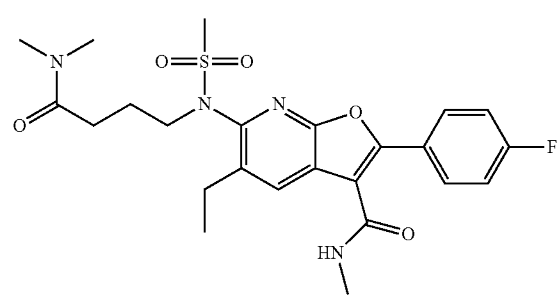 | 6-(N-(4-(dimethylamino)-4-oxobutyl)methylsulfonamido)-5-ethyl-2-(4-fluorophenyl)-N-methylfuro[2,3-b]pyridine-3-carboxamide |

TABLE 6-continued

| Ex. # | Structure | Name |
| --- | --- | --- |
| 22.97 | 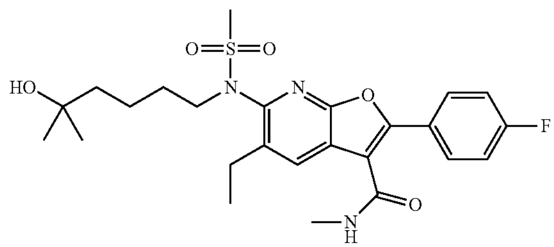 | 5-ethyl-2-(4-fluorophenyl)-6-(N-(5-hydroxy-5-methylhexyl)methylsulfonamido)-N-methylfuro[2,3-b]pyridine-3-carboxamide |
| 22.98 | 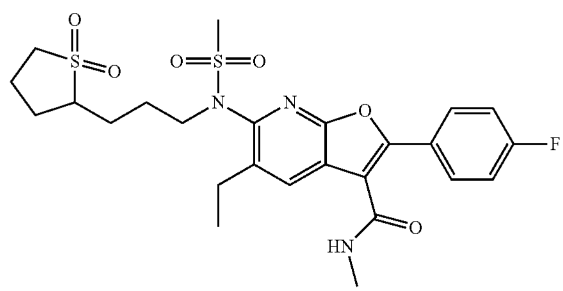 | 6-{[3-(1,1-Dioxo-tetrahydro-1lambdathiophen-2-yl)-propyl]-methanesulfonyl-amino}-5-ethyl-2-(4-fluoro-phenyl)-furo[2,3-b]pyridine-3-carboxylic acid methylamide |
| 22.99 | Enantiomer Peak 1 | 6-{[3-(1,1-Dioxo-tetrahydro-1lambdathiophen-2-yl)-propyl]-methanesulfonyl-amino}-5-ethyl-2-(4-fluoro-phenyl)-furo[2,3-b]pyridine-3-carboxylic acid methylamide |
| 22.991 | Enantiomer Peak 2 | 6-{[3-(1,1-Dioxo-tetrahydro-1lambdathiophen-2-yl)-propyl]-methanesulfonyl-amino}-5-ethyl-2-(4-fluoro-phenyl)-furo[2,3-b]pyridine-3-carboxylic acid methylamide |
| 22.992 | 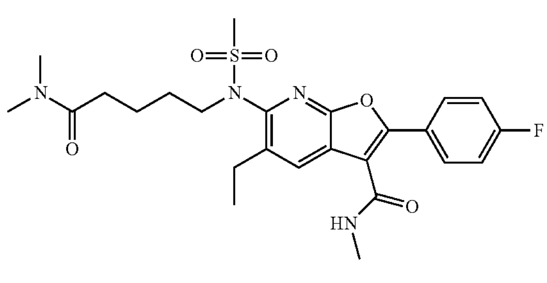 | 6-(N-(5-(dimethylamino)-5-oxopentyl)methylsulfonamido)-5-ethyl-2-(4-fluorophenyl)-N-methylfuro[2,3-b]pyridine-3-carboxamide |

TABLE 6-continued

| Ex. # | Structure | Name |
|---|---|---|
| 22.993 | 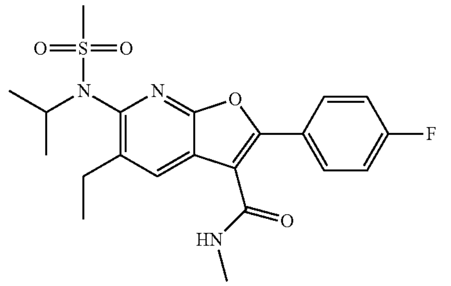 | 5-ethyl-2-(4-fluorophenyl)-6-(N-isopropylmethylsulfonamido)-N-methylfuro[2,3-b]pyridine-3-carboxamide |
| 22.994 | 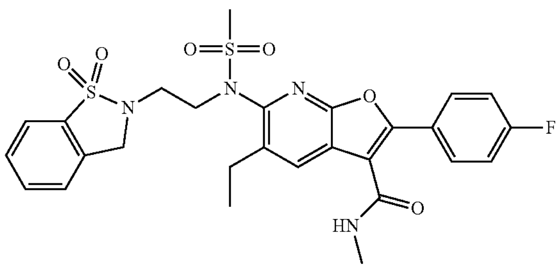 | 6-{[2-(1,1-Dioxo-1,3-dihydrobenzo[d]isothiazol-2-yl)-ethyl]-methanesulfonyl-amino}-5-ethyl-2-(4-fluoro-phenyl)-furo[2,3-b]pyridine-3-carboxylic acid methylamide |
| 22.995 | 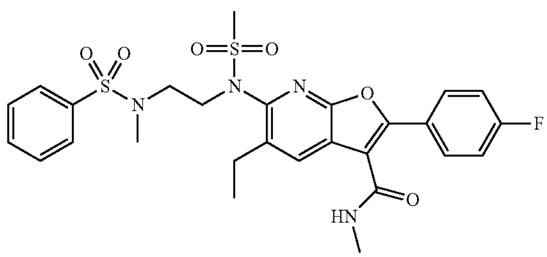 | 5-ethyl-2-(4-fluorophenyl)-N-methyl-6-(N-(2-(N-methylphenylsulfonamido)ethyl)methylsulfonamido)furo[2,3-b]pyridine-3-carboxamide |
| 22.996 | 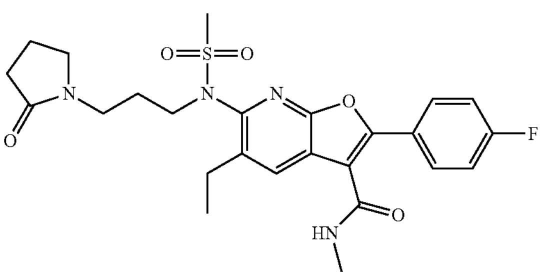 | 5-ethyl-2-(4-fluorophenyl)-N-methyl-6-(N-(3-(2-oxopyrrolidin-1-yl)propyl)methylsulfonamido)furo[2,3-b]pyridine-3-carboxamide |
| 22.997 | 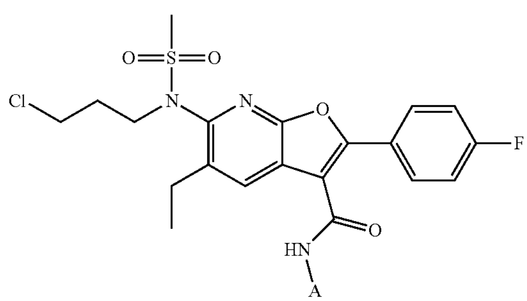 | 6-(N-(3-chloropropyl)methylsulfonamido)-5-ethyl-2-(4-fluorophenyl)-N-methylfuro[2,3-b]pyridine-3-carboximide |

In examples 21.2 and 21.4, the esters of examples 21.1 and 21, are hydrolyzed in analogy to example 19. In Examples 22.96 and 22.992, the acids in examples 21.2 and 21.4 are coupled with dimethylamine in analogy to example 4.3. In example 22.93, the ketone of Example 22.92 is reduced in analogy to Example 11. Examples 22.94 and 22.97 are derived from methyl-Grignard addition to the esters of examples 21.1 and 12, and example 22.95 is a byproduct obtained during the methyl-Grignard addition to the ester of example 21.1. The racemate of Example 22.98 is resolved into individual enantiomers by chiral HPLC on an IC 20×250 mm column with 18 mL/min 50% heptane 50% ethanol:

Example 22.99 elutes at 12.53 min and example 22.991 elutes at 14.85 min.

Example 23

5-Ethyl-2-(4-fluoro-phenyl)-6-[methanesulfonyl-(4-methanesulfonyl-butyl)-amino]-furo[2,3-b]pyridine-3-carboxylic acid methylamide A. 6-[(4-Bromo-butyl)-methanesulfonyl-amino]-5-ethyl-2-(4-fluoro-phenyl)-furo[2,3-b]pyridine-3-carboxylic acid methylamide

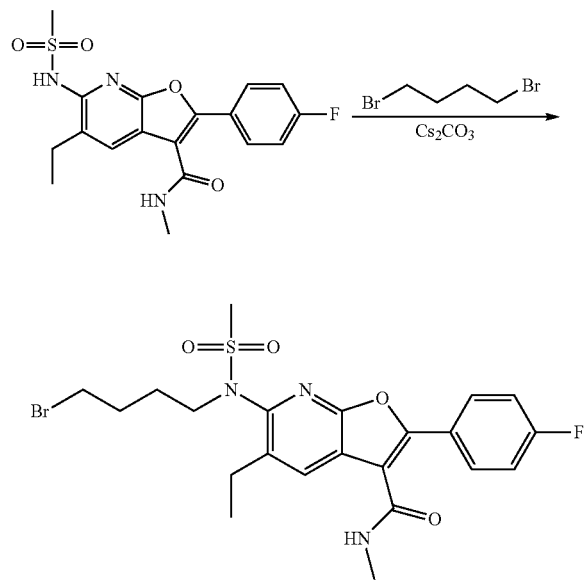

5-Ethyl-2-(4-fluoro-phenyl)-6-methanesulfonylamino-furo[2,3-b]pyridine-3-carboxylic acid methylamide (60 mg, 0.153 mmol), 1,4-dibromobutane (662 mg, 3.07 mmol) and cesium carbonate (52.4 mg, 0.161 mmol) in DMA (766 μL) are heated for 15 min at 120° C. by microwave. 1 mL CAN and 0.5 mL water are added and the mixture is filtered with a 0.45μ PTFE filter. Purification is achieved by reverse phase HPLC with a C8 column with 20-100% CAN//H$_2$O (0.1% TFA) over 15 min with 5 min hold to give 6-[(4-Bromo-butyl)-methanesulfonyl-amino]-5-ethyl-2-(4-fluoro-phenyl)-furo[2,3-b]pyridine-3-carboxylic acid methylamide (40.1 mg, 50%) MS (ESI) m/z 527.8 (M+1). Retention time=1.78 min, Method A.

B. 5-Ethyl-2-(4-fluoro-phenyl)-6-[methanesulfonyl-(4-methanesulfonyl-butyl)-amino]-furo[2,3-b]pyridine-3-carboxylic acid methylamide

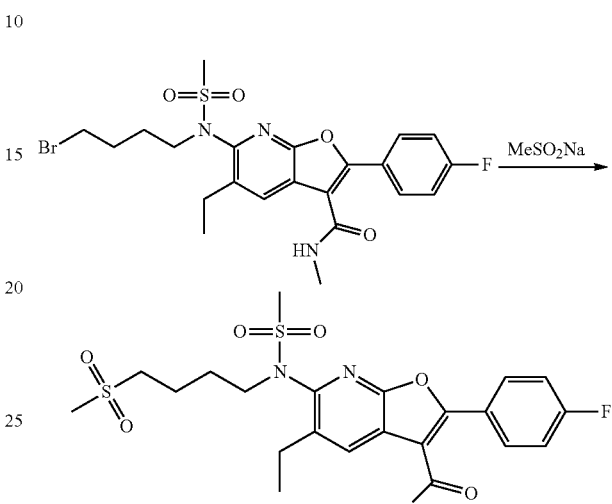

5-Ethyl-2-(4-fluoro-phenyl)-6-methanesulfonylamino-furo[2,3-b]pyridine-3-carboxylic acid methylamide (5 mg, 9.50 μmol) and methanesulfinate (9.70 mg, 0.095 mmol) are stirred in DMA (300 μL) overnight at room temperature. Added 1 ml CAN and 0.5 mL water and filtered with a 0.45μ filter. Purification is achieved by reverse phase HPLC with a C8 column with 20-100% CAN/water (0.1% NH$_4$OH) over 30 minutes (elution at 10.2 min) to give 5 mg (100%) of title compound. MS (ESI) m/z 526.0 (M+1). Retention time=1.41 min, Method A. $^1$H NMR (400 MHz, CD3CN) δ ppm 1.33 (2H, t) 1.55-1.65 (m, 2H) 1.78-1.89 (m, 2H) 2.41-2.18 (m, 2H) 2.83 (s, 3H) 2.92 (d, 3H) 2.90-3.04 (m, 2H) 3.10 (s, 3H) 3.77 (t, 2H) 6.85 (br s, 1H) 7.35 (t, 2H) 8.04 (t, 2H) 8.18 (s, 1H)

The compounds in Table 7 are prepared in analogy to Example 23.

TABLE 7

| Ex. # | Structure | Name |
|---|---|---|
| 23.1 | 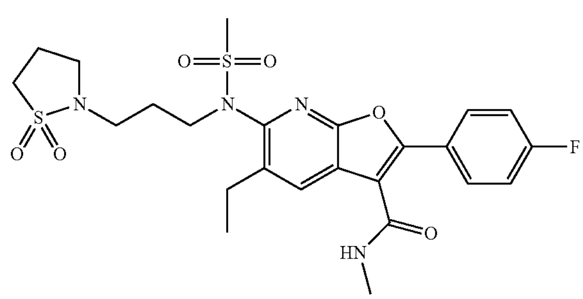 | 6-{[3-(1,1-Dioxo-isothiazolidin-2-yl)-propyl]-methanesulfonyl-amino}-5-ethyl-2-(4-fluoro-phenyl)-furo[2,3-b]pyridine-3-carboxylic acid methylamide |

| Ex. # | Structure | Name |
|---|---|---|
| 23.2 | 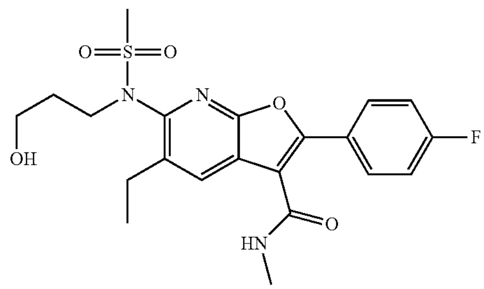 | 5-ethyl-2-(4-fluorophenyl)-6-(N-(3-hydroxypropyl)methylsulfonamido)-N-methylfuro[2,3-b]pyridine-3-carboxamide |
| 23.3 | 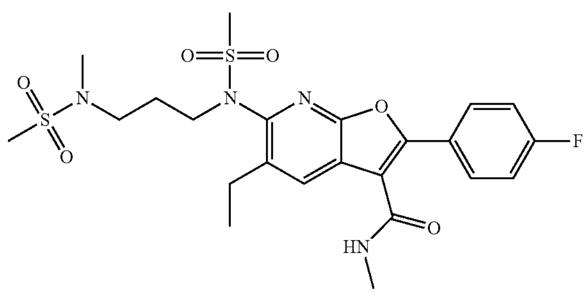 | 5-ethyl-2-(4-fluorophenyl)-N-methyl-6-(N-(3-(N-methylmethylsulfonamido)propyl)methylsulfonamido)furo[2,3-b]pyridine-3-carboxamide |
| 23.4 | 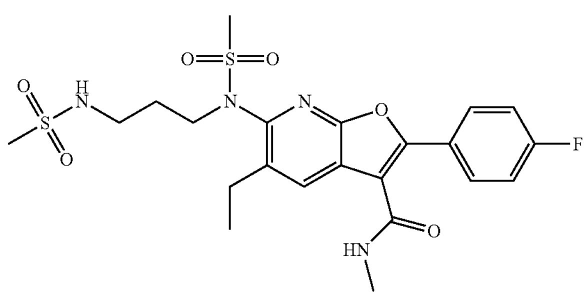 | 5-ethyl-2-(4-fluorophenyl)-N-methyl-6-(N-(3-(methylsulfonamido)propyl)methylsulfonamido)furo[2,3-b]pyridine-3-carboxamide |
| 23.5 | 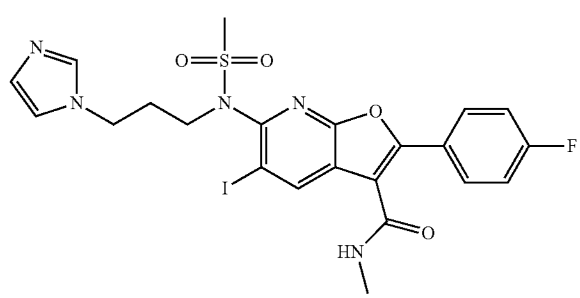 | 6-(N-(3-(1H-imidazol-1-yl)propyl)methylsulfonamido)-2-(4-fluorophenyl)-5-iodo-N-methylfuro[2,3-b]pyridine-3-carboxamide |
| 23.6 | 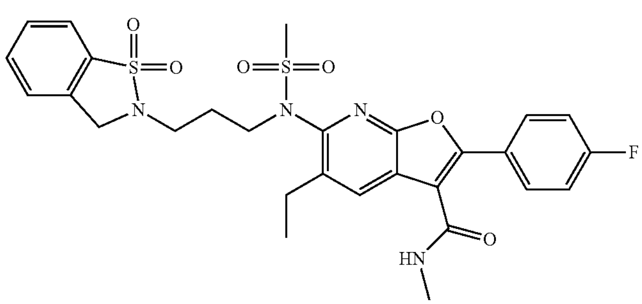 | 6-{[3-(1,1-Dioxo-1,3-dihydro-benzo[d]isothiazol-2-yl)-propyl]-methanesulfonyl-amino}-5-ethyl-2-(4-fluorophenyl)-furo[2,3-b]pyridine-3-carboxylic acid methylamide |

TABLE 7-continued

| Ex. # | Structure | Name |
|---|---|---|
| 23.6 | 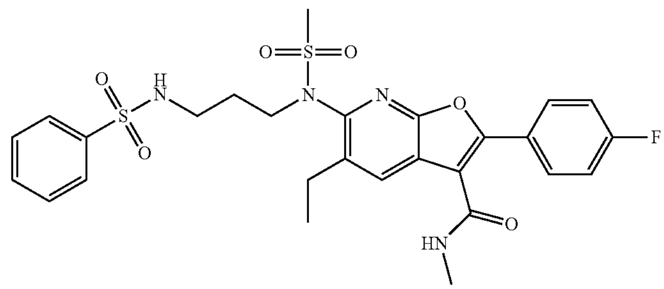 | 5-ethyl-2-(4-fluorophenyl)-N-methyl-6-(N-(3-(phenylsulfonamido)propyl)methylsulfonamido)furo[2,3-b]pyridine-3-carboxamide |
| 23.7 | 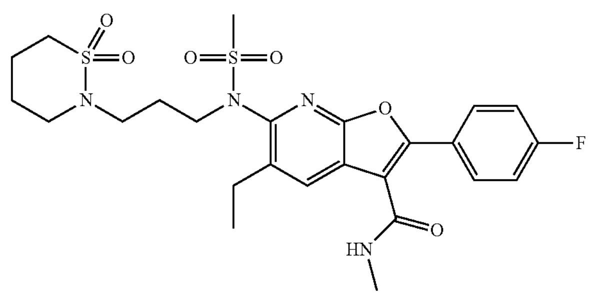 | 6-{[3-(1,1-Dioxo-[1,2]thiazinan-2-yl)-propyl]-methanesulfonyl-amino}-5-ethyl-2-(4-fluorophenyl)-furo[2,3-b]pyridine-3-carboxylic acid methylamide |
| 23.8 | 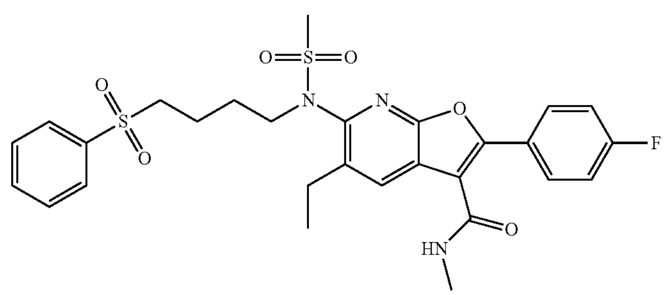 | 5-ethyl-2-(4-fluorophenyl)-N-methyl-6-(N-(4-(phenylsulfonyl)butyl)methylsulfonamido)furo[2,3-b]pyridine-3-carboxamide |
| 23.9 | 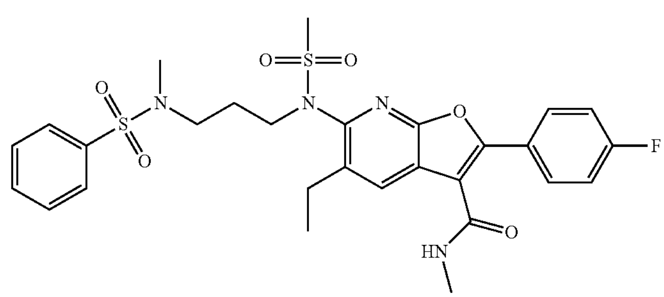 | 5-ethyl-2-(4-fluorophenyl)-N-methyl-6-(N-(3-(N-methylphenylsulfonamido)propyl)methylsulfonamido)furo[2,3-b]pyridine-3-carboxamide |
| 23.91 | 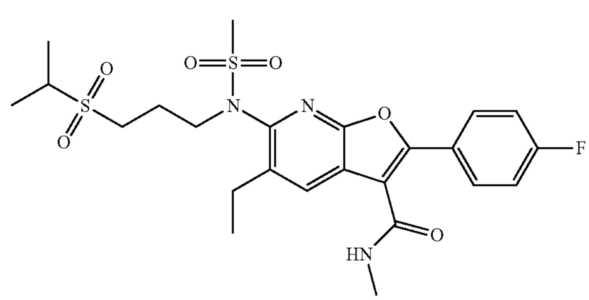 | 5-ethyl-2-(4-fluorophenyl)-6-(N-(3-(isopropylsulfonyl)propyl)methylsulfonamido)-N-methylfuro[2,3-b]pyridine-3-carboxamide |

TABLE 7-continued

| Ex. # | Structure | Name |
|---|---|---|
| 23.92 | 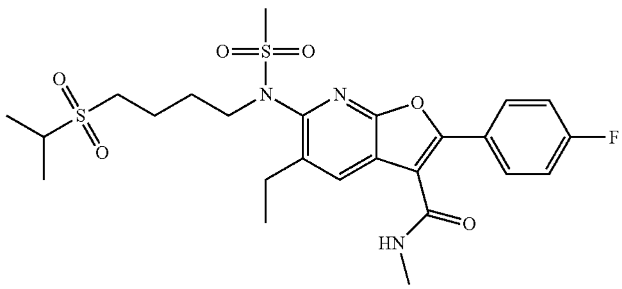 | 5-ethyl-2-(4-fluorophenyl)-6-(N-(4-(isopropylsulfonyl)butyl)methylsulfonamido)-N-methylfuro[2,3-b]pyridine-3-carboxamide |
| 23.93 | 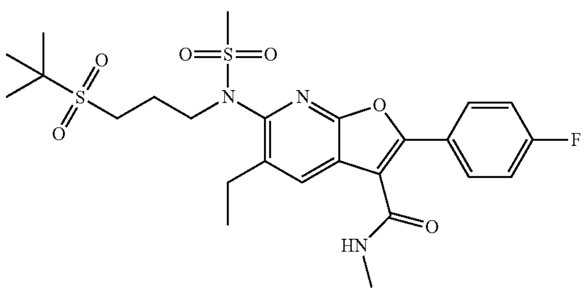 | 6-(N-(3-(tert-butylsulfonyl)propyl)methylsulfonamido)-5-ethyl-2-(4-fluorophenyl)-N-methylfuro[2,3-b]pyridine-3-carboxamide |
| 23.94 | 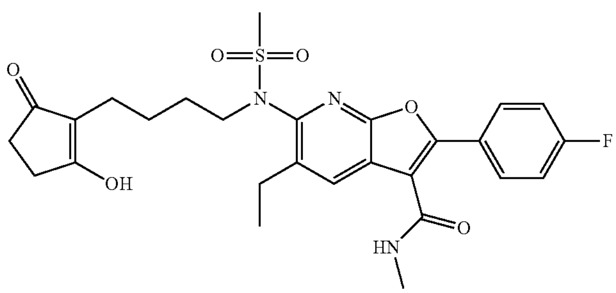 | 5-ethyl-2-(4-fluorophenyl)-6-(N-(4-(2-hydroxy-5-oxocyclopent-1-enyl)butyl)methylsulfonamido)-N-methylfuro[2,3-b]pyridine-3-carboxamide |
| 23.95 | 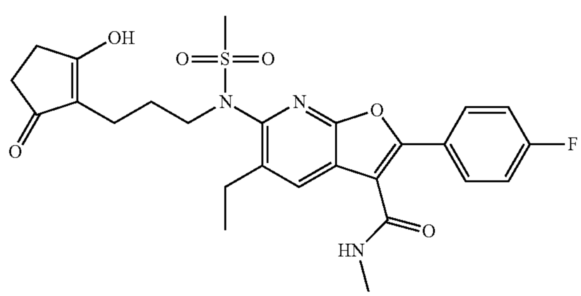 | 5-ethyl-2-(4-fluorophenyl)-6-(N-(3-(2-hydroxy-5-oxocyclopent-1-enyl)propyl)methylsulfonamido)-N-methylfuro[2,3-b]pyridine-3-carboxamide |
| 23.96 | 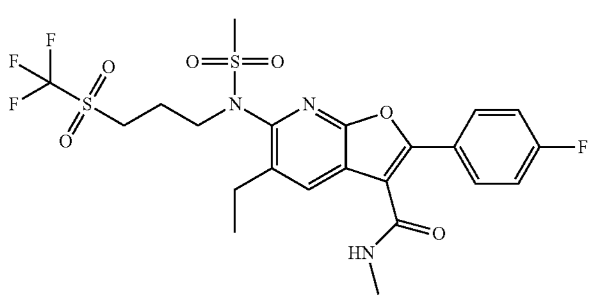 | 5-ethyl-2-(4-fluorophenyl)-N-methyl-6-(N-(3-(trifluoromethylsulfonyl)propyl)methylsulfonamido)furo[2,3-b]pyridine-3-carboxamide |

| Ex. # | Structure | Name |
|---|---|---|
| 23.97 | 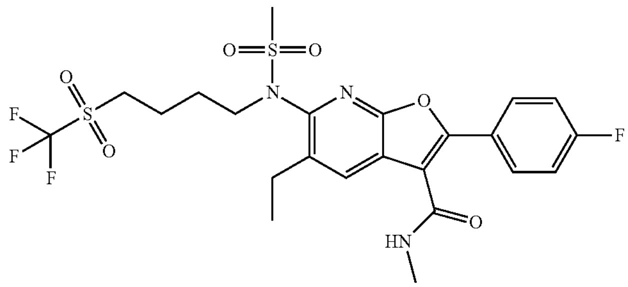 | 5-ethyl-2-(4-fluorophenyl)-N-methyl-6-(N-(4-(trifluoromethylsulfonyl)butyl)methylsulfonamido)furo[2,3-b]pyridine-3-carboxamide |
| 23.98 | 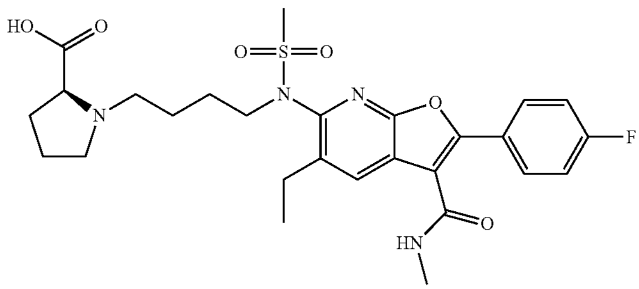 | (S)-1-(4-(N-(5-ethyl-2-(4-fluorophenyl)-3-(methylcarbamoyl)furo[2,3-b]pyridin-6-yl)methylsulfonamido)butyl)pyrrolidine-2-carboxylic acid |
| 23.99 | 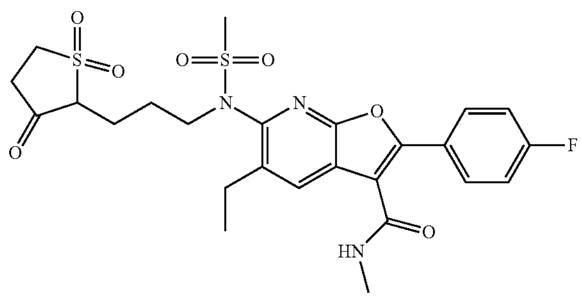 | 5-Ethyl-2-(4-fluoro-phenyl)-6-{methanesulfonyl-[3-(1,1,3-trioxo-tetrahydrothiophen-2-yl)-propyl]-amino}-furo[2,3-b]pyridine-3-carboxylic acid methylamide |
| 23.991 | 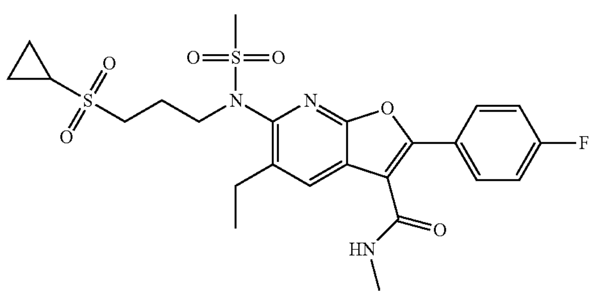 | 6-(N-(3-(cyclopropylsulfonyl)propyl)methylsulfonamido)-5-ethyl-2-(4-fluorophenyl)-N-methylfuro[2,3-b]pyridine-3-carboxamide |
| 23.992 | 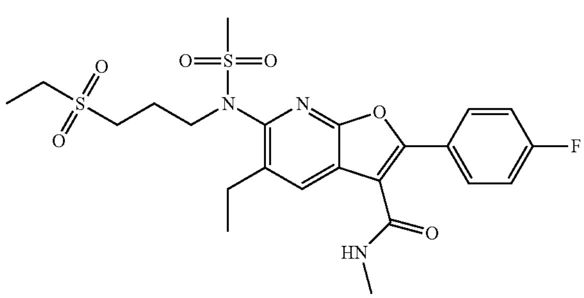 | 5-ethyl-6-(N-(3-(ethylsulfonyl)propyl)methylsulfonamido)-2-(4-fluorophenyl)-N-methylfuro[2,3-b]pyridine-3-carboxamide |

TABLE 7-continued

| Ex. # | Structure | Name |
|---|---|---|
| 23.993 | 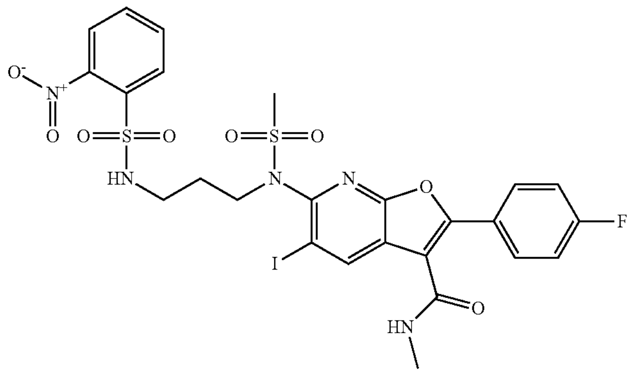 | 2-(4-fluorophenyl)-5-iodo-N-methyl-6-(N-(3-(2-nitrophenylsulfonamido)propyl)methylsulfonamido)furo[2,3-b]pyridine-3-carboxamide |
| 23.994 | 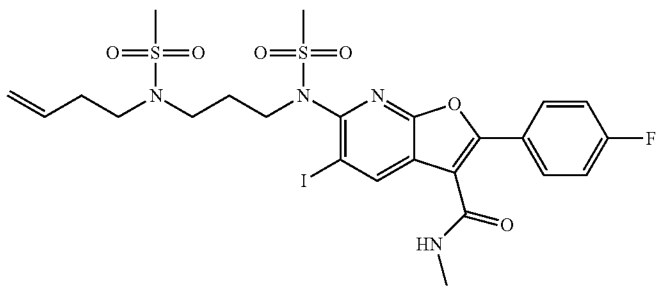 | 6-(N-(3-(N-(but-3-enyl)methylsulfonamido)propyl)methylsulfonamido)-2-(4-fluorophenyl)-5-iodo-N-methylfuro[2,3-b]pyridine-3-carboxamide |
| 23.995 | 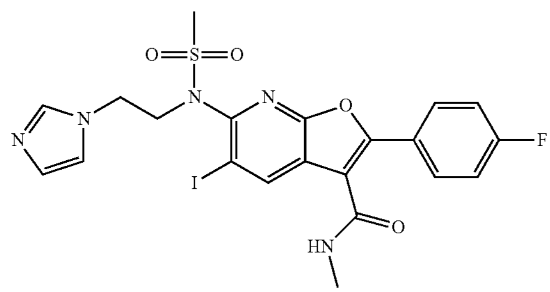 | 6-(N-(2-(1H-imidazol-1-yl)ethyl)methylsulfonamido)-2-(4-fluorophenyl)-5-iodo-N-methylfuro[2,3-b]pyridine-3-carboxamide |
| 23.996 | 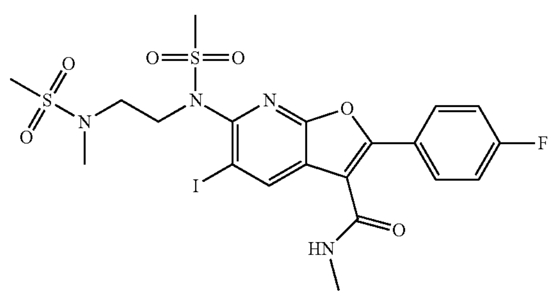 | 2-(4-fluorophenyl)-5-iodo-N-methyl-6-(N-(2-(N-methylmethylsulfonamido)ethyl)methylsulfonamido)furo[2,3-b]pyridine-3-carboxamide |
| 23.997 | 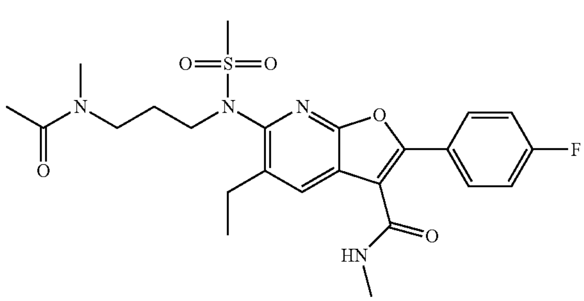 | 5-ethyl-2-(4-fluorophenyl)-N-methyl-6-(N-(3-(N-methylacetamido)propyl)methylsulfonamido)furo[2,3-b]pyridine-3-carboxamide |

TABLE 7-continued

| Ex. # | Structure | Name |
|---|---|---|
| 23.998 | 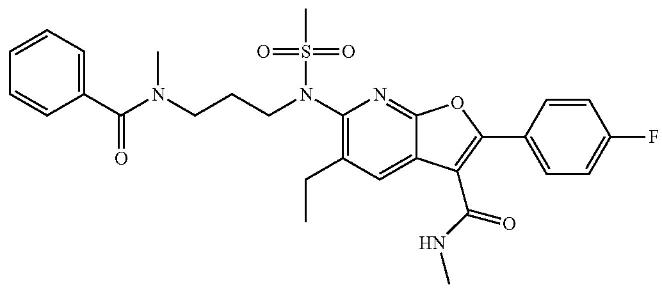 | 5-ethyl-2-(4-fluorophenyl)-N-methyl-6-(N-(3-(N-methylbenzamido)propyl)methylsulfonamido)furo[2,3-b]pyridine-3-carboxamide |
| 23.999 | 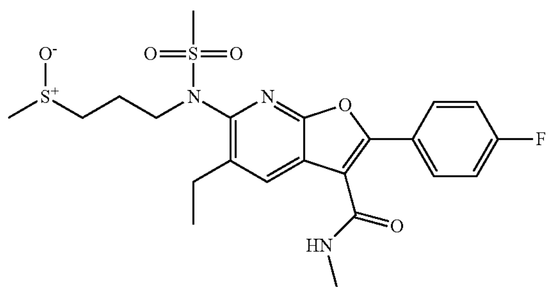 | 5-ethyl-2-(4-fluorophenyl)-N-methyl-6-(N-(3-(methylsulfinyl)propyl)methylsulfonamido)furo[2,3-b]pyridine-3-carboxamide |
| 23.9991 | 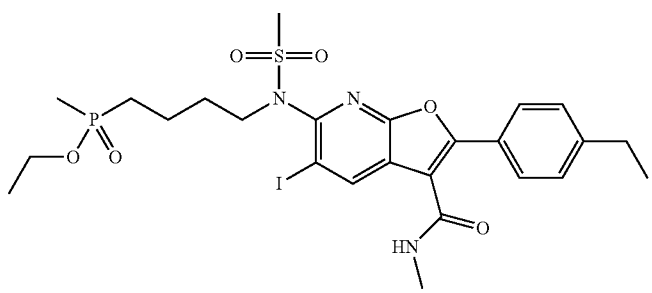 | ethyl 4-(N-(2-(4-ethylphenyl)-5-iodo-3-(methylcarbamoyl)furo[2,3-b]pyridin-6-yl)methylsulfonamido)butyl(methyl)phosphinate |
| 23.9992 | 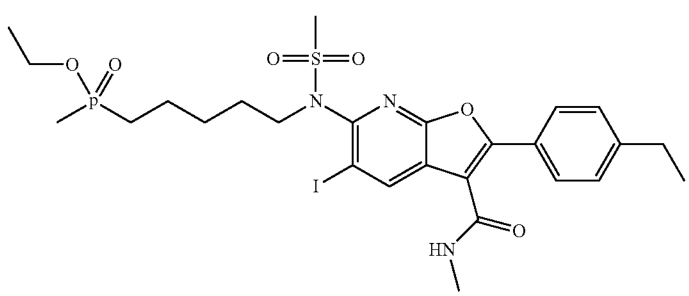 | ethyl 5-(N-(2-(4-ethylphenyl)-5-iodo-3-(methylcarbamoyl)furo[2,3-b]pyridin-6-yl)methylsulfonamido)pentyl(methyl)phosphinate |
| 23.9993 | 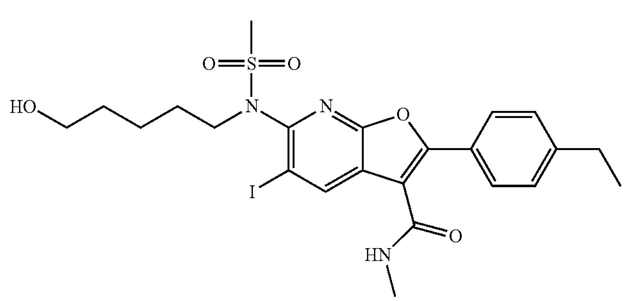 | 2-(4-ethylphenyl)-6-(N-(5-hydroxypentyl)methylsulfonamido)-5-iodo-N-methylfuro[2,3-b]pyridine-3-carboxamide |

| Ex. # | Structure | Name |
|---|---|---|
| 23.9994 | 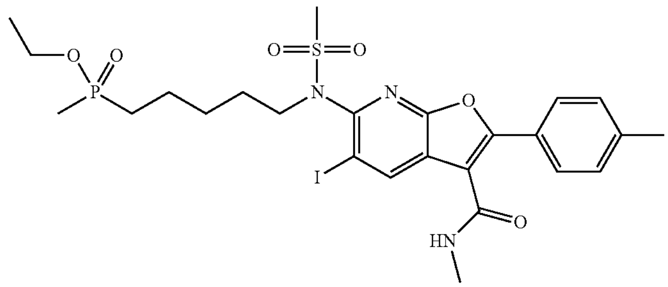 | ethyl 5-(N-(5-iodo-3-(methylcarbamoyl)-2-p-tolylfuro[2,3-b]pyridin-6-yl)methylsulfonamido)pentyl (methyl)phosphinate |
| 23.9995 | 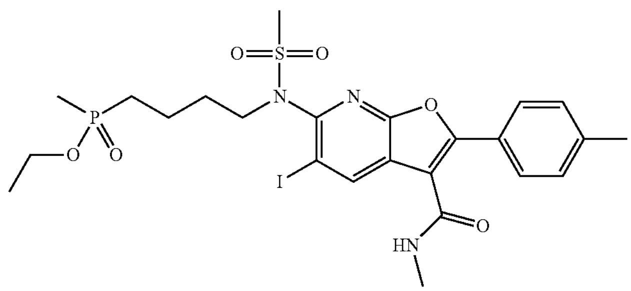 | ethyl 4-(N-(5-iodo-3-(methylcarbamoyl)-2-p-tolylfuro[2,3-b]pyridin-6-yl)methylsulfonamido)butyl (methyl)phosphinate |
| 23.9996 | 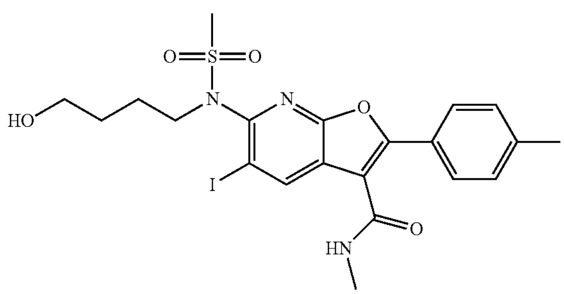 | 6-(N-(4-hydroxybutyl)methylsulfonamido)-5-iodo-N-methyl-2-p-tolylfuro[2,3-b]pyridine-3-carboxamide |
| 23.9997 | 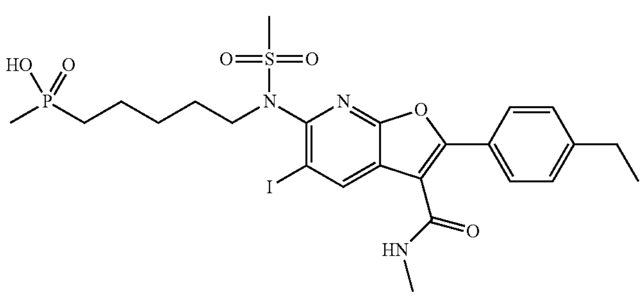 | 5-(N-(2-(4-ethylphenyl)-5-iodo-3-(methylcarbamoyl)furo[2,3-b]pyridin-6-yl)methylsulfonamido)pentyl (methyl)phosphinic acid |
| 23.9998 | 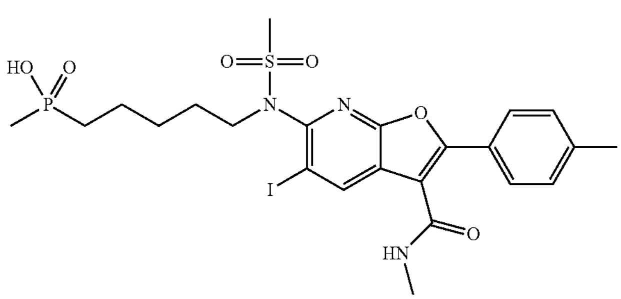 | 5-(N-(5-iodo-3-(methylcarbamoyl)-2-p-tolylfuro[2,3-b]pyridin-6-yl)methylsulfonamido)pentyl (methyl)phosphinic acid |

TABLE 7-continued

| Ex. # | Structure | Name |
|---|---|---|
| 23.9999 | 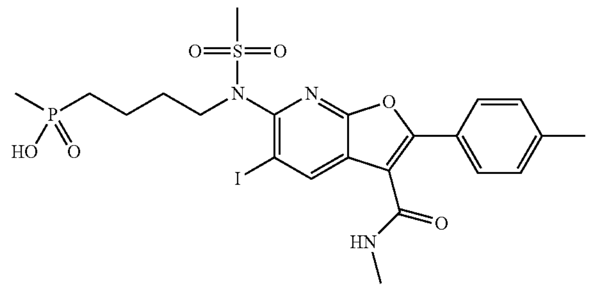 | 4-(N-(5-iodo-3-(methylcarbamoyl)-2-p-tolylfuro[2,3-b]pyridin-6-yl)methylsulfonamido)butyl(methyl)phosphinic acid |
| 23.99991 | 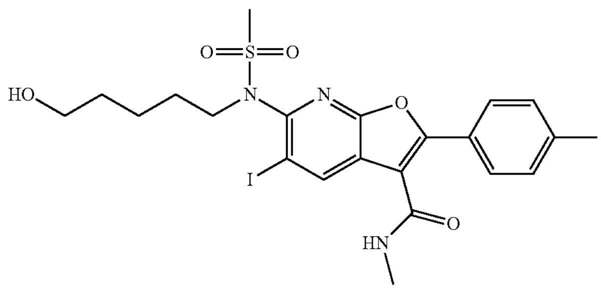 | 6-(N-(5-hydroxypentyl)methylsulfonamido)-5-iodo-N-methyl-2-p-tolylfuro[2,3-b]pyridine-3-carboxamide |
| 23.99992 | 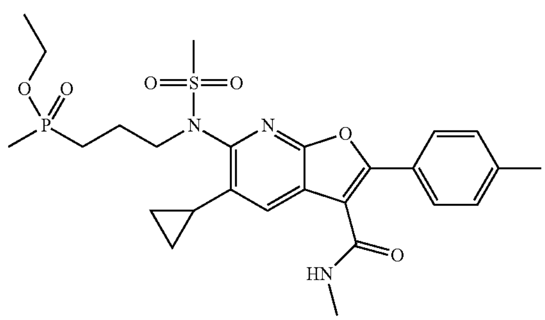 | ethyl 3-(N-(5-cyclopropyl-3-(methylcarbamoyl)-2-p-tolylfuro[2,3-b]pyridin-6-yl)methylsulfonamido)propyl(methyl)phosphinate |
| 23.99993 | 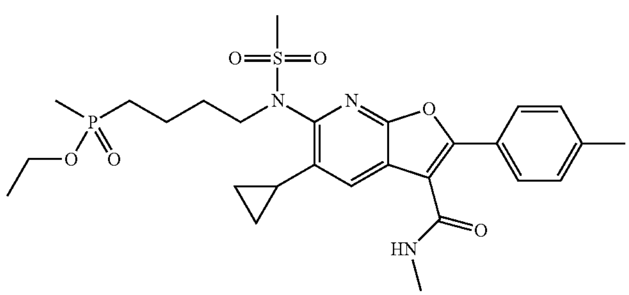 | ethyl 4-(N-(5-cyclopropyl-3-(methylcarbamoyl)-2-p-tolylfuro[2,3-b]pyridin-6-yl)methylsulfonamido)butyl(methyl)phosphinate |
| 23.99994 | 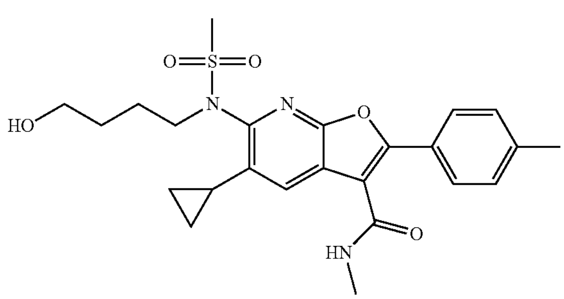 | 5-cyclopropyl-6-(N-(4-hydroxybutyl)methylsulfonamido)-N-methyl-2-p-tolylfuro[2,3-b]pyridine-3-carboxamide |

TABLE 7-continued

| Ex. # | Structure | Name |
|---|---|---|
| 23.99995 | 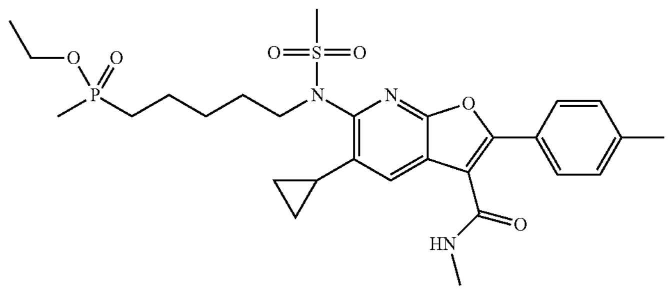 | ethyl 5-(N-(5-cyclopropyl-3-(methylcarbamoyl)-2-p-tolylfuro[2,3-b]pyridin-6-yl)methylsulfonamido)pentyl (methyl)phosphinate |
| 23.99996 | 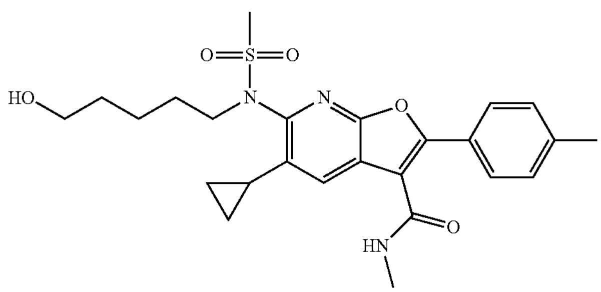 | 5-cyclopropyl-6-(N-(5-hydroxypentyl)methylsulfonamido)-N-methyl-2-p-tolylfuro[2,3-b]pyridine-3-carboxamide |
| 23.99997 | 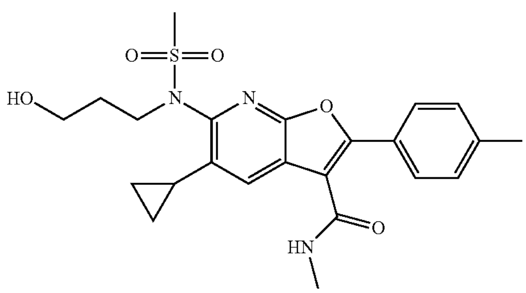 | 5-cyclopropyl-6-(N-(3-hydroxypropyl)methylsulfonamido)-N-methyl-2-p-tolylfuro[2,3-b]pyridine-3-carboxamide |
| 23.99998 | 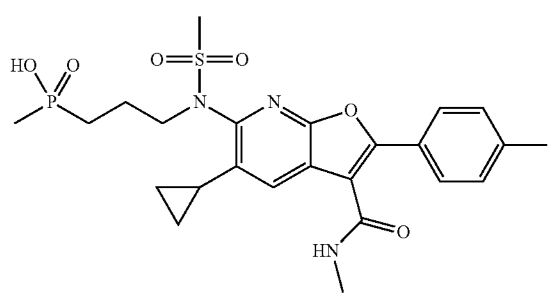 | 3-(N-(5-cyclopropyl-3-(methylcarbamoyl)-2-p-tolylfuro[2,3-b]pyridin-6-yl)methylsulfonamido)propyl (methyl)phosphinic acid |
| 23.99999 | 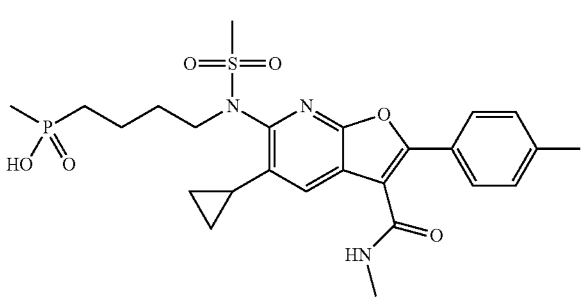 | 4-(N-(5-cyclopropyl-3-(methylcarbamoyl)-2-p-tolylfuro[2,3-b]pyridin-6-yl)methylsulfonamido)butyl (methyl)phosphinic acid |

TABLE 7-continued

| Ex. # | Structure | Name |
|---|---|---|
| 23.999991 | 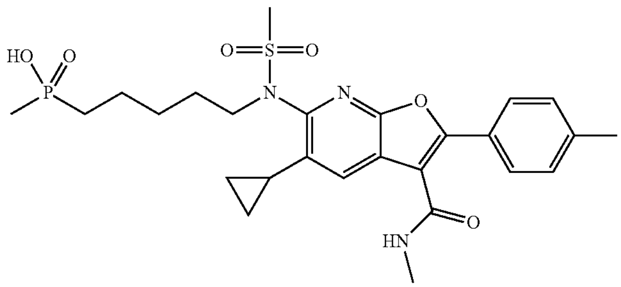 | 5-(N-(5-cyclopropyl-3-(methylcarbamoyl)-2-p-tolylfuro[2,3-b]pyridin-6-yl)methylsulfonamido)pentyl(methyl)phosphinic acid |
| 23.999992 | 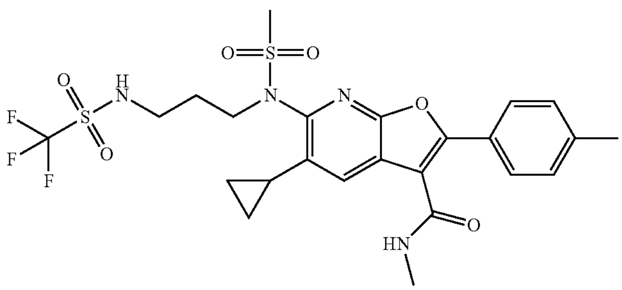 | 5-cyclopropyl-N-methyl-2-p-tolyl-6-(N-(3-(trifluoromethylsulfonamido)propyl)methylsulfonamido)furo[2,3-b]pyridine-3-carboxamide |
| 23.999993 | 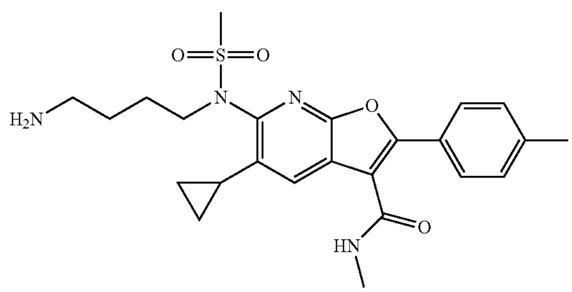 | 6-(N-(4-aminobutyl)methylsulfonamido)-5-cyclopropyl-N-methyl-2-p-tolylfuro[2,3-b]pyridine-3-carboxamide |
| 23.999994 | 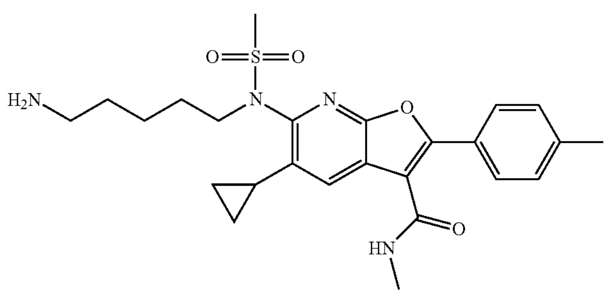 | 6-(N-(5-aminopentyl)methylsulfonamido)-5-cyclopropyl-N-methyl-2-p-tolylfuro[2,3-b]pyridine-3-carboxamide |
| 23.999995 | 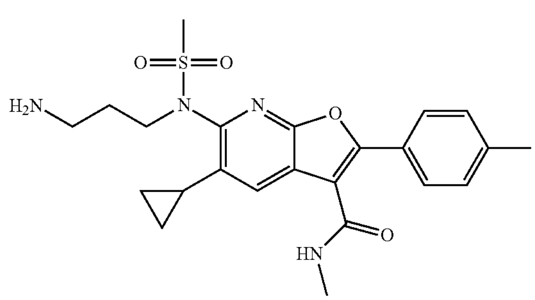 | 6-(N-(3-aminopropyl)methylsulfonamido)-5-cyclopropyl-N-methyl-2-p-tolylfuro[2,3-b]pyridine-3-carboxamide |

TABLE 7-continued

| Ex. # | Structure | Name |
|---|---|---|
| 23.999996 | 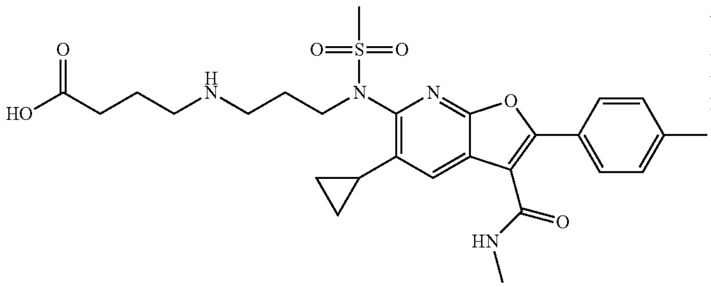 | 4-(3-(N-(5-cyclopropyl-3-(methylcarbamoyl)-2-p-tolylfuro[2,3-b]pyridin-6-yl)methylsulfonamido)propylamino)butanoic acid |
| 23.999997 | 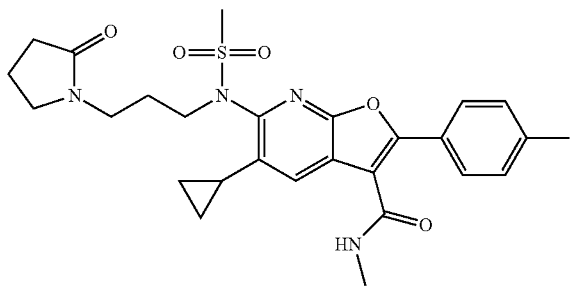 | 5-cyclopropyl-N-methyl-6-(N-(3-(2-oxopyrrolidin-1-yl)propyl)methylsulfonamido)-2-p-tolylfuro[2,3-b]pyridine-3-carboxamide |
| 23.999998 | 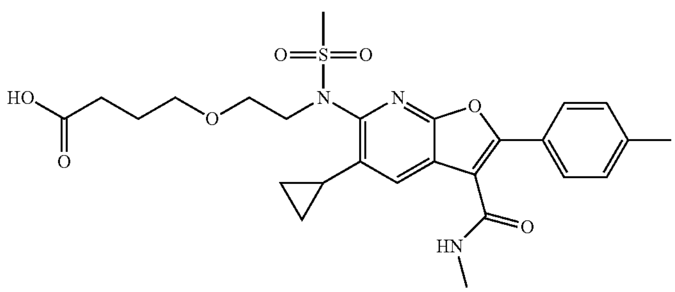 | 4-(2-(N-(5-cyclopropyl-3-(methylcarbamoyl)-2-p-tolylfuro[2,3-b]pyridin-6-yl)methylsulfonamido)ethoxy)butanoic acid |
| 23.999999 | 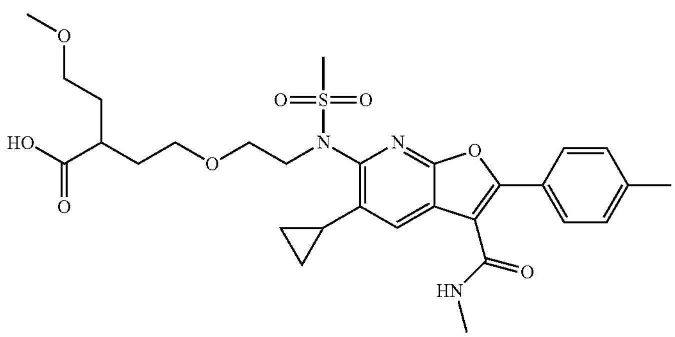 | 4-{2-[(5-Cyclopropyl-3-methylcarbamoyl-2-p-tolyl-furo[2,3-b]pyridin-6-yl)-methanesulfonyl-amino]-ethoxy}-2-(2-methoxy-ethyl)-butyric acid |

In Example 23.2, the sulfinate displacement gives a mixture of sulfone and sulfinic ester. The sulfinic ester is hydrolyzed to give the compound of example 23.2. Examples 23.997 and 23.998 are prepared by methylamine displacement of the alkyl bromide followed by acylation with acetic anhydride or benzoyl chloride. Example 23.999 is obtained using sodium thiomethoxide in the displacement of the alkylbromide, followed by partial oxidation with hydrogen peroxide. Example 23.999996 was obtained using 4-Aminobutyric acid ethyl ester in the displacement followed by ester hydrolysis with NaOH. Example 23.999997 was obtained as a byproduct in the synthesis of example 23.999996. Example 23.999998 was obtained using dimethylmalonate in the displacement, followed by hydrolysis using NaOH, decarboxylation at 150° C. in MeOH and hydrolysis using NaOH.

Example 23.999999 was obtained using dimethylmalonate in the displacement, alkylation of the product with 1-Bromo-2-methoxy-ethane, hydrolysis with NaOH, decarboxylation at 120° C. in MeOH and hydrolysis with NaOH.

Example 24

5-[(5-Cyclopropyl-3-methylcarbamoyl-2-p-tolyl-furo[2,3-b]pyridin-6-yl)-methanesulfonyl-amino]-2,2-dimethyl-pentanoic acid 5-iodo-N-methyl-6-(methylsulfonamido)-2-p-tolylfuro[2,3-b]pyridine-3-carboxamide is made in analogy to Example 1 2-(4-Fluoro-phenyl)-5-iodo-6-methanesulfonylamino-furo[2,3-b]pyridine-3-carboxylic acid methylamide by replacing 4-Fluorophenylacetylene with 4-methylphenylacetylene.

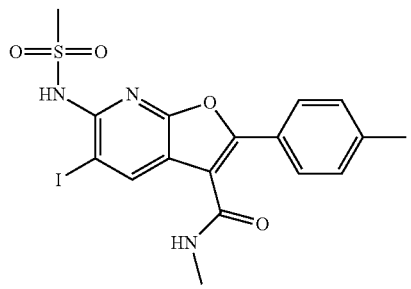 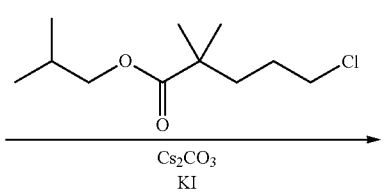

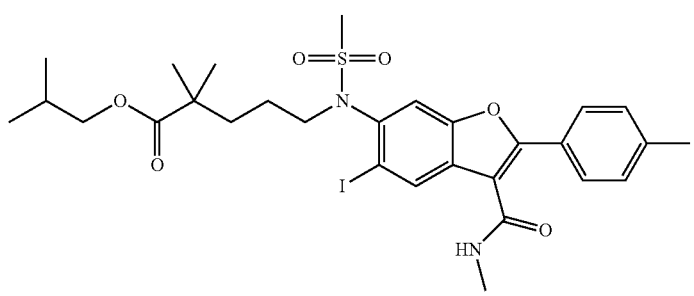

5-iodo-N-methyl-6-(methylsulfonamido)-2-p-tolylfuro[2,3-b]pyridine-3-carboxamide (136 mg, 0.28 mmol) and isobutyl 5-chloro-2,2-dimethylpentanoate (124 mg, 0.56 mmol) are dissolved in DMA (1 mL) and Cs$_2$CO$_3$ (183 mg, 0.56 mmol) and NaI (42 mg, 0.28 mmol) added. The mixture is microwaved at 150° C. for 20 min then diluted with water and extracted with EtOAc (3×20 mL). The organic is then washed with Brine (10 mL) and dried over Na$_2$SO$_4$ and concentrated. HPLC purification gives 70 mg (38% yield) of alkylated product isobutyl 5-(N-(5-iodo-3-(methylcarbamoyl)-2-p-tolylfuro[2,3-b]pyridin-6-yl)methylsulfonamido)-2,2-dimethylpentanoate. MS-ES [M+H]$^+$=670.2. This compound is used directly in the next step.

Isobutyl 5-(N-(5-iodo-3-(methylcarbamoyl)-2-p-tolylfuro[2,3-b]pyridin-6-yl)methylsulfonamido)-2,2-dimethylpentanoate (70 mg, 0.086 mmol) is dissolved in toluene (6 mL) and a premixed solution of potassium cyclopropyltrifluoroborate (155 mg, 1.045 mmol) and potassium carbonate (2M, 0.62 mL, 1.255 mmol) is added followed by Pd(Ph$_3$)$_4$ (3.6 mg, 3.14 umol). The mixture is degassed for 10 min then heated at 116° C. for 20 min in the microwave. The reaction mixture is then filtered through celite and aqueous extracted with EtOAc (3×15 mL). The organic is then washed with Brine (10 mL) and dried over Na$_2$SO$_4$ and concentrated. HPLC purification gives 50 mg (82% yield) of isobutyl 5-(N-(5-cyclopropyl-3-(methylcarbamoyl)-2-p-tolylfuro[2,3-b]pyridin-6-yl)methylsulfonamido)-2,2-dimethylpentanoate. MS-ES [M+H]$^+$=584.3. This compound is used directly in the next step.

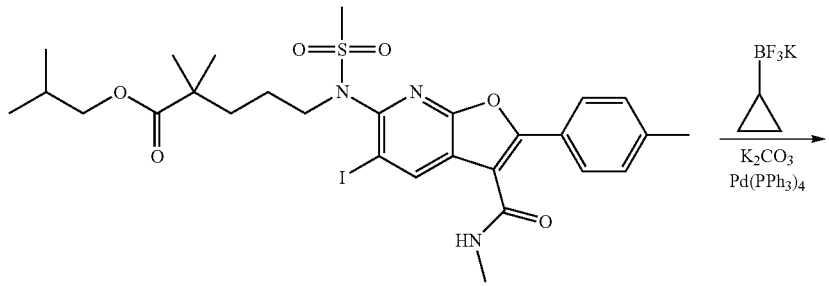

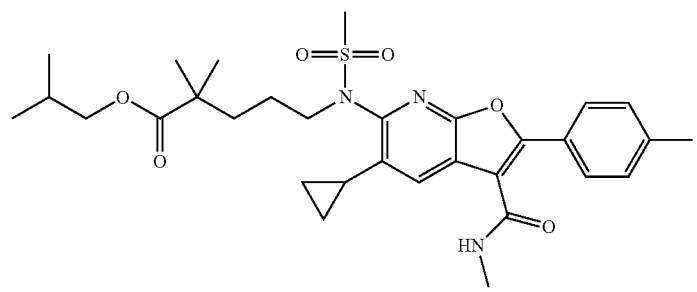

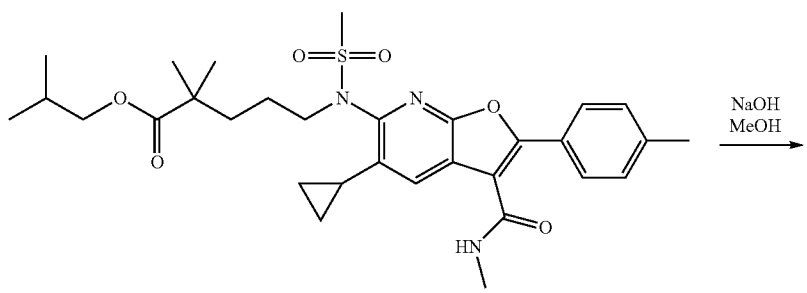

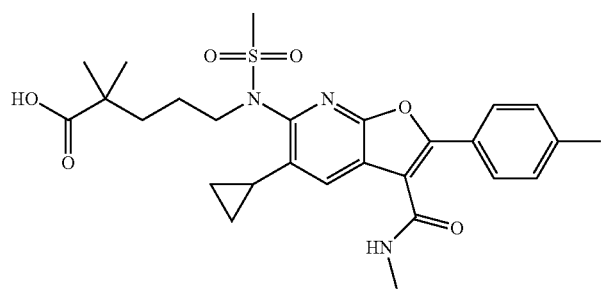

To isobutyl 5-(N-(5-cyclopropyl-3-(methylcarbamoyl)-2-p-tolylfuro[2,3-b]pyridin-6-yl)methylsulfonamido)-2,2-dimethylpentanoate 3 (50 mg, 0.086 mmol) in MeOH (2 mL) is added NaOH (3 mL, 2M, 6.00 mmol) and the reaction is heated at 60° C. overnight. The MeOH is removed by evaporation, and the solution is acidified to pH 5. The solid is collected by filtration then purified by HPLC to give 30 mg (64% yield) of 5-[(5-Cyclopropyl-3-methylcarbamoyl-2-p-tolyl-furo[2,3-b]pyridin-6-yl)-methanesulfonyl-amino]-2,2-dimethyl-pentanoic acid $^1$H-NMR (DMSO-d$^6$, 400 MHz) δ 12.05 (m, 1H), 8.49 (m, 1H), 7.74 (d, 2H, J=8 Hz), 7.55 (s, 1H), 7.36 (d, 2H, J=8 Hz), 3.65 (m, 2H), 3.16 (s, 3H), 2.83 (d, 3H, J=8 Hz), 2.43 (m, 1H), 2.38 (s, 3H), 1.48 (s, 2H), 1.38 (s, 2H), 1.04 (m, 2H), 1.00 (s, 6H), 0.7 (bm, 2H). MS-ES [M+H]$^+$=528.21.

The acid (28 mg, 0.055 mmol) is then dissolved in MeOH:CH$_3$CN:H$_2$O (3 mL, 1:1:1) and KHCO$_3$ (0.5M, 0.11 mL, 0.55 mmol) is added and the sample lyophilized overnight to give the potassium salt (30 mg).

Example 24.01

2-(4-Fluoro-phenyl)-6-[methanesulfonyl-(3-methanesulfonyl-propyl)-amino]-furo[2,3-b]pyridine-3-carboxylic acid methylamide A. 2-(4-Fluoro-phenyl)-5-iodo-6-[methanesulfonyl-(3-methanesulfonyl-propyl)-amino]-furo[2,3-b]pyridine-3-carboxylic acid methylamide

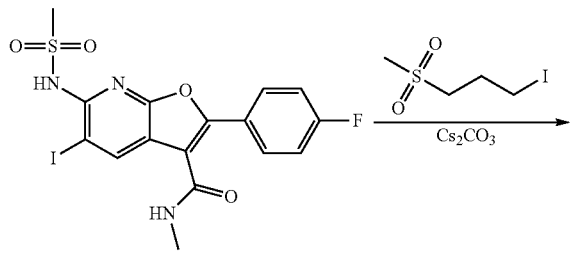

-continued

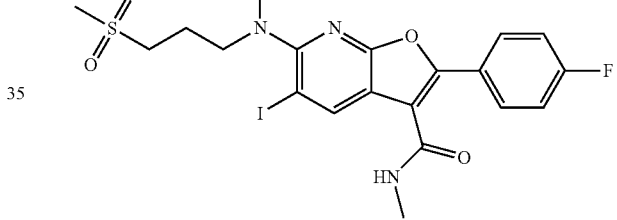

2-(4-Fluoro-phenyl)-5-iodo-6-methanesulfonylamino-furo[2,3-b]pyridine-3-carboxylic acid methylamide (162 mg, 0.331 mmol), 1-iodo-3-(methylsulfonyl)propane (82 mg, 0.331 mmol) and cesium carbonate (119 mg, 0.364 mmol) in DMF (1656 μL) are heated for 20 min at 150° C. by microwave. 3:1 Product/starting material. An additional 45 mg of alky iodide are added and 60 mg of cesium carbonate and heated for 20 min at 150° C. by microwave. LCMS indicates complete consumption of starting material. Acetonitrile and water are added and the mixture is filtered with 0.45μ PTFE filter. Purification is achieved by reverse phase HPLC with a C8 column with 20-50% ACN//H$_2$O (0.1% NH4OH) over 20 min. Elutes at 13-15 minutes to give the title compound (107 mg, 53%). MS (ESI) m/z 610.0 (M+1). Retention time=1.40 min, Method A.

B. 5-cyclopropyl-2-(4-fluorophenyl)-N-methyl-6-(N-(3-(methylsulfonyl)propyl)methylsulfonamidoguro[2,3-b]pyridine-3-carboxamide

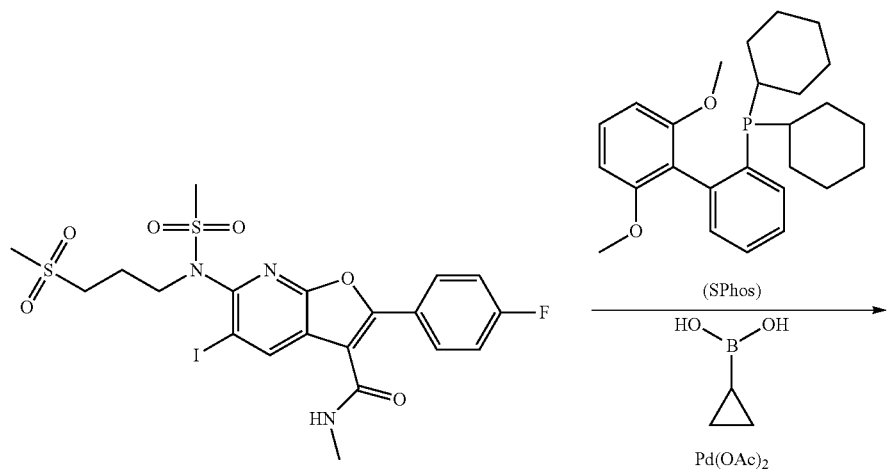

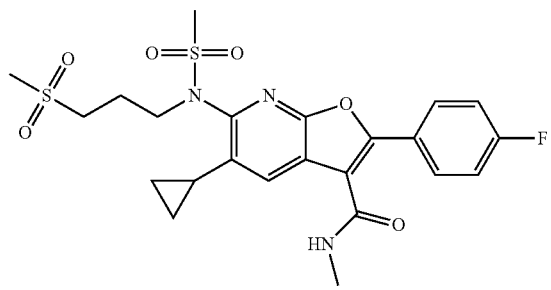

To 2-(4-Fluoro-phenyl)-5-iodo-6-[methanesulfonyl-(3-methanesulfonyl-propyl)-amino]-furo[2,3b]pyridine-3-carboxylic acid methylamide (100 mg, 0.164 mmol), in 200 μL toluene is added a premixed solution of S-Phos (6.74 mg, 0.016 mmol) and palladium(II) acetate (1.842 mg, 8.20 μmol) in 200 μL toluene. A premixed slurry of cyclopropylboronic acid (282 mg, 3.28 mmol) and SODIUM CARBONATE (472 μL, 0.943 mmol) are added in 420 μL toluene. The reaction mixture is heated under microwave irradiation at 120° C. for 20 minutes. 3 mL water is added and the mixture is extracted 3× with EtOAc and concentrated in vaccuo to give 200 mg crude product which is redissolved in 3 mL DMF and filtered with 0.45μ ptfe filter. Purification is achieved by reverse phase HPLC with a C18 column with ACN/water (0.1% NH$_4$OH) 20-50% over 15 min. elutes at 7.5 min. 60 mg (70%) MS (ESI) m/z 524.0 (M+1). Retention time=1.30 min, Method A. $^1$H NMR (400 MHz, CDCl$_3$) δ ppm 0.77-0.91 (br s, 1H) 1.15 (d, 1H) 1.54 (s, 1H) 2.05 (t, 2H) 2.51-2.60 (m, 1H) 2.91 (s, 3H) 3.00 (d, 3H) 3.12 (s, 3H) 3.22 (t, 2H) 3.50 (d, 1H) 3.97 (t, 2H) 5.75 (br s, 1H) 7.23 (t, 2H) 7.76 (s, 1H) 7.90 (t, 2H)

Example 25.1

5-(N-(5-cyclopropyl-3-(methylcarbamoyl)-2-p-tolyl-furo[2,3-b]pyridin-6-yl)methylsulfonamido)pentanoic acid A. 6-amino-5-iodo-2-p-tolylfuro[2,3-b]pyridine-3-carboxylic acid

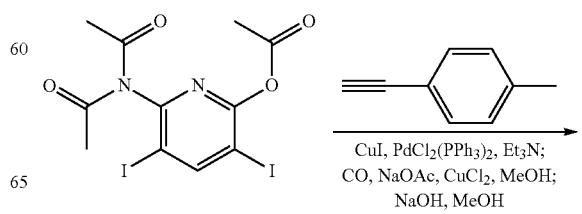

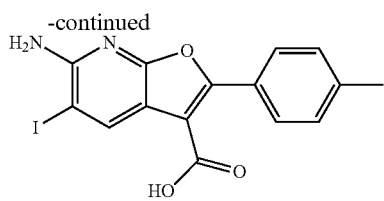

6-(N-acetylacetamido)-3,5-diiodopyridin-2-yl acetate (600 mg, 1.23 mmol) was dissolved in THF (40 mL) and copper(I) iodide (7.02 mg, 0.037 mmol) and bis(triphenylphosphine)palladium(II) chloride (25.9 mg, 0.037 mmol) were added. The mixture was bubbled under N2 at 0° C. for 5 min. Triethylamine (0.514 ml, 3.69 mmol) was added and the mixture was bubbled with N2 at 0° C. for 3 min. 1-ethynyl-4-methylbenzene (143 mg, 1.229 mmol) in THF (2 ml) was added and the mixture was stirred at 0° C. for 4 hr. Then mixture was warmed up to 23° C. and stirred for 16 hrs., then cooled to 0° C. Sodium acetate (403 mg, 4.92 mmol) and copper(II) chloride (496 mg, 3.69 mmol) were added, and 30 mL of methanol was added. The flask was purged with CO from a balloon and stirred at 23° C. overnight. The volatiles were removed under vacuum. 40 mL of 1.0N HCl and 100 mL of CH$_2$Cl$_2$ were added. The mixture was stirred at 23° C. for 30 min. The mixture was filtered and solid washed with 60 mL of CH$_2$Cl$_2$. The filtrates were combined and separated. The organic layer was dried over sodium sulfate, filtered and concentrated. The 440 mg of solid crude mixture including methyl 6-(N-acetylacetamido)-5-iodo-2-p-tolylfuro[2,3-b]pyridine-3-carboxylate and methyl 6-acetamido-5-iodo-2-p-tolylfuro[2,3-b]pyridine-3-carboxylate was dissolved in MeOH and stirred with SODIUM HYDROXIDE (8 ml, 8.00 mmol) at 60° C. for 2 hrs. The MeOH was removed under vacuum and 30 ml water was added. The aqueous was extracted with ethyl ether to remove neutral impurities. The aqueous layer was acidified to pH 4-5 and precipitate was filtered and washed w/water and dried under vacuum to afford 300 mg (0.76 mmol, 62%) 6-amino-5-iodo-2-p-tolylfuro[2,3-b]pyridine-3-carboxylic acid. MS-ES [M+H]$^+$=395.0; LC-RT=1.14 min, Method A

B. 5-iodo-N-methyl-6-(methylsulfonamido)-2-p-tolylfuro[2,3-b]pyridine-3-carboxamide

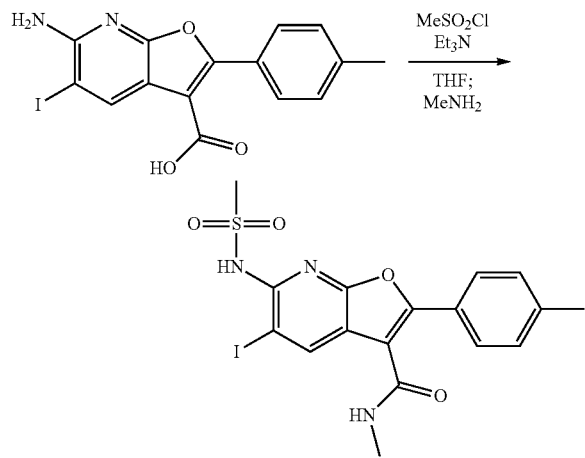

To 6-amino-5-iodo-2-p-tolylfuro[2,3-b]pyridine-3-carboxylic acid (2.5 g, 6.34 mmol) in THF at 0° C. was added triethylamine (9.72 ml, 69.8 mmol), and the mixture was stirred at 0° C. for 10 min. Methanesulfonyl chloride (4.94 ml, 63.4 mmol) was added and stirred at 23° C. for 20 hr. At this time, 2M methanamine in THF (31.7 ml, 63.4 mmol) was added and stirred at 23° C. for 60 min. The volatiles were removed under vacuum. 60 mL of water was added. The aqueous phase was acidified to PH<5 and extracted EtOAc, dried over sodium sulfate, filtered and concentrated to dryness. The solid was stirred in MeOH 50 mL and 15 mL of 1.0N NaOH at 23° C. for 30 min. The MeOH was removed and the mixture was acidified. The solid was filtered and washed with water and dried to give 2.06 g of solid (4.24 mmol, 67%, 90% pure) 5-iodo-N-methyl-6-(methylsulfonamido)-2-p-tolylfuro[2,3-b]pyridine-3-carboxamide.

C. methyl 5-(N-(5-iodo-3-(methylcarbamoyl)-2-p-tolylfuro[2,3-b]pyridin-6-yl)methylsulfonamido)pentanoate

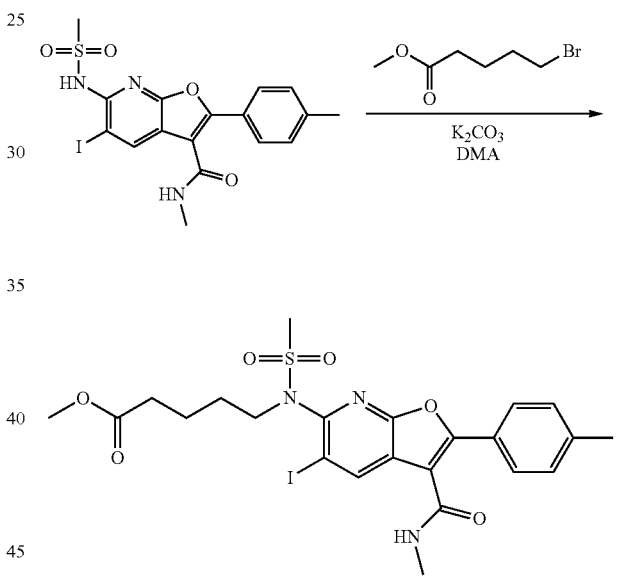

5-iodo-N-methyl-6-(methylsulfonamido)-2-p-tolylfuro[2,3-b]pyridine-3-carboxamide (100 mg, 0.206 mmol) was dissolved in dimethylacetamide (10 mL) and K2CO3 (39.9 mg, 0.288 mmol) was added then followed by methyl 5-bromopentanoate (0.059 mL, 0.412 mmol). The mixture was heated at 150° C. in the microwave for 20 min. Conversion approx 75% by LCMS, after which addition of additional methyl 5-bromopentanoate (3 eqs) and K2CO3 (2 eqs) did not result in additional conversion. Filtration and purification by HPLC (TFA/CH3CN/H$_2$O) afforded 57 mg (0.095 mmol, 46%) methyl 5-(N-(5-iodo-3-(methylcarbamoyl)-2-p-tolylfuro[2,3-b]pyridin-6-yl)methylsulfonamido)pentanoate MS-ES [M+H]$^+$=599.8, LC RT=1.61 min, Method A.

D. methyl 5-(N-(5-cyclopropyl-3-(methylcarbamoyl)-2-p-tolylfuro[2,3-b]pyridin-6-yl)methylsulfonamido)pentanoate

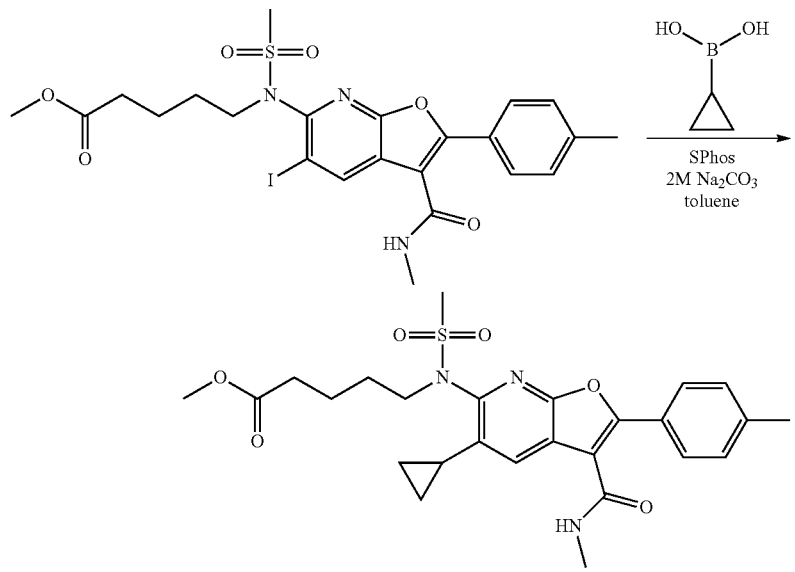

1. In a vial was added 1 mL Toluene and palladium acetate (0.5 mg, 0.002 mmol) and Dicyclohexyl-(2',6'-dimethoxy-biphenyl-2-yl)-phosphane (S-Phos 2.4 mg, 0.0058 mmol). The mixture stirred for 5 min.
2. In a second vial was 0.5 mL toluene and then the cylopropylboronic acid (50 mg, 0.584 mmol) and 2M aqueous sodium carbonate (0.584 mL, 1.17 mmol) and the mixture stirred for 5 min.

The methyl 5-(N-(5-iodo-3-(methylcarbamoyl)-2-p-tolyl-furo[2,3-b]pyridin-6-yl)methylsulfonamido)pentanoate (35 mg, 0.058 mmol) was suspended/dissolved in 1 mL toluene and added to 2. 1 was added to 2. The biphasic mixture was degassed for 5 min, then microwaved at 122° C. for 10 min. The mixture was then heated again at the same temperature for another 2×10 min. HPLC purification yielded methyl 5-(N-(5-cyclopropyl-3-(methylcarbamoyl)-2-p-tolylfuro[2,3-b]pyridin-6-yl)methylsulfonamido)pentanoate (20 mg, 0.039 mmol, 67%) MS-ES $[M+H]^+$=513.9, LC RT=1.60 min, Method A.

E. 5-(N-(5-cyclopropyl-3-(methylcarbamoyl)-2-p-tolylfuro[2,3-b]pyridin-6-yl)methylsulfonamido) pentanoic acid

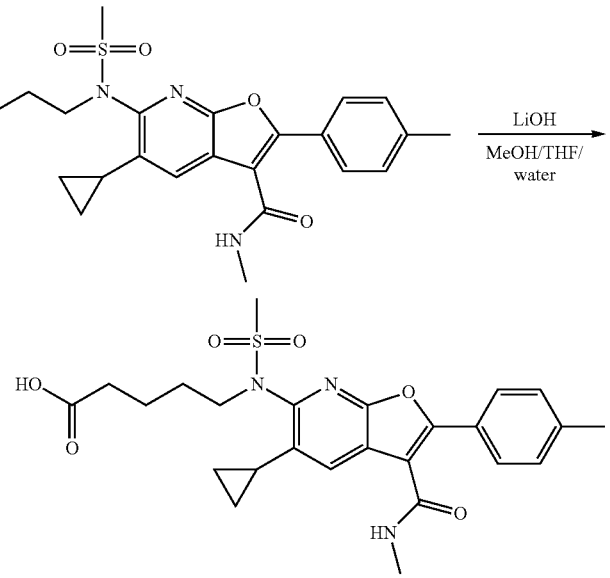

Methyl 5-(N-(5-cyclopropyl-3-(methylcarbamoyl)-2-p-tolylfuro[2,3-b]pyridin-6-yl)methylsulfonamido)pentanoate (17 mg, 0.033 mmol) was dissolved in MeOH/THF/H2O (2.33 mL, 3:1:3) and LiOH (0.13 mL, 0.13 mmol, 1M solution) was added and the mixture stirred at 23° C. overnight. The reaction was then neutralized by addition of NH$_4$Cl and the aqueous extracted with EtOAc (3×10 mL) then washed with brine and dried over Na$_2$SO$_4$ and evaporated to dryness. HPLC (Basic method/NH4OH/CH3CN/H2O) yielded 5-(N-(5-cyclopropyl-3-(methylcarbamoyl)-2-p-tolylfuro[2,3-b]pyridin-6-yl)methylsulfonamido)pentanoic acid (5 mg, 0.01 mmol, 30%).

F. 5-(N-(5-cyclopropyl-3-(methylcarbamoyl)-2-p-tolylfuro[2,3-b]pyridin-6-yl)methylsulfonamido) pentanoic acid arginine salt monohydrate 5-(N-(5-cyclopropyl-3-(methylcarbamoyl)-2-p-tolylfuro[2,3-b]pyridin-6-yl)methylsulfonamido)pentanoic acid (2.5 g) and L-arginine (0.871 g, 1 equiv) was suspended in 75 mL acetone. To the stirred mixture at room temperature was added 5 mL of water dropwise over 20 min. The mixture was stirred at room temperature over the weekend. The material was filtered and washed with 25 mL acetone. It was dried at 45° C. for 16 hrs under vacuum to obtain 3.4 g of crystalline monohydrate salt. Melting point: 214° C., elemental analysis: 53.99%; C, 6.55%; H, 14.88%; N, 4.51%; S.

The compounds in Table 8 were prepared in analogy to Example 24, 24.01 and 25.1.

TABLE 8

| Ex. | Structure | Name |
|---|---|---|
| 24.1 | 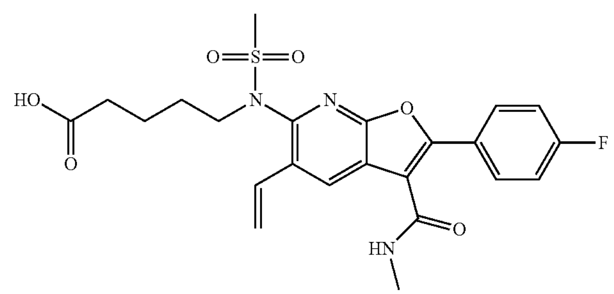 | 5-(N-(2-(4-fluorophenyl)-3-(methylcarbamoyl)-5-vinylfuro[2,3-b]pyridin-6-yl)methylsulfonamido)pentanoic acid |
| 24.2 | 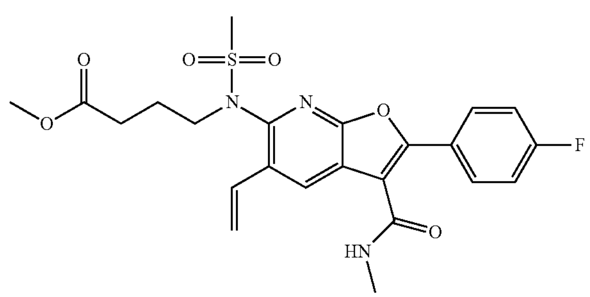 | methyl 4-(N-(2-(4-fluorophenyl)-3-(methylcarbamoyl)-5-vinylfuro[2,3-b]pyridin-6-yl)methylsulfonamido)butanoate |
| 24.3 | 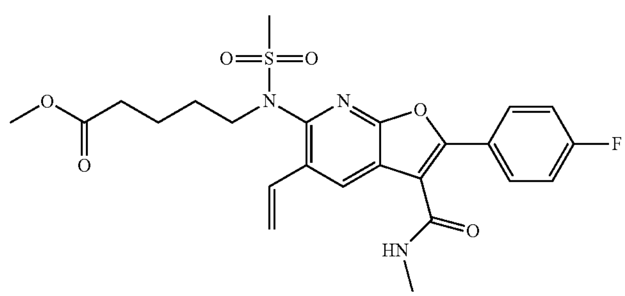 | methyl 5-(N-(2-(4-fluorophenyl)-3-(methylcarbamoyl)-5-vinylfuro[2,3-b]pyridin-6-yl)methylsulfonamido)pentanoate |
| 24.4 | 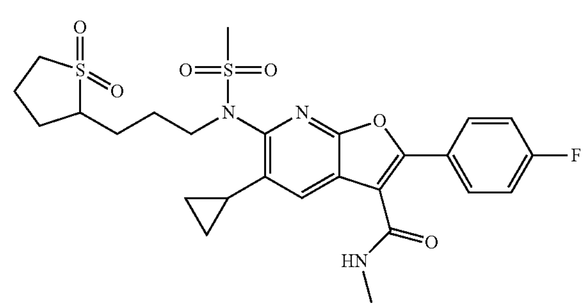 | 5-Cyclopropyl-6-{[3-1,1-dioxo-tetrahydrothiophen-2-yl)-propyl]-methanesulfonyl-amino}-2-(4-fluoro-phenyl)-furo[2,3-b]pyridine-3-carboxylic acid methylamide |

TABLE 8-continued

| Ex. | Structure | Name |
|---|---|---|
| 24.5 | 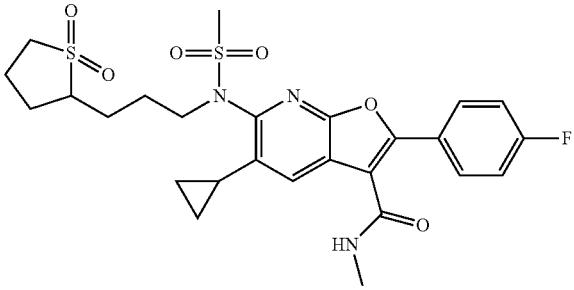 enantiomer 1 | 5-Cyclopropyl-6-{[3-(1,1-dioxo-tetrahydrothiophen-2-yl)-propyl]-methanesulfonyl-amino}-2-(4-fluoro-phenyl)-furo[2,3-b]pyridine-3-carboxylic acid methylamide |
| 24.6 | 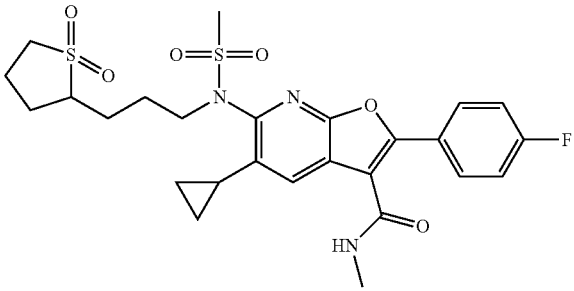 enantiomer 2 | 5-Cyclopropyl-6-{[3-(1,1-dioxo-tetrahydrothiophen-2-yl)-propyl]-methanesulfonyl-amino}-2-(4-fluoro-phenyl)-furo[2,3-b]pyridine-3-carboxylic acid methylamide |
| 24.7 | 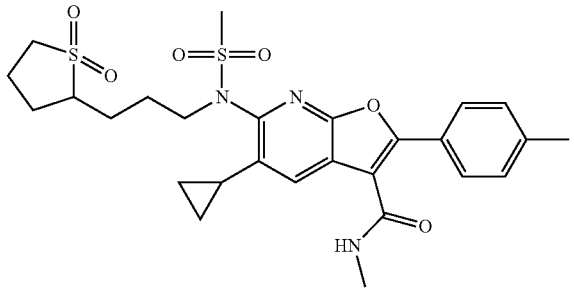 | 5-Cyclopropyl-6-{[3-((R)-1,1-dioxo-tetrahydrothiophen-2-yl)-propyl]-methanesulfonyl-amino}-2-p-tolyl-furo[2,3-b]pyridine-3-carboxylic acid methylamide |
| 24.8 | 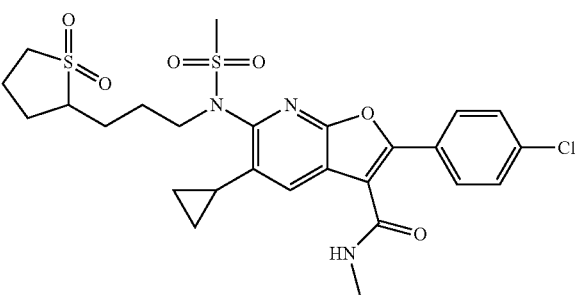 | 2-(4-Chloro-phenyl)-5-cyclopropyl-6-{[3-((R)-1,1-dioxo-tetrahydrothiophen-2-yl)-propyl]-methanesulfonyl-amino}-furo[2,3-b]pyridine-3-carboxylic acid methylamide |
| 24.9 | 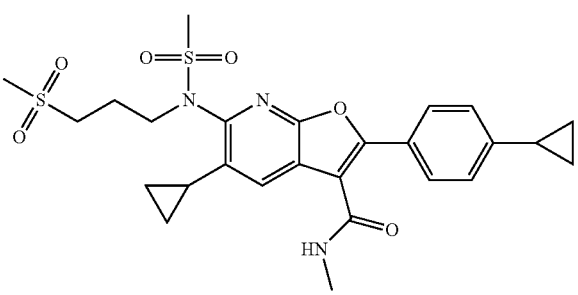 | 5-cyclopropyl-2-(4-cyclopropylphenyl)-N-methyl-6-(N-(3-(methylsulfonyl)propyl)methylsulfonamido)furo[2,3-b]pyridine-3-carboxamide |

TABLE 8-continued

| Ex. | Structure | Name |
|---|---|---|
| 25 | 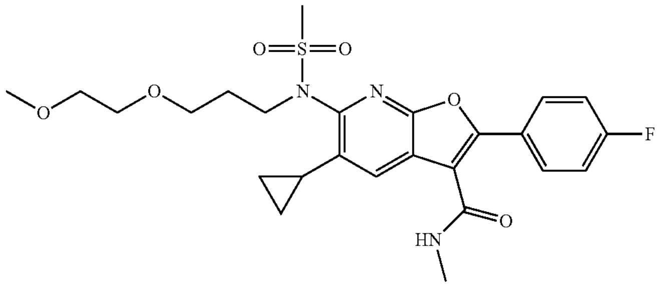 | 5-cyclopropyl-2-(4-fluorophenyl)-6-(N-(3-(2-methoxyethoxy)propyl)methylsulfonamido)-N-methylfuro[2,3-b]pyridine-3-carboxamide |
| 25.1 | 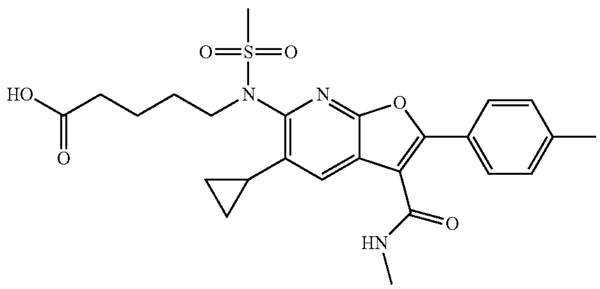 | 5-(N-(5-cyclopropyl-3-(methylcarbamoyl)-2-p-tolylfuro[2,3-b]pyridin-6-yl)methylsulfonamido)pentanoic acid |
| 25.2 | 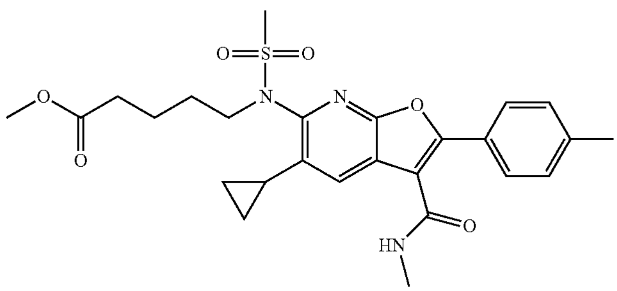 | methyl 5-(N-(5-cyclopropyl-3-(methylcarbamoyl)-2-p-tolylfuro[2,3-b]pyridin-6-yl)methylsulfonamido)pentanoate |
| 25.3 | 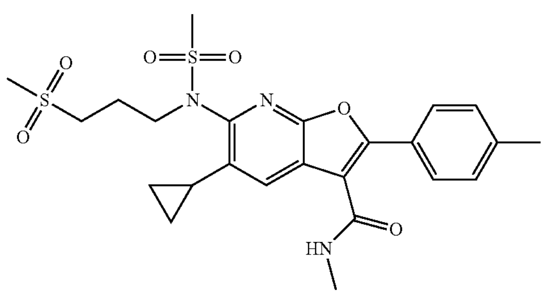 | 5-cyclopropyl-N-methyl-6-(N-(3-(methylsulfonyl)propyl)methylsulfonamido)-2-p-tolylfuro[2,3-b]pyridine-3-carboxamide |
| 25.4 | 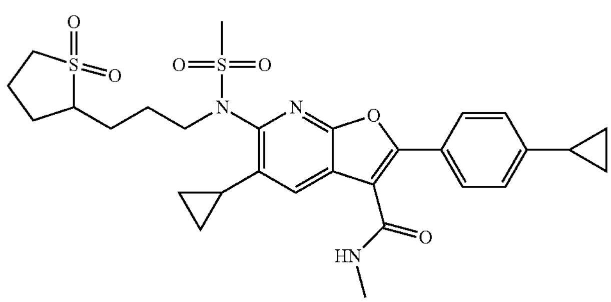 | 5-Cyclopropyl-2-(4-cyclopropyl-phenyl)-6-{[3-(1,1-dioxo-tetrahydro-thiophen-2-yl)-propyl]-methanesulfonyl-amino}-furo[2,3-b]pyridine-3-carboxylic acid methylamide |

TABLE 8-continued

| Ex. | Structure | Name |
|---|---|---|
| 25.5 | 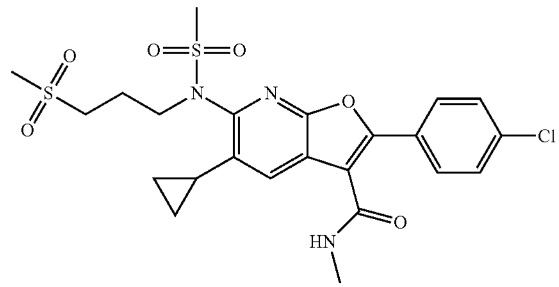 | 2-(4-chlorophenyl)-5-cyclopropyl-N-methyl-6-(N-(3-(methylsulfonyl)propyl)methylsulfonamido)furo[2,3-b]pyridine-3-carboxamide |
| 25.6 | 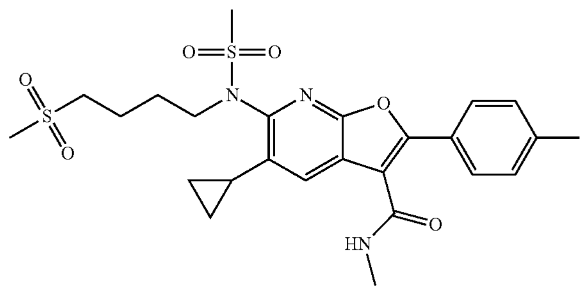 | 5-cyclopropyl-N-methyl-6-(N-(4-(methylsulfonyl)butyl)methylsulfonamido)-2-p-tolylfuro[2,3-b]pyridine-3-carboxamide |
| 25.7 | 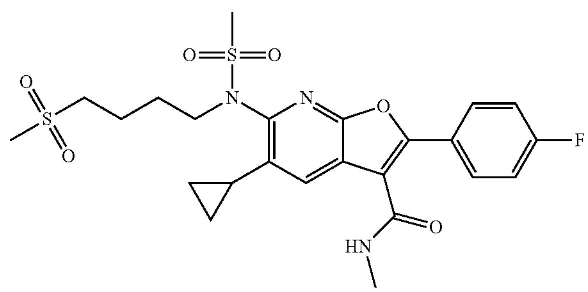 | 5-cyclopropyl-2-(4-fluorophenyl)-N-methyl-6-(N-(4-(methylsulfonyl)butyl)methylsulfonamido)furo[2,3-b]pyridine-3-carboxamide |
| 25.8 | 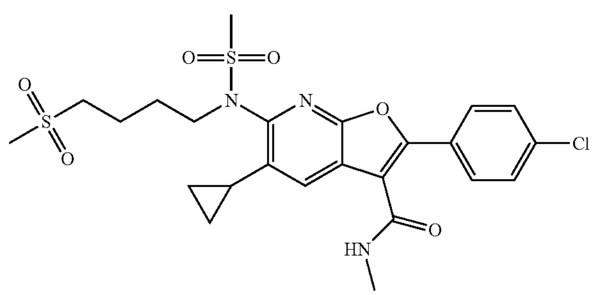 | 2-(4-chlorophenyl)-5-cyclopropy(-N-methyl-6-(N-(4-(methylsulfonyl)butyl)methylsulfonamido)furo[2,3-b]pyridine-3-carboxamide |
| 25.9 | 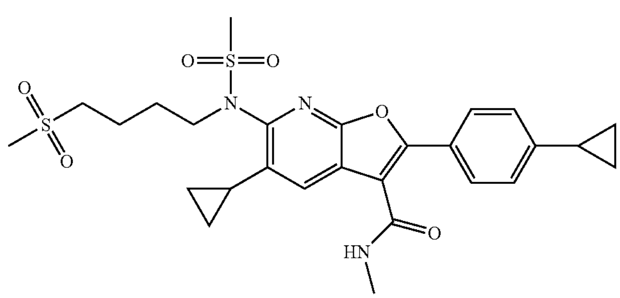 | 5-cyclopropyl-2-(4-cyclopropylphenyl)-N-methyl-6-(N-(4-(methylsulfonyl)butyl)methylsulfonamido)furo[2,3-b]pyridine-3-carboxamide |

TABLE 8-continued

| Ex. | Structure | Name |
|---|---|---|
| 25.9 | 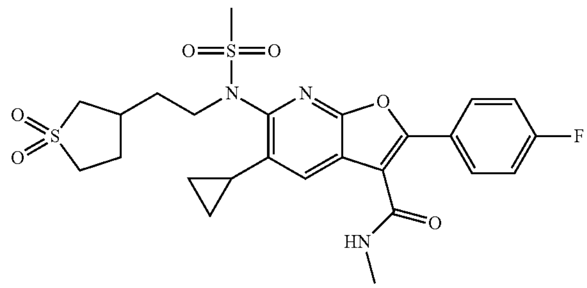 | 5-Cyclopropyl-6-{[2-(1,1-dioxo-tetrahydro-thiophen-3-yl)-ethyl]-methanesulfonyl-amino}-2-(4-fluoro-phenyl)-furo[2,3-b]pyridine-3-carboxylic acid methylamide |
| 26 | 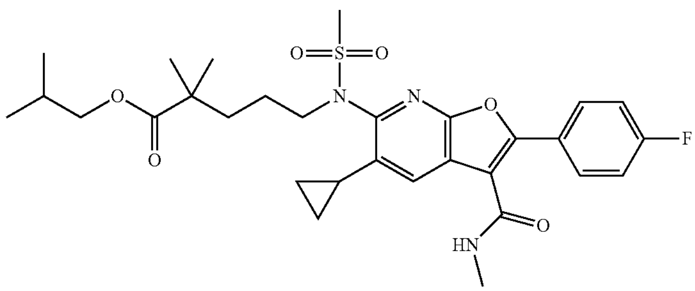 | isobutyl 5-(N-(5-cyclopropyl-2-(4-fluorophenyl)-3-(methylcarbamoyl)furo[2,3-b]pyridin-6-yl)methylsulfonamido)-2,2-dimethylpentanoate |
| 26.1 | 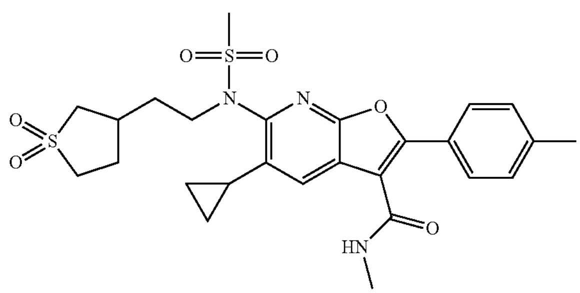 | 5-Cyclopropyl-6-{[2-(1,1-dioxo-tetrahydro-thiophen-3-yl)-ethyl]-methanesulfonyl-amino}-2-p-tolyl-furo[2,3-b]pyridine-3-carboxylic acid methylamide |
| 26.2 | 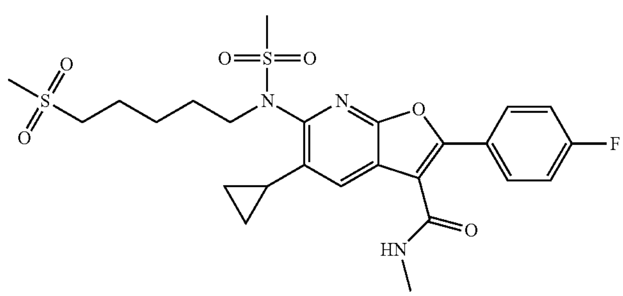 | 5-cyclopropyl-2-(4-fluorophenyl)-N-methyl-6-(N-(5-(methylsulfonyl)pentyl)methylsulfonamido)furo[2,3-b]pyridine-3-carboxamide |
| 26.3 | 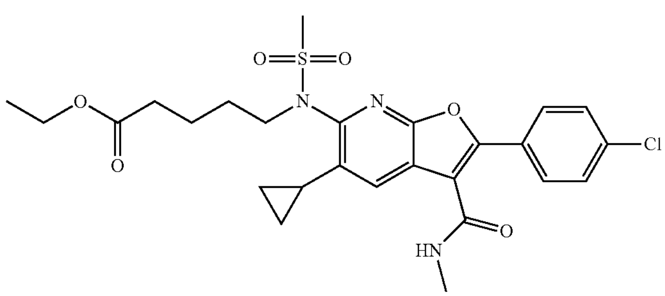 | ethyl 5-(N-(2-(4-chlorophenyl)-5-cyclopropyl-3-(methylcarbamoyl)furo[2,3-b]pyridin-6-yl)methylsulfonamido)pentanoate |

TABLE 8-continued

| Ex. | Structure | Name |
|---|---|---|
| 26.4 | 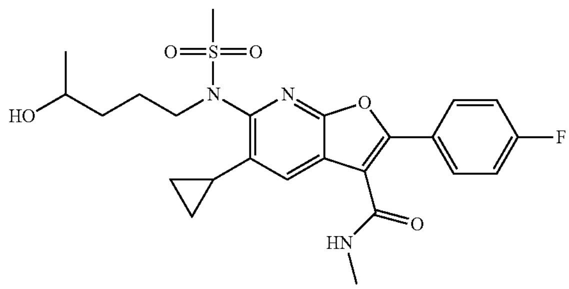 | 5-cyclopropyl-2-(4-fluorophenyl)-6-(N-(4-hydroxypentyl)methylsulfonamido)-N-methylfuro[2,3-b]pyridine-3-carboxamide |
| 26.5 | 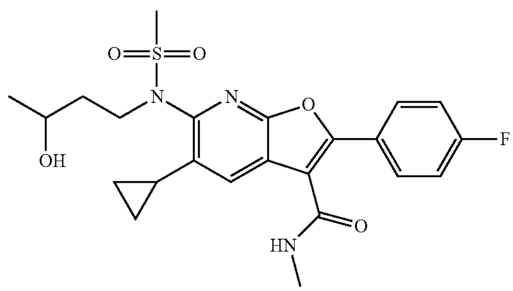 | 5-cyclopropyl-2-(4-fluorophenyl)-6-(N-(3-hydroxybutyl)methylsulfonamido)-N-methylfuro[2,3-b]pyridine-3-carboxamide |
| 26.6 | 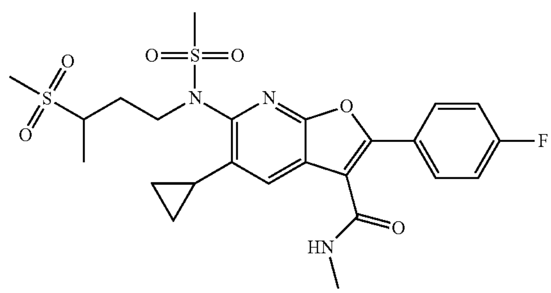 | 5-cyclopropyl-2-(4-fluorophenyl)-N-methyl-6-(N-(3-(methylsulfonyl)butyl)methylsulfonamido)furo[2,3-b]pyridine-3-carboxamide |
| 26.7 | 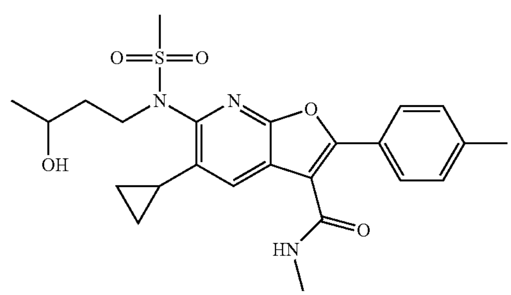 | 5-cyclopropyl-6-(N-(3-hydroxybutyl)methylsulfonamido)-N-methyl-2-p-tolylfuro[2,3-b]pyridine-3-carboxamide |
| 26.8 | 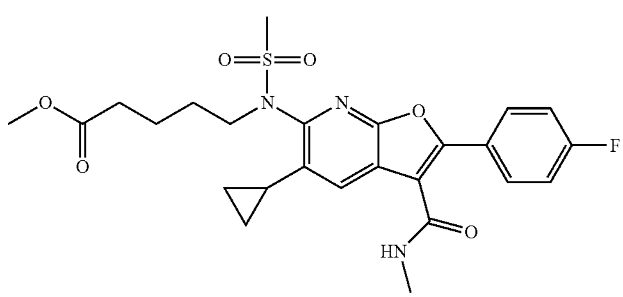 | methyl 5-(N-(5-cyclopropyl-2-(4-fluorophenyl)-3-(methylcarbamoyl)furo[2,3-b]pyridin-6-yl)methylsulfonamido)pentanoate |

TABLE 8-continued

| Ex. | Structure | Name |
|---|---|---|
| 26.9 | 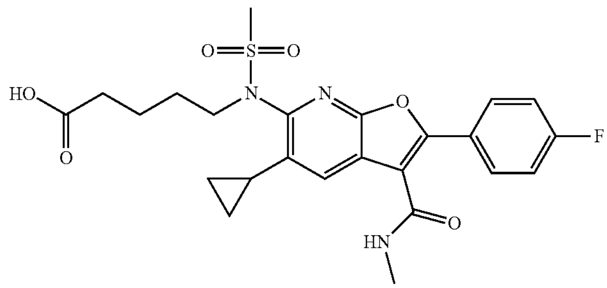 | 5-(N-(5-cyclopropyl-2-(4-fluorophenyl)-3-(methylcarbamoyl)furo[2,3-b]pyridin-6-yl)methylsulfonamido)pentanoic acid |
| 27 | 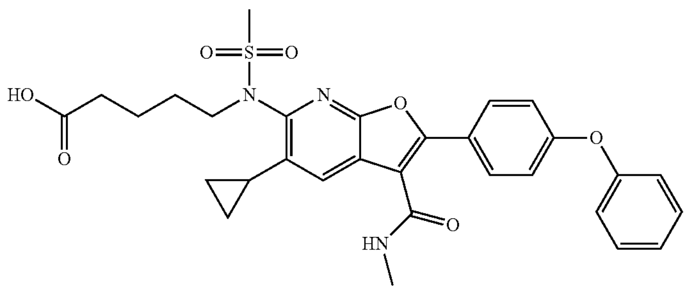 | 5-(N-(5-cyclopropyl-3-(methylcarbamoyl)-2-(4-phenoxyphenyl)furo[2,3-b]pyridin-6-yl)methylsulfonamido)pentanoic acid |
| 27.1 | 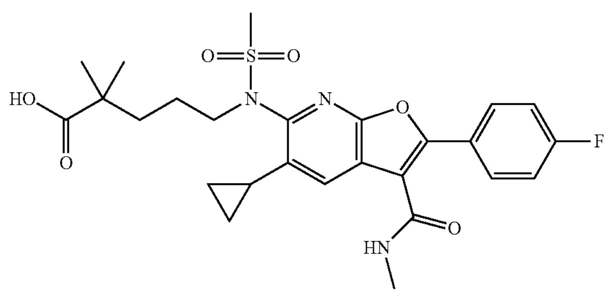 | 5-(N-(5-cyclopropyl-2-(4-fluorophenyl)-3-(methylcarbamoyl)furo[2,3-6]pyridin-6-yl)methylsulfonamido)-2,2-dimethylpentanoic acid |
| 27.2 | 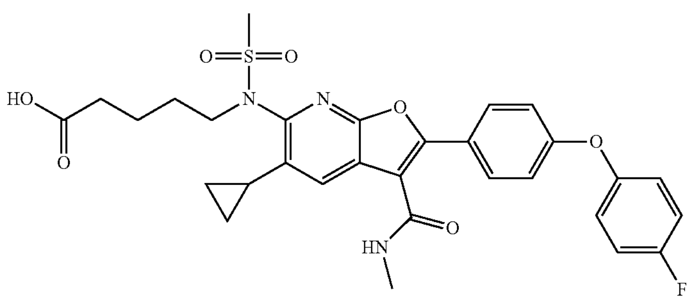 | 5-(N-(5-cyclopropyl-2-(4-(4-fluorophenoxy)phenyl)-3-(methylcarbamoyl)furo[2,3-b]pyridin-6-yl)methylsulfonamido)pentanoic acid |
| 27.3 | 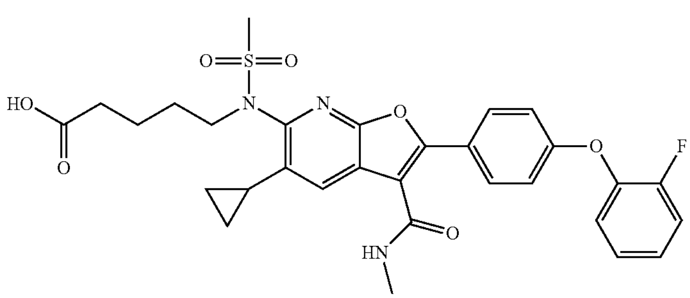 | 5-(N-(5-cyclopropyl-2-(4-(2-fluorophenoxy)phenyl)-3-(methylcarbamoyl)furo[2,3-b]pyridin-6-yl)methylsulfonamido)pentanoic acid |

TABLE 8-continued

| Ex. | Structure | Name |
|---|---|---|
| 27.4 | 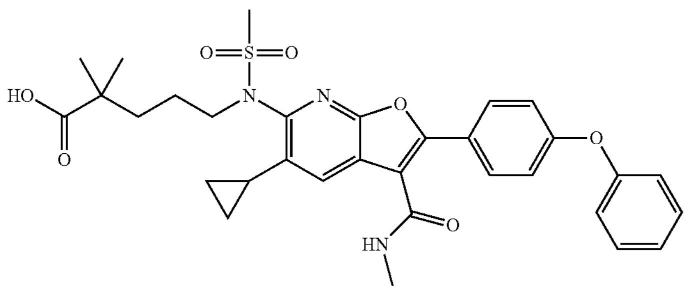 | 5-(N-(5-cyclopropyl-3-(methylcarbamoyl)-2-(4-phenoxyphenyl)furo[2,3-b]pyridin-6-yl)methylsulfonamido)-2,2-dimethylpentanoic acid |
| 27.5 | 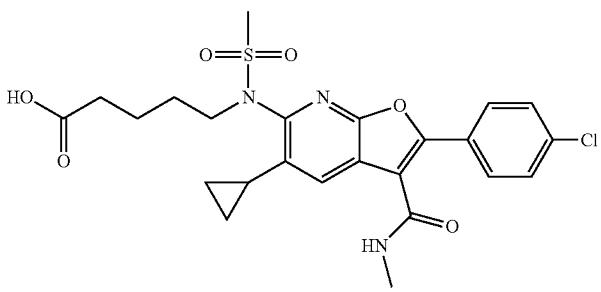 | 5-(N-(2-(4-chlorophenyl)-5-cyclopropyl-3-(methylcarbamoyl)furo[2,3-b]pyridin-6-yl)methylsulfonamido) pentanoic acid |
| 27.6 | 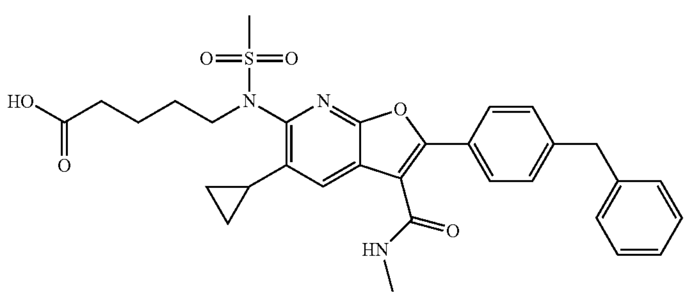 | 5-(N-(2-(4-benzylphenyl)-5-cyclopropyl-3-(methylcarbamoyl)furo[2,3-b]pyridin-6-yl)methylsulfonamido) pentanoic acid |
| 27.7 | 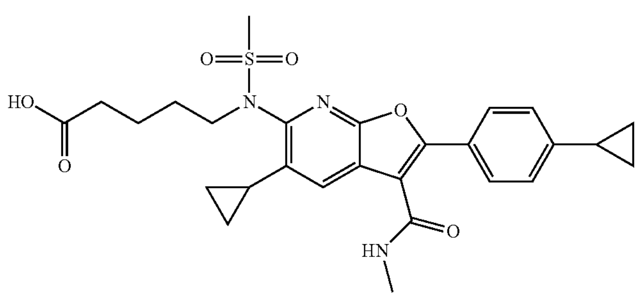 | 5-(N-(5-cyclopropyl-2-(4-cyclopropylphenyl)-3-(methylcarbamoyl)furo[2,3-b]pyridin-6-yl)methylsulfonamido) pentanoic acid |
| 27.8 | 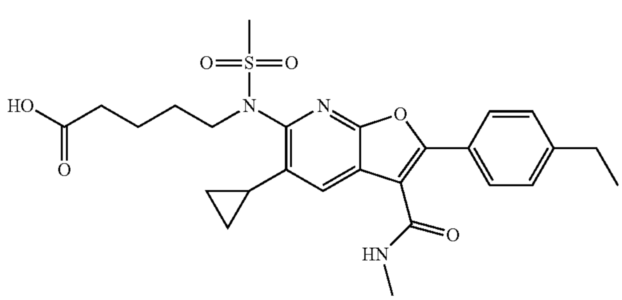 | 5-(N-(5-cyclopropyl-2-(4-ethylphenyl)-3-(methylcarbamoyl)furo[2,3-b]pyridin-6-yl)methylsulfonamido) pentanoic acid |

TABLE 8-continued

| Ex. | Structure | Name |
|---|---|---|
| 27.9 | 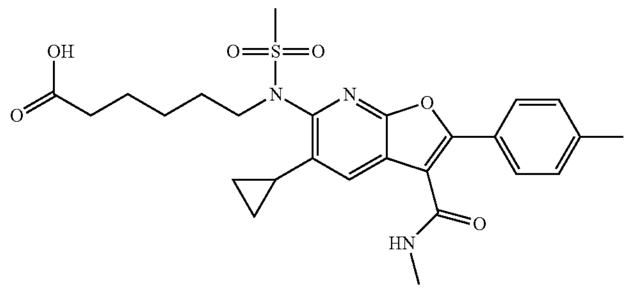 | 6-(N-(5-cyclopropyl-3-(methylcarbamoyl)-2-p-tolylfuro[2,3-b]pyridin-6-yl)methylsulfonamido)hexanoic acid |
| 28 | 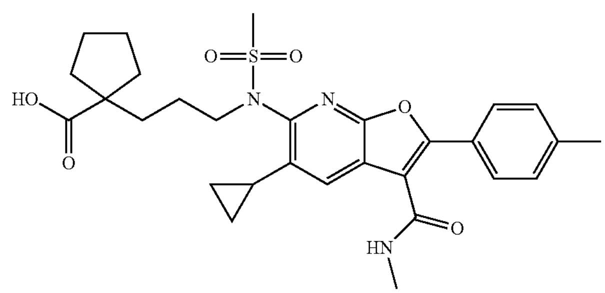 | 1-(3-(N-(5-cyclopropyl-3-(methylcarbamoyl)-2-p-tolylfuro[2,3-b]pyridin-6-yl)methylsulfonamido)propyl)cyclopentanecarboxylic acid |
| 28.1 | 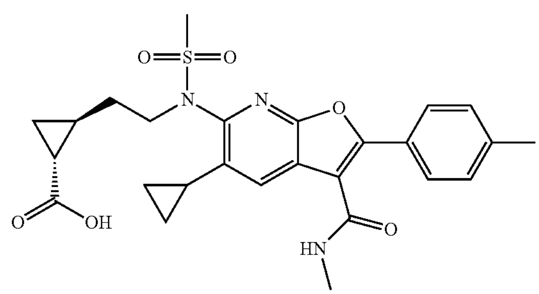 | (1R,2S)-2-(2-(N-(5-cyclopropyl-3-(methylcarbamoyl)-2-p-tolylfuro[2,3-b]pyridin-6-yl)methylsulfonamido)ethyl)cyclopropanecarboxylic acid |
| 28.2 | 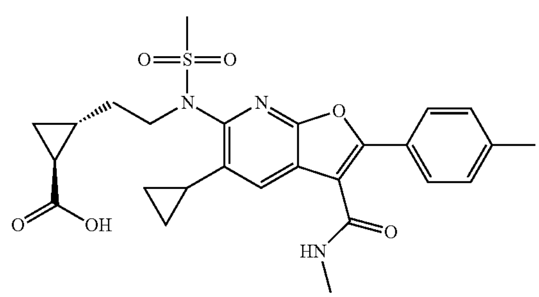 | (1S,2R)-2-(2-(N-(5-cyclopropyl-3-(methylcarbamoyl)-2-p-tolylfuro[2,3-b]pyridin-6-yl)methylsulfonamido)ethyl)cyclopropanecarboxylic acid |
| 28.3 | 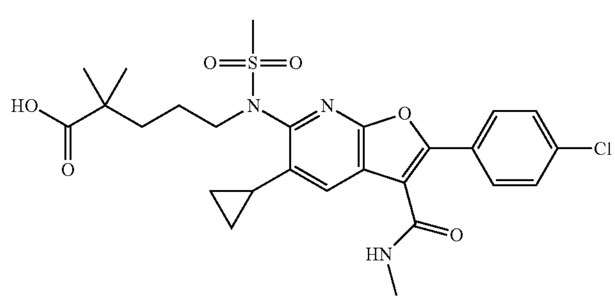 | 5-(N-(2-(4-chlorophenyl)-5-cyclopropyl-3-(methylcarbamoyl)furo[2,3-b]pyridin-6-yl)methylsulfonamido)-2,2-dimethylpentanoic acid |

TABLE 8-continued

| Ex. | Structure | Name |
|---|---|---|
| 28.4 | 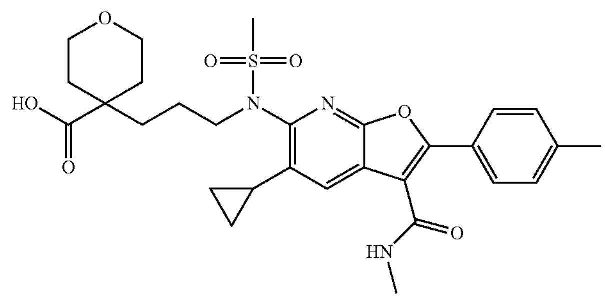 | 4-(3-(N-(5-cyclopropyl-3-(methylcarbamoyl)-2-p-tolylfuro[2,3-b]pyridin-6-yl)methylsulfonamido)propyl)tetrahydro-2H-pyran-4-carboxylic acid |
| 28.5 | 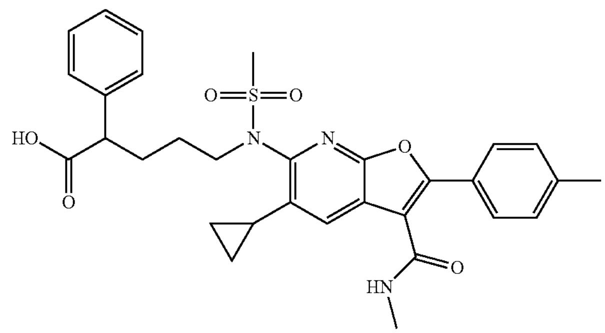 | 5-(N-(5-cyclopropyl-3-(methylcarbamoyl)-2-p-tolylfuro[2,3-b]pyridin-6-yl)methylsulfonamido)-2-phenylpentanoic acid |
| 28.6 | 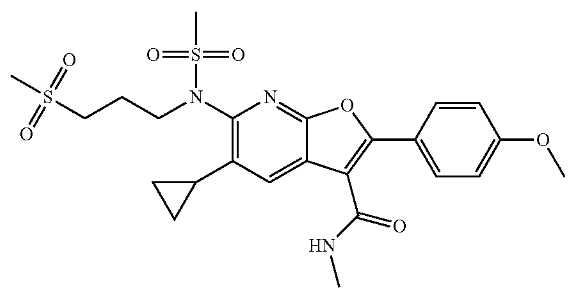 | 5-cyclopropyl-2-(4-methoxyphenyl)-N-methyl-6-(N-(3-(methylsulfonyl)propyl)methylsulfonamido)furo[2,3-b]pyridine-3-carboxamide |
| 28.9 | 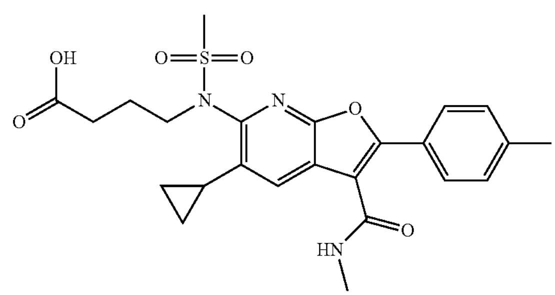 | 4-(N-(5-cyclopropyl-3-(methylcarbamoyl)-2-p-tolylfuro[2,3-b]pyridin-6-yl)methylsulfonamido)butanoic acid |
| 29 | 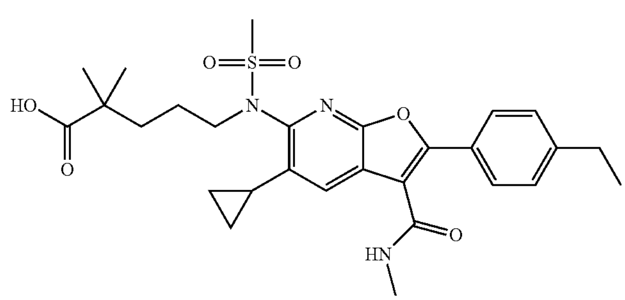 | 5-{[5-Cyclopropyl-2-(4-ethyl-phenyl)-3-methylcarbamoyl-furo[2,3-b]pyridin-6-yl]-methanesulfonyl-amino}-2,2-dimethyl-pentanoic acid |

TABLE 8-continued

| Ex. | Structure | Name |
| --- | --- | --- |
| 29.1 | 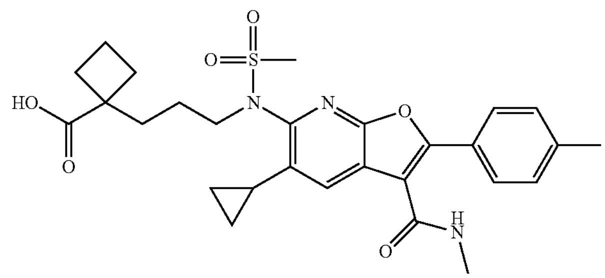 | 1-{3-[(5-Cyclopropyl-3-methylcarbamoyl-2-p-tolyl-furo[2,3-b]pyridin-6-yl)-methanesulfonyl-amino]-propyl}-cyclobutanecarboxylic acid |
| 29.2 | 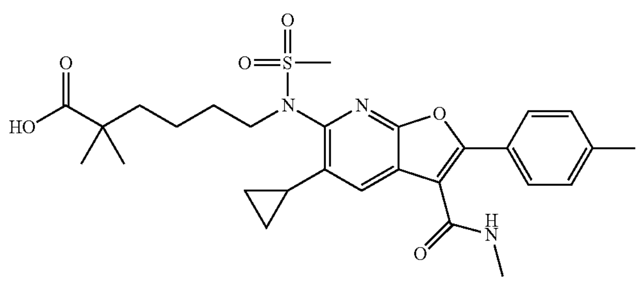 | 6-(N-(5-cyclopropyl-3-(methylcarbamoyl)-2-p-tolylfuro[2,3-b]pyridin-6-yl)methylsulfonamido)-2,2-dimethylhexanoic acid |
| 29.3 | 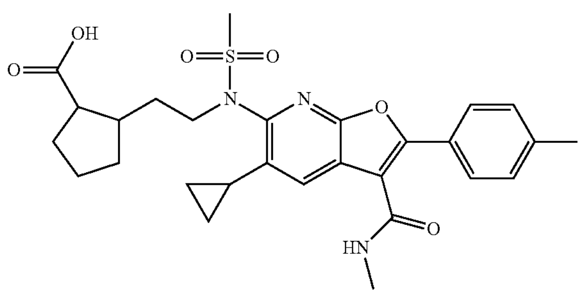 | 2-(2-(N-(5-cyclopropyl-3-(methylcarbamoyl)-2-p-tolylfuro[2,3-b]pyridin-6-yl)methylsulfonamido)ethyl)cyclopentanecarboxylic acid |
| 29.4 | 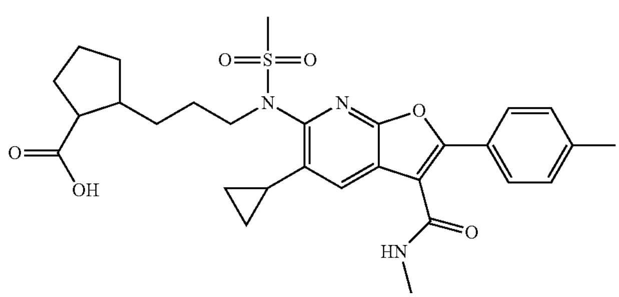 | 2-(3-(N-(5-cyclopropyl-3-(methylcarbamoyl)-2-p-tolylfuro[2,3-b]pyridin-6-yl)methylsulfonamido)propyl)cyclopentanecarboxylic acid |
| 29.5 | 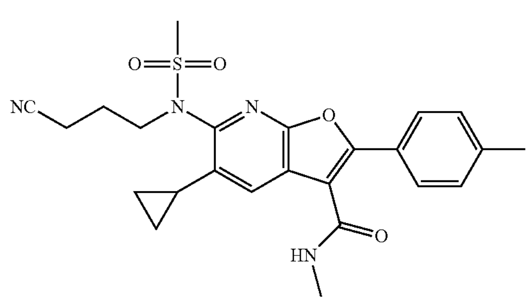 | 6-(N-(3-cyanopropyl)methylsulfonamido)-5-cyclopropyl-N-methyl-2-p-tolylfuro[2,3-b]pyridine-3-carboxamide |

TABLE 8-continued

| Ex. | Structure | Name |
|---|---|---|
| 29.6 | 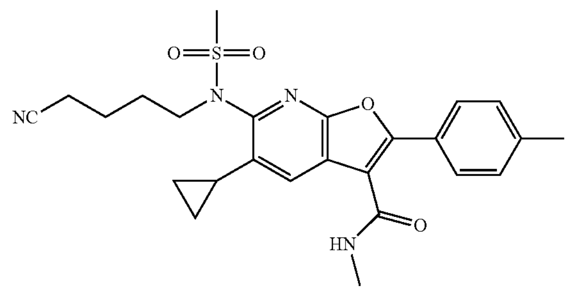 | 6-(N-(4-cyanobutyl)methylsulfonamido)-5-cyclopropyl-N-methyl-2-p-tolylfuro[2,3-b]pyridine-3-carboxamide |
| 29.7 | 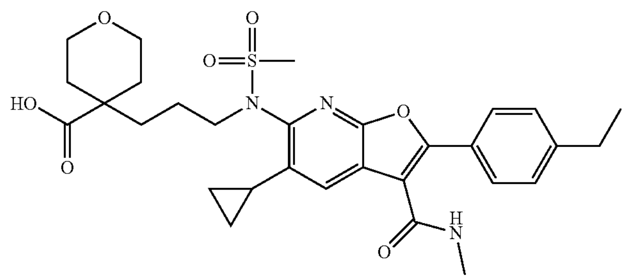 | 4-(3-(N-(5-cyclopropyl-2-(4-ethylphenyl)-3-(methylcarbamoyl)furo[2,3-b]pyridin-6-yl)methylsulfonamido)propyl)tetrahydro-2H-pyran-4-carboxylic acid |
| 29.8 | 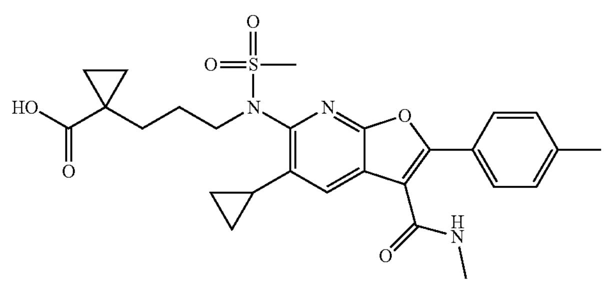 | 1-(3-(N-(5-cyclopropyl-3-(methylcarbamoyl)-2-p-tolylfuro[2,3-b]pyridin-6-yl)methylsulfonamido)propyl)cyclopropanecarboxylic acid |
| 29.9 | 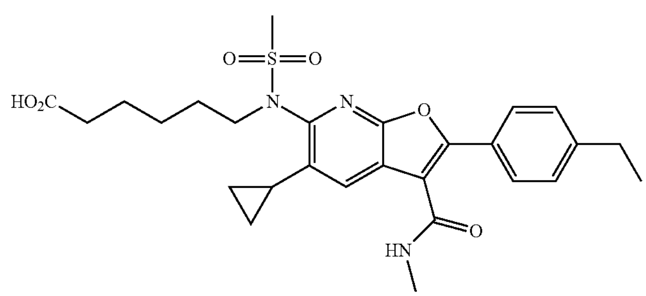 | 6-(N-(5-cyclopropyl-2-(4-ethylphenyl)-3-(methylcarbamoyl)furo[2,3-b]pyridin-6-yl)methylsulfonamido)hexanoic acid |
| 29.91 | 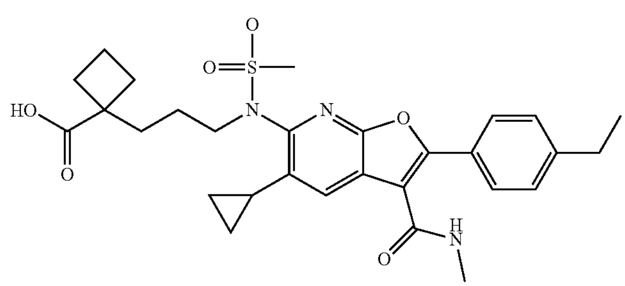 | 1-(3-(N-(5-cyclopropyl-2-(4-ethylphenyl)-3-(methylcarbamoyl)furo[2,3-b]pyridin-6-yl)methylsulfonamido)propyl)cyclobutanecarboxylic acid |

TABLE 8-continued

| Ex. | Structure | Name |
|---|---|---|
| 29.92 | 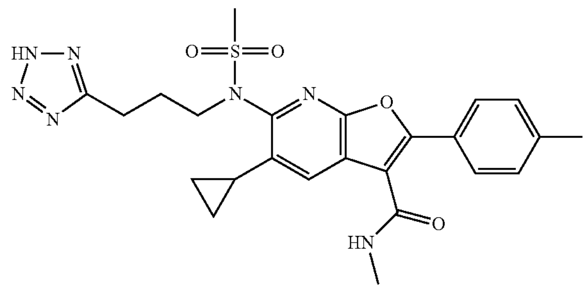 | 6-(N-(3-(2H-tetrazol-5-yl)propyl)methylsulfonamido)-5-cyclopropyl-N-methyl-2-p-tolylfuro[2,3-b]pyridine-3-carboxamide |
| 29.93 | 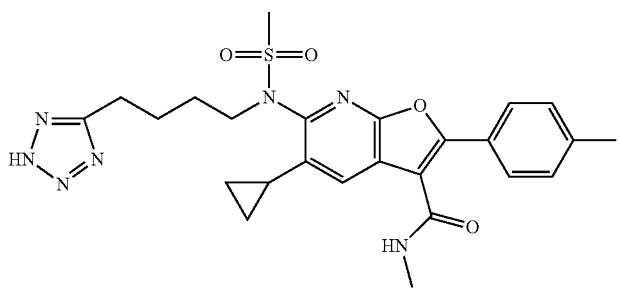 | 6-(N-(4-(2H-tetrazol-5-yl)butyl)methylsulfonamido)-5-cyclopropyl-N-methyl-2-p-tolylfuro[2,3-b]pyridine-3-carboxamide |
| 29.94 | 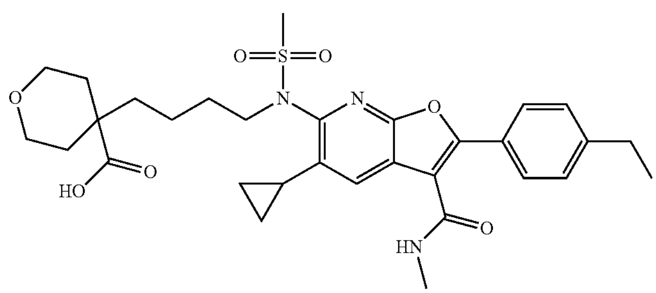 | 4-(4-(N-(5-cyclopropyl-2-(4-ethylphenyl)-3-(methylcarbamoyl)furo[2,3-b]pyridin-6-yl)methylsulfonamido)butyl)tetrahydro-2H-pyran-4-carboxylic acid |
| 29.95 | 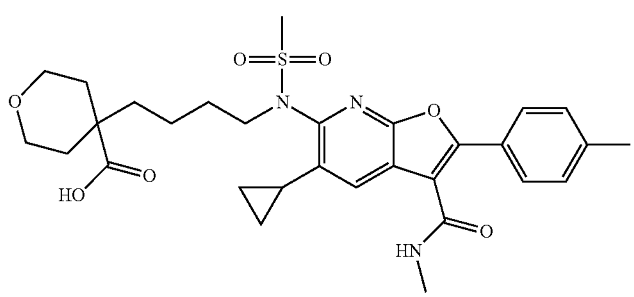 | 4-(4-(N-(5-cyclopropyl-3-(methylcarbamoyl)-2-p-tolylfuro[2,3-b]pyridin-6-yl)methylsulfonamido)butyl)tetrahydro-2H-pyran-4-carboxylic acid |
| 29.96 | 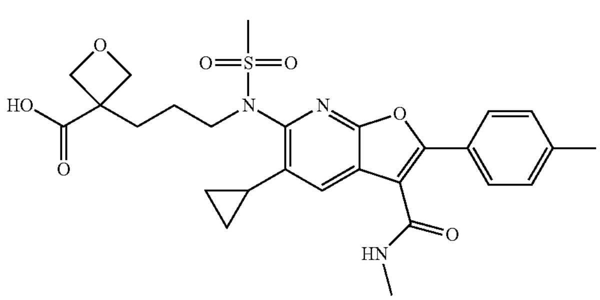 | 3-(3-(N-(5-cyclopropyl-3-(methylcarbamoyl)-2-p-tolylfuro[2,3-b]pyridin-6-yl)methylsulfonamido)propyl)oxetane-3-carboxylic acid |

US 8,324,239 B2

175                                                                 176

TABLE 8-continued

| Ex. | Structure | Name |
| --- | --- | --- |
| 29.97 | 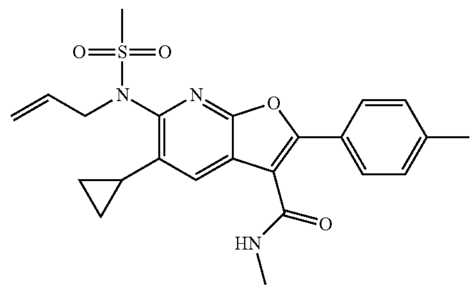 | 6-(N-allylmethylsulfonamido)-5-cyclopropyl-N-methyl-2-p-tolylfuro[2,3-b]pyridine-3-carboxamide |
| 29.98 | 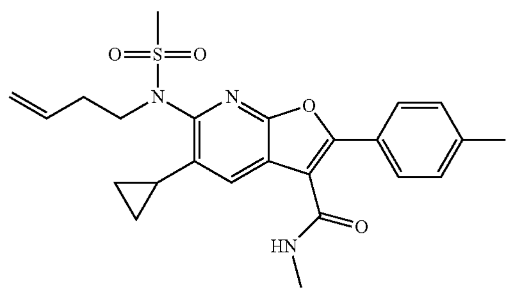 | 6-(N-(but-3-enyl)methylsulfonamido)-5-cyclopropyl-N-methyl-2-p-tolylfuro[2,3-b]pyridine-3-carboxamide |
| 29.99 | 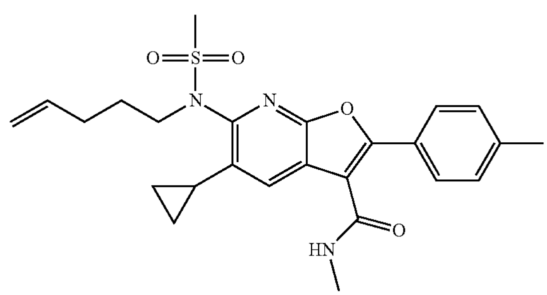 | 5-cyclopropyl-N-methyl-6-(N-(pent-4-enyl)methylsulfonamido)-2-p-tolylfuro[2,3-b]pyridine-3-carboxamide |
| 29.991 | 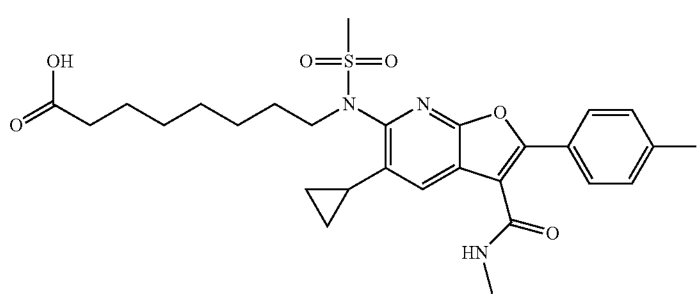 | 8-(N-(5-cyclopropyl-3-(methylcarbamoyl)-2-p-tolylfuro[2,3-b]pyridin-6-yl)methylsulfonamido)octanoic acid |
| 29.992 | 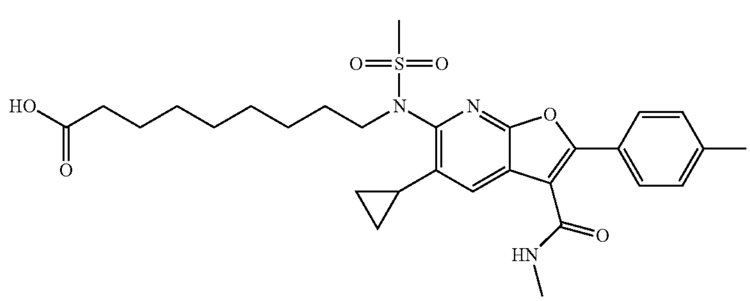 | 9-(N-(5-cyclopropyl-3-(methylcarbamoyl)-2-p-tolylfuro[2,3-b]pyridin-6-yl)methylsulfonamido)nonanoic acid |

TABLE 8-continued

| Ex. | Structure | Name |
|---|---|---|
| 29.993 | 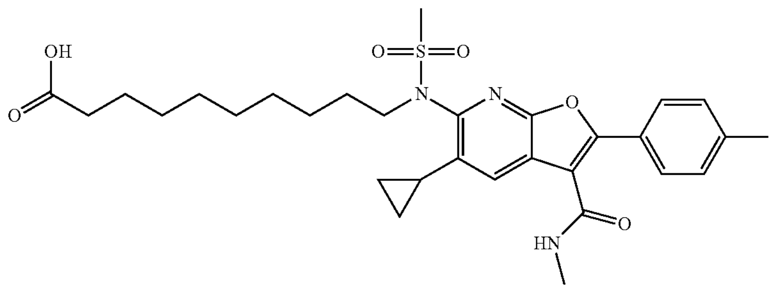 | 10-(N-(5-cyclopropyl-3-(methylcarbamoyl)-2-p-tolylfuro[2,3-b]pyridin-6-yl)methylsulfonamido)decanoic acid |
| 29.994 | 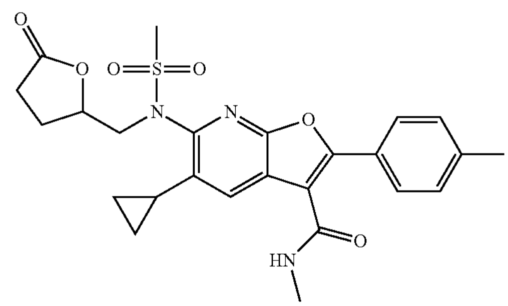 | 5-cyclopropyl-N-methyl-6-(N-((5-oxotetrahydrofuran-2-yl)methyl)methylsulfonamido)-2-p-tolylfuro[2,3-b]pyridine-3-carboxamide |
| 29.995 | 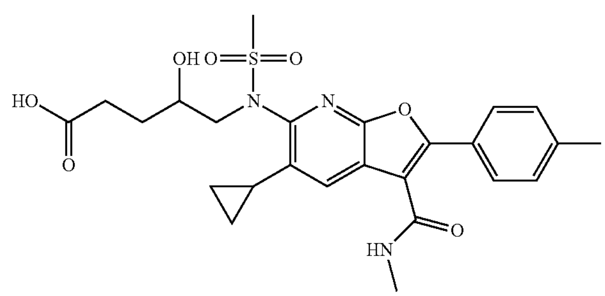 | 5-(N-(5-cyclopropyl-3-(methylcarbamoyl)-2-p-tolylfuro[2,3-b]pyridin-6-yl)methylsulfonamido)-4-hydroxypentanoic acid |
| 29.996 | 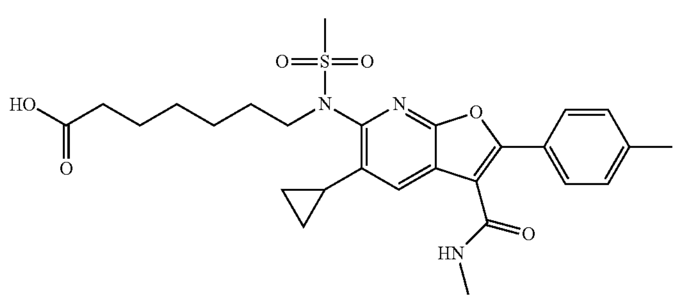 | 7-(N-(5-cyclopropyl-3-(methylcarbamoyl)-2-p-tolylfuro[2,3-b]pyridin-6-yl)methylsulfonamido)heptanoic acid |
| 29.997 | 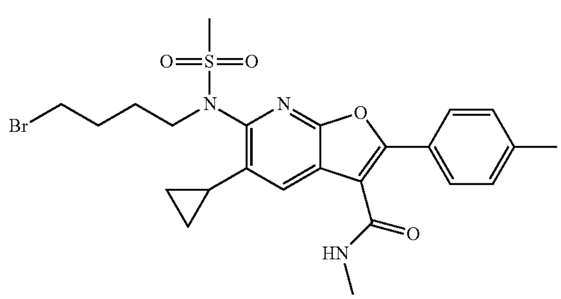 | 6-(N-(4-bromobutyl)methylsulfonamido)-5-cyclopropyl-N-methyl-2-p-tolylfuro[2,3-b]pyridine-3-carboxamide |

TABLE 8-continued

| Ex. | Structure | Name |
| --- | --- | --- |
| 29.998 | 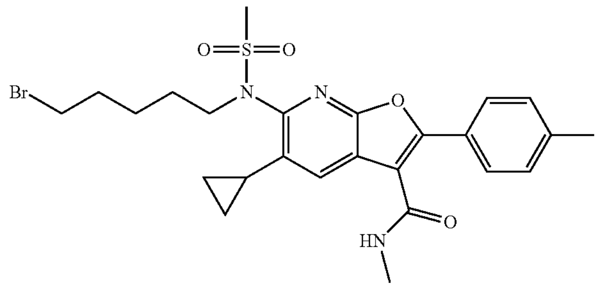 | 6-(N-(5-bromopentyl)methylsulfonamido)-5-cyclopropyl-N-methyl-2-p-tolylfuro[2,3-b]pyridine-3-carboxamide |
| 29.999 | 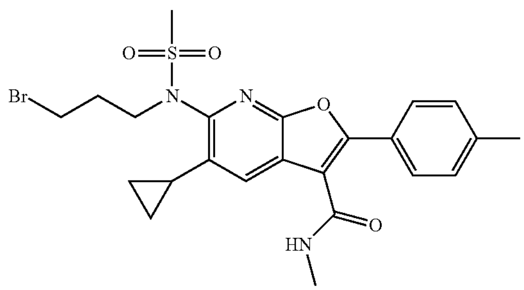 | 6-(N-(3-bromopropyl)methylsulfonamido)-5-cyclopropyl-N-methyl-2-p-tolylfuro[2,3-b]pyridine-3-carboxamide |
| 29.9991 | 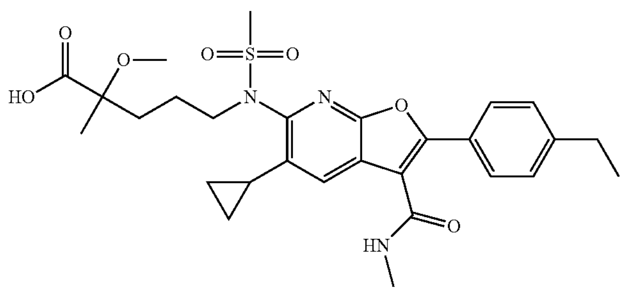 | 5-(N-(5-cyclopropyl-2-(4-ethylphenyl)-3-(methylcarbamoyl)furo[2,3-b]pyridin-6-yl)methylsulfonamido)-2-methoxy-2-methylpentanoic acid |
| 29.9992 | 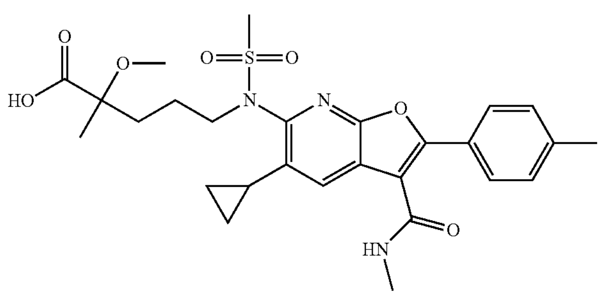 | 5-(N-(5-cyclopropyl-3-(methylcarbamoyl)-2-p-tolylfuro[2,3-b]pyridin-6-yl)methylsulfonamido)-2-methoxy-2-methylpentanoic acid |
| 29.9993 | 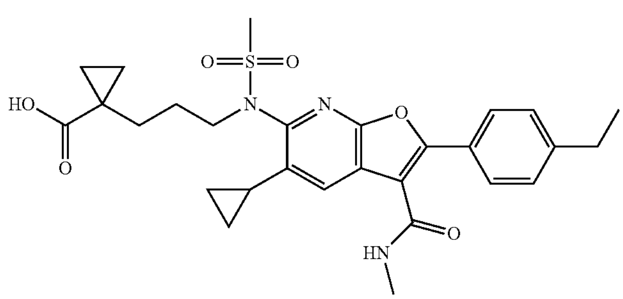 | 1-(3-(N-(5-cyclopropyl-2-(4-ethylphenyl)-3-(methylcarbamoyl)furo[2,3-b]pyridin-6-yl)methylsulfonamido)propyl)cyclopropanecarboxylic acid |

TABLE 8-continued

| Ex. | Structure | Name |
|---|---|---|
| 29.9994 | 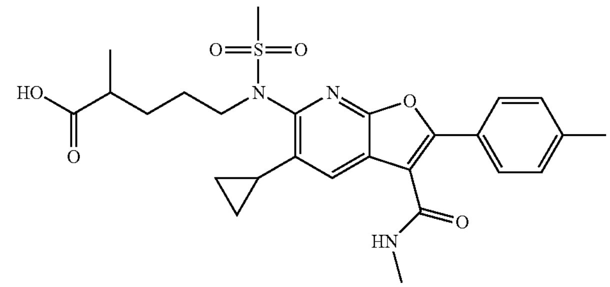 | 5-(N-(5-cyclopropyl-3-(methylcarbamoyl)-2-p-tolylfuro[2,3-b]pyridin-6-yl)methylsulfonamido)-2-methylpentanoic acid |
| 29.9995 | 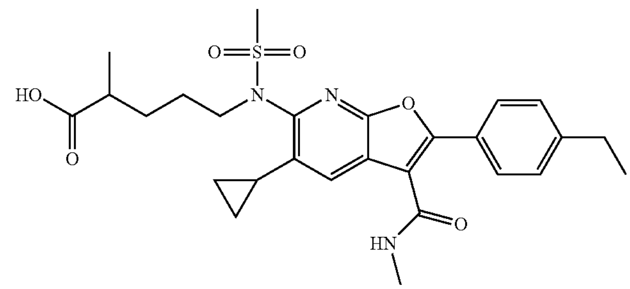 | 5-(N-(5-cyclopropyl-2-(4-ethylphenyl)-3-(methylcarbamoyl)furo[2,3-b]pyridin-6-yl)methylsulfonamido)-2-methylpentanoic acid |
| 29.9996 | 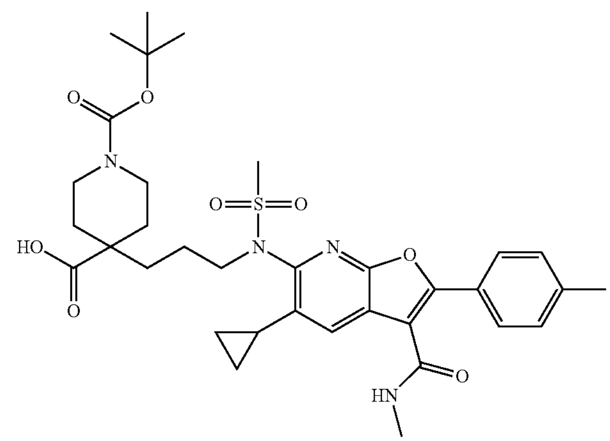 | 1-(tert-butoxycarbonyl)-4-(3-(N-(5-cyclopropyl-3-(methylcarbamoyl)-2-p-tolylfuro[2,3-b]pyridin-6-yl)methylsulfonamido)propyl)piperidine-4-carboxylic acid |
| 29.9997 | 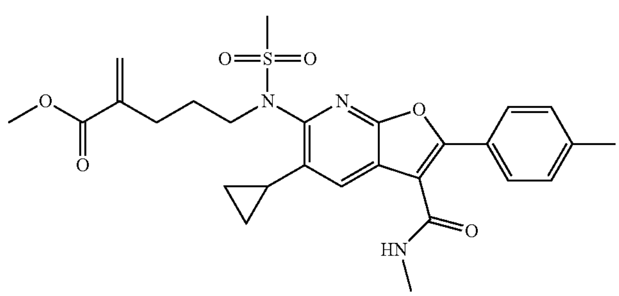 | methyl 5-(N-(5-cyclopropyl-3-(methylcarbamoyl)-2-p-tolylfuro[2,3-b]pyridin-6-yl)methylsulfonamido)-2-methylenepentanoate |
| 29.9998 | 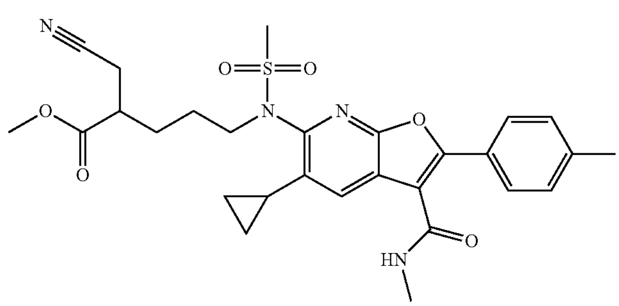 | methyl 2-(cyanomethyl)-5-(N-(5-cyclopropyl-3-(metfiylcarbamoyl)-2-p-tolylfuro[2,3-b]pyridin-6-yl)methylsulfonamido)pentanoate |

TABLE 8-continued

| Ex. | Structure | Name |
|---|---|---|
| 29.9999 | 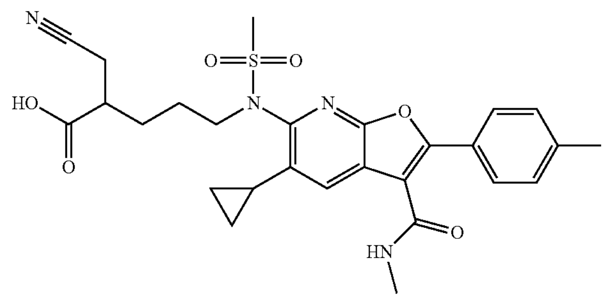 | 2-(cyanomethyl)-5-(N-(5-cyclopropyl-3-(methylcarbamoyl)-2-p-tolylfuro[2,3-b]pyridin-6-yl)methylsulfonamido)pentanoic acid |
| 29.99991 | 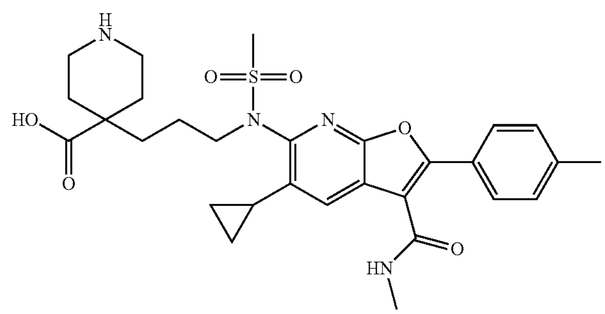 | 4-(3-(N-(5-cyclopropyl-3-(methylcarbamoyl)-2-p-tolylfuro[2,3-b]pyridin-6-yl)methylsulfonamido)propyl)piperidine-4-carboxylic acid |
| 29.99992 | 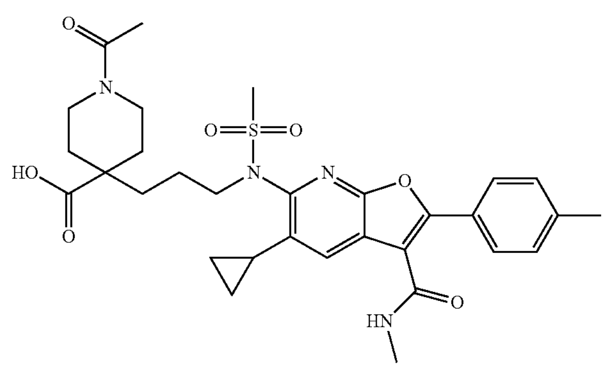 | 1-acetyl-4-(3-(N-(5-cyclopropyl-3-(methylcarbamoyl)-2-p-tolylfuro[2,3-b]pyridin-6-yl)methylsulfonamido)propyl)piperidine-4-carboxylic acid |
| 29.99993 | 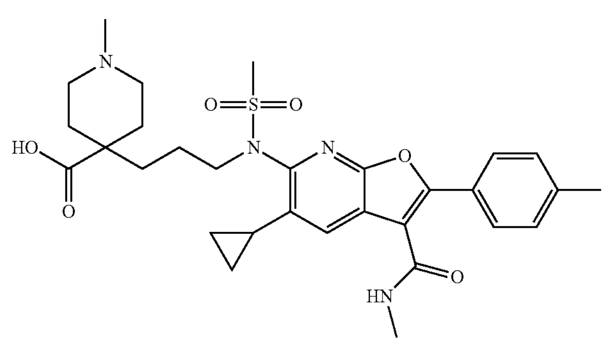 | 4-(3-(N-(5-cyclopropyl-3-(methylcarbamoyl)-2-p-tolylfuro[2,3-b]pyridin-6-yl)methylsulfonamido)propyl)-1-methylpiperidine-4-carboxylic acid |
| 29.99994 | 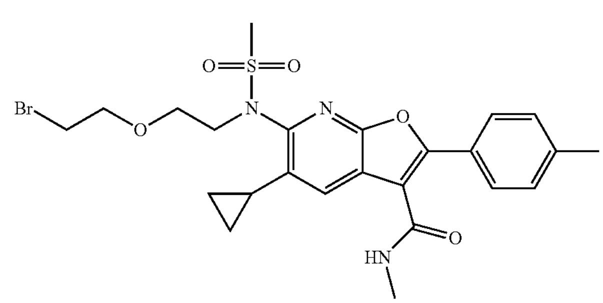 | 6-(N-(2-(2-bromoethoxy)ethyl)methylsulfonamido)-5-cyclopropyl-N-methyl-2-p-tolylfuro[2,3-b]pyridine-3-carboxamide |

TABLE 8-continued

| Ex. | Structure | Name |
|---|---|---|
| 29.99995 | 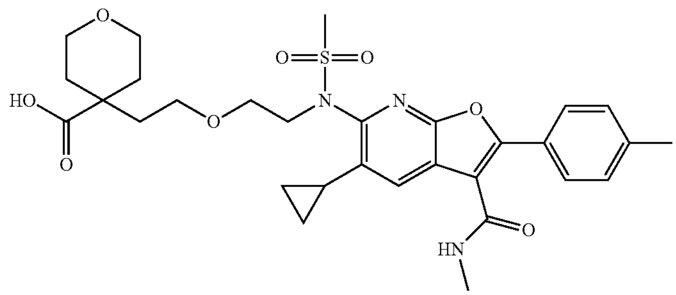 | 4-(2-(2-(N-(5-cyclopropyl-3-(methylcarbamoyl)-2-p-tolylfuro[2,3-b]pyridin-6-yl)methylsulfonamido)ethoxy)ethyl)tetrahydro-2H-pyran-4-carboxylic acid |
| 29.99996 | 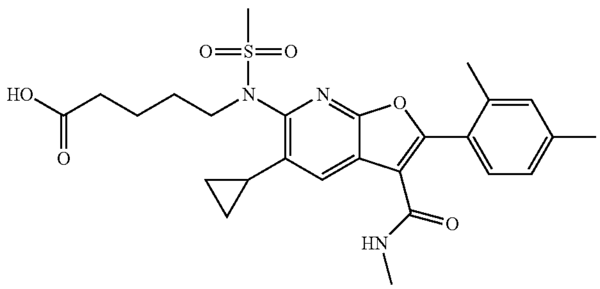 | 5-(N-(5-cyclopropyl-2-(2,4-dimethylphenyl)-3-(methylcarbamoyl)furo[2,3-b]pyridin-6-yl)methylsulfonamido)pentanoic acid |
| 29.99997 | 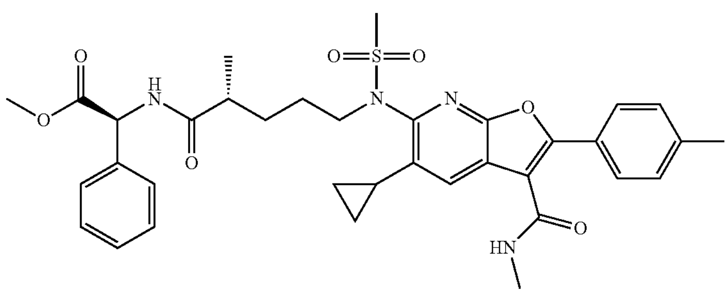 | (S)-methyl 2-((R)-5-(N-(5-cyclopropyl-3-(methylcarbamoyl)-2-p-tolylfuro[2,3-b]pyridin-6-yl)methylsulfonamido)-2-methylpentanamido)-2-phenylacetate |
| 29.99998 | 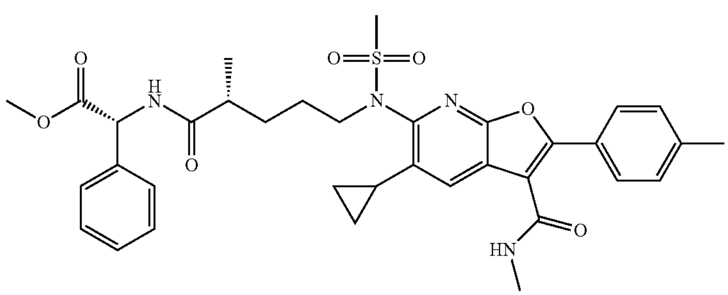 | (R)-methyl 2-((R)-5-(N-(5-cyclopropyl-3-(methylcarbamoyl)-2-p-tolylfuro[2,3-b]pyridin-6-yl)methylsulfonamido)-2-methylpentanamido)-2-phenylacetate |
| 29.99999 | 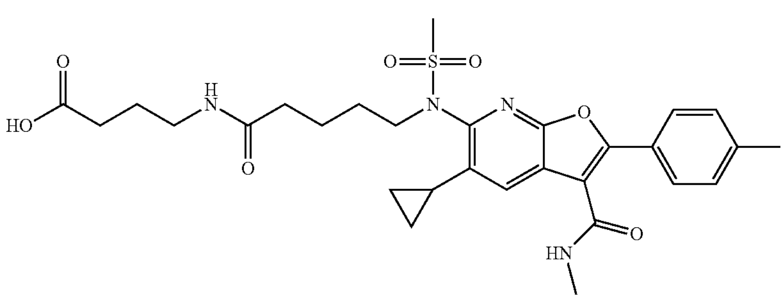 | 4-(5-(N-(5-cyclopropyl-3-(methylcarbamoyl)-2-p-tolylfuro[2,3-b]pyridin-6-yl)methylsulfonamido)pentanamido)butanoic acid |

TABLE 8-continued

| Ex. | Structure | Name |
|---|---|---|
| 29.999991 | 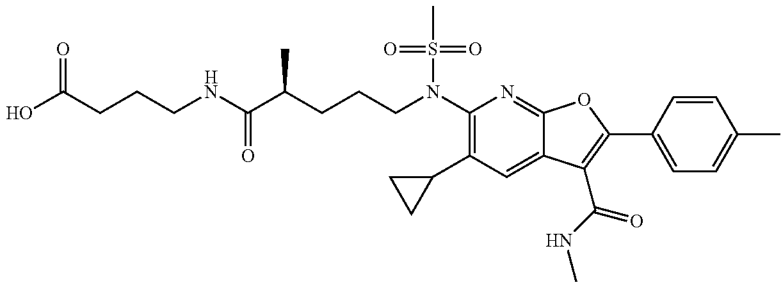 | (S)-4-(5-(N-(5-cyclopropyl-3-(methylcarbamoyl)-2-p-tolylfuro[2,3-b]pyridin-6-yl)methylsulfonamido)-2-methylpentanamido)butanoic acid |
| 29.999992 | 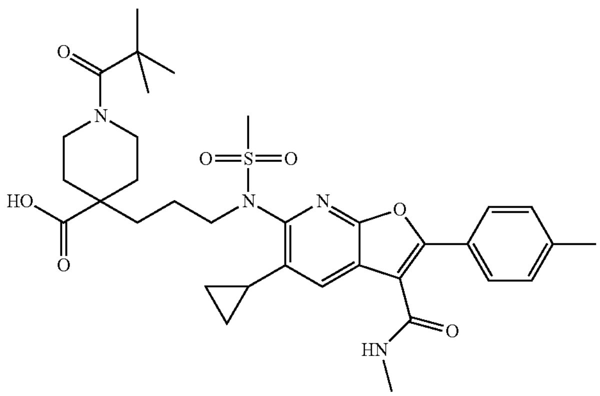 | 4-(3-(N-(5-cyclopropyl-3-(methylcarbamoyl)-2-p-tolylfuro[2,3-b]pyridin-6-yl)methylsulfonamido)propyl)-1-pivaloylpiperidine-4-carboxylic acid |
| 29.999993 | 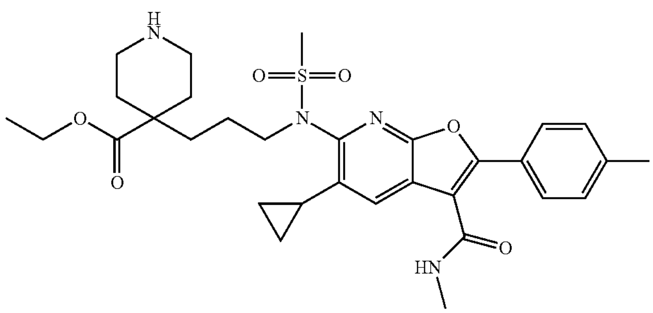 | ethyl 4-(3-(N-(5-cyclopropyl-3-(methylcarbamoyl)-2-p-tolylfuro[2,3-b]pyridin-6-yl)methylsulfonamido)propyl)piperidine-4-carboxylate |
| 29.999994 | 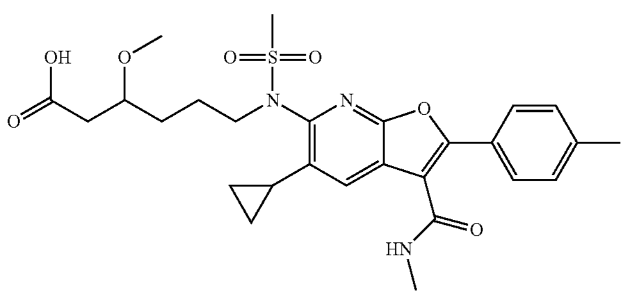 | 6-(N-(5-cyclopropyl-3-(methylcarbamoyl)-2-p-tolylfuro[2,3-b]pyridin-6-yl)methylsulfonamido)-3-methoxyhexanoic acid |
| 29.999995 | 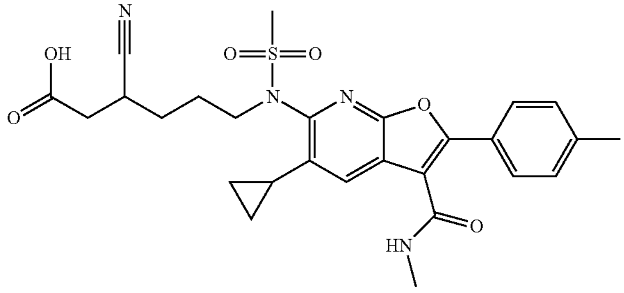 | 3-cyano-6-(N-(5-cyclopropyl-3-(methylcarbamoyl)-2-p-tolylfuro[2,3-b]pyridin-6-yl)methylsulfonamido)hexanoic acid |

TABLE 8-continued

| Ex. | Structure | Name |
|---|---|---|
| 29.999996 | 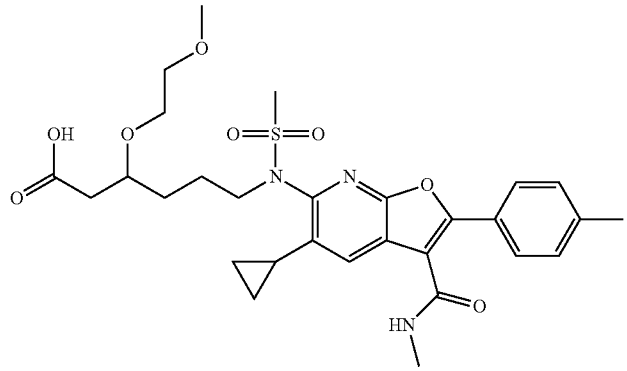 | 6-(N-(5-cyclopropyl-3-(methylcarbamoyl)-2-p-tolylfuro[2,3-b]pyridin-6-yl)methylsulfonamido)-3-(2-methoxyethoxy) hexanoic acid |
| 29.999997 | 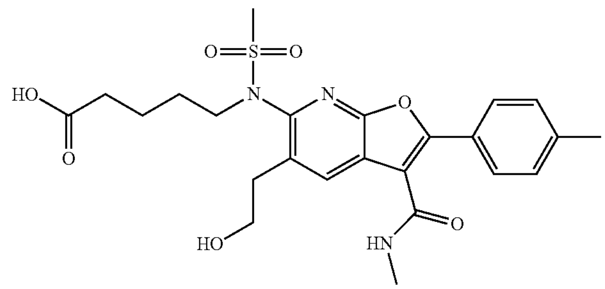 | 5-(N-(5-(2-hydroxyethyl)-3-(methylcarbamoyl)-2-p-tolylfuro[2,3-b]pyridin-6-yl)methylsulfonamido) pentanoic acid |
| 29.999998 | 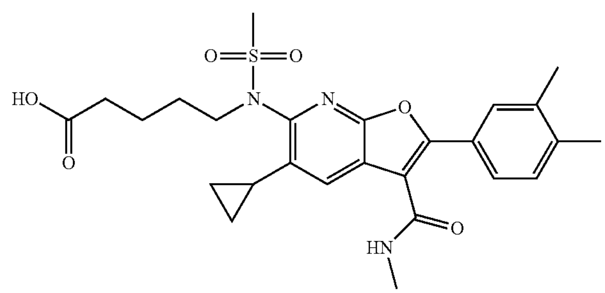 | 5-(N-(5-cyclopropyl-2-(3,4-dimethylphenyl)-3-(methylcarbamoyl)furo[2,3-b]pyridin-6-yl)methylsulfonamido) pentanoic acid |
| 29.999999 | 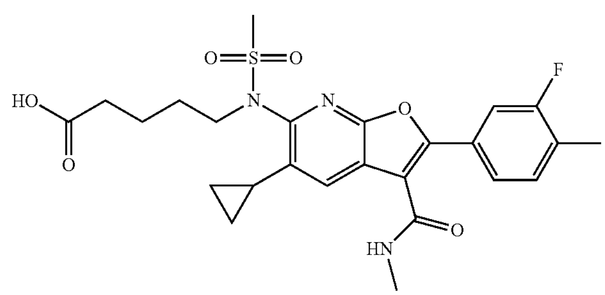 | 5-(N-(5-cyclopropyl-2-(3-fluoro-4-methylphenyl)-3-(methylcarbamoyl)furo[2,3-b]pyridin-6-yl)methylsulfonamido) pentanoic acid |

The racemate of Example 24.4 is resolved into individual enantiomers by chiral HPLC on an IC 21×250 mm column with 18 mL/min 60% heptane 40% ethanol: Example 24.5 eluted at 13.54 min, and Example 24.6 eluted at 15.68 min. In Examples 24.8, 25.5, 25.8, 26.3, Pd(PPh3)4 is used in place of Pd(OAc)$_2$ and S-Phos. In Examples 29.3 and 29.4, the side chains were prepared according to Synlett 2008, No 11, pp 1618-1622 to make methyl 2-allylcyclopentanecarboxylate followed by analogy to Examples 41 (ozonolysis, reduction, iodination) and to make methyl 2-(3-iodopropyl)cyclopentanecarboxylate and (hydroboration, iodination) methyl 2-(4-iodobutyl)cyclopentanecarboxylate.

In Example 28.4 and 29.7, the side chain is prepared as follows to make methyl 4-(3-chloropropyl)tetrahydro-2H-pyran-4-carboxylate To a solution of methyl tetrahydro-2H-pyran-4-carboxylate (2 g, 13.87 mmol) in THF (27.7 mL), cooled to −78° C., was added Sodium bis(trimethylsilyl)amide (25.4 mL, 15.26 mmol) dropwise. Upon complete, the mixture was allowed warm up to 0° C. and cooled again to −78° C., and 1-bromo-3-chloropropane (2.62 g, 16.65 mmol) was added dropwise. Upon complete, the mixture was allowed warm up to 0° C., stirred for 3 hr. To the reaction mixture was added water (200 ml) and extracted with diethyl ether (300 ml×3). The ether layers was combined, dried over MgSO4 and concentrated to give crude product which was used for next step without further purification.

Examples 29.8, 29.91, 29.94, 29.95 and were prepared in analogy to Example 29.7.

Examples 29.92 and 29.93 were prepared from the compounds of Examples 29.5 and 29.6 respectively according to the following procedure.

6-(N-(3-cyanopropyl)methylsulfonamido)-5-cyclopropyl-N-methyl-2-p-tolylfuro[2,3-b]pyridine-3-carboxamide (15 mg, 0.032 mmol) is dissolved in DME (1.5 ml), dibutylstannanone (4.0 mg, 0.016 mmol) and azidotrimethylsilane (7.5 mg, 0.064 mmol) are added together then heated in the microwave for 20 min at 150.0 C. The mixture is then filtered through a bed of celite and the solid is washed with EtOAc (25 mL). The combined organic is then washed with H2O (10 mL), Brine (10 mL) and dried over Na2SO4, followed by evaporation of the solvent and purification by HPLC (CH3CN/H2O/0.1% TFA).

Example 29.96

Side Chain Methyl 3-(3-iodopropyl)oxetane-3-carboxylate was Prepared as Follows

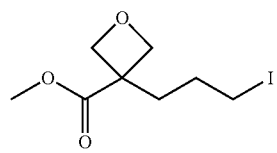

A. 2,2-Bis(hydroxymethyl)pent-4-enoic acid

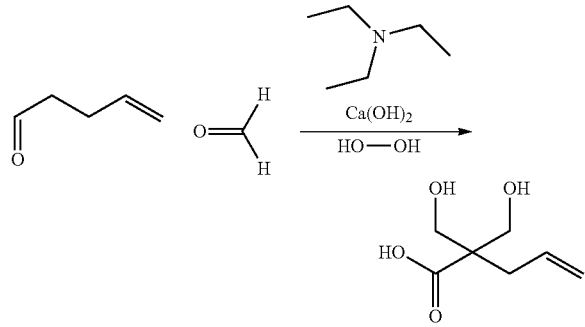

To a mixture of Ca(OH)$_2$ (0.05 eq., 221 mg), TEA (0.05 eq., 0.42 ml) and formalin (37% aqueous solution, 2.2 eq., 9.8 ml) at room temperature was slowly added pent-4-enal (1 eq., 5.02 g). The reaction mixture was stirred at room temperature for 4 h, and fomic acid was added until pH 7. The resulting mixture was concentrated to dryness to remove volatile starting materials. Water (31 ml) and H$_2$O$_2$ (30% aqueous solution, 2 eq., 12 ml) were added. The mixture was stirred at room temperature for 48 h. Concentrated HCl was added until pH 3. The resulting mixture was concentrated to dryness, triturated with EtOAc and filtered. The filtrated was concentrated to yield the crude product (8.72 g) used directly in next step.

B. Methyl 2,2-bis(hydroxymethyl)pent-4-enoate

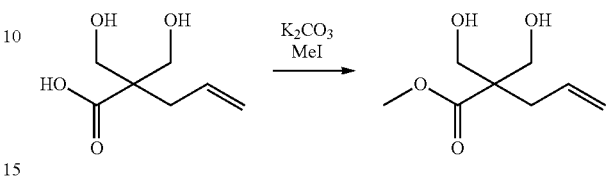

A mixture of crude 2,2-bis(hydroxymethyl)pent-4-enoic acid (1 eq., 8.72 g), K$_2$CO$_3$ (3 eq., 22.9 g) and acetone (109 ml) was stirred at room temperature for 30 min. MeI (6 eq., 46.4 g) was added at 0° C. The mixture was stirred at room temperature for 2 days and concentrated. Water and EtOAc were added. The aqueous layer was extracted with 3×EtOAc. The organic layers were dried over MgSO$_4$. Silica gel chromatography using 4-40% ACN (containing 5% MeOH)-DCM yields the title compound as colorless oil (2.2 g, 23% for two steps).

C. Methyl 3-allyloxetane-3-carboxylate

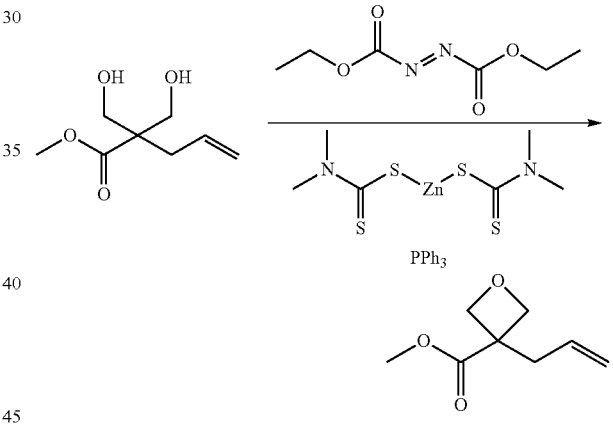

DEAD (1.2 eq., 2.64 g) was added to a solution of methyl 2,2-bis(hydroxymethyl)pent-4-enoate (1 eq., 2.2 g), Ziram® (1.2 eq., 4.64 g) and triphenylphosphine (1.2 eq., 3.98 g) in PhMe (32 ml). The mixture was stirred at room temperature for 2 days and filtered. The filter cake was washed with 3×DCM. The filtrate was concentrated at 50 torr and 40° C. Silica gel chromatography using straight DCM yields the title compound as colorless oil (1.27 g, 64%).

D. Methyl 3-(3-hydroxypropyl)oxetane-3-carboxylate

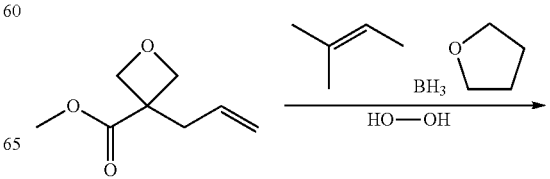

193
-continued

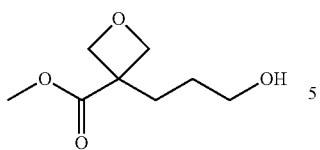

The title compound was prepared analogous to ethyl 5-hydroxy-2-(2-methoxyethyl)-2-methylpentanoate.

E. Methyl 3-(3-iodopropyl)oxetane-3-carboxylate

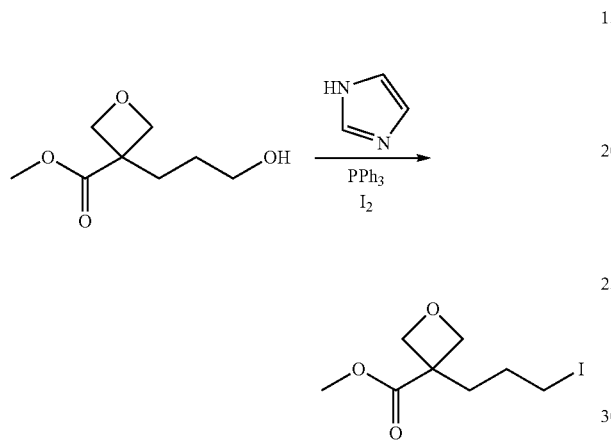

The title compound was prepared analogous to methyl 3-(2-iodoethoxy)-2,2-dimethylpropanoate.

The side chains for examples 29.9991, 29.9992, 29.9993, 29.9996 were prepared by analogy to example 29.7.

The side chains for examples 29.9994 and 29.9995 were prepared by analogy to 29.96 steps D and E.

Example 29.9997 was a byproduct in the synthesis of Example 29.96. Example 29.9998 was prepared from the compound of example 29.9997 using KCN in 1:1 tert-butanol:DMSO, and example 29.9999 was prepared by NaOH hydrolysis of example 29.9998.

Example 29.99991 was prepared from the compound of example 29.9996 using trifluoroacetic acid:dichloromethane 1:4. Example 29.99992 was prepared from the compound of example 29.99991 with acetic anhydride/pyridine. Example 29.99993 was prepared from the example of 29.99991 with formaldehyde and sodium triacetoxy borohydride. Example 29.999993 was prepared using trifluoroacetic acid:dichloromethane 1:4 with the alkylation product prior to hydrolysis en route to 29.9996.

Examples 29.99997, 29.99998, 29.99999 and 29.999991 were prepared by amide couplings to Example 25.1 using HATU, and diisopropylethylamine in DMF, with Examples 29.99999 and 29.999991 followed by hydrolysis using NaOH aq.

Examples 29.999994 and 29.999996 were prepared by stirring the compound of example 44.1 with MeOH and DBU 3:1 at 60° C., and hydrolysis with NaOH 2M aq at 60° C.

Example 29.999995 was prepared by stirring the compound of example 44.1 with KCN in tBuOH:DMSO 1:1 at 60° C. and hydrolysis with NaOH 2M aq at 60° C. Example 29.999997 was obtained by analogy to example 25.1, example 2.1 and example 42 step B.

194

Example 30

2-(4-Fluoro-phenyl)-9-methanesulfonyl-5-methyl-6,7,8,9-tetrahydro-5H-1-oxa-9,10-diaza-cyclohepta[f]indene-3-carboxylic acid methylamide A. 2-(4-Fluoro-phenyl)-5-iodo-6-(methanesulfonyl-pent-4-enyl-amino)-furo[2,3-b]pyridine-3-carboxylic acid methylamide

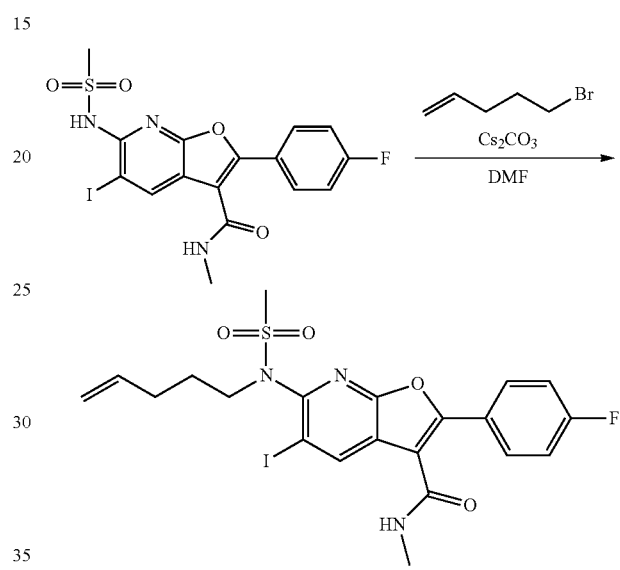

A mixture of 2-(4-fluorophenyl)-5-iodo-N-methyl-6-(methylsulfonamido)furo[2,3-b]pyridine-3-carboxamide (440 mg), Cs$_2$CO$_3$ (322 mg, 1.1 eq.), 5-bromopent-1-ene (402 mg, 3 eq.) and dry DMF (4.5 ml) was stirred in a microwave reactor at 150° C. for 15 min and cooled to rt. Water was added and the mixture was extracted with methylene chloride. The organic layer was washed with 2× water. Silica gel flash chromatography using 0-11% ether-methylene chloride yielded the title compound (250 mg, 55%). MS (ESI) m/z 558.1 (M+1). Retention time=1.33 min (Method A).

B. Mixture of 2-(4-Fluoro-phenyl)-9-methanesulfonyl-5-methylene-6,7,8,9-tetrahydro-5H-1-oxa-9,10-diaza-cyclohepta[f]indene-3-carboxylic acid methylamide and 2-(4-Fluoro-phenyl)-9-methanesulfonyl-5-methyl-8,9-dihydro-7H-1-oxa-9,10-diaza-cyclohepta[f]indene-3-carboxylic acid methylamide

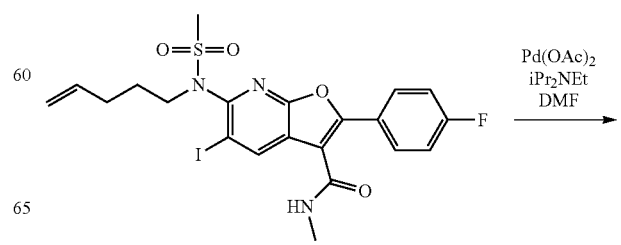

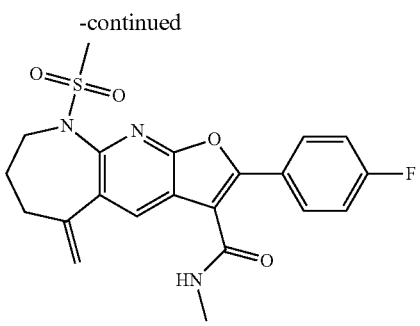

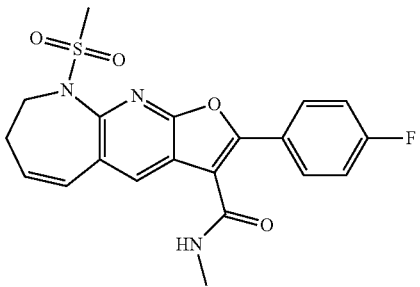

A mixture of 2-(4-fluoro-phenyl)-5-iodo-6-(methane-sulfonyl-pent-4-enyl-amino)-furo[2,3-b]pyridine-3-carboxylic acid methylamide (250 mg), triethylamine (0.069 ml, 1.1 eq.), Pd(OAc)₂ (20 mg, 0.2 eq.) and dry DMF (2.2 ml) was stirred in a microwave reactor at 120° C. for 45 min. The cooled reaction mixture was purified to yield a mixture of isomers using a Shimadzu preparative HPLC with a Waters XBridge C₈ 30×100 mm column and a water (containing 0.1% ammonium hydroxide)-acetonitrile mobile phase. Gradient time: 15 min. 35% isocratic. MS (ESI) m/z 430.1 (M+1). Retention time=1.42 min (Method A).

C. 2-(4-Fluoro-phenyl)-9-methanesulfonyl-5-methyl-6,7,8,9-tetrahydro-5H-1-oxa-9,10-diaza-cyclohepta[f]indene-3-carboxylic acid methylamide

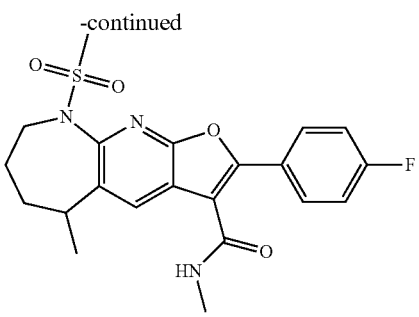

The mixture of 2-(4-fluoro-phenyl)-9-methanesulfonyl-5-methylene-6,7,8,9-tetrahydro-5H-1-oxa-9,10-diaza-cyclohepta[f]indene-3-carboxylic acid methylamide and 2-(4-fluoro-phenyl)-9-methanesulfonyl-5-methyl-8,9-dihydro-7H-1-oxa-9,10-diaza-cyclohepta[f]indene-3-carboxylic acid methylamide (15 mg), Pd(OH)₂ (20% on carbon, 4.9 mg), MeOH (0.56 ml) and EtOAc (0.14 ml) was stirred under hydrogen for 1.5 h at rt. The mixture was filtered through a 0.2 μM PTFE syringe filter and concentrated to give the title compound as an off-white solid. MS (ESI) m/z 432.3 (M+1). Retention time=1.23 min (Method A). ¹H-NMR (400 MHz, CDCl₃) δ ppm 8.13 (s, 1H), 7.94-7.86 (m, 2H), 7.31-7.23 (m, 2H), 5.88 (br, 1H), 3.51 (s, 3H), 3.39-3.31 (m, 1H), 2.10-1.62 (m, 6H), 1.49 (d, 3H).

Example 31

2-(4-Fluoro-phenyl)-6-hydroxy-9-methanesulfonyl-5-methyl-6,7,8,9-tetrahydro-5H-1-oxa-9,10-diaza-cyclohepta[f]indene-3-carboxylic acid methylamide and Example 32

2-(4-Fluoro-phenyl)-5-hydroxy-9-methanesulfonyl-5-methyl-6,7,8,9-tetrahydro-5H-1-oxa-9,10-diaza-cyclohepta[f]indene-3-carboxylic acid methylamide

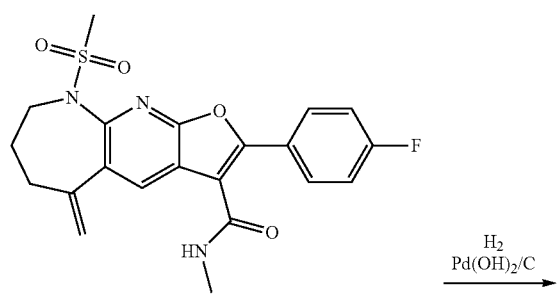

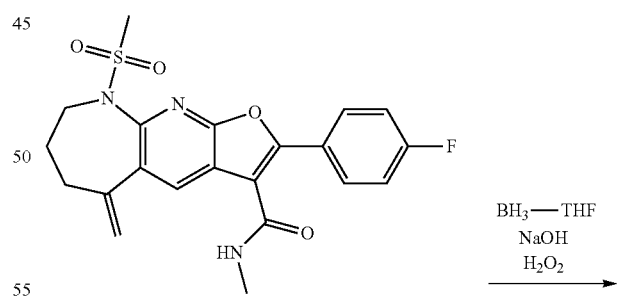

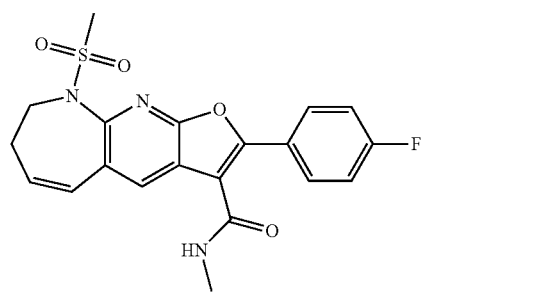

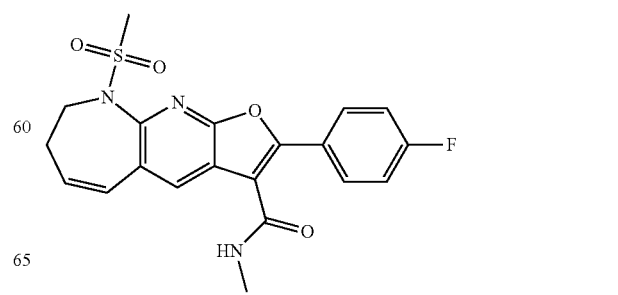

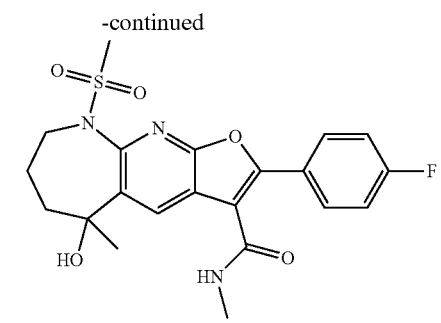

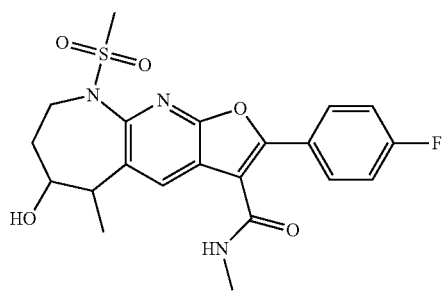

To a mixture of 2-(4-fluoro-phenyl)-9-methanesulfonyl-5-methylene-6,7,8,9-tetrahydro-5H-1-oxa-9,10-diaza-cyclohepta[f]indene-3-carboxylic acid methylamide and 2-(4-fluoro-phenyl)-9-methanesulfonyl-5-methyl-8,9-dihydro-7H-1-oxa-9,10-diaza-cyclohepta[f]indene-3-carboxylic acid methylamide (30 mg) was added solution of BH$_3$.THF in THF (1 M, 0.14 ml, 2 eq.) at 0° C. The mixture was stirred at 5° C. for 16 h. NaOH (10% aq. solution, 2 eq.) and H$_2$O$_2$ (30% aq. solution, 0.030 ml, 4 eq.) were slowly added. The mixture was stirred at rt for 2 h. The reaction mixture was then diluted with EtOAc and the layers were separated. The aqueous phase was extracted with EtOAc. The combined organic phases were washed with brine, dried (Na$_2$SO$_4$), and concentrated in vacuo. The residue was purified using a Shimadzu preparative HPLC with a Waters XBridge C$_8$ 30×100 mm column and a water (containing 0.1% ammonium hydroxide)-acetonitrile mobile phase. Gradient 25-35% over 10 min.

Example 31 MS (ESI) m/z 448.1 (M+1). Retention time=1.28 min, Method A. $^1$H-NMR (400 MHz, CD$_3$CN) δ ppm 8.17 (s, 1H), 8.03-7.97 (m, 2H), 7.33-7.27 (m, 2H), 6.81 (br, 1H), 3.92 (br, 1H), 3.78 (br, H), 3.55 (br, 1H), 3.44 (s, 3H), 3.30 (br, 1H), 3.01 (br, 1H), 2.90 (d, 3H), 1.90-1.73 (m, 2H), 1.41 (d, 3H).

Example 32 MS (ESI) m/z 448.1 (M+1). Retention time=1.33 min, Method A. NMR (400 MHz, CD$_3$CN) δ ppm 8.57 (s, 1H), 8.04-7.98 (m, 2H), 7.33-7.27 (m, 2H), 6.81 (br, 1H), 4.11-4.01 (m, 1H), 3.44 (s, 3H), 3.13-3.07 (m, 1H), 2.91 (d, 3H), 2.52 (s, 1H), 2.08-1.79 (m, 4H), 1.62 (s, 3H).

Example 33

(5R,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide and Example 34: (5S,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide A. 2-(4-fluorophenyl)-N-methyl-6-(methylsulfonamido)-5-(prop-1-en-2-yl)furo[2,3-b]pyridine-3-carboxamide

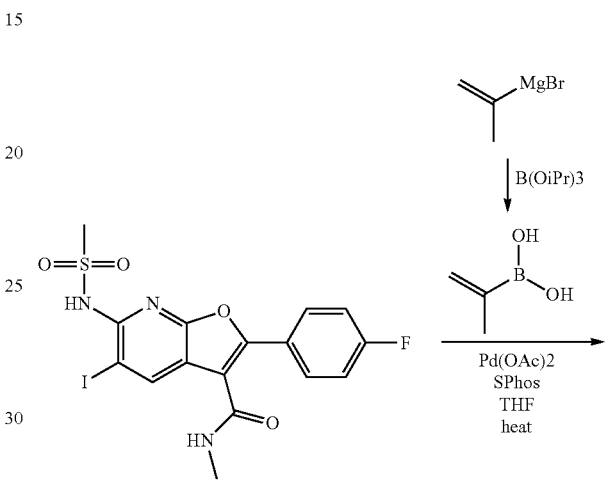

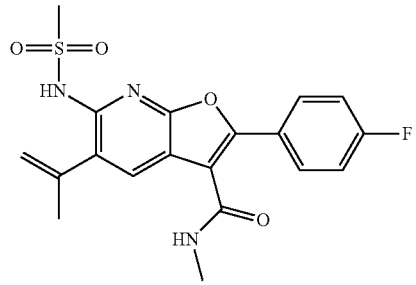

To prop-1-en-2-ylmagnesium bromide (0.5 M THF solution, 6.1 ml, 5 eq.) in a heatgun-dried microwave tube at 0° C. was added triisopropyl borate (0.71 ml, 5 eq.). The mixture was stirred at 0° C. for 15 min and warmed to rt. K$_2$CO$_3$ (2 M aq. solution, 1.5 ml, 5 eq.) was added. The mixture was stirred at rt for 15 min. 2-(4-Fluorophenyl)-5-iodo-N-methyl-6-(methylsulfonamido)furo[2,3-b]pyridine-3-carboxamide (300 mg, 1 eq.) and Pd(PPh$_3$)$_4$ (106 mg, 0.15 eq.) were added. The mixture was degassed, stirred in a microwave reactor at 120° C. for 20 min and cooled. Water was added followed by LiOH (1 M aq. solution, 1.8 ml). The mixture was washed with ether. (It took a long time for layers to settle. There may be a solid meta-phase which can be filtered out as pure product.) Aq. layer was acidified to pH 3.5 using saturated citric acid. Precipitate was filtered, washed with water and lyophilized to give the title compound as an off-white solid (180 mg, 73%). MS (ESI) m/z 404.2 (M+1). Retention time=1.23 min (Method A).

B. Example 35
(S)-6-(N-(2-(benzyloxy)but-3-enyl)methylsulfonamido)-2-(4-fluorophenyl)-N-methyl-5-(prop-1-en-2-yl)furo[2,3-b]pyridine-3-carboxamide

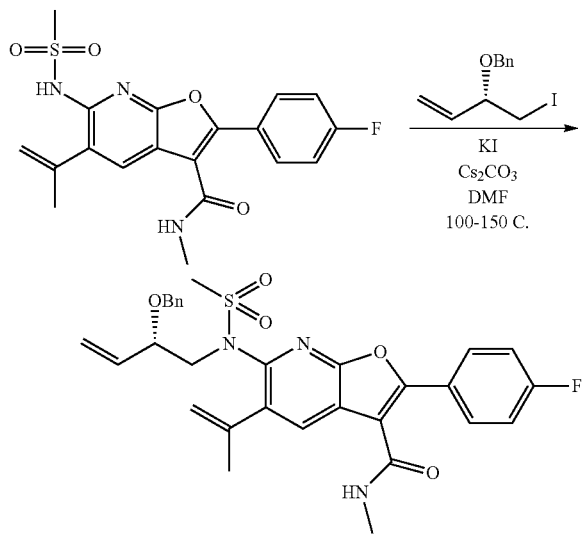

2-(4-fluorophenyl)-N-methyl-6-(methylsulfonamido)-5-(prop-1-en-2-yl)furo[2,3-b]pyridine-3-carboxamide (87 mg, 0.216 mmol), (S)-((1-iodobut-3-en-2-yloxy)methyl)benzene (62.1 mg, 0.216 mmol) and cesium carbonate (70.3 mg, 0.216 mmol) are heated under microwave irradiation for 30 min at 120° C. HPLC affords (S)-6-(N-(2-(benzyloxy)but-3-enyl)methylsulfonamido)-2-(4-fluorophenyl)-N-methyl-5-(prop-1-en-2-yl)furo[2,3-b]pyridine-3-carboxamide (70 mg, 0.124 mmol, 57.6% yield)

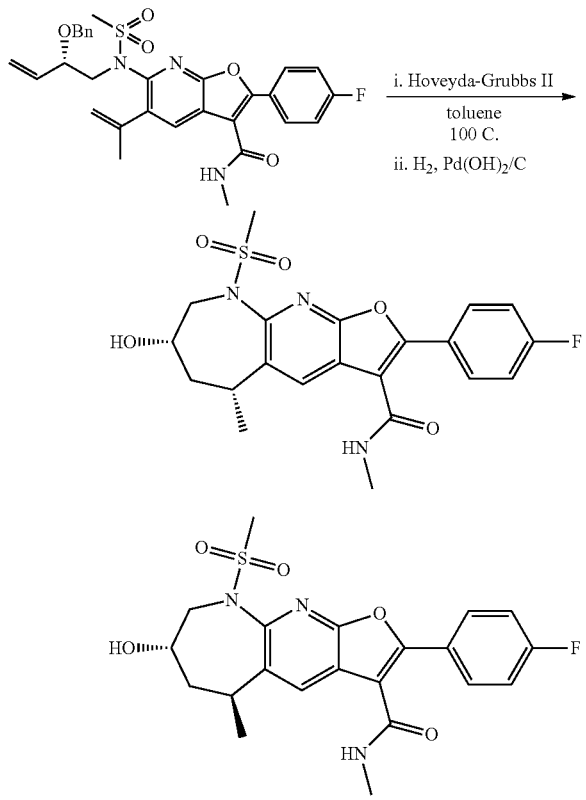

To a solution of (S)-6-(N-(2-(benzyloxy)but-3-enyl)methylsulfonamido)-2-(4-fluorophenyl)-N-methyl-5-(prop-1-en-2-yl)furo[2,3-b]pyridine-3-carboxamide (543 mg, 0.963 mmol) in toluene is added Hoveyda-Grubbs $2^{nd}$ generation catalyst (6 mg, 0.0096 mmol), and the reaction mixture is heated to 100° C. for 18 h. After the reaction is judged complete by LCMS, the toluene is removed in vacuo, and the solid is triturated with methanol to afford (S)-7-Benzyloxy-2-(4-fluoro-phenyl)-9-methanesulfonyl-5-methyl-8,9-dihydro-7H-1-oxa-9,10-diaza-cyclohepta[f]indene-3-carboxylic acid methylamide that is taken directly to the next step.

To a solution of (S)-7-Benzyloxy-2-(4-fluoro-phenyl)-9-methanesulfonyl-5-methyl-8,9-dihydro-7H-1-oxa-9,10-diaza-cyclohepta[f]indene-3-carboxylic acid methylamide (252 mg, 0.471 mmol) in 10:1 ethyl acetate-ethanol is added 25 mg 5% Pd/C and the reaction mixture is stirred under a balloon of $H_2$ until it is judged complete by LCMS. The reaction mixture is filtered, evaporated to dryness and resolved on IA semiprep with 40% EtOH/heptane.

Peak 1 elutes at 7.41 min: Example 34 (5S,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide Peak 2 elutes at 15.47 min: Example 33 (5R,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide (51 mg, 0.114 mmol)

Example 36

A. 2-(4-Fluorophenyl)-N-methyl-6-(methylsulfonamido)-5-vinylfuro[2,3-b]pyridine-3-carboxamide is prepared by analogy to 2-(4-Fluorophenyl)-N-methyl-6-(methylsulfonamido)-5-(prop-1-en-2-yl)furo[2,3-b]pyridine-3-carboxamide, step A of Example 33. Potassium vinyltrifluoroborate may be used as the coupling partner.

B. 2-(4-fluorophenyl)-N-methyl-6-(N-(pent-4-enyl)methylsulfonamido)-5-vinylfuro[2,3-b]pyridine-3-carboxamide

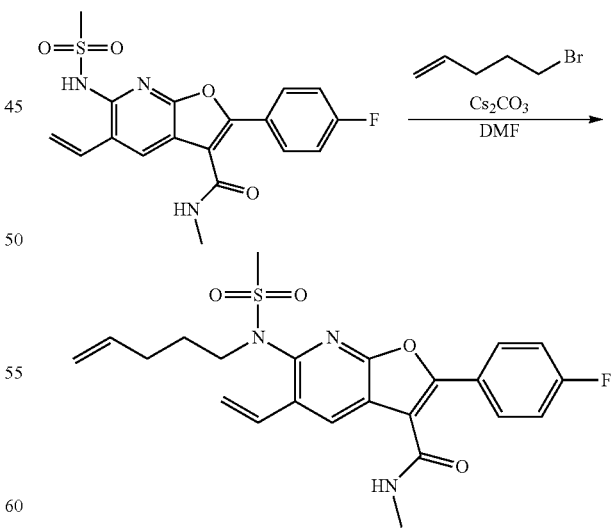

The title compound was prepared analogous to 2-(4-fluoro-phenyl)-5-iodo-6-(methanesulfonyl-pent-4-enyl-amino)-furo[2,3-b]pyridine-3-carboxylic acid methylamide. MS (ESI) m/z 458.2 (M+1). Retention time 1.66 min (Method A).

C. (Z)-2-(4-Fluoro-phenyl)-10-methanesulfonyl-7,8,9,10-tetrahydro-1-oxa-10,11-diaza-cycloocta[f]indene-3-carboxylic acid methylamide

D. 2-(4-Fluoro-phenyl)-10-methanesulfonyl-5,6,7,8,9,10-hexahydro-1-oxa-10,11-diaza-cycloocta[f]indene-3-carboxylic acid methylamide

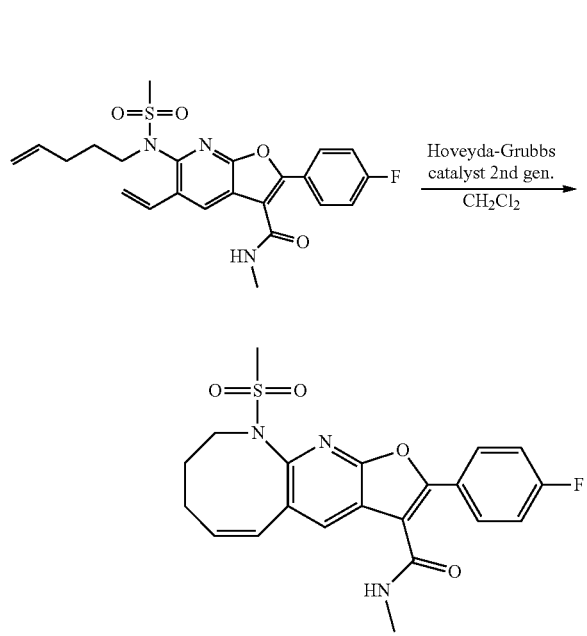

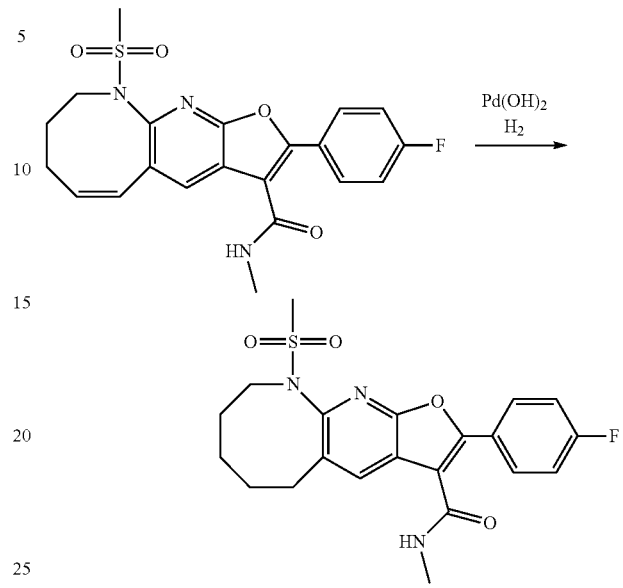

A mixture of 2-(4-fluorophenyl)-N-methyl-6-(N-(pent-4-enyl)methylsulfonamido)-5-vinylfuro[2,3-b]pyridine-3-carboxamide (5.0 mg, 1 eq.), Hoveyda-Grubbs catalyst $2^{nd}$ generation (0.7 mg, 0.1 eq.) and methylene chloride (0.55 ml) was degassed and stirred in a microwave reactor at 100° C. for 15 min. The reaction mixture was diluted with EtOAc, filtered through a 0.2 μM PTFE syringe filter and concentrated to yield the crude title compound which was used without purification in the next step.

The title compound was prepared analogous to 2-(4-Fluoro-phenyl)-9-methanesulfonyl-5-methyl-6,7,8,9-tetrahydro-5H-1-oxa-9,10-diaza-cyclohepta[f]indene-3-carboxylic acid methylamide. The reaction mixture was purified using a Shimadzu preparative HPLC with a Waters XBridge $C_8$ 30×100 mm column and a water (containing 0.1% ammonium hydroxide)-acetonitrile mobile phase. Gradient: 25-35% over 10 min. MS (ESI) m/z 432.0 (M+1). Retention time 1.45 min (Method A). $^1$H NMR (400 MHz, CDCl$_3$) δ ppm 8.13 (s, 1H), 7.97-7.90 (m, 2H), 7.27-7.20 (m, 2H), 5.72 (br, 1H), 4.75-4.70 (m, 1H), 4.15-4.10 (m, 1H), 3.66-3.61 (2H), 3.31 (s, 3H), 3.01 (d, 3H), 1.80-1.30 (m, 6H).

The compounds in Table 9 were prepared in analogy to Example 30 and Example 36.

TABLE 9

| Ex. | Structure | Name |
|---|---|---|
| 36.1 | 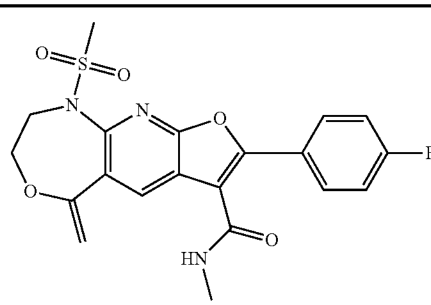 | 2-(4-Fluoro-phenyl)-9-methanesulfonyl-5-methylene-5,7,8,9-tetrahydro-1,6-dioxa-9,10-diaza-cyclohepta[f]indene-3-carboxylic acid methylamide |
| 36.2 | 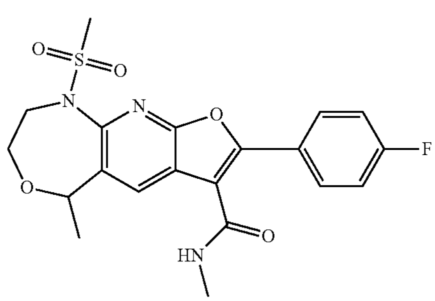 | 2-(4-Fluoro-phenyl)-9-methanesulfonyl-5-methyl-5,7,8,9-tetrahydro-1,6-dioxa-9,10-diaza-cyclohepta[f]indene-3-carboxylic acid methylamide |

TABLE 9-continued

| Ex. | Structure | Name |
|---|---|---|
| 36.3 | 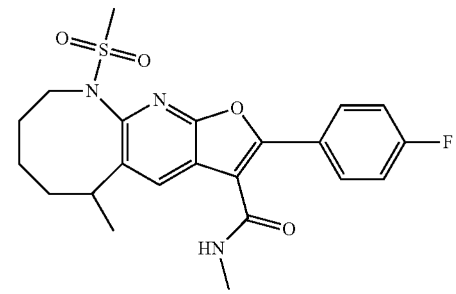 | 2-(4-Fluoro-phenyl)-10-methanesulfonyl-5-methyl-5,6,7,8,9,10-hexahydro-1-oxa-10,11-diaza-cycloocta[f]indene-3-carboxylic acid methylamide |
| 36.4 | 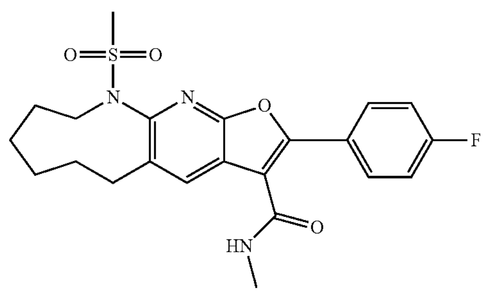 | 2-(4-Fluoro-phenyl)-11-methanesulfonyl-6,7,8,9,10,11-hexahydro-5H-1-oxa-11,12-diaza-cyclonona[f]indene-3-carboxylic acid methylamide |
| 36.5 | 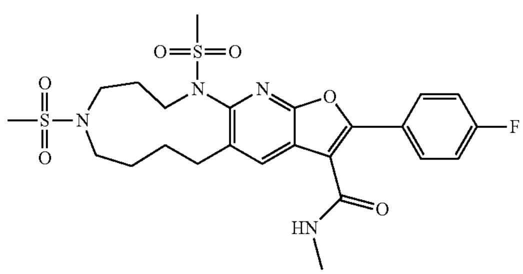 | 2-(4-Fluoro-phenyl)-9,13-bis-methanesulfonyl-6,7,8,9,10,11,12,13-octahydro-5H-1-oxa-9,13,14-triaza-cycloundeca[f]indene-3-carboxylic acid methylamide |
| 36.6 | 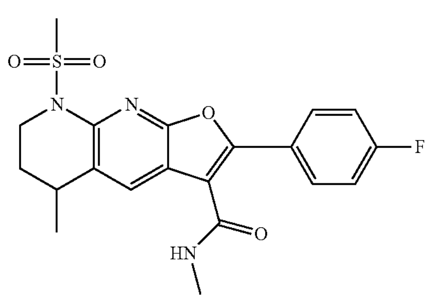 | 2-(4-fluorophenyl)-N,5-dimethyl-8-(methylsulfonyl)-5,6,7,8-tetrahydrofuro[2,3-b][1,8]naphthyridine-3-carboxamide |

Example 36.5 is prepared in analogy to example 30 from the compound of example 23.994.

Example 37

2-(4-Fluoro-phenyl)-1'-methanesulfonyl-5-methyl-6,7,8,9,10,11-hexahydro-5H-1-oxa-11,12-diaza-cyclonona[f]indene-3-carboxylic acid methylamide A. 2-(4-Fluorophenyl)-6-(N-(hex-5-enyl)methylsulfonamido)-5-iodo-N-methylfuro[2,3-b]pyridine-3-carboxamide

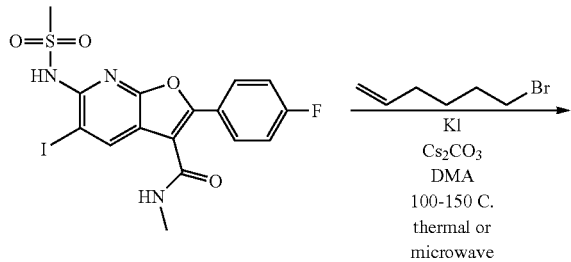

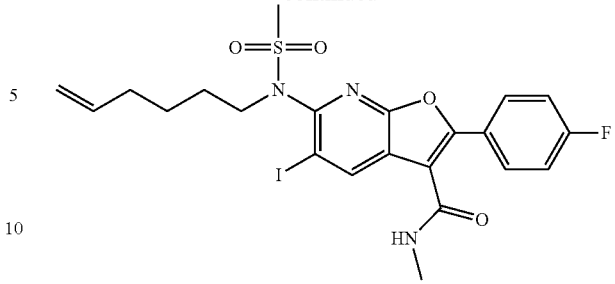

The title compound was prepared analogous to 2-(4-fluorophenyl)-6-(N-(pent-4-enyl)methylsulfonamido)-5-iodo-N-methylfuro[2,3-b]pyridine-3-carboxamide. MS (ESI) m/z 571.9 (M+1). Retention time=1.63 min (Method A).

B. 2-(4-Fluorophenyl)-5-iodo-N-methyl-6-(N-(6-(4,4,5,5-tetramethyl-1,3,2-dioxaborolan-2-yl)hept-5-enyl)methylsulfonamidoguro[2,3-b]pyridine-3-carboxamide

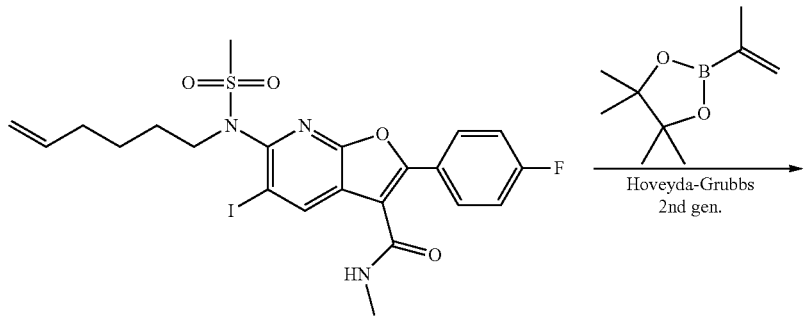

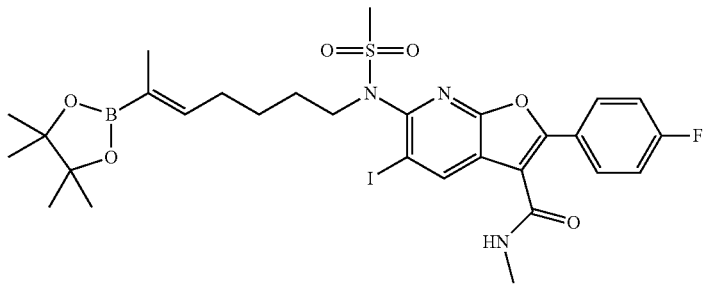

A mixture of 2-(4-fluorophenyl)-6-(N-(hex-5-enyl)methylsulfonamido)-5-iodo-N-methylfuro[2,3-b]pyridine-3-carboxamide (95 mg, 1 eq.), 4,4,5,5-tetramethyl-2-(prop-1-en-2-yl)-1,3,2-dioxaborolane (140 mg, 5 eq.), Hoveyda-Grubbs catalyst ($2^{nd}$ generation) (10 mg, 0.1 eq.) and methylene chloride (17 ml) was degassed and stirred in a microwave reactor at 100° C. for 15 min. The cooled reaction mixture was purified using a Shimadzu preparative HPLC with a Waters XBridge $C_8$ 30×100 mm column and a water (containing 0.1% ammonium hydroxide)-acetonitrile mobile phase. Gradient time: 15 min. MS (ESI) m/z 712.0 (M+1). Retention time=1.51 min (Method 8).

C. (E)-2-(4-Fluoro-phenyl)-1'-methanesulfonyl-5-methyl-8,9,10,11-tetrahydro-7H-1-oxa-11,12-diaza-cyclonona[f]indene-3-carboxylic acid methylamide

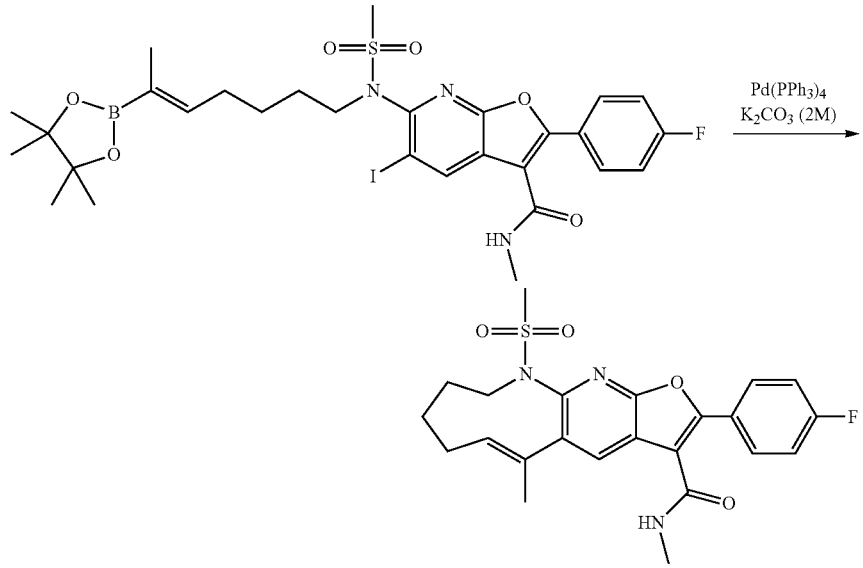

A mixture of 2-(4-fluorophenyl)-5-iodo-N-methyl-6-(N-(6-(4,4,5,5-tetramethyl-1,3,2-dioxaborolan-2-yl)hept-5-enyl)methylsulfonamido)furo[2,3-b]pyridine-3-carboxamide (18 mg, 1 eq.), K$_2$CO$_3$ (2 M aq. solution, 0.025 ml, 2 eq.), Pd(PPh$_3$)$_4$ (7.1 mg, 0.2 eq.) and THF (13 ml) was degassed and stirred in a microwave reactor at 130° C. for 1 h. The mixture was cooled and water was added. The mixture was extracted with EtOAc. The EtOAc layer was dried over MgSO$_4$ and concentrated to yield the crude title compound which was used in next step with no purification. MS (ESI) m/z 458.1 (M+1). Retention time 1.07 min (Method 8).

D. 2-(4-Fluoro-phenyl)-11-methanesulfonyl-5-methyl-6,7,8,9,10,11-hexahydro-5H-1-oxa-11,12-diaza-cyclonona[f]indene-3-carboxylic acid methylamide

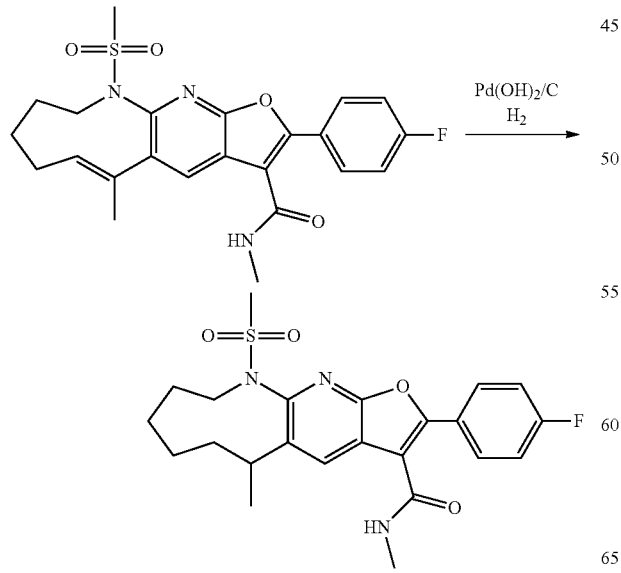

The title compound was prepared analogous to 2-(4-Fluoro-phenyl)-9-methanesulfonyl-5-methyl-6,7,8,9-tetrahydro-5H-1-oxa-9,10-diaza-cyclohepta[f]indene-3-carboxylic acid methylamide. The reaction mixture was purified using a Shimadzu preparative HPLC with a Waters XBridge C$_8$ 30×100 mm column and a water (containing 0.1% ammonium hydroxide)-acetonitrile mobile phase. Gradient time: 10 min. MS (ESI) m/z 460.1 (M+1). Retention time 1.59 min (Method A).

Example 38

2-(4-Fluoro-phenyl)-6-hydroxy-11-methanesulfonyl-5-methyl-6,7,8,9,10,11-hexahydro-5H-1-oxa-11,12-diaza-cyclonona[f]indene-3-carboxylic acid methylamide

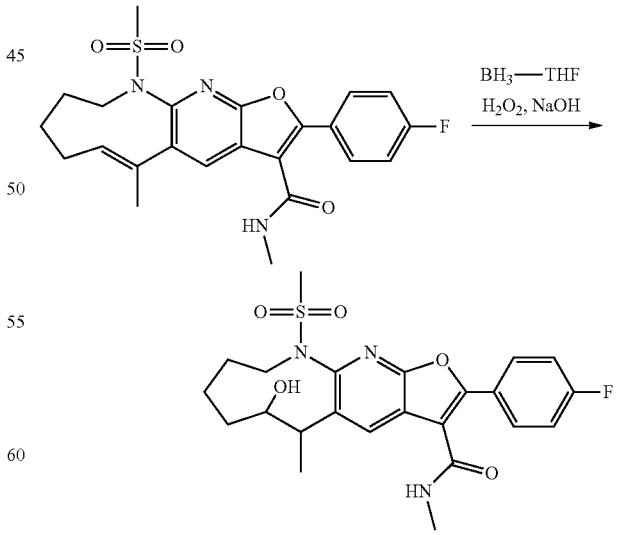

The title compound was prepared analogous to 2-(4-fluoro-phenyl)-6-hydroxy-9-methanesulfonyl-5-methyl-6,7,8,9-tetrahydro-5H-1-oxa-9,10-diaza-cyclohepta[f]indene-3-carboxylic acid methylamide. The reaction mixture was purified using a Shimadzu preparative HPLC with a Waters XBridge C$_8$ 30×100 mm column and a water (containing 0.1% ammonium hydroxide)-acetonitrile mobile phase. Gradient: 26-30% over 15 min. MS (ESI) m/z 476.3 (M+1). Retention time 1.34 min (Method A). $^1$H NMR (400 MHz, CD$_3$CN) δ ppm 8.17 (s, 1H), 8.09-8.01 (m, 2H), 7.34-7.26 (m, 2H), 4.17-4.12 (m, 1H), 3.93-3.88 (m, 1H), 3.55-3.47 (m, 1H), 3.34-3.28 (m, 2H), 3.13 (s, 3H), 2.92 (d, 3H), 1.89-1.75 (m, 6H), 1.42 (d, 3H).

Example 39

2-(4-Fluoro-phenyl)-9-methanesulfonyl-6,7,8,9-tetrahydro-5H-1-oxa-9,10-diaza-cyclohepta[f]indene-3-carboxylic acid methylamide is made by analogy to Example 36. MS (ESI) m/z 418.0 (M+1). Retention time 1.41 min (Method A).

Example 40

2-(4-Fluoro-phenyl)-7,10-bis-methanesulfonyl-5-methyl-5,6,7,8,9,10-hexahydro-1-oxa-7,10,11-triaza-cycloocta[f]indene-3-carboxylic acid methylamide A. N-Allyl-N-(2-bromo-ethyl)-2-nitro-benzenesulfonamide

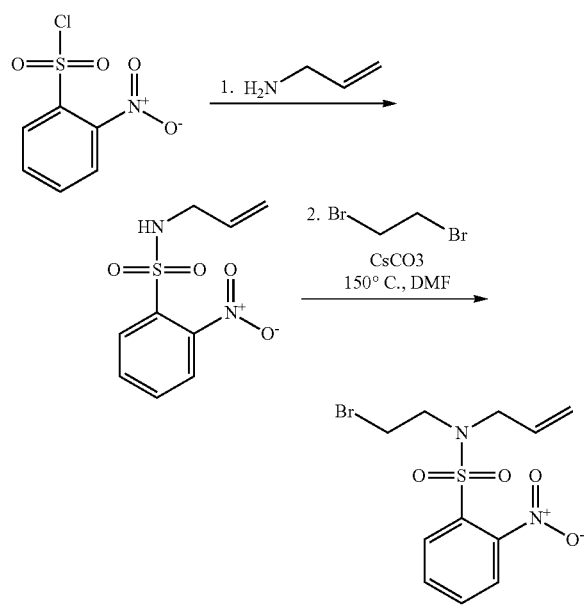

N-Allyl-2-nitro-benzenesulfonamide is prepared following the procedure reported by Cluzeau et al (Cluzeau, J.; Oishi, S.; Ohno, H.; Wang, Z.; Evans, B.; Peiper, S. C.; Fujii, N. *Org. Biomol. Chem.* 2007, 5, 1915-1923.)

N-Allyl-2-nitro-benzenesulfonamide (570 mg, 2.35 mmol) is dissolved in DMF (5 mL) and then CsCO3 (920 mg, 2.82 mmol) and 1,2-dibromoethane (884 mg, 4.71 mmol) is added. The mixture is then microwaved for 30 min at 150° C., then filtered and the solid washed with EtOAc (30 mL). The organic is washed with Brine (20 mL) and then dried over Na2SO4 and then concentrated to dryness. HPLC (CH3CN/H2O/0.1% TFA) provides N-Allyl-N-(2-bromo-ethyl)-2-nitro-benzenesulfonamide (400 mg, 48%). MS-ES [M+H]$^+$=351.1.

B. 6-({2-[Allyl-(2-nitro-benzenesulfonyl)-amino]-ethyl}-methanesulfonyl-amino)-2-(4-fluoro-phenyl)-5-iodo-furo[2,3-b]pyridine-3-carboxylic acid methylamide

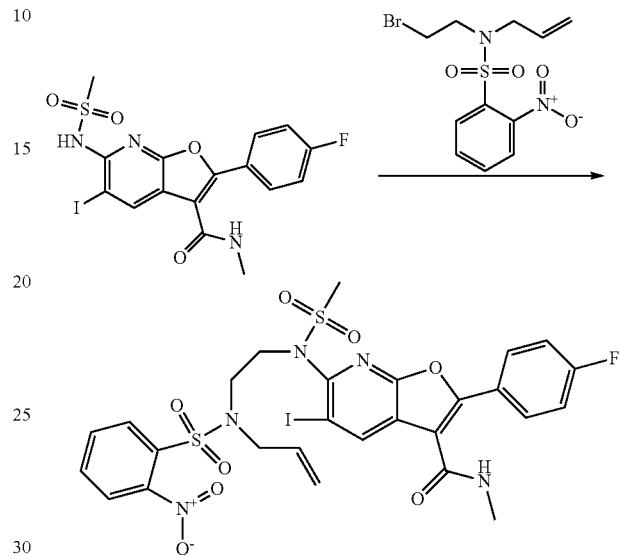

2-(4-Fluoro-phenyl)-5-iodo-6-methanesulfonylamino-furo[2,3-b]pyridine-3-carboxylic acid methylamide (150 mg, 0.31 mmol) is dissolved in DMA (4 mL) and Cs2CO3 (110 mg, 0.34 mmol) and N-Allyl-N-(2-bromo-ethyl)-2-nitro-benzenesulfonamide (214 mg, 0.61 mmol) is added and the mixture is placed in the microwave for 30 min at 150° C. The mixture is then filtered and the solid is washed with EtOAc (30 mL). The organic is washed with H2O (10 mL) then Brine (20 mL) and then dried over Na2SO4 then concentrated to dryness. HPLC (CH3CN/H$_2$O/0.1% TFA) provides 6-({2-[Allyl-(2-nitro-benzenesulfonyl)-amino]-ethyl}-methanesulfonyl-amino)-2-(4-fluoro-phenyl)-5-iodo-furo[2,3-b]pyridine-3-carboxylic acid methylamide (45 mg, 19%). MS-ES [M+H]$^+$=758.3.

C. 2-(4-Fluoro-phenyl)-10-methanesulfonyl-5-methylene-7-(2-nitro-benzenesulfonyl)-5,6,7,8,9,10-hexahydro-1-oxa-7,10,11-triaza-cycloocta[f]indene-3-carboxylic acid methylamide and 2-(4-Fluoro-phenyl)-5-iodo-6-{methanesulfonyl-[2-(2-nitro-benzenesulfonylamino)-ethyl]-amino}-furo[2,3-b]pyridine-3-carboxylic acid methylamide

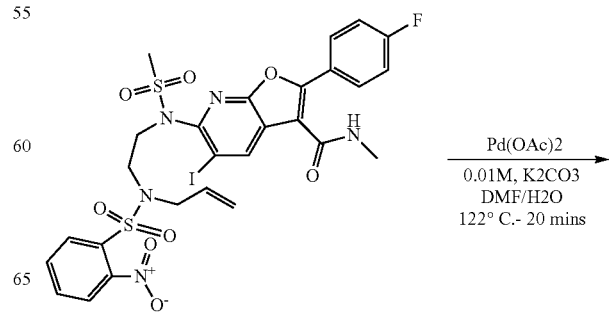

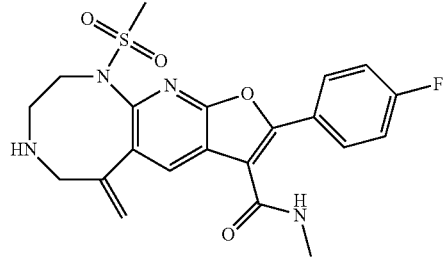

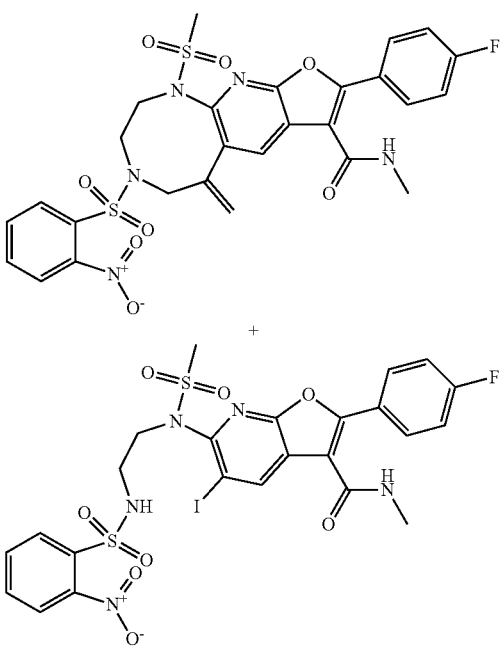

6-({2-[Allyl-(2-nitro-benzenesulfonyl)-amino]-ethyl}-methanesulfonyl-amino)-2-(4-fluoro-phenyl)-5-iodo-furo[2,3-b]pyridine-3-carboxylic acid methylamide (50 mg, 0.07 mmol) is dissolved in DMF/H₂O (10:1, 2 mL: 0.2 mL) and diacetoxypalladium (0.5 mg, 2.64 umol), 1,3-bis(diphenylphosphino)propane (8.17 mg, 0.02 mmol) and potassium carbonate (13.7 mg, 0.10 mmol) are added together then heated in the microwave for 20 min at 122° C. The mixture is then filtered through a bed of celite and the solid is washed with EtOAc (25 mL). The combined organic is then washed with H2O (10 mL), Brine (10 mL) and dried over Na2SO4, followed by evaporation of the solvent. HPLC (CH3CN/H2O/0.1% TFA) provides 2-(4-Fluoro-phenyl)-10-methanesulfonyl-5-methylene-7-(2-nitro-benzenesulfonyl)-5,6,7,8,9,10-hexahydro-1-oxa-7,10,11-triaza-cycloocta[f]indene-3-carboxylic acid methylamide (10 mg, 27%). MS-ES [M+H]⁺=632.3 and 2-(4-Fluoro-phenyl)-5-iodo-6-{methanesulfonyl-[2-(2-nitro-benzenesulfonylamino)-ethyl]-amino}-furo[2,3-b]pyridine-3-carboxylic acid methylamide (3 mg, 7%). MS-ES [M+H]⁺=718.0.

D. 2-(4-Fluoro-phenyl)-10-methanesulfonyl-5-methylene-5,6,7,8,9,10-hexahydro-1-oxa-7,10,11-triaza-cycloocta[f]indene-3-carboxylic acid methylamide

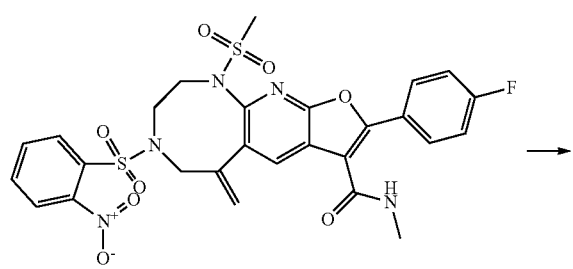

2-(4-Fluoro-phenyl)-10-methanesulfonyl-5-methylene-7-(2-nitro-benzenesulfonyl)-5,6,7,8,9,10-hexahydro-1-oxa-7,10,11-triaza-cycloocta[f]indene-3-carboxylic acid methylamide (4 mg, 7.94 umol) is dissolved in anhydrous THF (0.5 mL) and to this solution Cs2CO3 (25.9 mg, 0.08 mmol) followed by PS-thiophenol (Cardullo et. al Synlett 2005) (100 mg of resin with a 2 mmol/g of loading). This amount of resin is previously treated by shaking for 30 min in a sealed vial with 2 mL of a 0.7M solution of PPh3 in dry deoxygenated THF. The resin is filtered on a sintered glass, washed with dry THF and then used immediately without drying. The mixture is then stirred slowly overnight. The solid is filtered then washed several times with THF (25 mL) and CH2Cl2 (20 mL). The combined organic is evaporated to afford 2-(4-Fluoro-phenyl)-10-methanesulfonyl-5-methylene-5,6,7,8,9,10-hexahydro-1-oxa-7,10,11-triaza-cycloocta[f]indene-3-carboxylic acid methylamide (2 mg, 56%). MS-ES [M+H]⁺=444.9.

Cardullo, F.; Donati, D.; Merlo, G.; Paio, A.; Salaris, M.; Taddei, M.; *Synlett*. 2005, 19, 2996-2998.

E. 2-(4-Fluoro-phenyl)-7,10-bis-methanesulfonyl-5-methylene-5,6,7,8,9,10-hexahydro-1-oxa-7,10,11-triaza-cycloocta[f]indene-3-carboxylic acid methylamide

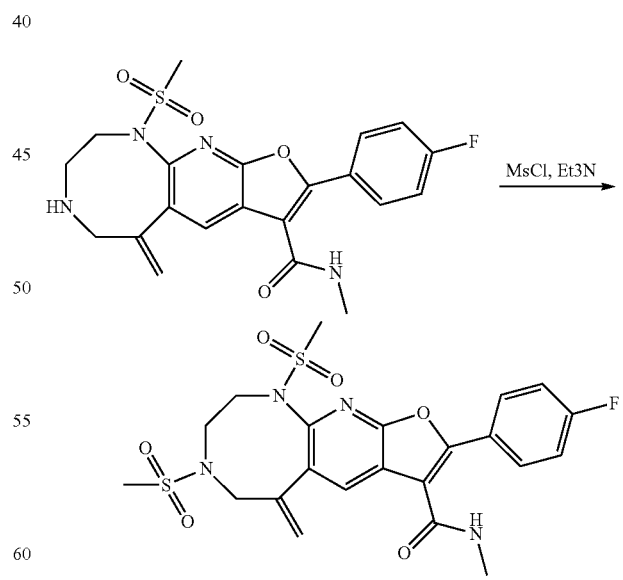

2-(4-Fluoro-phenyl)-10-methanesulfonyl-5-methylene-5,6,7,8,9,10-hexahydro-1-oxa-7,10,11-triaza-cycloocta[f]indene-3-carboxylic acid methylamide (6.0 mg, 0.013 mmol) is dissolved in DCM (2 mL) and the solution is cooled to 0° C. Methanesulfonyl chloride (7.7 mg, 0.07 mmol) is added followed by triethylamine (6.83 mg, 0.07 mmol) and the reaction is allowed to warm up to RT over 3 h then evaporated to dryness and placed on the high vacuum overnight. The sample is then redissolved in EtOAc (25 mL) and then washed with 1N HCl (10 mL), then Brine (20 mL) and dried over Na2SO4. The organic is concentrated to afford 2-(4-Fluoro-phenyl)-7,10-bis-methanesulfonyl-5-methylene-5,6,7,8,9,10-hexahydro-1-oxa-7,10,11-triaza-cycloocta[f]indene-3-carboxylic acid methylamide (3 mg, 42%). MS-ES [M+H]$^+$=523.0.

F. 2-(4-Fluoro-phenyl)-7,10-bis-methanesulfonyl-5-methyl-5,6,7,8,9,10-hexahydro-1-oxa-7,10,11-triaza-cycloocta[f]indene-3-carboxylic acid methylamide

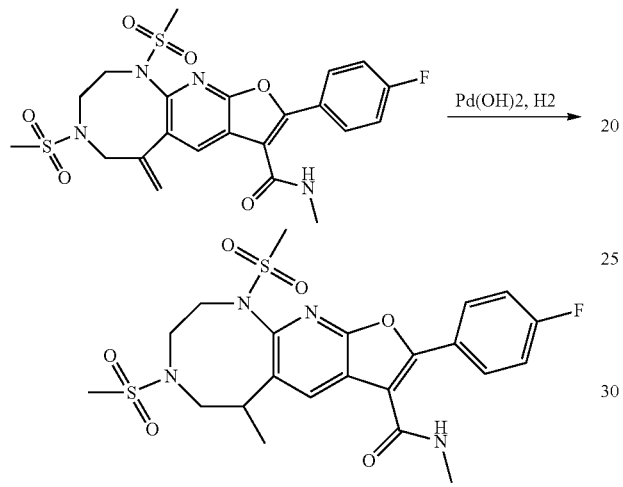

To 2-(4-Fluoro-phenyl)-7,10-bis-methanesulfonyl-5-methylene-5,6,7,8,9,10-hexahydro-1-oxa-7,10,11-triaza-cycloocta[f]indene-3-carboxylic acid methylamide (3 mg, 5.74 umol) dissolved in MeOH:EtOAc (1:1 1 mL) was added Dihydroxypalladium (0.5 mg, 2.87 umol). The reaction was fitted with a balloon of H2 and then stirred overnight. The mixture was filtered through a bed of celite and washed with additional MeOH (10 mL) and EtOAc (10 mL) and then concentrated and purified by HPLC CH3CN/H2O/0.1% TFA) to provide 2-(4-Fluoro-phenyl)-7,10-bis-methanesulfonyl-5-methyl-5,6,7,8,9,10-hexahydro-1-oxa-7,10,11-triaza-cycloocta[f]indene-3-carboxylic acid methylamide (140 ug, 3%). MS-ES [M+H]$^+$=525.2.

Example 41

3-(2-(N-(5-cyclopropyl-3-(methylcarbamoyl)-2-p-tolylfuro[2,3-b]pyridin-6-yl)methylsulfonamido)ethoxy)-2,2-dimethylpropanoic acid

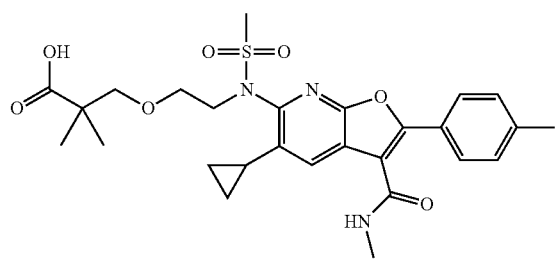

A. Methyl 3-(allyloxy)-2,2-dimethylpropanoate

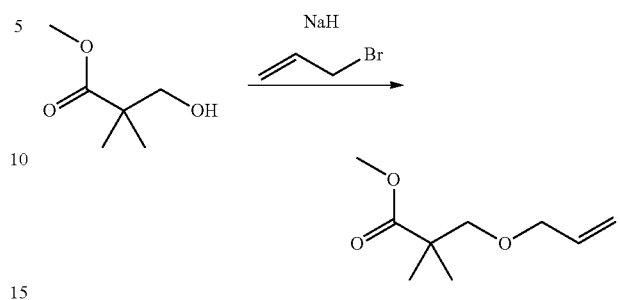

To a mixture of methyl 3-hydroxy-2,2-dimethylpropanoate (5.59 g, 1 eq.) and DMF (42 ml) at 0° C. was slowly added NaH (60% in mineral oil, 1.69 g, 1 eq.). After 30 min, 3-bromoprop-1-ene (5.12 g, 1 eq.) was added. The reaction mixture was warmed to room temperature and stirred overnight. Water was carefully added. The resulting mixture was extracted with EtOAc, dried over MgSO$_4$ and concentrated to yield a light-yellow oil to be used in the next step without purification.

B. Methyl 3-(2-hydroxyethoxy)-2,2-dimethylpropanoate

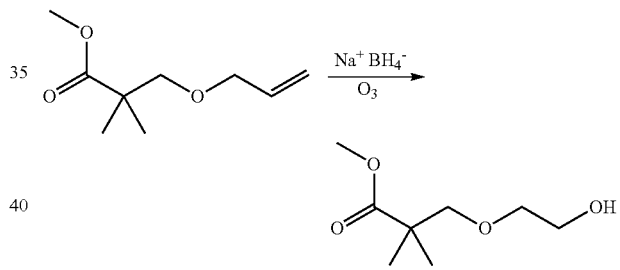

A mixture of crude methyl 3-(allyloxy)-2,2-dimethylpropanoate (7.28 g, 1 eq.), MeOH (63 ml), DCM (63 ml) and pyridine (16 ml) was cooled to −78° C. O$_3$ was passed through the reaction mixture until the colorless solution turned light blue. N$_2$ was passed for 1 min. NaBH$_4$ (4.00 g, 2.5 eq.) was added. The reaction mixture was stirred at 0° C. for 3 h. Saturated aqueous NH$_4$Cl was carefully added. The resulting mixture was extracted with EtOAc, dried over MgSO$_4$ and concentrated. Silica gel chromatography using 6-66% EtOAc-heptane yields the title compound as a colorless oil (7.45 g, 31%).

C. Methyl 3-(2-iodoethoxy)-2,2-dimethylpropanoate

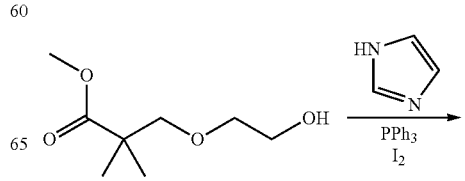

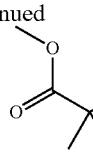

To a mixture of methyl 3-(2-hydroxyethoxy)-2,2-dimethylpropanoate (2.30 g, 1 eq.), 1H-imidazole (1.07 g, 1.2 eq.) and DCM (100 ml) was slowly added resin-bound triphenylphosphine (1.2 eq.) and iodine (3.98 g, 1.2 eq.). The reaction mixture was stirred at room temperature overnight and filtered. The filtrate was concentrated and subject to silica gel chromatography using 0-25% ether-heptane to yield the title compound as a colorless oil (3.73 g, 62%).

D. 3-(2-(N-(5-cyclopropyl-3-(methylcarbamoyl)-2-p-tolylfuro[2,3-b]pyridin-6-yl)methylsulfonamido)ethoxy)-2,2-dimethylpropanoic acid The title compound was prepared analogous to Example 24.01. MS (ESI) m/z 544.0 (M+1). Retention time=1.14 min, Method A.

Example 41.1

3-(2-(N-(5-Cyclopropyl-2-(4-ethylphenyl)-3-(methylcarbamoyl)furo[2,3-b]pyridin-6-yl)methylsulfonamido)ethoxy)-2,2-dimethylpropanoic acid

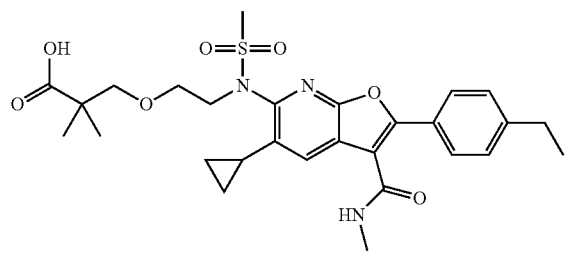

The title compound was prepared analogous to Example 41 MS (ESI) m/z 558.0 (M+1). Retention time=1.23 min, Method A.

Example 42

5-(N-(5-Cyclopropyl-2-(4-ethylphenyl)-3-(methylcarbamoyl)furo[2,3-b]pyridin-6-yl)methylsulfonamido)-2-(2-methoxyethyl)-2-methylpentanoic acid

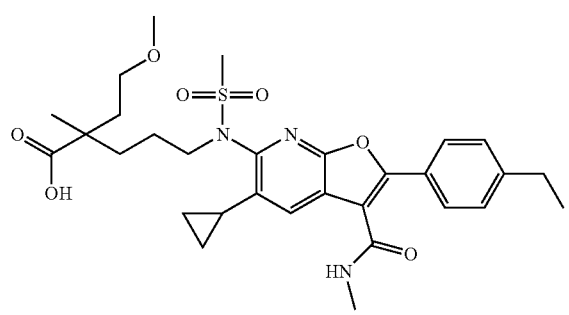

A. Ethyl 2-(2-methoxyethyl)-2-methylpent-4-enoate

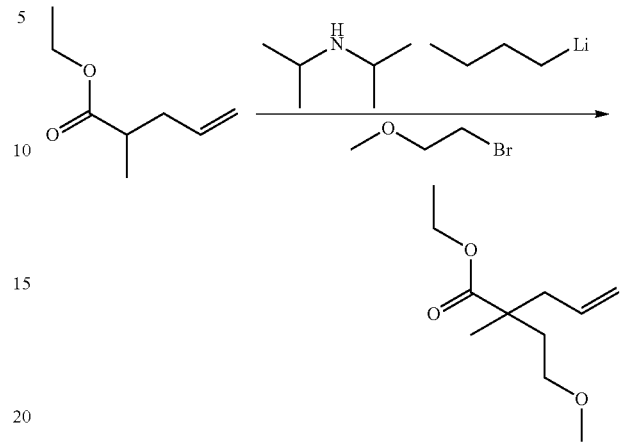

The title compound was prepared analogous to the side chain of Example 29.7 and Example 43 step A.

B. Ethyl 5-hydroxy-2-(2-methoxyethyl)-2-methylpentanoate

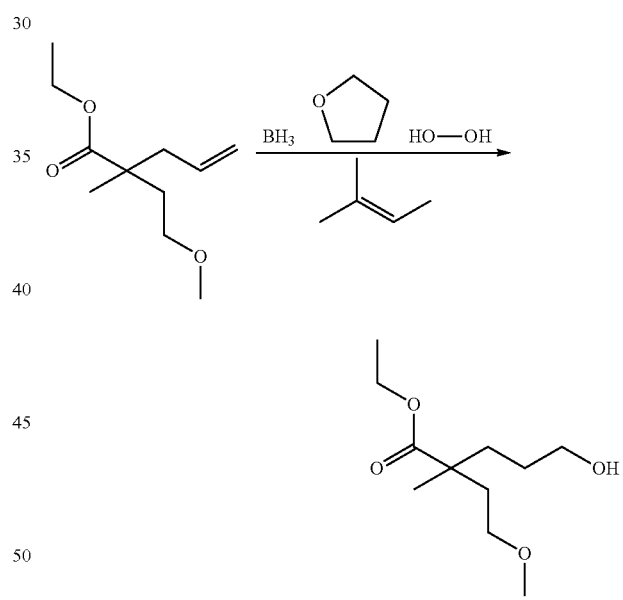

BH$_3$.THF (1 M in THF, 16.5 ml, 1.1 eq.) was added dropwise to a stirred solution of 2-methyl-2-butene (1.75 ml, 1.1 eq.) in dry THF (15 ml) at 0° C. An hour later, a cold solution of ethyl 2-(2-methoxyethyl)-2-methylpent-4-enoate (3.00 g, 1 eq.) in THF (15 ml) was rapidly added. After the reaction mixture had been stirred at room temperature for 1 h, it was quenched with MeOH at 0° C., and then buffer (pH 7, 0.5 M phosphate solution, 18 ml) and H$_2$O$_2$ (30% in water, 18.4 ml, 12 eq.) were added. The reaction mixture was stirred at room temperature for 14 h, poured into brine and extracted with ether. The combined organic phase was washed with saturated aqueous Na$_2$S$_2$O$_3$ solution, water and brine, dried over Na2SO4, and concentrated. Silica gel chromatography using 5-50% ether-DCM yields the title compound (3.27 g, 39%).

C. Ethyl 5-iodo-2-(2-methoxyethyl)-2-methylpentanoate

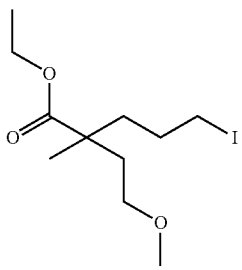

The title compound was prepared analogous to methyl 3-(2-iodoethoxy)-2,2-dimethylpropanoate.

D. 5-(N-(5-Cyclopropyl-2-(4-ethylphenyl)-3-(methylcarbamoyl)furo[2,3-b]pyridin-6-yl)methylsulfonamido)-2-(2-methoxyethyl)-2-methylpentanoic acid The title compound was prepared analogous to Example 24.01. MS (ESI) m/z 586.2 (M+1). Retention time=1.52 min, Method A. The enantiomers were separated using Chiral LC (IA 4.6×100 mm column, 40% isopropanol-hexane, 10 min) and both had 2 nM IC50s.

Example 42.1

5-(N-(5-cyclopropyl-3-(methylcarbamoyl)-2-p-tolyl-furo[2,3-b]pyridin-6-yl)methylsulfonamido)-2-(2-methoxyethyl)-2-methylpentanoic acid

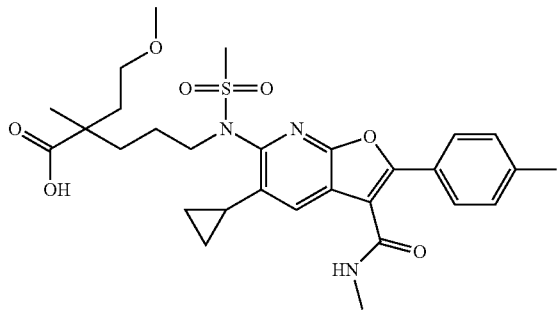

The title compound was prepared analogous to Example 42

Example 43

5-(N-(5-Cyclopropyl-2-(4-ethylphenyl)-3-(methylcarbamoyl)furo[2,3-b]pyridin-6-yl)methylsulfonamido)-2-(methoxymethyl)-2-methylpentanoic acid

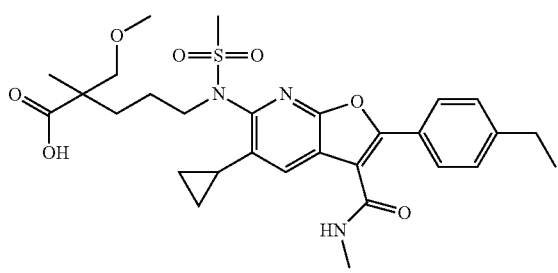

A. Methyl 3-(2-iodoethoxy)-2,2-dimethylpropanoate

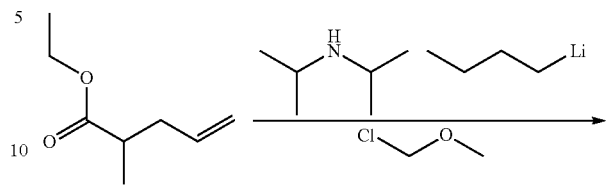

Diisopropylamine (11.0 ml, 1 eq.) was dissolved in THF (100 mL) and cooled to 0° C. n-BuLi (1.6 M in hexanes, 48 ml, 1 eq.) was added, and the mixture was stirred for 30 min. The mixture was cooled to −78° C., and ethyl 2-methylpent-4-enoate (11.0 g, 1 eq.) was added. The reaction mixture was allowed to proceed for 1 h at this temperature, and then chloro(methoxy)methane (5.85 ml, 1 eq.) was added dropwise over 10 min. The reaction mixture was allowed to warm up to room temperature overnight, added to a cooled solution of aqueous NH$_4$Cl, extracted with ether, washed with brine and dried over MgSO$_4$. The filtrate was concentrated and subject to silica gel chromatography using 0-30% ether-pentane to yield the title compound as a colorless oil.

B. Ethyl 5-iodo-2-(methoxymethyl)-2-methylpentanoate

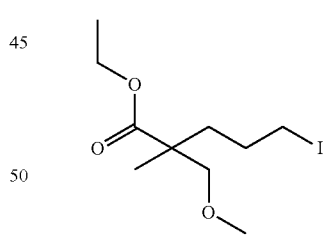

The title compound was prepared analogous to methyl 3-(2-iodoethoxy)-2,2-dimethylpropanoate.

C. 5-(N-(5-Cyclopropyl-2-(4-ethylphenyl)-3-(methylcarbamoyl)furo[2,3-b]pyridin-6-yl)methylsulfonamido)-2-(methoxymethyl)-2-methylpentanoic acid The title compound was prepared analogous to Example 24.01. MS (ESI) m/z 572.1 (M+1). Retention time=1.47 min, Method A. The enantiomers were separated using Chiral LC (IA 4.6×100 mm column, 40% isopropanol-hexane, 10 min) and both had 2 nM IC50.

Example 43.1

5-(N-(5-cyclopropyl-3-(methylcarbamoyl)-2-p-tolyl-furo[2,3-b]pyridin-6-yl)methylsulfonamido)-2-(methoxymethyl)-2-methylpentanoic acid

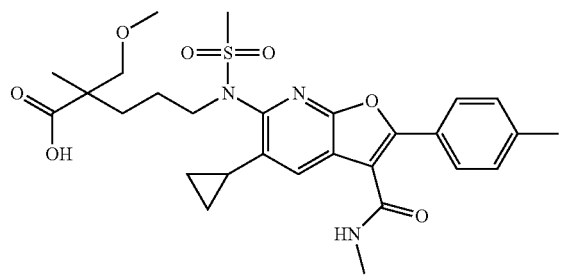

The title compound was prepared by analogy to example 43, and both enantiomers have 2 nM IC50.

Example 44

5-[(5-Cyclopropyl-3-methylcarbamoyl-2-p-tolyl-furo[2,3-b]pyridin-6-yl)-methanesulfonyl-amino]-3-dimethylamino-pentanoic acid

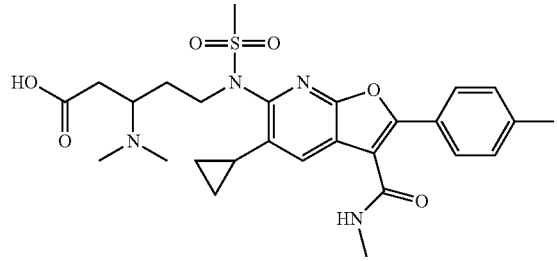

A. 6-(But-3-enyl-methanesulfonyl-amino)-5-cyclopropyl-2-p-tolyl-furo[2,3-b]pyridine-3-carboxylic acid methylamide

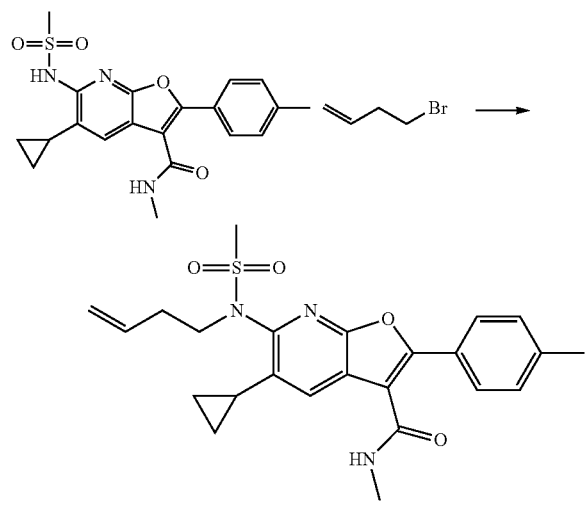

To a solution of 5-cyclopropyl-6-methanesulfonylamino-2-p-tolyl-furo[2,3-b]pyridine-3-carboxylic acid methylamide (900 mg, 2.25 mmol, 1.0 equiv) in DMA (2.0 mL) was added NaI (169 mg, 1.12 mmol, 0.5 equiv) and Cs$_2$CO$_3$ (2.2 g, 6.76 mmol, 3.0 equiv) and the resulting mixture was heated at 110° C. for 1 hour. The mixture was then diluted with EtOAc and washed with water, brine, dried over MgSO$_4$ and concentrated. The residue wad purified by silica gel column chromatography, EtOAc/heptane (70%) to give product 760 mg. MS (ESI) m/z 454.5 (M+1). Retention time=1.58 min, Method LC-C8 broad range-NpH.

B. 5-[(5-Cyclopropyl-3-methylcarbamoyl-2-p-tolyl-furo[2,3-b]pyridin-6-yl)-methanesulfonyl-amino]-pent-2-enoic acid methyl ester

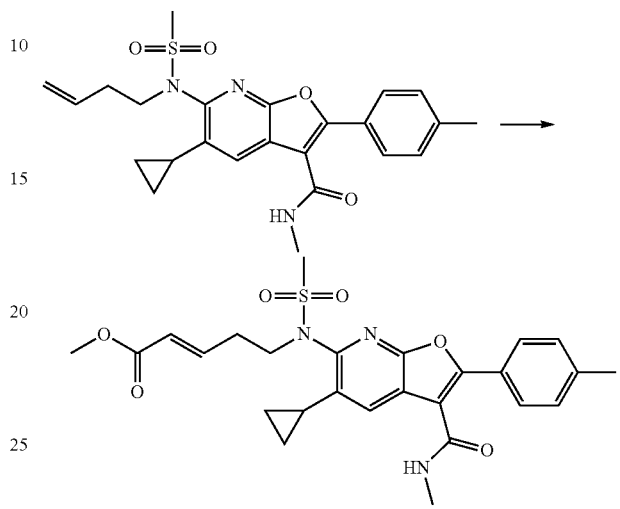

To a solution of Grubbs II catalyst (4.7 mg, 0.005 mmol, 0.05 equiv) in DCM (1.0 mL) was added methyl acrylate (95 mg, 1.1 mmol, 10 equiv) followed by a solution of 6-(But-3-enyl-methanesulfonyl-amino)-5-cyclopropyl-2-p-tolyl-furo[2,3-b]pyridine-3-carboxylic acid methylamide (50 mg, 0.11 mmol, 1.0 equiv) in DCM (1.0 mL). The solution was stirred at room temperature for 2 hours, after which the solvent was removed under vacuum. The residue was purified by silica gel column chromatography, EtOAc/heptane 70% to give product 35 mg. MS (ESI) m/z 512.6 (M+1). Retention time=1.50 min, Method LC-C8 broad range-NpH.

C. 5-[(5-Cyclopropyl-3-methylcarbamoyl-2-p-tolyl-furo[2,3-b]pyridin-6-yl)-methanesulfonyl-amino]-3-dimethylamino-pentanoic acid

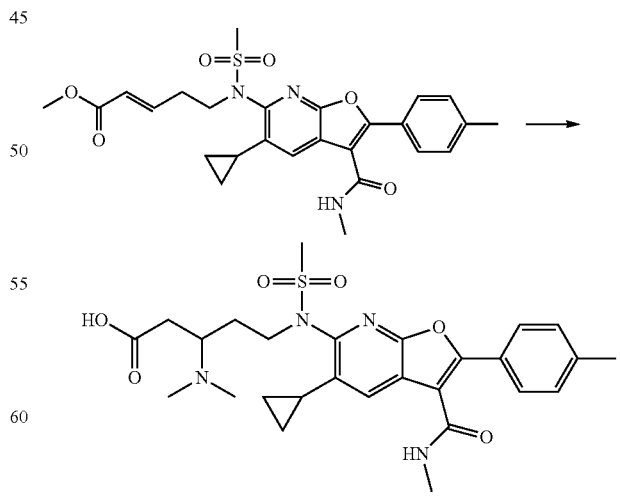

To a solution of 5-[(5-cyclopropyl-3-methylcarbamoyl-2-p-tolyl-furo[2,3-b]pyridin-6-yl)-methanesulfonyl-amino]-pent-2-enoic acid methyl ester (26 mg, 0.051 mmol, 1.0 equiv) in DCM (0.5 mL) was added dimethyl amine (0.10 mL, 2.0 M in THF, 0.2 mmol, 4.0 equiv) and LiClO₄ (10.8 mg, 0.1 mmol, 2.0 equiv). The mixture was stirred at room temperature for 24 hours. The reaction mixture was then diluted with THF (0.3 mL), water (0.3 mL), MeOH (0.3 mL) and to the solution was added LiOH (4.9 mg, 0.2 mmol, 5.0 equiv). The mixture was heated at 55° C. for 20 minutes. The solution was neutralized to pH=7 by addition of 1.0 N HCl aq. solution. The mixture was extracted with $CH_2Cl_2$. The organic layer was dried over $Na_2SO_4$ and concentrated. The residue was purified by reverse phase HPLC with ammonium hydroxide as modifier to give product 6.0 mg. MS (ESI) m/z 543.6 (M+1). Retention time=1.09 min, Method A. ¹H NMR (400 MHz, MeOD) d ppm 0.77-0.92 (m, 2H) 1.09-1.20 (m, 2H) 1.61-1.75 (m, 1 H) 2.00-2.11 (m, 1H) 2.37-2.47 (m, 4H) 2.48-2.58 (m, 2H) 2.68 (s, 6H) 2.93 (s, 3 H) 3.17 (s, 3H) 3.51-3.62 (m, 1H) 3.82-3.94 (m, 1H) 3.94-4.04 (m, 1H) 7.35 (d, J=8.03 Hz, 2H) 7.59 (s, 1H) 7.79 (d, J=8.53 Hz, 2H)

Example 44.1

(E)-ethyl 6-(N-(5-cyclopropyl-3-(methylcarbamoyl)-2-p-tolylfuro[2,3-b]pyridin-6-yl)methylsulfonamido)hex-2-enoate

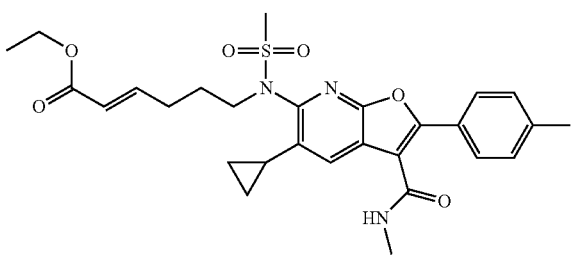

The title compound was prepared by analogy to example 44A and B.

Example 45

2-(2-(N-(5-cyclopropyl-3-(methylcarbamoyl)-2-(p-tolyl)furo[2,3-b]pyridin-6-yl)methylsulfonamido)ethyl)benzoic acid A. 6-(N-(2-chlorophenethyl)methylsulfonamido)-5-iodo-N-methyl-2-(p-tolyl)furo[2,3-b]pyridine-3-carboxamide

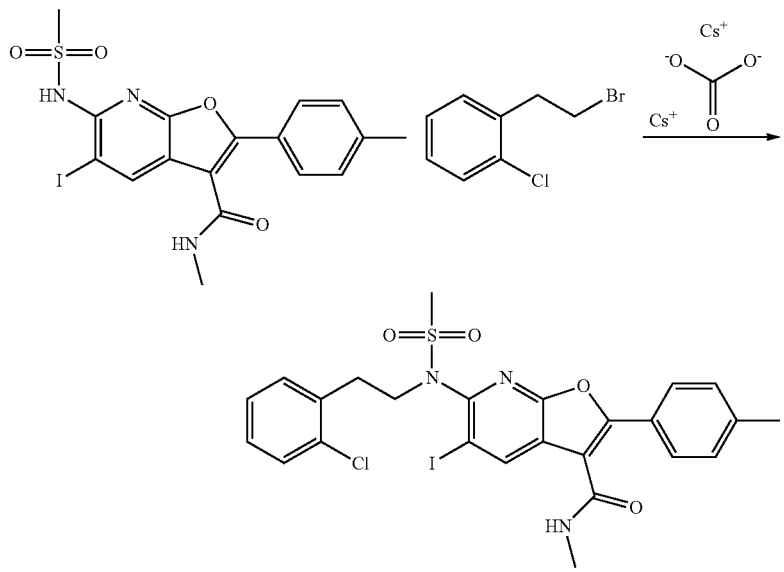

To 5-iodo-N-methyl-6-(methylsulfonamido)-2-(p-tolyl)furo[2,3-b]pyridine-3-carboxamide (150 mg, 0.309 mmol) was added 1-(2-bromoethyl)-2-chlorobenzene (678 mg, 3.09 mmol) and CESIUM CARBONATE (101 mg, 0.309 mmol) was heated at 150° C. µwave 10 min. LCMS showed 1:1 SM/Prod and 1:2 styrene/Br. Added CESIUM CARBONATE (101 mg, 0.309 mmol) and heated additional 10 min at 150° C. µwave. Added water and extracted with EtOAc. Conc. on vac. Added ACN/water and filtered with 0.45 µPTFE filter Purified via HPLC C18 40-70% ACN/water (0.1% NH₄OH) 40 mL/min over 20 min. Elutes at 19 min. (or 50-70% over 15 min) 69.2 mg of 6-(N-(2-chlorophenethyl)methylsulfonamido)-5-iodo-N-methyl-2-(p-tolyl)furo[2,3-b]pyridine-3-carboxamide.

B. 6-(N-(2-chlorophenethyl)methylsulfonamido)-5-cyclopropyl-N-methyl-2-(p-tolyl)furo[2,3-b]pyridine-3-carboxamide

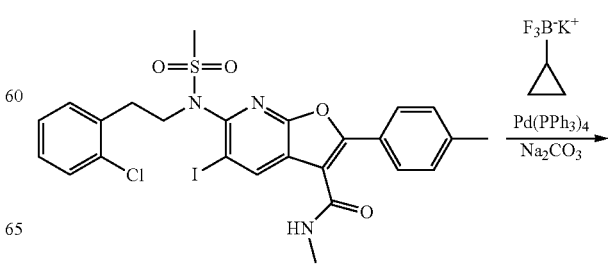

-continued

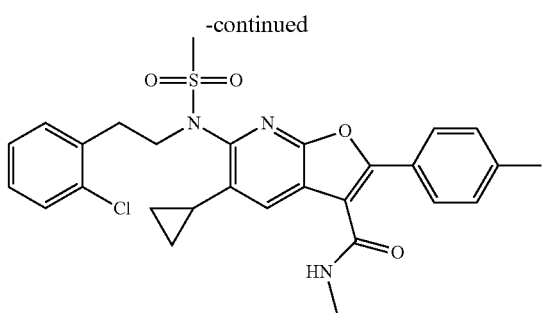

To 6-(N-(2-chlorophenethyl)methylsulfonamido)-5-iodo-N-methyl-2-(p-tolyl)furo[2,3-b]pyridine-3-carboxamide (32 mg, 0.051 mmol) and Tetrakis (5.93 mg, 5.13 µmol) in toluene (513 µL) was added a premixed solution of 2N SODIUM CARBONATE (385 µL, 0.769 mmol) and Potassium cyclopropyltriflruoroborate (76 mg, 0.513 mmol) in toluene (513 µL).

Bubbled with N2 for 5 min and heated at 120° C. in microwave for 20 minutes.

LCMS showed 2:1 Prod/SM-I Added water 50 mL and extracted 4× with EtOAc. Conc on vac.Taken up in ACN (precipitated) solid is Prod and Ph3P (Conc. on vac. and reconstituted in DMF with 10% ACN and water. Purified via HPLC C18 40-75% ACN/water (0.1% NH4OH) 40 mL/min over 20 min to give 6-(N-(2-chlorophenethyl)methylsulfonamido)-5-cyclopropyl-N-methyl-2-(p-tolyl)furo[2,3-b]pyridine-3-carboxamide C. 5-cyclopropyl-N-methyl-2-(p-tolyl)-6-(N-(2-vinylphenethyl)methylsulfonamido)furo[2,3-b]pyridine-3-carboxamide

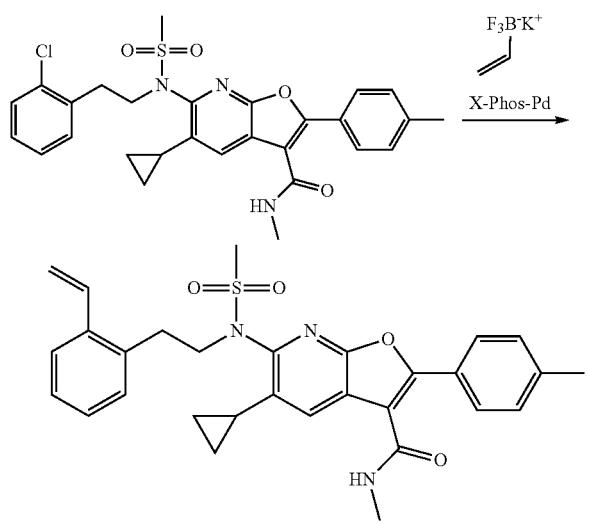

Combined 6-(N-(2-chlorophenethyl)methylsulfonamido)-5-cyclopropyl-N-methyl-2-(p-tolyl)furo[2,3-b]pyridine-3-carboxamide (38 mg, 0.071 mmol), Potassium phosphate Tribasic (nH2O) (244 mg, 1.059 mmol) and Pd-catalyst (42.4 mg, 0.071 mmol) in 3.4 mL 2:1 THF/water. Heated at 120° C. µwave for 20 min. Added water 50 mL and extracted 4× with EtOAc. Conc on vac. Taken up in DMF/ACN/drop of water Purified via HPLC C18 40-75% ACN/water (0.1% NH4OH) 40 mL/min over 20 min to give 10.4 mg 5-cyclopropyl-N-methyl-2-(p-tolyl)-6-(N-(2-vinylphenethyl)methylsulfonamido)furo[2,3-b]pyridine-3-carboxamide D. 2-(2-(N-(5-cyclopropyl-3-(methylcarbamoyl)-2-(p-tolyl)furo[2,3-b]pyridin-6-yl)methylsulfonamido)ethyl)benzoic acid

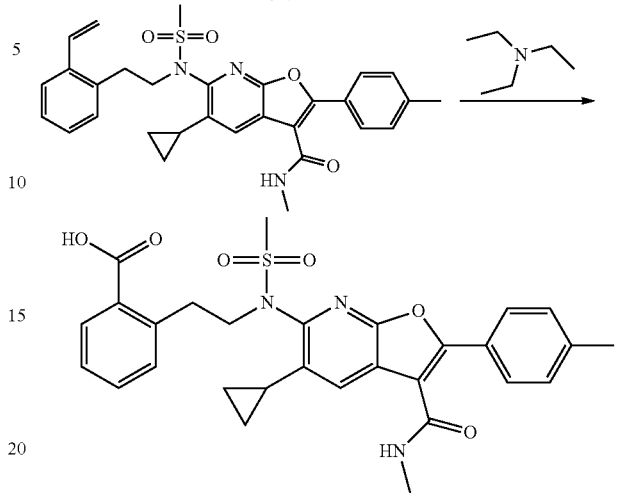

5-cyclopropyl-N-methyl-2-(p-tolyl)-6-(N-(2-vinylphenethyl)methylsulfonamido)furo[2,3-b]pyridine-3-carboxamide (5.5 mg, 10.38 µmol) was bubbled with a stream of Ozone for 10 seconds. LCMS showed 1:2:1 CHO(+)532/(+)580 intermed./(+)626 Bubbled with N2 for 5 minutes. Added triethylamine (14.47 µL, 0.104 mmol) and stirred 15 min. LCMS showed 2:4:1 (+)548 COOH/(+)532 CHO/(+)580 intermed Concentrated under nitrogen. Added ACN and filtered with 0.45pPTFE filter. Purified via HPLC C18 10-70% ACN/water (0.1% NH4OH) over 30 min 40 mL/min. to give 2-(2-(N-(5-cyclopropyl-3-(methylcarbamoyl)-2-(p-tolyl)furo[2,3-b]pyridin-6-yl)methylsulfonamido)ethyl)benzoic acid eluted at 10 min, Example 46
6-(N-(5-cyclopropyl-3-(methylcarbamoyl)-2-(p-tolyl)furo[2,3-b]pyridin-6-yl)methylsulfonamido)-2-(methylsulfonyl)hexanoic acid A. 6-(N-(4-bromobutyl)methylsulfonamido)-5-iodo-N-methyl-2-(p-tolyl)furo[2,3-b]pyridine-3-carboxamide

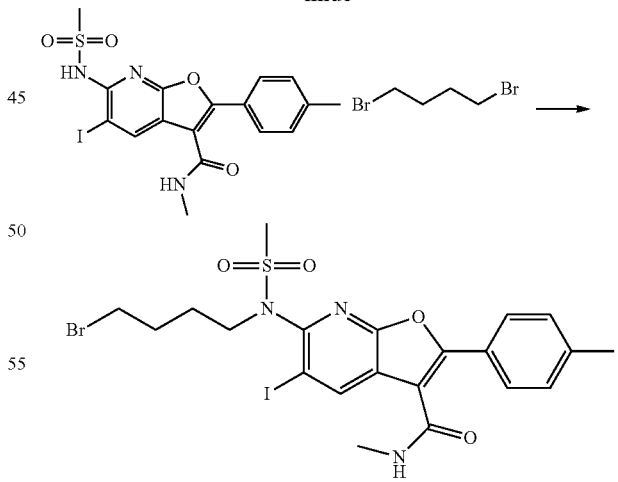

To 5-iodo-N-methyl-6-(methylsulfonamido)-2-(p-tolyl)furo[2,3-b]pyridine-3-carboxamide (crude ~20%) (400 mg, 0.824 mmol) was added 1,4-dibromobutane (1780 mg, 8.24 mmol) and CESIUM CARBONATE (537 mg, 1.648 mmol) and DMF (4 ml) Heated at 120° C. 30 min. Added water and extracted with EtOAc. Conc. on vac to oil. Added 3 mL ACN and 1 mL water. Filtered with 0.45p filter Purified via HPLC C8 40-80% ACN/H2O (0.1% NH4OH) 40 mL/min over 10 min. to give 6-(N-(4-bromobutyl)methylsulfonamido)-5-iodo-N-methyl-2-(p-tolyl)furo[2,3-b]pyridine-3-carboxamide B. 6-(N-(4-bromobutyl)methylsulfonamido)-5-cyclopropyl-N-methyl-2-(p-tolyl)furo[2,3-b]pyridine-3-carboxamide

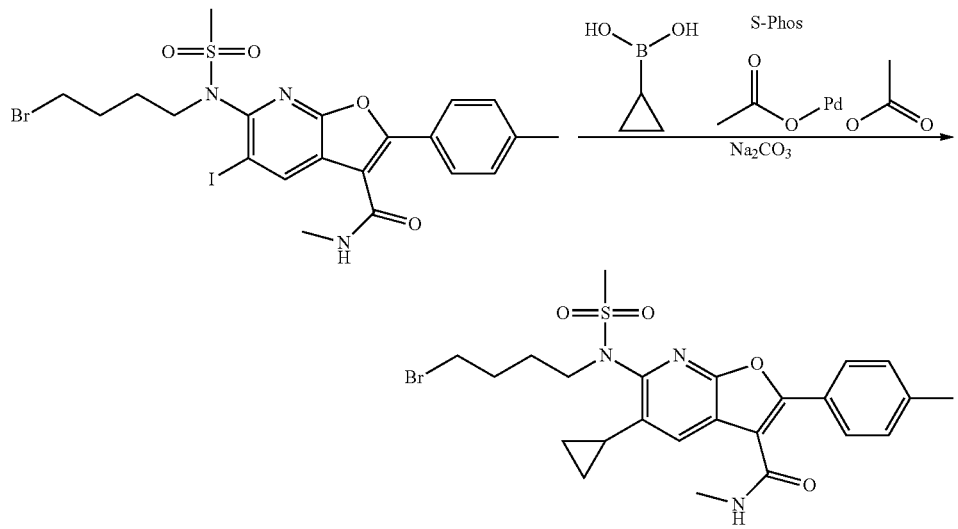

To 6-(N-(4-bromobutyl)methylsulfonamido)-5-iodo-N-methyl-2-(p-tolyl)furo[2,3-b]pyridine-3-carboxamide (57 mg, 0.092 mmol) was added a premixed solution of S-Phos (3.77 mg, 9.19 μmol) and Pd(OAc)$_2$ (0.825 mg, 3.68 μmol) in toluene (300 μL). Added a premixed solution of 2N SODIUM CARBONATE (919 μL, 1.838 mmol) and cyclopropylboronic acid (118 mg, 1.378 mmol) in toluene (900 μL). Degassed with N2 for 60 minutes.

Conc. on vac. Extracted with EtOAc. Conc.on vac and dissolved in ACN/water/DMF

Purified via HPLC C18 40-100% ACN/water (0.1% NH4OH) 40 mL/min over 15 min. Eluted 6-(N-(4-bromobutyl)methylsulfonamido)-5-cyclopropyl-N-methyl-2-(p-tolyl)furo[2,3-b]pyridine-3-carboxamide product at 7 min 19 mg, (eliminated bromide comes right in front).

C. ethyl 6-(N-(5-cyclopropyl-3-(methylcarbamoyl)-2-(p-tolyl)furo[2,3-b]pyridin-6-yl)methylsulfonamido)-2-(methylsulfonyl)hexanoate

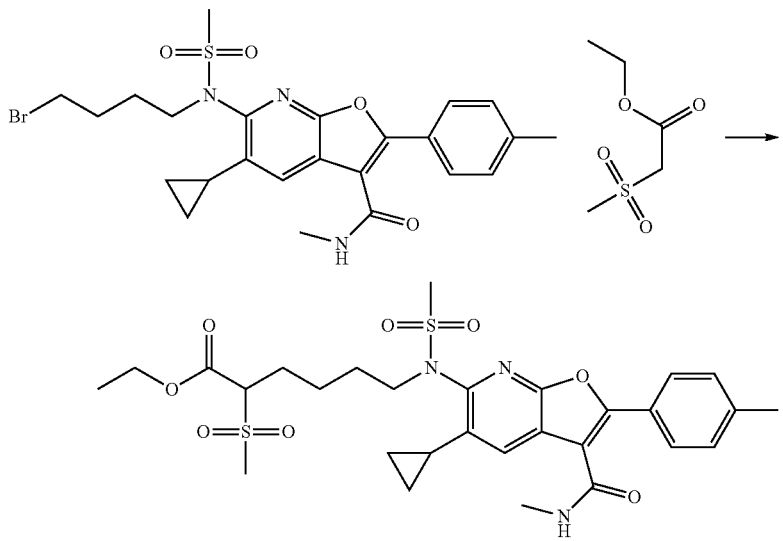

To 6-(N-(4-bromobutyl)methylsulfonamido)-5-cyclopropyl-N-methyl-2-(p-tolyl)furo[2,3-b]pyridine-3-carboxamide (4.5 mg, 8.42 µmol) was added ethyl 2-(methylsulfonyl)acetate (1.399 mg, 8.42 µmol) and CESIUM CARBONATE (5.49 mg, 0.017 mmol) and KI (1.398 mg, 8.42 µmol) and DMF Heated at 120° C. 20 min. Added water and extracted with EtOAc. Conc. on vac to oil. Added 3 mL ACN and 1 mL water. Filtered with 0.45µ filter Purified via HPLC C18 40-100% ACN/H2O (0.1% NH4OH) 40 mL/min over 10 min. to give ethyl 6-(N-(5-cyclopropyl-3-(methylcarbamoyl)-2-(p-tolyl)furo[2,3-b]pyridin-6-yl)methylsulfonamido)-2-(methylsulfonyl)hexanoate.

D. ethyl 6-(N-(5-cyclopropyl-3-(methylcarbamoyl)-2-(p-tolyl)furo[2,3-b]pyridin-6-yl)methylsulfonamido)-2-(methylsulfonyl)hexanoate

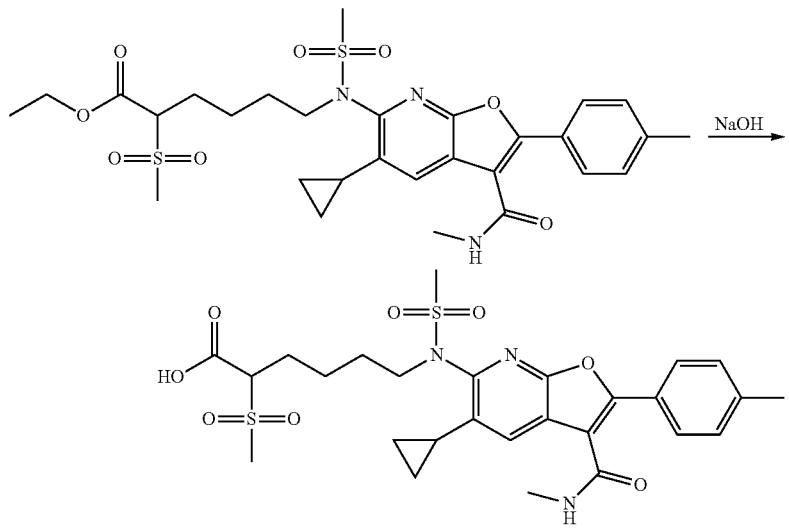

To ethyl 6-(N-(5-cyclopropyl-3-(methylcarbamoyl)-2-(p-tolyl)furo[2,3-b]pyridin-6-yl)methylsulfonamido)-2-(methylsulfonyl)hexanoate was added 1 mL 50% NaOH and 3 mL EtOH. Stirred at RT ON Removed organic solvent on vac. Added 10 mL EtOAc. Added 20 mL conc. NH4OH and 5 mL 1N HCl and extracted with EtOAc. Washed with brine. Dried over Na2SO4, and conc. on vac. To give 6-(N-(5-cyclopropyl-3-(methylcarbamoyl)-2-(p-tolyl)furo[2,3-b]pyridin-6-yl)methylsulfonamido)-2-(methylsulfonyl)hexanoic acid.

Example 46.1

(Z)-6-(N-(5-cyclopropyl-3-(methylcarbamoyl)-2-(p-tolyl)furo[2,3-b]pyridin-6-yl)methylsulfonamido)-2-(1-hydroxyethylidene)hexanoic acid

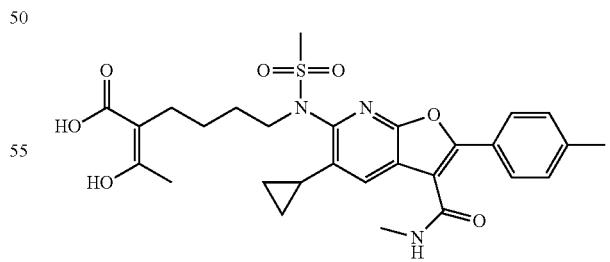

Prepared similarly to Example 46 6-(N-(5-cyclopropyl-3-(methylcarbamoyl)-2-(p-tolyl)furo[2,3-b]pyridin-6-yl)methylsulfonamido)-2-(methylsulfonyl)hexanoic acid, by using ethyl 3-oxobutanoate in the alkylation with 6-(N-(4-bromobutyl)methylsulfonamido)-5-cyclopropyl-N-methyl-2-(p-tolyl)furo[2,3-b]pyridine-3-carboxamide, followed by hydrolysis.

Example 47

(S)-5-(N-(5-cyclopropyl-3-(methylcarbamoyl)-2-p-tolylfuro[2,3-b]pyridin-6-yl)methylsulfonamido)-2-methylpentanoic acid

A. 4-Benzyl-3-(5-bromo-pentanoyl)-oxazolidin-2-one

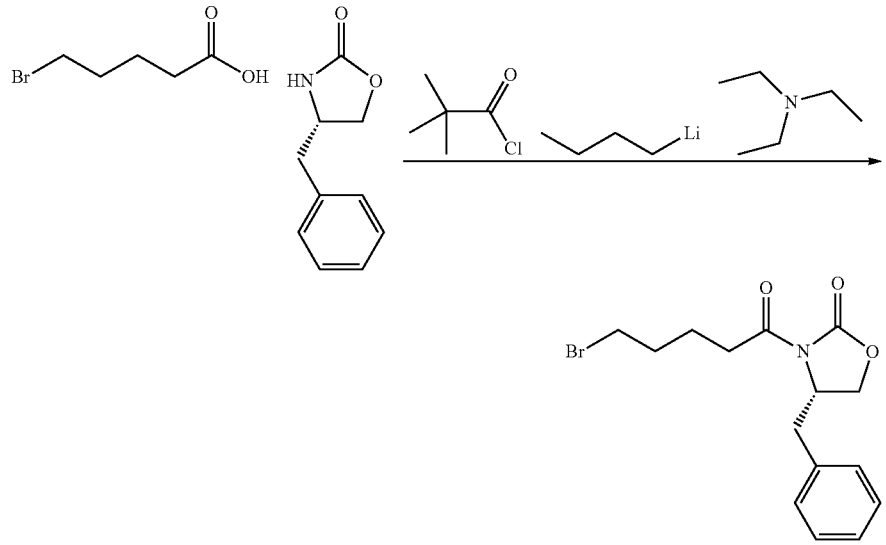

*Syn Comm* 35, 1675-1680 2005

To a round bottom flask containing 5-bromopentanoic acid (33.33 g, 184 mmol) was added THF (552 mL) and purged with N2 and cooled to −78° C. Added TEA (2.72 mL, 228 mmol) followed by dropwise pivaloyl chloride (23.79 mL, 193 mmol). Stirred at 0° C. 1 hr.

In a separate flask, (S)-4-benzyloxazolidin-2-one (32.6 g, 184 mmol) and THF (184 mL) were purged with N2 and cooled to −78° C. Added n-butyllithium (1.6M hexanes) (138 mL, 221 mmol) and stirred 5 min. Cannulated the second flask to the flask containing activated acid at −78° C. (added 20 mL more THF to aid transfer). Stirred at −78° C. for 1 hr. Allowed to warm to RT. Conc. on vac. then partitioned between DCM and 0.1M phosphate buffer pH=7. Extracted 3× with DCM and Conc. on vac. Purified on silica 0-50% EtOAc./Hept over 15 column volumes (330 g×2 columns, 80 ml/min). to give 44.35 g (75%) white/clear oil

B. (S)-4-benzyl-3-((S)-5-bromo-2-methylpentanoyl)oxazolidin-2-one

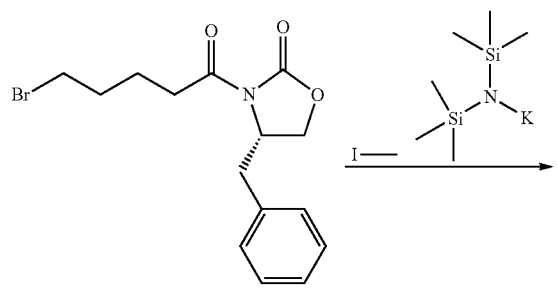

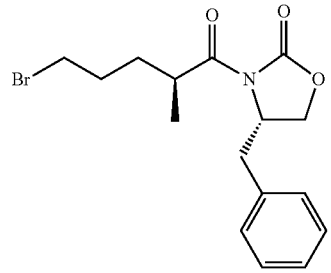

Syn Comm 35, 1675-1680 2005

To a round bottom flask containing KHMDS (25.3 g, 127 mmol) and purged with N2. was added in THF (132 mL) then cooled to −78° C. Added (S)-4-benzyl-3-(5-bromopentanoyl)oxazolidin-2-one (10.78 g, 31.7 mmol) in THF (26.4 mL) Stirred at −78° C. for 30 min Added MeI (19.81 mL, 317 mmol) dropwise stirred for 1 hr at −78° C. quenched with acetic acid. (9.01 mL 158 mmlol) Allowed to warm to RT. over 2 hr. Conc. on vac. then partitioned between DCM and half conc. brine. Extracted 3× with DCM and Conc. on vac. yellow oil. Purified on silica 10-50% EtOAc./Hept over 10 column volumes.

C. 6-(N—((S)-5-((S)-4-benzyl-2-oxooxazolidin-3-yl)-4-methyl-5-oxopentyl)methylsulfonamido)-5-iodo-N-methyl-2-p-tolylfuro[2,3-b]pyridine-3-carboxamide

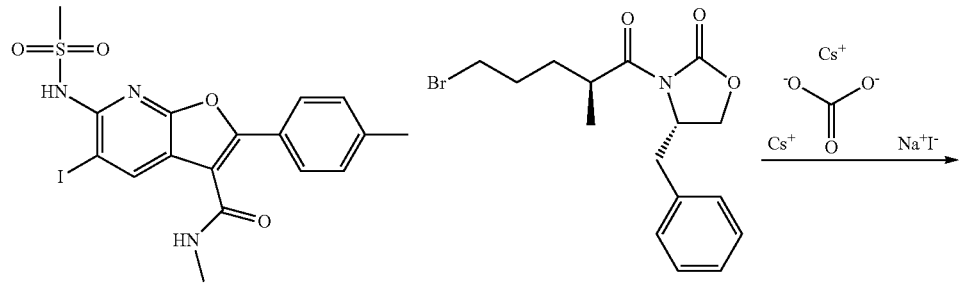

To 5-iodo-N-methyl-6-(methylsulfonamido)-2-p-tolylfuro[2,3-b]pyridine-3-carboxamide (1 g, 2.061 mmol) was added (S)-4-benzyl-3-((S)-5-bromo-2-methylpentanoyl)oxazolidin-2-one (0.730 g, 2.061 mmol) and CESIUM CARBONATE (2.014 g, 6.18 mmol) and NaI (0.309 g, 2.061 mmol) and DMA (4.12 mL). Heated 100° C. 2 hr (note: done at 1 hr) Added 30 mL 1N HCl and extracted with EtOAc, washed with brine, and conc. on vac. 3.05 g crude brown oil. Taken up in minimum EtOAc 30 mL and triturated into a stirring solution of 200 mL heptanes. to give a white solid which is filtered. Purified on 120 g Silica: 0-20% DCM/ether 15 column volumes 964 mg 6-(N—((S)-5-((S)-4-benzyl-2-oxooxazolidin-3-yl)-4-methyl-5-oxopentyl)methylsulfonamido)-5-iodo-N-methyl-2-p-tolylfuro[2,3-b]pyridine-3-carboxamide

D. 6-(N—((S)-5-((S)-4-benzyl-2-oxooxazolidin-3-yl)-4-methyl-5-oxopentyl)methylsulfonamido)-5-cyclopropyl-N-methyl-2-p-tolylfuro[2,3-b]pyridine-3-carboxamide

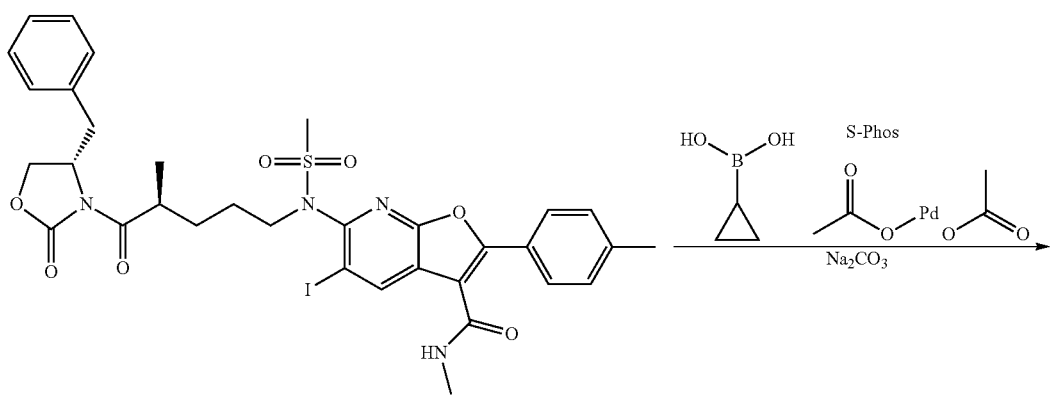

-continued

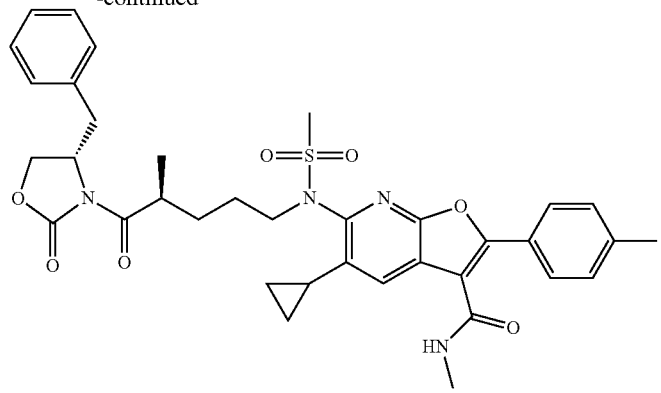

To 6-(N—((S)-5-((S)-4-benzyl-2-oxooxazolidin-3-yl)-4-methyl-5-oxopentyl)methylsulfonamido)-5-iodo-N-methyl-2-p-tolylfuro[2,3-b]pyridine-3-carboxamide (964 mg, 1.271 mmol) was added a premixed solution of S-Phos (52.2 mg, 0.127 mmol) and Pd(OAc)2 (11.41 mg, 0.051 mmol) in toluene (2.139 mL) Added a premixed solution of 2N SODIUM CARBONATE (12.71 mL, 25.4 mmol) and cyclopropylboronic acid (1637 mg, 19.06 mmol) in toluene (6.42 mL).

Degassed with N2 for 30 minutes. Heated sealed tube at 120° C. for 30 minutes (NOTE: rxn actually decreased from 120° C. to 70° C. over 30 minutes due to hotplate malfunction) Conc. on vac. Extracted with EtOAc and conc. on vac to give 810 mg crude Dissolved in DCM and purified on 120 g silica with 0-30% ether/DCM over 15 column volumes. 386.3 mg of 6-(N—((S)-5-((S)-4-benzyl-2-oxooxazolidin-3-yl)-4-methyl-5-oxopentypmethylsulfonamido)-5-cyclopropyl-N-methyl-2-p-tolylfuro[2,3-b]pyridine-3-carboxamide E. (R)-5-(N-(5-cyclopropyl-3-(methylcarbamoyl)-2-(p-tolyl)furo[2,3-b]pyridin-6-yl)methylsulfonamido)-2-methylpentanoic acid

*Synthetic Comm.* 35 1675-1680 2005

H2O2 (30%) (0.222 mL, 2.170 mmol) was added to a solution of 6-(N—((S)-5-((S)-4-benzyl-2-oxooxazolidin-3-yl)-4-methyl-5-oxopentyl)methylsulfonamido)-5-cyclopropyl-N-methyl-2-p-tolylfuro[2,3-b]pyridine-3-carboxamide (365 mg, 0.543 mmol) in 6.4 mL of 7:3 THF/water at 0° C. Added LiOH (26.0 mg, 1.085 mmol) Stirred at 0° C. for 15 min. Quenched with sodium sulfite (342 mg, 2.71 mmol) in 2 mL water followed by sodium bicarbonate (0.5 M) (5.43 mL, 2.71 mmol) Added DCM and extracted AQ layer Treated AQ layer with 1N HCl and then extracted with EtOAc. Concentrated Chiral HPLC using a 20-250 mm IA column running 40% EtOH in heptane gave 294 mg (0.572 mmol) desired enantiomer at 9.4 min. and 120 mg of undesired enantiomer at 13.3 min. The desired enantiomer was taken up in 2 mL MeOH and salted with 0.5 N KHCO3 and lyophylized.

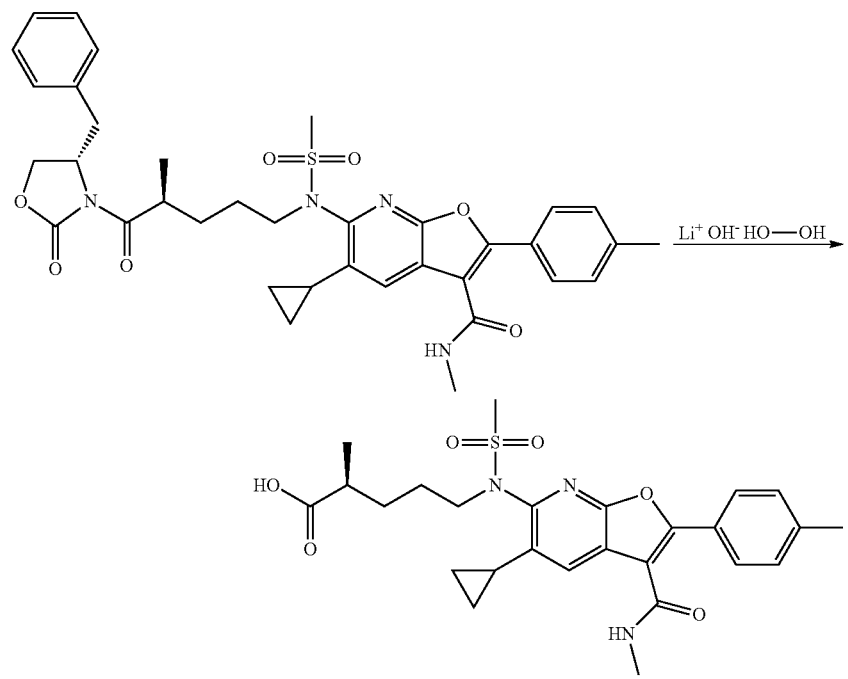

Example 47.1

5-cyclopropyl-6-(N—((R)-5-(R)-1-hydroxy-3-phenylpropan-2-ylamino)-4-methyl-5-oxopentyl)methylsulfonamido)-N-methyl-2-p-tolylfuro[2,3-b]pyridine-3-carboxamide

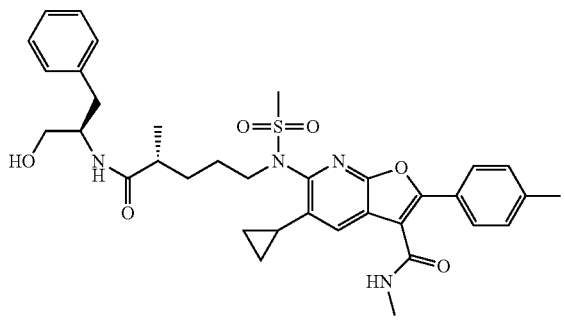

The title compound was obtained in a similar synthesis from non-optically pure starting material and by omitting the H2O2 as described in *Tetrahedron Asymmetry* 19 (2008) 838-846 example 4.6

Example 47.2

5-cyclopropyl-6-(N—((S)-5-(R)-1-hydroxy-3-phenylpropan-2-ylamino)-4-methyl-5-oxopentyl)methylsulfonamido)-N-methyl-2-p-tolylfuro[2,3-b]pyridine-3-carboxamide

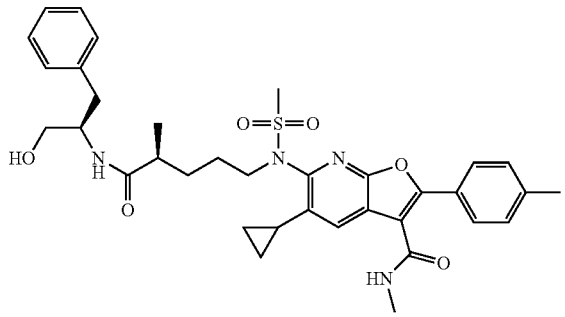

The title compound was obtained in a similar synthesis from non-optically pure starting material and by omitting the H2O2 as described in *Tetrahedron Asymmetry* 19 (2008) 838-846 example 4.6

Example 47.3

(R)-5-(N-(5-cyclopropyl-3-(methylcarbamoyl)-2-p-tolylfuro[2,3-b]pyridin-6-yl)methylsulfonamido)-2-methylpentanoic acid

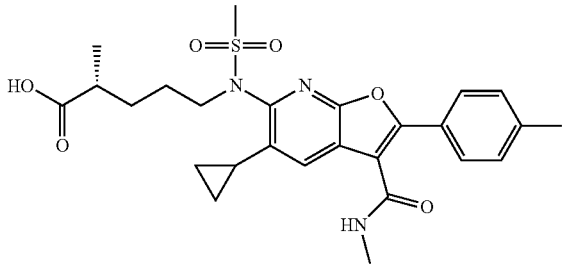

Synthesized analogous to example 47.

Example 47.4

(S)-6-(N-(5-Cyclopropyl-2-(4-ethylphenyl)-3-(methylcarbamoyl)furo[2,3-b]pyridin-6-yl)methylsulfonamido)-2-(methoxymethyl)hexanoic acid

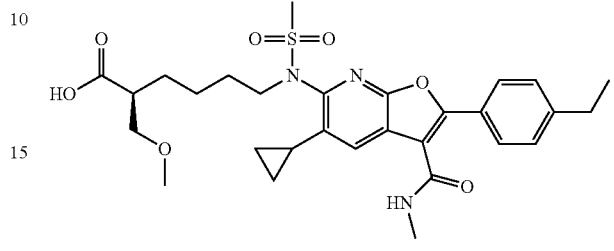

A. (R)-4-Benzyl-3-(6-bromohexanoyl)oxazolidin-2-one

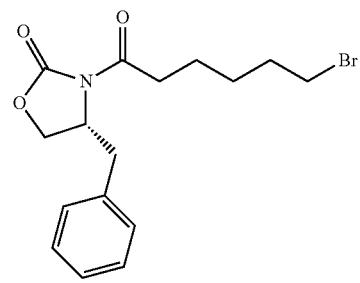

The title compound was prepared analogous to a literature method in *Synthetic Communications*, 35(12), 1675-1680; 2005.

B. (R)-4-Benzyl-3-((S)-6-bromo-2-(methoxymethyl)hexanoyl)oxazolidin-2-one

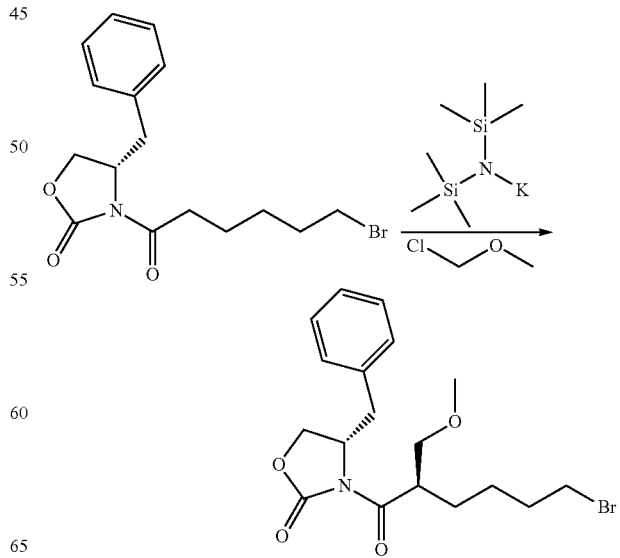

To a round-bottom flask containing THF (80 ml) cooled to −78° C. and purged with a continuous stream of N₂ gas was added KHMDS (1 M in THF, 22.6 ml, 4 eq.). In a separate flask purged with a continuous stream of N₂ gas was added (R)-4-benzyl-3-(6-bromohexanoyl)oxazolidin-2-one (2.00 g, 1 eq.) dissolved in THF (10 ml) and cooled to −78° C. The solution containing (R)-4-benzyl-3-(6-bromohexanoyl)oxazolidin-2-one was transferred to the KHMDS solution, and chloro(methoxy)methane (7.2 g, 15.8 eq.) was added dropwise. The reaction mixture was allowed to stir for an additional 2 h, quenched with saturated aqueous NH₄Cl and concentrated. Water was added. The mixture was extracted with EtOAc. The organic layers were dried over MgSO₄ and concentrated. Silica gel chromatography using 30-100% DCM-heptane yields the title compound.

C. (S)-6-(N-(5-Cyclopropyl-2-(4-ethylphenyl)-3-(methylcarbamoyl)furo[2,3-b]pyridin-6-yl)methylsulfonamido)-2-(methoxymethyl)hexanoic acid The title compound was prepared analogous to Example 47. MS (ESI) m/z 572.2 (M+1). Retention time=1.36 min, Method A.

Example 47.5

(R)-6-(N-(5-Cyclopropyl-3-(methylcarbamoyl)-2-p-tolylfuro[2,3-b]pyridin-6-yl)methylsulfonamido)-2-(methoxymethyl)hexanoic acid

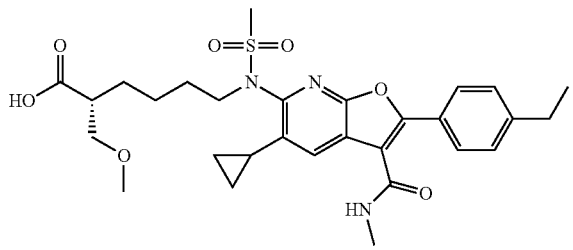

The title compound was prepared analogous to Example 47.4. MS (ESI) m/z 558.2 (M+1). Retention time=1.32 min, Method A.

Example 47.6

5-Cyclopropyl-6-(N—((R)-6-((S)-1-hydroxy-3-phenylpropan-2-ylamino)-5-(methoxymethyl)-6-oxohexyl)methylsulfonamido)-N-methyl-2-p-tolylfuro[2,3-b]pyridine-3-carboxamide

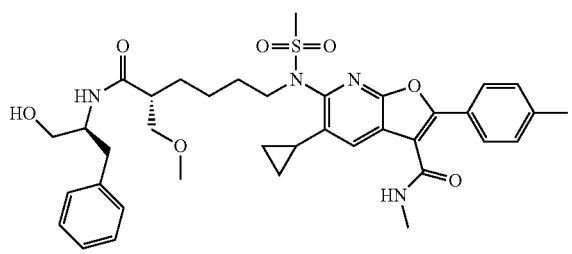

The title compound was a byproduct in the synthesis of 47.5. MS (ESI) m/z 691.3 (M+1). Retention time=1.55 min, Method A.

Example 47.7

(R)-5-(N-(5-Cyclopropyl-3-(methylcarbamoyl)-2-p-tolylfuro[2,3-b]pyridin-6-yl)methylsulfonamido)-2-(methoxymethyl)pentanoic acid

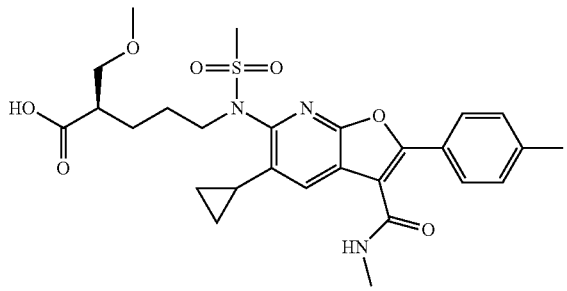

A. (S)-4-Benzyl-3-(5-bromopentanoyl)oxazolidin-2-one

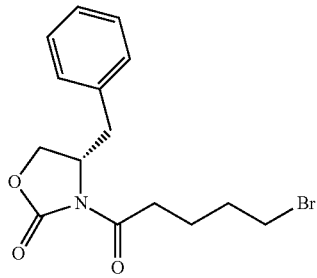

The title compound was prepared according to *Synthetic Communications*, 35(12), 1675-1680; 2005.

B. (S)-4-Benzyl-3-((R)-5-bromo-2-(methoxymethyl)pentanoyl)oxazolidin-2-one

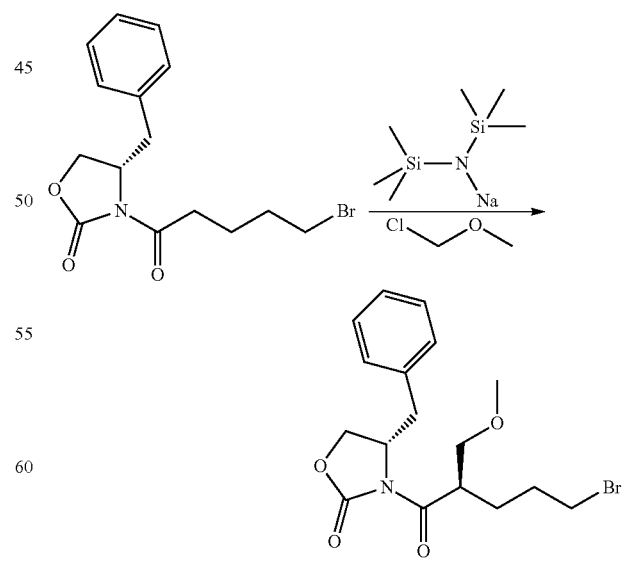

To a solution (S)-4-benzyl-3-(5-bromopentanoyl)oxazolidin-2-one (4.00 g, 1 eq.) and THF (100 ml) was added NaH- MDS (1 M in THF, 53 ml, 4.5 eq.) at −78° C. After 30 min chloro(methoxy)methane (12.3 g, 13 eq.) was added dropwise. The reaction mixture was stirred at −10° C. for 2 days. Concentrated aqueous HCl solution was carefully added. The resulting mixture was concentrated and extracted with EtOAc. The organic layers were dried over MgSO$_4$ and concentrated. Silica gel chromatography using 60-80% DCM-heptane yields the title compound (1.06 g, 23%).

C. Example 47.71

6-(N—((R)-5-(S)-4-Benzyl-2-oxooxazolidin-3-yl)-4-(methoxymethyl)-5-oxopentyl)methylsulfonamido)-5-iodo-N-methyl-2-p-tolylfuro[2,3-b]pyridine-3-carboxamide

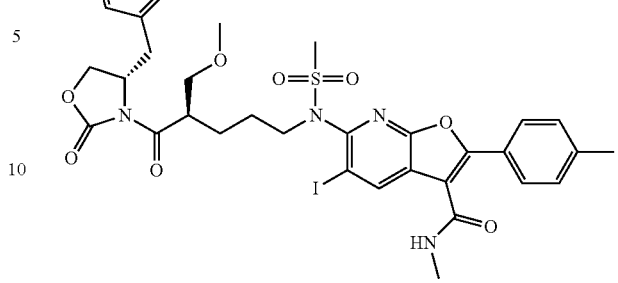

The title compound was prepared analogous to Example 47. MS (ESI) m/z 789.3 (M+1). Retention time=1.72 min, Method A.

D. Example 47.72

6-(N—((R)-5-(S)-4-Benzyl-2-oxooxazolidin-3-yl)-4-(methoxymethyl)-5-oxopentyl)methylsulfonamido)-5-cyclopropyl-N-methyl-2-p-tolylfuro[2,3-b]pyridine-3-carboxamide

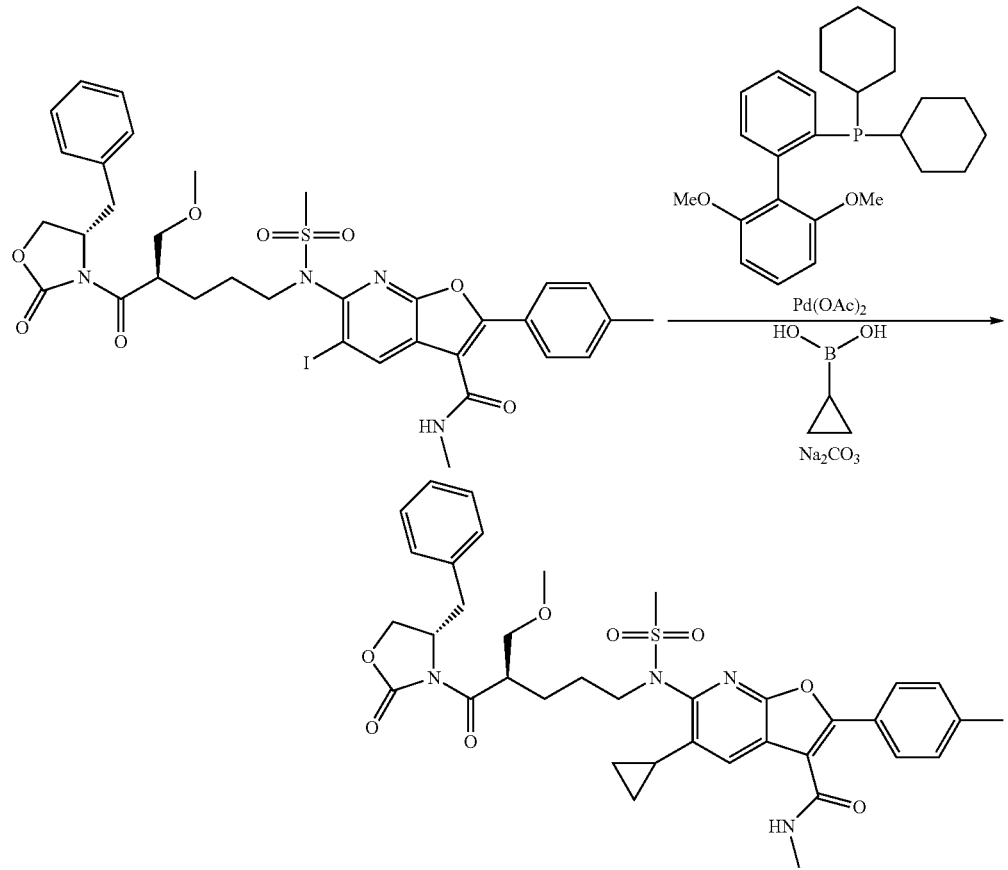

The title compound was prepared analogous to Example 47. MS (ESI) m/z 703.3 (M+1). Retention time=1.69 min, Method A.

E. (R)-5-(N-(5-Cyclopropyl-3-(methylcarbamoyl)-2-p-tolylfuro[2,3-b]pyridin-6-yl)methylsulfonamido)-2-(methoxymethyl)pentanoic acid

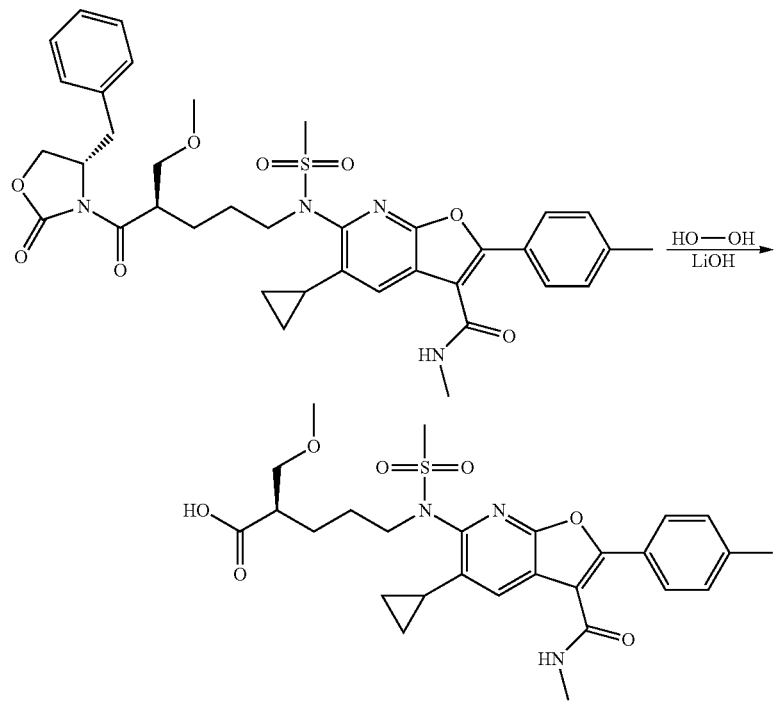

The title compound was prepared analogous to Example 47. MS (ESI) m/z 544.1 (M+1). Retention time=1.50 min, Method A.

Example 48

2-(4-(3-(N-(5-cyclopropyl-3-(methylcarbamoyl)-2-p-tolylfuro[2,3-b]pyridin-6-yl)methylsulfonamido)propyl)tetrahydro-2H-pyran-4-yl)acetic acid A: -cyclopropyl-6-(N-(3-(4-(2-diazoacetyl)tetrahydro-2H-pyran-4-yl)propyl)methylsulfonamido)-N-methyl-2-p-tolylfuro[2,3-b]pyridine-3-carboxamide

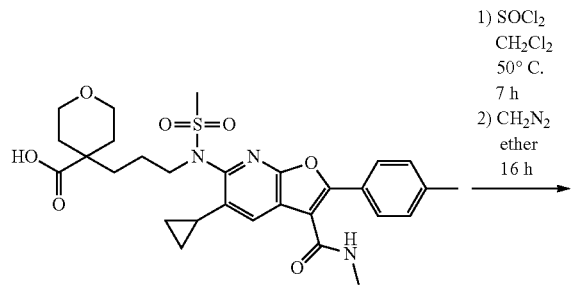

To a solution of 4-(3-(N-(5-cyclopropyl-3-(methylcarbamoyl)-2-p-tolylfuro[2,3-b]pyridin-6-yl)methylsulfonamido)propyl)tetrahydro-2H-pyran-4-carboxylic acid (Example 28.4, 0.35 g, 0.869 mmol) in DCM (4 mL) was added thionyl chloride (0.124 g, 1.043 mmol) slowly under $N_2$ atmosphere. Then the reaction mass was heated to 50° C. for 7 h. The reaction was monitored by TLC. After reaction is completed reaction mass was concentrated to dryness under N2. To this was added Acetonitrile (2 mL) followed by Diazomethane in ether (8 mL) slowly at −5° C. and allowed to stir at RT for 16 h. The reaction was monitored by TLC. The reaction mass was diluted with ether (10 mL), added 10% aqueous citric acid solution (2 mL), washed with bicarbonate solution (5 mL) followed by brine wash (5 mL). The organic layer was dried over sodium sulphate and concentrated to give crude product (0.19 g, 0.118 mmol) as a light yellow syrup. Yield (0.19 g, 55.88%). TLC (70% EtOAc in Hexane; Rf=0.60)

*Preparation of Diazomethane in ether: 25 ml of 50% KOH solution and 80 ml of ether were taken in a 250 ml two neck RB flask fitted with a distillation condenser. The other end of condenser is kept in 20 ml of ether.

8 g of NMU was added to the KOH-ether layer. Diazomethane generated was allowed to pass to the receiver, dried under KOH pellets and this collected diazomethane in ether was used for the reaction.

[M+H]$^+$=594.5

$^1$H NMR (400 MHz, CDCl$_3$): δ 7.77 (s, 1H), 7.73 (d, 2H, J=8.1 Hz), 7.33 (d, 2H, J=8.1 Hz), 5.81 (br d, 1H, NH), 3.71-3.78 (m, 4H), 3.44 (t, 2H, J=10.8 Hz), 3.09 (s, 3H), 2.95 (d, 3H, J=4.8 Hz), 2.51-2.59 (m, 1H), 2.45 (s, 3H), 1.86 (m, 2H), 1.35-1.65 (m, 5H), 1.24-1.31 (m, 2H), 1.11-1.14 (m, 2H), 0.81-0.88 (m, 2H).

B. Methyl2-(4-(3-(N-(5-cyclopropyl-3-(methylcarbamoyl)-2-p-tolylfuro[2,3-b]pyridin-6-yl)methylsulfonamido)propyl)tetrahydro-2H-pyran-4-yl)acetate

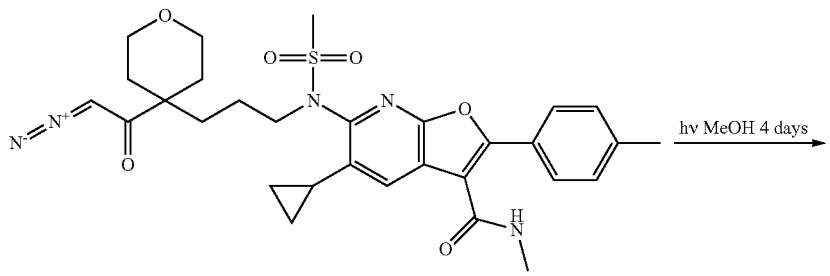

5-cyclopropyl-6-(N-(3-(4-(2-diazoacetyl)tetrahydro-2H-pyran-4-yl)propyl)methylsulfonamido)-N-methyl-2-p-tolylfuro[2,3-b]pyridine-3-carboxamide (0.19 g, 0.118 mmol) was taken in Methanol (5 mL) in a round-bottom flask fitted with a condenser under N₂ atmosphere. Then the reaction mass was heated under UV light for 4 days. The reaction was monitored by TLC. The reaction mass was concentrated to dryness to get the crude product (0.35 g) as a light yellow solid. TLC (70% EtOAc in Hexane; Rf=0.75)

[M+H]⁺=598.2

¹H NMR (300 MHz, CDCl₃): δ 7.78 (s, 1H), 7.72 (d, 2H, J=8.4 Hz), 7.34 (d, 2H, J=8.4 Hz), 5.83 (br s, 1H, NH), 3.56-3.82 (m, 7H), 3.34 (t, J=10.5 Hz, 2H), 3.11 (d, J=10.5 Hz, 3H), 2.95 (d, 3H, J=4.8 Hz), 2.53-2.62 (m, 1H), 2.44 (s, 3H), 2.30 (s, 2H), 2.00 (t, J=12.3 Hz, 3H), 0.55-1.70 (m, 9H).

C. 2-(4-(3-(N-(5-cyclopropyl-3-(methylcarbamoyl)-2-p-tolylfuro[2,3-b]pyridin-6-yl)methylsulfonamido)propyl)tetrahydro-2H-pyran-4-yl)acetic acid

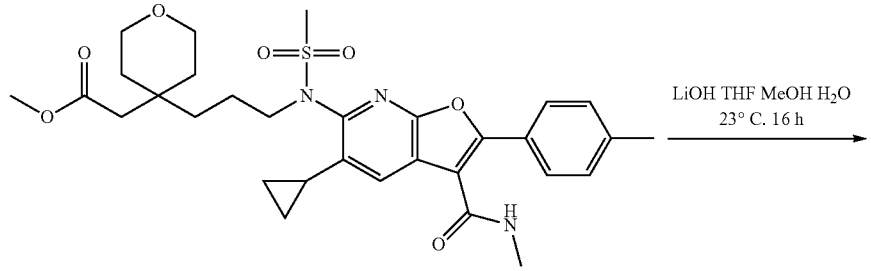

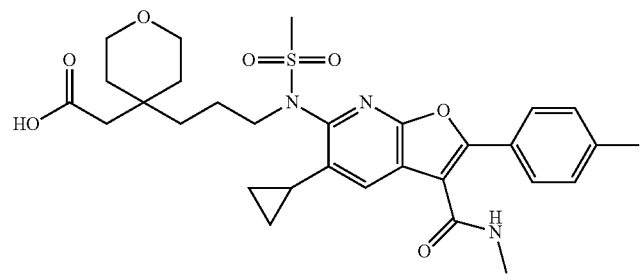

To a solution of methyl 2-(4-(3-(N-(5-cyclopropyl-3-(methylcarbamoyl)-2-p-tolylfuro[2,3-b]pyridin-6-yl)methylsulfonamido)propyl)tetrahydro-2H-pyran-4-yl)acetate (0.35 g, 0.586 mmol) in THF (2.5 mL): MeOH (1 mL): H₂O (0.5 mL) was added Lithium hydroxide (0.098 g, 2.34 mmol) slowly. Then reaction mass was allowed to stir at RT for 16 h. The reaction was monitored by TLC. The reaction mass was concentrated to dryness, added water (5 mL) and washed with ethyl acetate (10 mL). The aqueous layer was acidified with 1NHCl and extracted with ethyl acetate (2×10 mL) followed by brine wash. The organic layer was dried over sodium sulphate and concentrated to give crude product. The crude product was purified by Prep HPLC (Method A). 52 mg of product was isolated with 91% HPLC purity and 100 mg of product with 45% HPLC purity and then this was again purified by prep-HPLC (Method B) to get 30 mg of product with 95% HPLC-purity. Yield (82 mg, 24%). TLC (70% EtOAc in Hexane; Rf=0.35).

¹H NMR (400 MHz, CDCl₃): δ 7.75 (s, 1H), 7.73 (d, 2H, J=8.4 Hz), 7.33 (d, 2H, J=8.0 Hz), 5.83 (br d, 1H, NH), 3.74-3.78 (m, 2H), 3.55-3.68 (m, 4H), 3.13 (s, 3H), 2.95 (d, 3H, J=4.8 Hz), 2.52-2.62 (m, 1H), 2.44 (s, 3H), 2.31 (s, 2H), 1.40-1.55 (m, 6H), 1.24-1.35 (m, 2H), 1.10-1.12 (m, 2H), 0.51-0.80 (m, 2H).

Example 49

(S)-(phosphonooxy)methyl 5-(N-(5-cyclopropyl-3-(methylcarbamoyl)-2-(p-tolyl)furo[2,3-b]pyridin-6-yl)methylsulfonamido)-2-methylpentanoate A. Example 49.1

(S)-((bis(benzyloxy)phosphoryl)oxy)methyl 5-(N-(5-cyclopropyl-3-(methylcarbamoyl)-2-(p-tolyl)furo[2,3-b]pyridin-6-yl)methylsulfonamido)-2-methylpentanoate

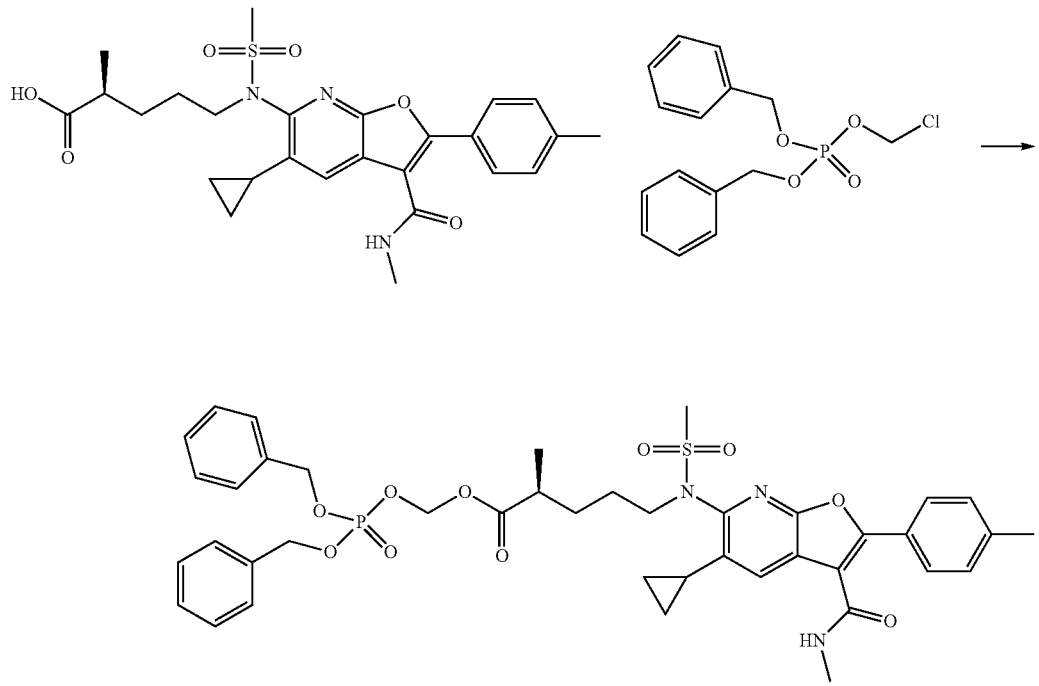

(S)-5-(N-(5-cyclopropyl-3-(methylcarbamoyl)-2-p-tolyl-furo[2,3-b]pyridin-6-yl)methylsulfonamido)-2-methylpentanoic acid (Example 47, 50 mg, 0.090 mmol) and [dibenzyl chloromethyl phosphate (32.5 mg, 0.1 mmol) were stirred in DMF at RT LCMS-80% done at 1 hr Stirred at RT ON-95% done, trace SM and trace mono-de-benzylated side prod.(+) 714 Added 800 μL ACN and 200 μL water Purified on HPLC C18 20-100% ACN/water 1% NH4OH 40 mL/min over 10 min Conc. on vac at 30° C.—no degradation. To give (S)-((bis(benzyloxy)phosphoryl)oxy)methyl 5-(N-(5-cyclopropyl-3-(methylcarbamoyl)-2-(p-tolyl)furo[2,3-b]pyridin-6-yl)methylsulfonamido)-2-methylpentanoate B. (S)-(phosphonooxy)methyl 5-(N-(5-cyclopropyl-3-(methylcarbamoyl)-2-(p-tolyl)furo[2,3-b]pyridin-6-yl)methylsulfonamido)-2-methylpentanoate

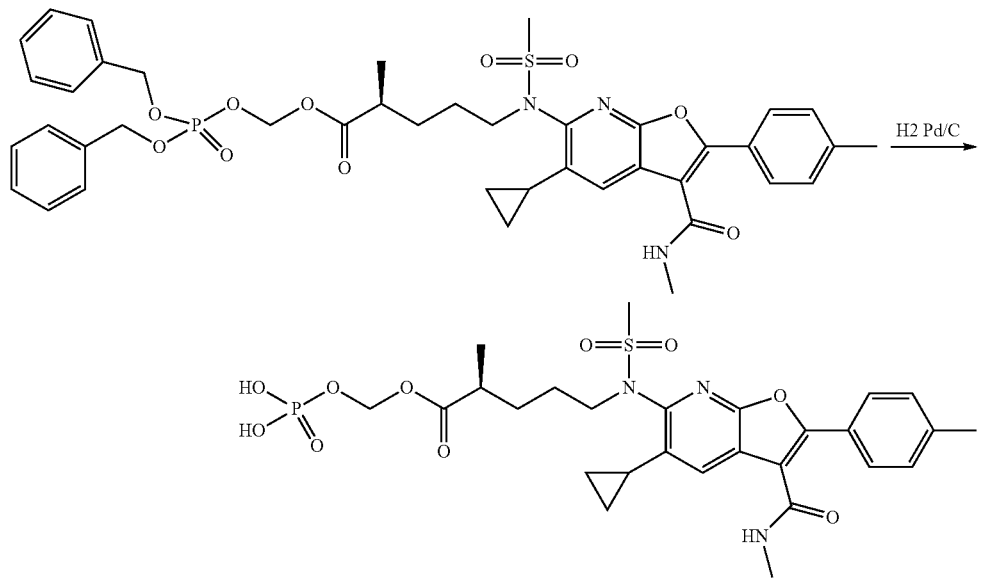

(S)-((bis(benzyloxy)phosphoryl)oxy)methyl 5-(N-(5-cyclopropyl-3-(methylcarbamoyl)-2-(p-tolyl)furo[2,3-b]pyridin-6-yl)methylsulfonamido)-2-methylpentanoate (10 mg, 0.012 mmol) and Pd—C (10% wt) (1.3 mg) in EtOAc (250 μL) with NaHCO3 (1.045 mg, 0.012 mmol) was placed under N2 and then evacuated and backfilled with H2 and kept under an H2 balloon at RT for 2 hrs (trace COOH side prod.) Filtered through 0.45μ PTFE filter to give (S)-(phosphonooxy)methyl 5-(N-(5-cyclopropyl-3-(methylcarbamoyl)-2-(p-tolyl)furo[2,3-b]pyridin-6-yl)methylsulfonamido)-2-methylpentanoate.

Example 50

6-(N-(5-cyclopropyl-3-(methylcarbamoyl)-2-p-tolylfuro[2,3-b]pyridin-6-yl)methylsulfonamido)-3-hydroxy-2,2-dimethylhexanoic acid

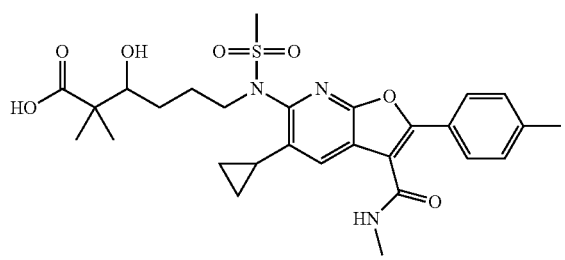

A. 6-(N-(4-hydroxybutyl)methylsulfonamido)-5-iodo-N-methyl-2-p-tolylfuro[2,3-b]pyridine-3-carboxamide

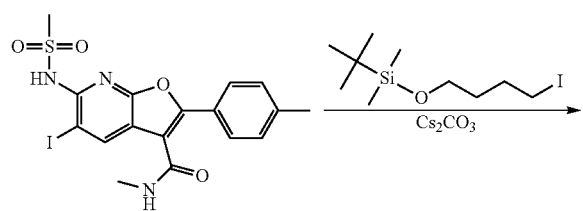

-continued

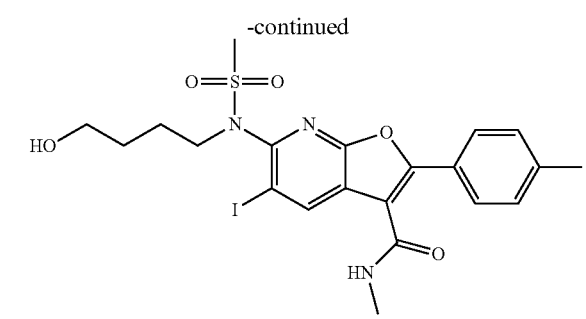

The title compound was prepared analogous to Example 24.01, first stage.

B. 5-iodo-N-methyl-6-(N-(4-oxobutyl)methylsulfonamido)-2-p-tolylfuro[2,3-b]pyridine-3-carboxamide

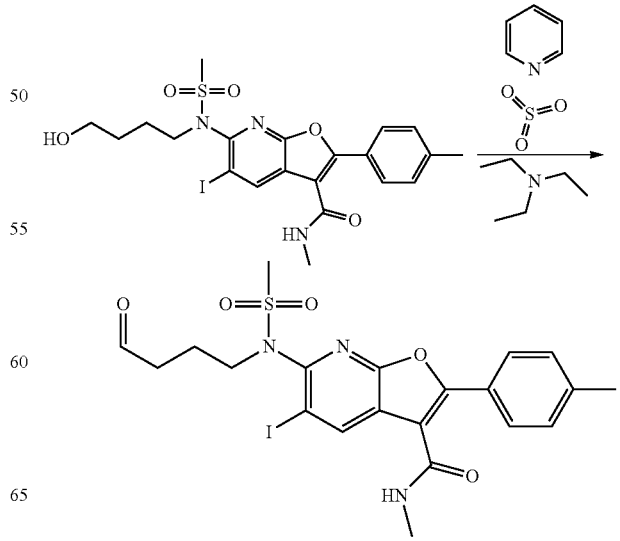

To a solution of 6-(N-(4-hydroxybutyl)methylsulfonamido)-5-iodo-N-methyl-2-p-tolylfuro[2,3-b]pyridine-3-carboxamide (1 eq., 190 mg) in DMSO (1.7 ml) was added triethyl amine (8 eq., 0.38 ml) and pyridine sulfur trioxide (3 eq., 163 mg). The mixture was stirred at room temperature for 1 h. Water was added. The mixture was extracted with EtOAc. The organic layer was washed with water three times, dried over MgSO$_4$ and concentrated to yield the crude title compound which was used in next step without purification.

C. Ethyl 3-hydroxy-6-(N-(5-iodo-3-(methylcarbamoyl)-2-p-tolylfuro[2,3-b]pyridin-6-yl)methylsulfonamido)-2,2-dimethylhexanoate

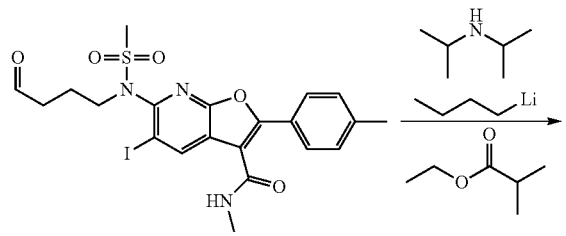

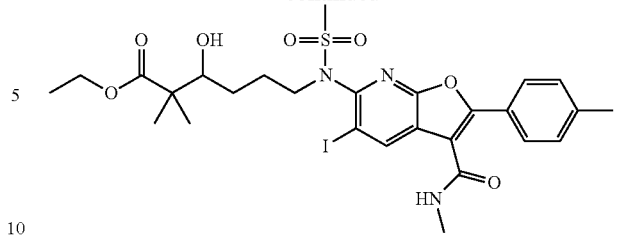

To a solution of diisopropylamine (1.4 eq., 18 μl) in THF (0.5 ml) cooled at 0° C. was added n-BuLi (1.6 M in hexane, 1.2 eq., 68 μl). The resultant solution was stirred at 0° C. for 10 min and cooled to −78° C., and then a solution of ethyl isobutyrate (1 eq., 10.5 mg) in THF (0.5 ml) was added. After the reaction mixture was stirred at −78° C. for 1 h, a solution of 5-iodo-N-methyl-6-(N-(4-oxobutyl)methylsulfonamido)-2-p-tolylfuro[2,3-b]pyridine-3-carboxamide (1 eq., 50.0 mg) in THF (1 ml) was introduced. The reaction mixture was stirred at −78° C. for 1 h, quenched with saturated aqueous NH$_4$Cl, and extracted with diethyl ether. The combined ethereal layers were washed with brine, dried over MgSO$_4$, filtered, and concentrated to yield the crude title compound which was used in next step without purification.

D. 6-[(5-Cyclopropyl-3-methylcarbamoyl-2-p-tolyl-furo[2,3-b]pyridin-6-yl)-methanesulfonyl-amino]-3-hydroxy-2,2-dimethyl-hexanoic acid ethyl ester

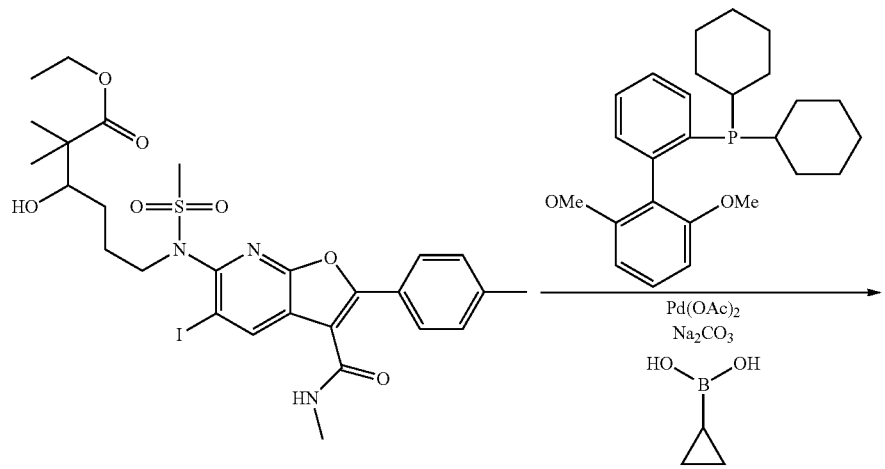

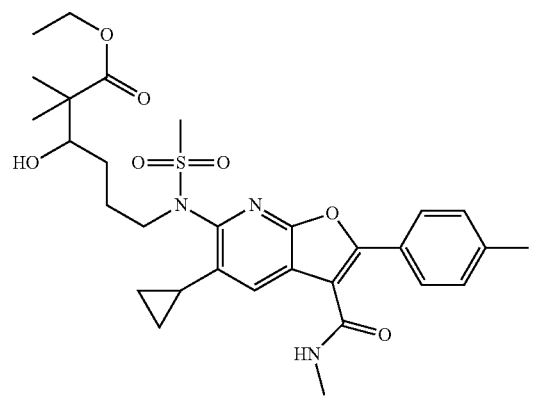

To a solution of S-Phos (0.4 eq., 15 mg), Pd(OAc)$_2$ (0.2 eq., 4.0 mg) and PhMe (3 ml) was added ethyl 3-hydroxy-6-(N-(5-iodo-3-(methylcarbamoyl)-2-p-tolylfuro[2,3-b]pyridin-6-yl)methylsulfonamido)-2,2-dimethylhexanoate (1 eq., 60 mg). A solution of boronic acid (30 eq., 232 mg) and Na$_2$CO$_3$ (2 N aqueous solution, 40 eq., 0.54 ml) was added. The mixture was heated in a sealed tube under nitrogen at 115° C. for 60 min, cooled, and diluted with DCM and water. The aqueous layer was extracted with DCM. Orgnic layers were washed with saturated aqueous Na$_2$CO$_3$ solution and concentrated to yield the crude title compound which was used in next step without purification.

E. 6-(N-(5-cyclopropyl-3-(methylcarbamoyl)-2-p-tolylfuro[2,3-b]pyridin-6-yl)methylsulfonamido)-3-hydroxy-2,2-dimethylhexanoic acid

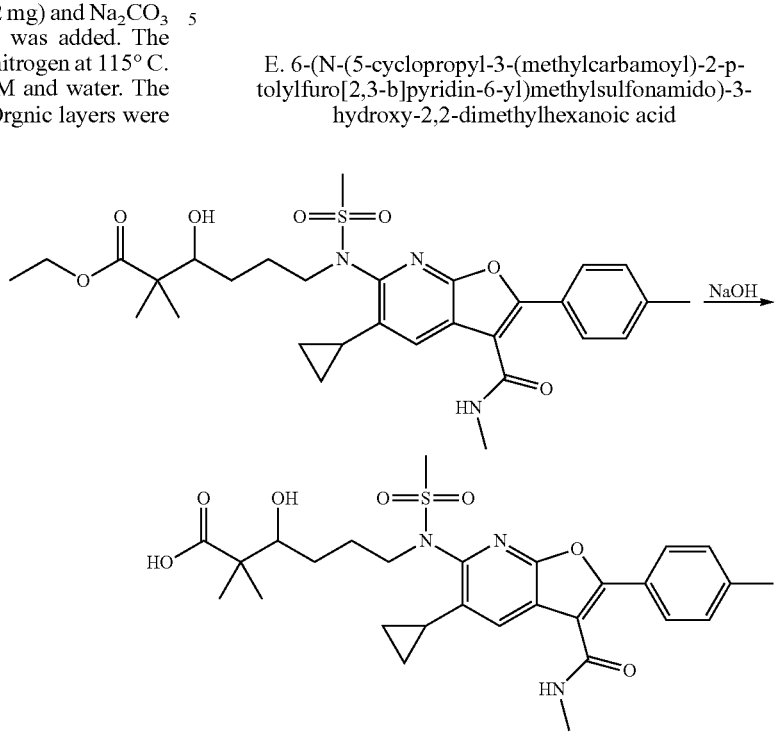

The title compound was prepared analogous to Example 24.01, second stage.

NMR data for additional compounds are Tabulated in Table 10

TABLE 10

| Example | $^1$H NMR (400 MHz) |
|---|---|
| 2.1 | (400 MHz, CDCl$_3$) d ppm 8.18 (s, 1H), 7.96-7.92 (m, 2H), 7.25-7.20 (m, 2H), 5.79 (br s, 1H), 3.32 (s, 3H), 3.19 (s, 3H), 2.99-2.98 (d, 3H), 2.96-2.91 (q, 2H), 1.33-1.29 (t, 3H) |
| 2.2 | (400 MHz, CD$_3$CN) d ppm 8.03-8.01 (m, 2H), 7.68 (s, 1H), 7.32-7.27 (m, 2H), 6.83 (br s, 1H), 3.88-3.85 (m, 2H), 3.61-3.57 (m, 2H), 3.22 (s, 3H), 2.92-2.90 (d, 3H), 2.53-2.48 (m, 1H), 1.11-1.09 (m, 2H), 0.84 (m, 2H) |
| 2.4 | (400 MHz, CD$_3$CN) d ppm 8.36 (s, 1H), 8.10-8.02 (m, 2H), 7.34-7.28 (m, 2H), 6.83 (br s, 1H), 5.37-5.35 (m, 1H), 5.16-5.15 (m, 1H), 3.29 (s, 3H), 3.25 (s, 3H), 2.93-2.90 (d, 3H) |
| 2.5 | (400 MHz, CD$_3$CN) d ppm 8.19 (s, 1H), 8.07-8.02 (m, 2H), 7.35-7.29 (m, 2H), 6.84 (br s, 1H), 6.38 (s, 1H), 5.99 (s, 1H), 3.22 (s, 3H), 3.19 (s, 3H), 2.90-2.89 (d, 3H) |
| 2.6 | (400 MHz, CDCl3) d ppm 8.01-7.97 (m, 2H), 7.93 (s, 1H), 7.30-7.25 (m, 2H), 5.80 (br s, 2H), 3.38 (s, 3H), 3.26 (s, 3H), 2.52 (m, 1H), 1.16 (m, 2H), 0.82 (m, 2H) |
| 2.7 | CDCl3 d ppm 7.93-7.90 (m, 2H), 7.80 (s, 1H), 7.23-7.19 (m, 2H), 5.86 (br s, 1H), 3.34 (s, 3H), 3.23 (s, 3H), 3.19-3.15 (m, 2H), 2.48 (m, 1H), 1.19 (m, 3H), 1.13 (m, 2H), 0.77 (m, 2H) |
| 2.8 | CDCl3 d ppm 7.89 (s, 1H), 7.88-7.86 (m, 2H), 7.55-7.53 (m, 3H), 5.75 (m, 1H), 3.35 (s, 3H), 3.24 (s, 3H), 2.97 (d, 3H), 2.23 (m, 1H), 1.11 (m, 2H), 0.78 (m, 2H) |
| 2.9 | CDCl3 d ppm 8.75 (s, 1H), 7.68-7.66 (d, 2H), 7.28-7.26 (d, 2H), 5.75 (br s, 1H), 3.21 (s, 3H), 3.17 (s, 3H), 2.89-2.88 (d, 3H), 2.38 (s, 3H). |
| 2.91 | DMSO d ppm 9.31 (s, 1H), 8.76-8.74 (d, 2H), 8.44-8.42 (d, 2H), 7.45 (br s, 1H), 3.81 (s, 3H), 3.80 (s, 3H), 3.49-3.48 (d, 3H) |
| 2.92 | CDCl3 d ppm 8.17 (s, 1H), 7.99 (m, 2H), 7.25 (m, 2H), 5.82 (m, 1H), 3.32 (s, 3H), 3.19 (s, 3H), 3.03 (d, J = 4 Hz, 3H), 2.57 (s, 3H). |
| 2.93 | CDCl3 d ppm 7.81 (s, 1H), 7.68-7.65 (d, 2H), 7.27-7.25 (d, 2H), 5.70 (br s, 1H), 3.26 (s, 3H), 3.15 (s, 3H), 2.88-2.87 (d, 3H), 2.41-2.38 (m, 1H), 2.37 (s, 3H), 1.06-1.00 (m, 2H), 0.74-0.68 (m, 2H) |
| 2.94 | CDCl3 d ppm 7.80 (s, 1H), 7.69-7.67 (d, 2H), 7.29-7.27 (d, 2H), 5.72 (br s, 1H), 3.26 (s, 3H), 3.14 (s, 3H), 2.88-2.87 (d, 3H), 2.69-2.62 (q, 2H), 2.43-2.35 (m, 1H), 1.24-1.20 (t, 3H), 1.04-0.98 (m, 2H), 0.73-0.67 (m, 2H). |

TABLE 10-continued

| Example | $^1$H NMR (400 MHz) |
|---|---|
| 2.96 | CDCl3 d ppm 7.88-7.86 (d, 2H), 7.82 (s, 1H), 7.53-7.51 (d, 2H), 5.78 (br s, 1H), 3.36 (s, 3H), 3.25 (s, 3H), 3.02-3.01 (d, 3H), 2.53-2.46 (m, 1H), 1.16-1.10 (m, 2H), 0.82-0.76 (m, 2H). |
| 4.4 | CD3CN d ppm 8.18 (m, 1H), 8.07-8.01 (m, 2H), 7.33-7.26 (m, 2H), 6.92 (br s, 1H), 6.48 (br s, 2H), 5.64 (br s, 1H), 4.30-4.26 (m, 1H), 3.60-3.51 (m, 2H), 3.26 (s, 3H), 3.17 (s, 3H), 2.92 (d, 3H), 2.57-2.51 (m, 2H), 2.43-2.38 (m, 2H), 2.30-1.77 (m, 6H) |
| 4.5 | CD3CN d ppm 8.13 (m, 1H), 8.08-8.01 (m, 2H), 7.33-7.28 (m, 2H), 6.91 (br s, 1H), 3.28 (s, 3H), 3.17 (s, 3H), 3.12 (s, 3H), 2.93 (d, 3H), 2.96-2.90 (m, 2H), 2.40-2.32 (m, 2H), 1.81-1.78 (m, 2H) |
| 4.6 | CD3CN d ppm 8.17 (m, 1H), 8.06-8.02 (m, 2H), 7.32-7.26 (m, 2H), 6.89 (br s, 1H), 4.36-4.31 (m, 1H), 3.63 (s, 3H), 3.61-3.52 (m, 2H), 3.27 (s, 3H), 3.16 (s, 3H), 2.93-2.88 (m, 2H), 2.92 (d, 3H), 2.50-2.44 (m, 2H), 2.00-1.59 (m, 6H) |
| 4.7 | CD3CN d ppm 8.17 (m, 1H), 8.04-7.99 (m, 2H), 7.32-7.26 (m, 2H), 6.91 (br s, 1H), 4.42-4.38 (m, 1H), 3.60-3.48 (m, 2H), 3.25 (s, 3H), 3.16 (s, 3H), 2.93-2.88 (m, 2H), 2.91 (d, 3H), 2.53-2.48 (m, 2H), 2.10-1.60 (m, 6H) |
| 4.8 | CD3CN d ppm 8.18 (m, 1H), 8.06-8.02 (m, 2H), 7.32-7.26 (m, 2H), 6.91 (br s, 1H), 6.48 (br s, 1H), 5.63 (br s, 1H), 4.33-4.27 (m, 1H), 3.62-3.42 (m, 2H), 3.25 (s, 3H), 3.16 (s, 3H), 2.93-2.88 (m, 2H), 2.92 (d, 3H), 2.52-2.43 (m, 2H), 2.10-1.60 (m, 6H) |
| 4.95 | CD3CN d ppm 8.15 (m, 1H), 8.07-8.01 (m, 2H), 7.94 (br s, 1H), 7.33-7.27 (m, 2H), 6.90 (br s, 1H), 6.19 (br s, 1H), 5.54 (br s, 1H), 3.26 (s, 3H), 3.18 (s, 3H), 2.92 (s, 3H), 2.94-2.88 (m, 2H), 2.23-1.61 (m, 6H) |
| 5 | CDCl3 d ppm 11.66 (s, 1H), 9.5 (s, 1H), 8.73 (d, 1H), 8.27 (d, 1H), 8.01 (t, 1H), 7.50 (m, 1H), 3.31 (s, 3H), 3.28 (s, 3H), 3.07 (d, 3H). |
| 6.1 | (400 MHz, CD$_3$CN) d ppm 8.32 (s, 1H), 8.05-7.99 (m, 2H), 7.37-7.29 (m, 2H), 6.88 (br s, 1H), 4.55-4.43 (m, 1H), 3.28 (s, 3H), 3.12 (s, 3H), 2.92-2.91 (d, 3H), 1.59-1.58 (d, 3H) |
| 6.2 | (400 MHz, CD$_3$CN) d ppm 8.18 (s, 1H), 8.08-7.99 (m, 2H), 7.33-7.29 (m, 2H), 6.87 (br s, 1H), 3.66-3.59 (m, 1H), 3.27 (s, 3H), 3.17 (s, 3H), 2.94-2.92 (d, 3H), 1.33-1.31 (d, 6H) |
| 18.1 | (400 MHz, CD$_3$CN) d ppm 8.72 (s, 1H), 8.09-8.03 (m, 2H), 7.35-7.29 (m, 2H), 6.85 (br s, 1H), 3.88-3.85 (m, 2H), 3.67-3.59 (m, 2H), 3.27 (s, 3H), 2.92-2.91 (d, 3H) |
| 18.3 | (400 MHz, CDCl$_3$) d ppm 8.77 (s, 1H), 7.97-7.93 (m, 2H), 7.24-7.21 (m, 2H), 5.77 (br s, 1H), 5.79-5.70 (m, 1H), 5.09-5.00 (m, 2H), 3.83-3.80 (m, 2H), 3.16 (s, 3H), 3.01-3.00 (d, 3H), 2.33 (m, 2H) |
| 18.4 | (400 MHz, MeOD) δ ppm 8.69 (s, 1H), 7.99 (br s, 2H), 7.31 (br s, 2H), 4.19 (m, 2H), 3.64-4.03 (M, 6H), 3.51 (m, 4H), 3.27 (s, 3H), 2.96 (s, 3H) |
| 18.5 | CD3CN d ppm 8.71 (s, 1H), 8.04-8.07 (m, 2H), 7.32 (t, 2H), 6.84 (br s, 1H), 5.77-5.84 (m, 1H), 4.95-5.06 (m, 2H), 3.73 (t, 2H), 3.14 (s, 3H), 2.91 (d, 3H), 2.00-2.08 (m, 2H), 1.57-1.61 (m, 2H) |
| 18.6 | CD3CN d ppm 8.71 (s, 1H), 8.09-8.05 (m, 2H), 7.34-7.30 (m, 2H), 7.18-7.16 (m, 1H), 7.11-7.09 (m, 1H), 6.90-6.88 (m, 1H), 6.83-6.81 (m, 1H), 3.96-3.92 (m, 2H), 3.76 (s, 3H), 3.15 (s, 3H), 2.92-2.91 (d, 3H), 2.8-2.7 (very broad m, 2H) |
| 18.7 | CD3CN d ppm 8.71 (s, 1H), 8.02-8.07 (m, 2H), 7.32 (t, 2H), 6.86 (br s, 1H), 3.75 (t, 2H), 3.60 (s, 3H), 3.16 (s, 3H), 2.95 (d, 3H), 2.50 (t, 2H), 1.73-1.81 (m, 2H) |
| 18.8 | CD3CN d ppm 8.53 (s, 1H), 8.29-8.39 (m, 2H), 7.84 (s, 1H), 7.75 (d, 1H), 7.52 (d, 1H), 7.27-7.37 (m, 3H), 6.85 (br s, 2H), 6.12 (br s, 1H), 4.96 (br s, 2H), 3.21 (s, 3H), 2.88 (d, 3H) |
| 18.91 | CD3CN d ppm 8.71 (s, 1H), 8.08-8.03 (m, 2H), 7.34-7.28 (m, 2H), 6.86 (br s, 1H), 4.68 (br s, 1H), 3.76-3.73 (m, 2H), 3.39-3.22 (m, 6H), 3.17 (s, 3H), 3.12-3.05 (m, 2H), 2.92-2.91 (d, 3H) |
| 18.92 | CD3CN d ppm 8.69 (s, 1H), 8.02-8.05 (m, 2H), 7.31 (t, 2H), 6.86 (br s, 1H), 3.63-3.74 (m, 4H), 3.13 (s, 3H), 2.96 (d, 3H), 2.23 (s, 9H), 1.19-1.44 (m, 5H) |
| 18.93 | CD3CN d ppm 8.71 (s, 1H), 8.03-8.08 (m, 2H), 7.30 (t, 2H), 6.88 (br s, 1H), 3.75 (t, 2H), 3.51 (br s, 1H), 3.24-3.43 (m, 2H), 3.15 (s, 3H), 2.90 (d, 3H), 2.71-2.81 (m, 2H), 1.50-1.60 (m, 2H) |
| 18.95 | CDCl3 d ppm 8.78 (s, 1H), 7.95 (t, 2H), 7.00-7.20 (m, 2H), 3.54 (t, 2H), 3.14 (s, 3H), 3.01 (d, 3H), 2.57 (t, 2H), 0.81-0.92 (m, 2H) |
| 18.96 | MeOD d ppm 8.54 (s, 1H), 8.00 (m, 2H), 7.28, (t, 2H), 3.89 (t, 2H), 3.54-3.62 (m, 2H), 3.20, (s, 3H), 3.08-3.11 (m, 2H), 3.12 (d, 3H), 2.23 (t, 2H) |
| 21 | CD3CN d ppm 8.17 (s, 1H), 8.00-8.05 (m, 2H), 7.33.(T, 2H), 6.88 (br s, 1H), 3.75 (t, 2H), 3.58 (s, 3H), 3.09 (s, 3H), 2.92 (d, 3H), 2.92-2.98 (m 2H), 2.28 (t, 2H), 1.81 (t, 2H), 1.45-1.52 (m, 2H), 1.33 (t, 3H) |
| 21.1 | CD3CN d ppm 8.18 (s, 1H), 8.01-8.06 (m, 2H), 7.33 (t, 2H), 6.85 (br s, 1H), 3.76 (t, 2H), 3.60 (s, 3H), 3.09 (s, 3H), 2.92-2.98 (m, 2H), 2.92 (d, 3H), 2.35 (t, 2H), 1.72 (t, 2H), 1.33 (t, 3H) |
| 21.2 | MeOD d ppm 8.10 (s, 1H), 7.95-7.99 (m, 2H), 7.28 (t, 2H), 3.76 (t, 2H), 3.08 (s, 3H), 2.96 (s, 3H), 2.90-2.99 (m, 2H), 2.13 (t, 2H), 1.60-1.64 (m, 2H), 1.38-1.47 (m, 2H), 1.31 (t, 2H) |
| 24.1 | CD3CN d ppm 8.44 (s, 1H), 8.01-8.05 (m, 2H), 7.30-7.32 (m, 2H), 7.27-7.30 (m, 1H), 5.95 (d, 1H), 5.46 (d, 1H), 3.72 (t, 2H), 3.13 (s, 3H), 2.94 (s, 3H), 2.43 (t, 2H), 1.73-1.83 (m, 2H), 1.45-1.56 (m, 2H) |
| 24.2 | CD3CN d ppm 8.47 (s, 1H), 8.03-8.08 (m, 2H), 7.32 (t, 2H), 7.25 (t, 1H), 6.91 (br s, 1H), 5.97 (d, 1H), 5.49 (d, 1H), 3.76 (t, 2H), 3.59 (s, 3H), 3.11 (s, 3H), 2.94 (d, 3H), 2.36 (t, 2H), 1.79 (t, 2H) |

TABLE 10-continued

| Example | ¹H NMR (400 MHz) |
|---|---|
| 24.3 | CD3CN d ppm 8.33 (s, 1H), 7.89-7.94 (m, 2H), 7.16 (t, 2H), 7.10 (t, 1H), 6.79 (br s, 1H), 5.82 (d, 1H), 5.33 (d, 1H), 3.61 (t, 2H), 3.44 (s, 3H), 2.97 (s, 3H), 2.80 (d, 3H), 2.13 (t, 2H), 1.44-1.48 (m, 2H), 1.20-1.30 (m, 2H), 1.09 (t, 2H) |
| 25.1 | CDCl3: d 7.70 (s, 1H), 7.65 (d, 2H, J = 8 Hz), 7.24 (d, 2H, J = 8 Hz), 5.75 (m, 1H), 3.73 (m, 2H), 3.05 (s, 3H), 2.89 (d, 3H, J = 4 Hz), 2.50 (m, 1H), 2.34 (s, 3H), 2.29 (m, 2H), 1.62 (m, 2H), 1.48 (m, 2H), 1.12 (m, 2H), 0.69 (m, 2H). |
| 27.4 | DMSO-d6 d ppm 8.62-8.58 (q, 1H), 8.02-7.97 (m, 2H), 7.54 (s, 1H), 7.47-7.43 (m, 2H), 7.29-7.22 (m, 1H), 7.15-7.08 (m, 4H), 3.57 (br, 2H), 3.33 (s, 3H), 3.14-3.13 (d, 3H), 2.82-2.80 (m, 2H), 1.30-1.20 (m, 4H), 1.05-1.01 (m, 2H), 0.79 (s, 6H). |
| 27.5 | DMSO-d6 d ppm 8.56-8.52 (q, 1H), 7.97-7.94 (m, 2H), 7.53-7.48 (m, 3H), 3.61-3.57 (t, 2H), 3.17 (s, 3H), 2.83-2.81 (d, 3H), 2.49-2.40 (m, 2H), 2.20-2.13 (t, 2H), 1.60-1.50 (m, 2H), 1.53-1.47 (m, 2H), 1.06-1.01 (m, 2H). |
| 27.6 | CD3OD d ppm 7.83-7.79 (m, 2H), 7.58 (s, 1H), 7.37-7.35 (m, 2H), 7.29-7.15 (m, 5H), 4.02 (s, 2H), 3.80-3.76 (t, 2H), 3.14 (s, 3H), 2.92-2.90 (d, 3H), 2.55-2.47 (m, 1H), 2.23-2.17 (t, 2H), 1.70-1.60 (m, 2H), 1.55-1.45 (m, 2H), 1.12-1.07 (m, 2H), 0.78 (br, 2H). |
| 27.8 | CD3OD d ppm 7.83-7.79 (m, 2H), 7.59 (s, 1H), 7.38-7.36 (m, 2H), 3.81-3.78 (t, 2H), 3.17 (s, 3H), 2.96-2.94 (d, 3H), 2.77-2.69 (q, 2H), 2.56-2.49 (m, 1H), 2.15-2.09 (t, 2H), 1.68-1.60 (m, 2H), 1.57-1.48 (m, 2H), 1.29-1.25 (t, 3H), 1.11-1.09 (m, 2H), 0.81 (br, 2H). |
| 27.9 | MeOH-d⁴ δ ppm 7.79 (d, 2H, J = 8 Hz), 7.59 (s, 1H), 7.35 (d, 2H, J = 8 Hz), 3.79 (m, 2H), 3.15 (s, 3H), 2.94 (s, 3H), 2.54 (m, 1H), 2.42 (s, 3H), 2.24 (m, 2H), 1.63-1.35 (m, 6H), 1.10 (m, 2H), 0.78 (bm, 2H) |
| 28 | MeOH-d⁴ δ ppm 7.78 (d, 2H, J = 8 Hz), 7.58 (s, 1H), 7.35 (d, 2H, J = 8 Hz), 3.74 (m, 2H), 3.15 (s, 3H), 2.94 (s, 3H), 2.53 (m, 1H), 2.42 (s, 3H), 2.07 (m, 2H), 1.68-1.55 (m, 6H), 1.50-1.30 (m, 4H), 1.10 (m, 2H), 0.81 (bm, 2H) |
| 28.3 | CD3OD d ppm 7.96-7.94 (m, 2H), 7.66 (s, 1H), 7.59-7.57 (m, 2H), 3.83-3.79 (t, 2H), 3.21 (s, 3H), 3.00 (br, 3H), 2.60-2.55 (m, 1H), 1.61-1.52 (m, 4H), 1.17-1.15 (m, 2H), 1.12 (s, 6H), 0.87 (br, 2H). |
| 29 | CD3OD d ppm 7.83-7.80 (m, 2H), 7.59 (s, 1H), 7.38-7.36 (m, 2H), 3.78-3.74 (t, 2H), 3.16 (s, 3H), 2.95-2.94 (d, 3H), 2.76-2.69 (q, 2H), 2.56-2.49 (m, 1H), 1.60-1.42 (m, 4H), 1.57-1.48 (m, 2H), 1.29-1.23 (t, 3H), 1.11-1.09 (m, 2H), 1.05 (s, 6H), 0.81 (br, 2H). |
| 29.1 | MeOH-d⁴ δ ppm 7.79 (d, 2H, J = 8 Hz), 7.58 (s, 1H), 7.34 (d, 2H, J = 8 Hz), 3.77 (m, 2H), 3.25 (s, 3H), 2.93 (s, 3H), 2.53 (m, 1H), 2.42 (s, 3H), 2.34 (m, 2H), 1.82 (m, 6H), 1.41 (m, 2H), 1.10 (m, 2H), 0.81 (bm, 2H). |
| 36.6 | CD₃CN d ppm 8.01-7.97 (m, 2H), 8.00 (s, 1H), 7.30-7.26 (m, 2H), 6.76 (br s, 1H), 3.97 (m, 2H), 3.51 (s, 3H), 3.15-3.10 (m, 1H), 2.91-2.90 (d, 3H), 1.83-1.76 (m, 2H), 1.40-1.38 (d, 2H) |
| 39 | CDCl₃ δ ppm 8.12 (s, 1H), 7.98-7.90 (m, 2H), 7.28-7.20 (m, 2H), 5.78 (br, 1H), 3.62 (br, 2H), 3.51 (s, 3H), 3.02 (d, 3H), 2.98-2.91 (m, 2H), 2.08-2.01 (m, 2H), 1.80-1.72 (m, 2H). |

Example 51

Liquid Microemulsion Formulation of Compound of Example 25.1

5-(N-(5-cyclopropyl-3-(methylcarbamoyl)-2-p-tolylfuro[2,3-b]pyridin-6-yl)methylsulfonamido)pentanoic acid (125 mg) from Example 25.1, step E was combined with 1.0N aqueous potassium hydroxide (500 microliters) and water (1.3 mL). The mixture was sonicated for 10 to 20 minutes. A preconcentrate solution (5 mL) consisting of 58.1% w/w Cremophor RH40, 16.9% Labrafil M2125CS, 8.3% Propylene glycol and 16.7% ethanol was added to the mixture and the resultant solution sonicated until clear. Citrate buffer (3.2 mL of 50 mM pH5) was added and stirred until a homogeneous viscosity obtained.

Example 52

Suspension Microemulsion Formulation of Compound of Example 25.1

5-(N-(5-cyclopropyl-3-(methylcarbamoyl)-2-p-tolylfuro[2,3-b]pyridin-6-yl)methylsulfonamido)pentanoic acid arginine monohydrate (100 mg) from Example 25.1, step F was combined with a preconcentrate solution (2.5 mL) consisting of 58.1% w/w Cremophor RH40, 16.9% Labrafil M2125CS, 8.3% Propylene glycol and 16.7% ethanol. The mixture was sonicated until homogeneous and then diluted 1:1 with 50 mM pH 7.4 tris buffer.

Example 53

Solid Microemulsion Formulation of Compound of Example 25.1

Step A:

Solid microemulsion excipient prepared by combining 19.7% Lauroglycol FCC, 19.7% Cremophor EL, 19.7% Lauroglycol 90, 19.7% PEG3350, and 21.2% Vitamin E-TPGS on percent weight basis and heating the mixture to 65 to 75° C. The mixture was stirred until a homogeneous clear liquid was obtained.

Step B:

5-(N-(5-cyclopropyl-3-(methylcarbamoyl)-2-p-tolylfuro[2,3-b]pyridin-6-yl)methylsulfonamido)pentanoic acid arginine monohydrate (5.4 g) from Example 25.1, step F was combined with microemulsion excipient prepared in Step A and stirred at 65° C. for one hour. The liquid formulation was then placed in hard gelatin capsules which were cooled to room temperature. Final formulation composition by weight percent: 27% 5-(N-(5-cyclopropyl-3-(methylcarbamoyl)-2-p-tolylfuro[2,3-b]pyridin-6-yl)methylsulfonamido)pentanoic acid arginine monohydrate, 14.4% Lauroglycol FCC, 14.4% Cremophor EL, 14.4% Lauroglycol 90, 14.4% PEG3350 and 15.50% vitamin E-TPGS.

Biological Examples

Biological Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al. In vitro assays have been reported in Ferrari et al. *Jnl. of Vir.*, 73:1649-1654, 1999; Ishii et al., *Hepatology*, 29:1227-1235, 1999; Lohmann et al., *Jnl of Bio. Chem.*, 274:10807-10815, 1999; and Yamashita et al., *Jnl. of Bio. Chem.*, 273:15479-15486, 1998.

WO 97/12033, filed on Sep. 27, 1996, by Emory University, listing C. Hagedorn and A. Reinoldus as inventors, which claims priority to U.S. Provisional Patent Application Ser. No. 60/004,383, filed on September 1995, described an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996: 1(Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al.

Biological Example 2

Replicon Assay

A cell line, ET (Huh-lucubineo-ET) is used for screening of compounds for inhibiting HCV RNA dependent RNA polymerase. The ET cell line is stably transfected with RNA transcripts harboring a $I_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T12801; K1846T) (Krieger at al, 2001 and unpublished). The ET cells are grown in DMEM (Dulbeco's Modified Eagle's Medium), supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). Reagents are all available through Life Technologies (Bethesda, Md.). The cells are plated at $0.5-1.0 \times 10^4$ cells/well in the 96 well plates and incubated for 24 hrs before adding test compound. The compounds are added to the cells to achieve a final concentration of 0.1 nM to 50 µM and a final DMSO (dimethylsulfoxide) concentration of 0.5%. Luciferase activity is measured 48 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication data is plotted relative to no compound control. To determine the $EC_{50}$ (effective concentration at which 50% of the maximum inhibition is observed), a 10 point, 3-fold serial dilution for each compound is used, which spans a concentration range of 1000 fold. $EC_{50}$ values were calculated by fitting % inhibition at each concentration to the following equation:

$$\% \text{ inhibition}=100\%/[(EC_{50}/[I])^b+1]$$

where b is Hill's coefficient.

In some aspects, certain compounds of Formula (I), exhibited $EC_{50}$ of equal to or less than 50 µM when tested according to the assay of Example 2. In other aspects the $EC_{50}$ was equal to or less than 10 µM. In still other aspects the $EC_{50}$ was equal to or less than 1 µM.

Biological Example 3

Cloning and Expression of Recombinant HCV-NS5b

The coding sequence of NS5b protein is cloned by PCR from pFKI$_{389}$luc/NS3-3'/ET as described by Lohmann, V., et al. (1999) *Science* 285, 110-113 using the primers shown on page 266 of WO 2005/012288.

The cloned fragment is missing the C terminus 21 amino acid substituents. The cloned fragment is inserted into an IPTG-inducible (isopropyl-β-D-thiogalactopyranoside) expression plasmid that provides an epitope tag (His)6 at the carboxy terminus of the protein.

The recombinant enzyme is expressed in XL-1 cells and after induction of expression, the protein is purified using affinity chromatography on a nickel-NTA (nitrilotriacetic acid) column. Storage conditions are 10 mM Tris-HCl pH 7.5, 50 mM NaCl, 0.1 mM EDTA (ethylenediaminetetraacetic acid), 1 mM DTT (dithiothreotol), and 20% glycerol at −20° C.

Biological Example 4

HCV-NS5b Enzyme Assay Using Heteropolymer Substrate

The polymerase activity is assayed by measuring incorporation of radiolabeled UTP into a RNA product using a biotinylated, heteropolymeric template, which included a portion of the HCV genome. Typically, the assay mixture (50 µL) contained 10 mM Tris-HCl (pH 7.5), 5 mM MgCl$_2$, 0.2 mM EDTA, 10 mM KCl, 1 unit/µL RNAsin, 1 mM DTT, 10 µM each of NTP (nucleoside triphosphate), including [$^3$H]-UTP (uridine triphosphate), and 10 ng/µL heteropolymeric template. Test compounds are initially dissolved in 100% DMSO and further diluted in aqueous buffer containing 5% DMSO. Typically, compounds are tested at concentrations between 1 nM and 100 µM. Reactions are started with addition of enzyme and allowed to continue at 37° C. for 2 hours. Reactions are quenched with 8 µL of 100 mM EDTA and reaction mixtures (30 µL) are transferred to streptavidin-coated scintillation proximity microtiter plates (FlashPlates) and incubated at room temperature overnight. Incorporation of radioactivity is determined by scintillation counting.

Biological Example 5

HCV-NS5b Enzyme Assay Using Homopolymer Substrate

The polymerase activity is assayed by measuring incorporation of radiolabeled UTP into a RNA product using a biotinylated, homopolymeric template. The template is formed by annealing adenosine homopolymer to uridine 20-mer capped with a 5'-biotin group (biotin-U[20]) in the ratio of 1:4. Typically, the assay mixture (50 µL) contained 25 mM Tris-HCl (pH 7.5), 40 mM KCl, 0.3 mM $MgCl_2$, 0.05 mM EDTA, 0.2 unit/µL Superase RNAse Inhibitor, 5 mM DTT, 30 µM UTP (Uridine triphosphate), including [$^3$H]-UTP (uridine triphosphate) at 0.4 µCi/µL with final concentration of 1 µM, and 50 nM of homopolymeric template. Test compounds are initially dissolved in 100% DMSO and further diluted in aqueous buffer containing 5% DMSO. Typically, compounds are tested at concentrations between 2 nM and 50 µM. Reactions are started with addition of enzyme and allowed to continue at 30° C. for 90 minutes. Reactions are quenched with 8 µL of 100 mM EDTA and reaction mixtures (30 µL) are transferred to streptavidin-coated scintillation proximity microtiter plates (Flash Plates) and incubated at room temperature overnight. Incorporation of radioactivity is determined by scintillation counting.

Inhibitor $IC_{50}$ values are determined by adding test compound as ten point, two-fold serial dilutions in 100% DMSO with a final reaction concentration of 5%. $IC_{50}$ values are calculated by plotting the % inhibition against compound concentration and fitting the data to a constrained four parameter sigmoidal curve, equivalent to the "four parameter logistic equation", where Bottom is the minimum Y value, Top is the maximum Y value, and Hillslope is the slope of the linear portion of the semi-log curve. Top and Bottom are constrained to values of 0% and 100%, respectively. These analyses are performed using Graphpad Prism v.4.0 (Graphpad Software, Inc.) in conjunction with DS Accord for EXCEL 6.0 (Accelrys, Microsoft Corp.).

Biological Example 6

The polymerase activity is also assayed by measuring incorporation of radiolabeled GTP into an RNA product using a biotinylated oligoG13 primer with a polycytidylic acid RNA template. Typically, the assay mixture (40 µL) contains 50 mM HEPES (pH 7.3), 2.5 mM magnesium acetate, 2 mM sodium chloride, 37.5 mM potassium acetate, 5 mM DTT, 0.4 U/mL RNasin, 2.5% glycerol, 3 nM NS5B, 20 nM polyC RNA template, 20 nM biotin-oligoG13 primer, and 0.2 µM tritiated guanosine triphosphate. Test compounds are initially dissolved and diluted in 100% DMSO and further diluted into aqueous buffer, producing a final concentration of 5% DMSO. Typically, compounds are tested at concentrations between 0.2 nM and 10 µM. Reactions are started with addition of tritiated guanosine triphosphate and allowed to continue at 30° C. for 2 hours. Reactions are quenched with 100 µL stop buffer containing 10 mM EDTA and 1 µg/mL streptavidin-coated scintillation proximity beads. Reaction plates are incubated at 4° C. for 10 hours and then incorporation of radioactivity was determined by scintillation counting.

Compounds in Table 11 supra have been tested in the polymerase assay of Biological Example 1 and the $IC_{50}$ values for each compound are provided therein. Most of the compounds of Table 11 exhibit an $IC_{50}$ of 1 µM or less or an $IC_{50}$ of 500 nM or less in the replicon assay of Biological Example 2 provided herein. For example, the compounds of Example numbers 1, 2.1, 2.2, 2.9, 2.93, 2.94, 2.95, 2.96, 2.97, 2.98, 4.9, 6, 14.1, 16, 18.97, 18.98, 18.99, 18.994, 18.995, 18.996, 18.997, 21.97, 21.992, 22.92, 22.95, 22.98, 22.99, 22.991, 23, 23.1, 23.7, 23.91, 23.92, 23.99, 23.994, 24, 24.01, 24.2, 24.3, 24.4, 24.5, 24.6, 24.7, 24.8, 24.9, 25, 25.1, 25.2, 25.3, 25.4, 25.5, 25.5, 25.6, 25.7, 25.8, 25.9, 26, 26.1, 26.2, 26.3, 26.4, 26.5, 26.6, 26.7, 26.8, 27, 27.2, 27.4, 27.5, 27.6, 27.7, 27.8, 27.9, 28, 28.1, 28.2, 28.3, 28.5, 28.7, 30, 31, 34, 36, 36.2, 36.3, and 36.4 exhibit an $IC_{50}$ of 100 nM or less in the replicon assay of Biological Example 2. Compounds of Examples 4, 4.5, 4.7, 4.91, 5, 9, 18.95, 18.96, 19, 21.99, 23.98 exhibit an $IC_{50}$ of 5 µM or more in the replicon assay of Biological Example 2.

TABLE 11

| Example # | NS5B polymerase IC50 µM | Mass observed | Ion | Retention time | LC-method |
|---|---|---|---|---|---|
| 1 | 0.016 | 418.0 | M + H | 1.43 | A |
| 2 | 0.163 | 503.9 | M + H | 1.40 | A |
| 2.1 | 0.012 | 404.3 | M + H | 1.27 | A |
| 2.2 | 0.054 | 448.0 | M + H | 1.27 | A |
| 2.3 | 0.408 | 487.1 | M + H | 1.20 | A |
| 2.4 | 0.132 | 418.3 | M + H | 1.23 | A |
| 2.5 | 0.662 | 472.0 | M + H | 1.45 | A |
| 2.6 | 0.297 | 404.1 | M + H | 1.22 | A |
| 2.7 | 0.044 | 432.1 | M + H | 1.33 | A |
| 2.8 | 0.030 | 400.2 | M + H | 1.57 | A |
| 2.9 | 0.016 | 500.0 | M + H | 1.41 | A |
| 2.91 | 0.802 | 554.0 | M + H | 1.49 | A |
| 2.92 | 0.256 | 393.1 | M + H | 1.33 | A |
| 2.93 | 0.004 | 414.3 | M + H | 1.42 | A |
| 2.94 | 0.003 | 428.1 | M + H | 1.60 | A |
| 2.95 | 0.008 | 537.7 | M + H | 1.46 | A |
| 2.96 | 0.024 | 434.1 | M + H | 1.49 | A |
| 2.97 | 0.004 | 451.8 | M + H | 1.58 | A |
| 2.98 | 0.005 | 457.8 | M + H | 1.62 | A |
| 2.99 | 0.071 | 428.0 | M + H | 1.23 | A |
| 3 | 0.034 | 506.3 | M + H | 1.28 | A |
| 4 | 0.049 | 478.1 | M + H | 1.03 | A |
| 4.1 | 0.112 | 575.2 | M + H | 1.25 | A |
| 4.2 | 0.128 | 418.0 | M + H | 1.36 | A |
| 4.3 | 0.132 | 463.1 | M + H | 1.10 | A |
| 4.4 | 0.200 | 560.2 | M + H | 1.15 | A |
| 4.5 | 0.206 | 541.1 | M + H | 1.01 | A |
| 4.6 | 0.113 | 589.2 | M + H | 1.28 | A |
| 4.7 | 0.051 | 575.4 | M + H | 1.08 | A |
| 4.8 | 0.051 | 574.4 | M + H | 1.14 | A |
| 4.9 | 0.075 | 536.3 | M + H | 1.28 | A |
| 4.91 | 0.010 | 570.2 | M + H | 1.10 | A |
| 4.92 | 0.223 | 480.2 | M + H | 1.13 | A |
| 4.93 | 0.216 | 464.3 | M + H | 1.19 | A |
| 4.94 | 0.208 | 498.2 | M + H | 1.12 | A |
| 4.95 | 0.016 | 477.2 | M + H | 1.11 | A |
| 4.96 | 0.078 | 420.3 | M + H | 1.35 | A |
| 5 | 0.256 | 474.1 | M + H | 1.22 | A |
| 6 | 0.020 | 406.3 | M + H | 1.25 | A |
| 6.1 | 0.043 | 474.0 | M + H | 1.45 | A |
| 6.2 | 0.058 | 420.0 | M + H | 1.38 | A |
| 7 | 0.060 | 402.1 | M + H | 1.19 | A |
| 8 | 0.125 | 442.1 | M + H | 1.28 | A |
| 9 | 2.324 | 452.0 | M + H | 1.07 | A |
| 9.1 | 0.117 | 431.9 | M + H | 1.13 | A |
| 9.2 | 0.082 | | M + H | | A |
| 10 | 0.467 | 420.1 | M + H | 1.16 | A |
| 11 | 0.825 | 422.3 | M + H | 1.14 | A |
| 12 | 0.734 | 434.1 | M + H | 1.15 | A |
| 13 | 0.273 | 429.3 | M + H | 1.19 | A |
| 14 | 0.147 | 431.1 | M + H | 1.18 | A |
| 14.3 | 0.498 | 463.2 | M + H | 1.12 | A |
| 15 | 0.532 | 435.1 | M + H | 1.00 | A |
| 16 | 0.003 | 492.3 | M + H | 1.59 | A |
| 17 | 0.128 | 480.2 | M + H | 1.59 | A |
| 18 | 0.115 | 576.9 | M + H | 0.96 | A |
| 18.1 | 0.451 | 533.9 | M + H | 1.36 | A |
| 18.2 | 0.061 | 557.1 | M + H | 1.14 | A |
| 18.3 | 0.103 | 544.0 | M + H | 1.41 | A |
| 18.4 | 0.260 | 603.0 | M + H | 1.24 | A |
| 18.5 | 0.449 | 558.0 | M + H | 1.44 | A |
| 18.6 | 0.573 | 624.2 | M + H | 1.36 | A |
| 18.7 | 0.076 | 590.0 | M + H | 1.25 | A |
| 18.8 | 0.051 | 623.0 | M + H | 1.16 | A |
| 18.9 | 0.109 | 571.0 | M + H | 1.22 | A |
| 18.91 | 0.133 | 616.2 | M + H | 1.16 | A |

TABLE 11-continued

| Example # | NS5B polymerase IC50 μM | Mass observed | Ion | Retention time | LC-method |
|---|---|---|---|---|---|
| 18.92 | 1.015 | 587.0 | M + H | 1.20 | A |
| 18.93 | 0.108 | 592.0 | M + H | 1.06 | A |
| 18.94 | 0.243 | 578.0 | M + H | 1.02 | A |
| 18.95 | 0.112 | 604.0 | M + H | 0.96 | A |
| 18.96 | 0.034 | 653.0 | M + H | 0.97 | A |
| 18.97 | 0.032 | 649.9 | M + H | 1.36 | A |
| 18.98 | 0.004 | 666.0 | M + H | 1.52 | A |
| 18.99 | 0.005 | 646.0 | M + H | 1.46 | A |
| 18.991 | 0.029 | 625.9 | M + H | 1.46 | A |
| 18.992 | 0.237 | 606.0 | M + H | 1.51 | A |
| 18.993 | 0.112 | 610.0 | M + H | 1.39 | A |
| 18.994 | 0.014 | 605.8 | M + H | 1.39 | A |
| 18.995 | 0.014 | 639.7 | M + H | 1.46 | A |
| 18.996 | 0.004 | 619.7 | M + H | 1.44 | A |
| 18.997 | 0.022 | 623.7 | M + H | 1.39 | A |
| 18.998 | 0.039 | 575.9 | M + H | 1.45 | A |
| 18.999 | 0.004 | 626.1 | M + H | 1.26 | A |
| 18.9991 | 0.005 | 640.3 | M + H | 1.17 | B |
| 19 | 0.009 | 590.2 | M + H | 1.03 | A |
| 20 | 1.839 | 561.0 | M + H | 1.00 | A |
| 21 | 0.010 | 506.1 | M + H | 1.51 | A |
| 21.1 | 0.052 | 492.1 | M + H | 1.45 | A |
| 21.2 | 0.012 | 492.1 | M + H | 1.19 | A |
| 21.3 | 0.134 | 576.2 | M + H | 1.56 | A |
| 21.4 | 0.007 | 520.1 | M + H | 1.43 | A |
| 21.5 | 0.191 | 551.3 | M + H | 1.56 | A |
| 21.6 | 0.948 | 555.2 | M + H | 1.61 | A |
| 21.7 | 0.531 | 555.2 | M + H | 1.61 | A |
| 21.8 | 0.688 | 494.3 | M + H | 1.40 | A |
| 21.9 | 0.772 | 526.3 | M + H | 1.71 | A |
| 21.91 | 0.570 | 542.1 | M + H | 1.68 | A |
| 21.92 | 0.352 | 556.1 | M + H | 1.59 | A |
| 21.93 | 0.186 | 519.2 | M + H | 1.65 | A |
| 21.94 | 0.077 | 532.2 | M + H | 1.55 | A |
| 21.95 | 0.119 | 537.1 | M + H | 1.60 | A |
| 21.96 | 0.072 | 565.2 | M + H | 1.65 | A |
| 21.97 | 0.003 | 574.1 | M + H | 1.63 | A |
| 21.98 | 0.037 | 583.1 | M + H | 1.61 | A |
| 21.99 | 4.544 | 507.0 | M + H | 1.65 | A |
| 21.991 | 0.074 | 459.0 | M + H | 1.59 | A |
| 21.992 | 0.065 | 512.1 | M + H | 1.32 | A |
| 21.993 | 0.228 | 526.0 | M + H | 1.65 | A |
| 21.994 | 0.147 | 490.1 | M + H | 1.49 | A |
| 21.995 | 0.155 | 601.1 | M − H | 1.73 | A |
| 21.996 | 0.094 | 497.0 | M + H | 1.45 | A |
| 21.997 | 0.148 | 587.0 | M − H | 1.70 | A |
| 21.998 | 0.428 | 604.1 | M + H | 1.67 | A |
| 21.999 | 0.112 | 618.2 | M + H | 1.66 | A |
| 22 | 0.169 | 517.0 | M + H | 1.50 | A |
| 22.1 | 0.034 | 570.1 | M + H | 1.66 | A |
| 22.2 | 0.281 | 556.0 | M + H | 1.58 | A |
| 22.3 | 0.089 | 521.1 | M + H | 1.57 | A |
| 22.4 | 0.033 | 590.1 | M + H | 1.41 | A |
| 22.5 | 0.083 | 570.0 | M + H | 1.25 | A |
| 22.6 | 0.251 | 570.0 | M + H | 1.28 | A |
| 22.7 | 0.053 | 570.0 | M + H | 1.26 | A |
| 22.8 | 0.045 | 563.0 | M + H | 1.56 | A |
| 22.9 | 0.023 | 568.0 | M + H | 1.62 | A |
| 22.91 | 0.034 | 567.0 | M + H | 1.48 | A |
| 22.92 | 0.032 | 490.3 | M + H | 1.42 | A |
| 22.93 | 0.047 | 492.0 | M + H | 1.49 | A |
| 22.94 | 0.031 | 492.0 | M + H | 1.50 | A |
| 22.95 | 0.040 | 476.0 | M + H | 1.45 | A |
| 22.96 | 0.131 | 505.0 | M + H | 1.41 | A |
| 22.97 | 0.046 | 506.0 | M + H | 1.51 | A |
| 22.98 | 0.011 | 552.0 | M + H | 1.37 | A |
| 22.99 | 0.015 | 555.2 | M + H | 1.39 | A |
| 22.991 | 0.007 | 555.2 | M + H | 1.39 | A |
| 22.992 | 0.041 | 519.1 | M + H | 1.47 | A |
| 22.993 | 1.064 | 434.1 | M + H | 1.57 | A |
| 22.994 | 1.062 | 587.0 | M + H | 1.48 | A |
| 22.995 | 0.024 | 589.3 | M + H | 1.50 | A |
| 22.996 | 0.059 | 517.3 | M + H | 1.34 | A |
| 22.997 | 0.083 | 465.9 | M + H | 1.56 | A |
| 23 | 0.022 | 526.0 | M + H | 1.41 | A |
| 23.1 | 0.045 | 553.1 | M + H | 1.59 | A |
| 23.2 | 0.144 | 450.3 | M + H | 1.26 | A |
| 23.3 | 0.058 | 541.3 | M + H | 1.39 | A |
| 23.4 | 0.125 | 527.0 | M + H | 1.33 | A |
| 23.5 | 0.151 | 598.2 | M + H | 1.31 | A |
| 23.5 | 0.035 | 601.0 | M + H | 1.51 | A |
| 23.6 | 0.093 | 589.0 | M + H | 1.51 | A |
| 23.7 | 0.005 | 567.3 | M + H | 1.39 | A |
| 23.8 | 0.058 | 588.2 | M + H | 1.55 | A |
| 23.9 | 0.074 | 603.0 | M + H | 1.53 | A |
| 23.91 | 0.018 | 540.1 | M + H | 1.41 | A |
| 23.92 | 0.011 | 554.0 | M + H | 1.43 | A |
| 23.93 | 0.044 | 554.1 | M + H | 1.81 | A |
| 23.94 | 0.044 | 544.0 | M + H | 1.43 | A |
| 23.95 | 0.029 | 530.0 | M + H | 1.43 | A |
| 23.96 | 0.189 | 565.9 | M + H | 1.57 | A |
| 23.97 | 0.035 | 579.9 | M + H | 1.58 | A |
| 23.98 | 0.166 | 561.0 | M + H | 1.19 | A |
| 23.99 | 0.026 | 566.0 | M + H | 1.35 | A |
| 23.991 | 0.061 | 537.9 | M + H | 1.41 | A |
| 23.992 | 0.067 | 525.9 | M + H | 1.38 | A |
| 23.993 | 0.125 | 732.2 | M + H | 1.44 | A |
| 23.994 | 0.057 | 679.0 | M + H | 1.48 | A |
| 23.995 | 0.114 | 583.8 | M + H | 1.32 | A |
| 23.996 | 0.242 | 624.9 | M + H | 1.36 | A |
| 23.997 | 0.058 | 505.3 | M + H | 1.33 | A |
| 23.998 | 0.184 | 567.3 | M + H | 1.47 | A |
| 23.999 | 0.079 | 512.0 | M + H | 1.33 | A |
| 23.9991 | 0.026 | 662.0 | M + H | 1.21 | A |
| 23.9992 | 0.020 | 676.1 | M + H | 1.26 | A |
| 23.9993 | 0.026 | 586.0 | M + H | 1.25 | A |
| 23.9994 | 0.038 | 662.1 | M + H | 1.35 | A |
| 23.9995 | 0.017 | 648.0 | M + H | 1.15 | A |
| 23.9996 | 0.019 | 558.0 | M + H | 1.15 | A |
| 23.9997 | 0.012 | 648.0 | M + H | 1.17 | A |
| 23.9998 | 0.011 | 634.0 | M + H | 1.10 | A |
| 23.9999 | 0.013 | 620.0 | M + H | 0.89 | A |
| 23.99991 | 0.009 | 572.0 | M + H | 1.35 | A |
| 23.99992 | 0.007 | 548.1 | M + H | 1.15 | A |
| 23.99993 | 0.011 | 562.2 | M + H | 1.32 | A |
| 23.99994 | 0.003 | 472.2 | M + H | 1.30 | A |
| 23.99995 | 0.009 | 576.2 | M + H | 1.21 | A |
| 23.99996 | 0.002 | 486.1 | M + H | 1.20 | A |
| 23.99997 | 0.004 | 458.0 | M + H | 1.10 | A |
| 23.99998 | 0.005 | 520.0 | M + H | 0.90 | A |
| 23.99999 | 0.006 | 534.1 | M + H | 0.89 | A |
| 23.999991 | 0.004 | 548.1 | M + H | 0.92 | A |
| 23.999992 | 0.002 | 589.0 | M + H | 1.41 | A |
| 23.999993 | 0.016 | 470.9 | M + H | 0.96 | A |
| 23.999994 | 0.014 | 485.0 | M + H | 1.00 | A |
| 23.999995 | 0.014 | 457.0 | M + H | 0.97 | A |
| 23.999996 | 0.016 | 543.0 | M + H | 1.00 | A |
| 23.999997 | 0.005 | 525.0 | M + H | 1.14 | A |
| 23.999998 | 0.005 | 529.9 | M + H | 0.96 | A |
| 23.999999 | 0.020 | 588.0 | M + H | 0.94 | A |
| 24 | 0.001 | 528.2 | M + H | 1.46 | A |
| 24.01 | 0.001 | 524.0 | M + H | 1.30 | A |
| 24.1 | 0.078 | 490.0 | M + H | 1.36 | A |
| 24.2 | 0.042 | 490.0 | M + H | 1.47 | A |
| 24.3 | 0.057 | 504.0 | M + H | 1.50 | A |
| 24.4 | 0.009 | 564.0 | M + H | 1.37 | A |
| 24.5 | 0.001 | 564.0 | M + H | 1.43 | A |
| 24.6 | 0.000 | 564.0 | M + H | 1.43 | A |
| 24.7 | 0.005 | 560.2 | M + H | 1.51 | A |
| 24.8 | 0.001 | 580.1 | M + H | 1.54 | A |
| 24.9 | 0.003 | 546.2 | M + H | 1.51 | A |
| 25 | 0.005 | 520.0 | M + H | 1.51 | A |
| 25.1 | 0.002 | 499.9 | M + H | 1.31 | A |
| 25.2 | 0.003 | 513.9 | M + H | 1.68 | A |
| 25.3 | 0.001 | 520.0 | M + H | 1.41 | A |
| 25.4 | 0.001 | 586.2 | M + H | 1.57 | A |
| 25.5 | 0.001 | 540.0 | M + H | 1.46 | A |
| 25.6 | 0.002 | 533.9 | M + H | 1.45 | A |
| 25.7 | 0.001 | 537.8 | M + H | 1.41 | A |
| 25.8 | 0.001 | 555.7 | M + H | 1.49 | A |
| 25.9 | 0.003 | 559.9 | M + H | 1.53 | A |
| 25.91 | 0.003 | 549.8 | M + H | 1.45 | A |

TABLE 11-continued

| Example # | NS5B polymerase IC50 μM | Mass observed | Ion | Retention time | LC-method |
|---|---|---|---|---|---|
| 26 | 0.006 | 588.3 | M + H | 1.45 | B |
| 26.1 | 0.001 | 546.2 | M + H | 0.94 | B |
| 26.2 | 0.004 | 552.2 | M + H | 1.47 | A |
| 26.3 | 0.003 | 548.2 | M + H | 1.39 | B |
| 26.4 | 0.005 | 490.2 | M + H | 1.5 | A |
| 26.5 | 0.010 | 476.2 | M + H | 1.47 | A |
| 26.6 | 0.004 | 538.1 | M + H | 1.47 | A |
| 26.7 | 0.002 | 472.2 | M + H | 1.57 | A |
| 26.8 | 0.005 | 518.1 | M + H | 1.54 | A |
| 26.9 | 0.003 | 503.8 | M + H | 1.27 | A |
| 27 | 0.001 | 578.3 | M + H | 1.57 | A |
| 27.1 | 0.012 | 532.2 | M + H | 1.46 | A |
| 27.2 | 0.001 | 596.9 | M + H | 1.45 | A |
| 27.3 | 0.023 | 597 | M + H | 1.44 | A |
| 27.4 | 0.001 | 606 | M + H | 1.58 | A |
| 27.5 | 0.001 | 520.1 | M + H | 1.53 | A |
| 27.6 | 0.001 | 576.2 | M + H | 1.79 | A |
| 27.7 | 0.001 | 526.3 | M + H | 1.67 | A |
| 27.8 | 0.001 | 514.2 | M + H | 1.68 | A |
| 27.9 | 0.002 | 514.3 | M + H | 0.76 | A |
| 28 | 0.001 | 554 | M + H | 0.68 | A |
| 28.1 | 0.002 | 511.9 | M + H | 1.41 | C |
| 28.2 | 0.002 | 511.9 | M + H | 1.39 | C |
| 28.3 | 0.002 | 548.2 | M + H | 1.63 | A |
| 28.4 | 0.003 | 570.3 | M + H | 1.6 | A |
| 28.5 | 0.001 | 576.3 | M + H | 1.63 | A |
| 28.7 | 0.005 | 535.9 | M + H | 1.47 | A |
| 28.9 | 0.002 | 485.9 | M + H | 1.3 | A |
| 29 | 0.001 | 542.2 | M + H | 1.64 | A |
| 29.1 | 0.002 | 540.2 | M + H | 1.6 | A |
| 29.2 | 0.001 | 542.2 | M + H | 1.13 | B |
| 29.3 | 0.006 | 540.3 | M + H | 1.07 | B |
| 29.4 | 0.003 | 544.0 | M + H | 1.06 | A |
| 29.5 | 0.002 | 467.2 | M + H | 1.12 | B |
| 29.6 | 0.002 | 481.2 | M + H | 1.18 | B |
| 29.7 | 0.002 | 584.1 | M + H | 1.56 | A |
| 29.8 | 0.002 | 526.0 | M + H | 1.49 | A |
| 29.9 | 0.002 | 528.0 | M + H | 1.59 | A |
| 29.91 | 0.002 | 554.0 | M + H | 1.71 | A |
| 29.92 | 0.002 | 509.9 | M + H | 1.39 | A |
| 29.93 | 0.003 | 524.0 | M + H | 1.41 | A |
| 29.94 | 0.003 | 598.1 | M + H | 1.60 | A |
| 29.95 | 0.003 | 584.1 | M + H | 1.53 | A |
| 29.96 | 0.005 | 541.9 | M + H | 0.97 | A |
| 29.97 | 0.003 | 440.0 | M + H | 1.36 | A |
| 29.98 | 0.017 | 454.0 | M + H | 1.41 | A |
| 29.99 | 0.014 | 467.9 | M + H | 1.50 | A |
| 29.991 | 0.004 | 542.0 | M + H | 1.11 | A |
| 29.992 | 0.007 | 556.0 | M + H | 1.21 | A |
| 29.993 | 0.002 | 570.0 | M + H | 1.22 | A |
| 29.994 | 0.006 | 497.9 | M + H | 1.23 | A |
| 29.995 | 0.013 | 515.9 | M + H | 1.09 | A |
| 29.996 | 0.007 | 528.9 | M + H | 1.10 | A |
| 29.997 | 0.002 | 535.8 | M + H | 1.45 | A |
| 29.998 | 0.003 | 549.8 | M + H | 1.64 | A |
| 29.999 | 0.004 | 521.8 | M + H | 1.55 | A |
| 29.9991 | 0.003 | 558.1 | M + H | 0.77 | B |
| 29.9992 | 0.004 | 544.1 | M + H | 1.34 | A |
| 29.9993 | 0.002 | 540.1 | M + H | 1.59 | A |
| 29.9994 | 0.002 | 514.1 | M + H | 1.35 | A |
| 29.9995 | 0.002 | 528.1 | M + H | 1.43 | A |
| 29.9996 | 0.117 | 669.1 | M + H | 1.20 | A |
| 29.9997 | 0.015 | 525.9 | M + H | 1.47 | A |
| 29.9998 | 0.005 | 553.0 | M + H | 1.38 | A |
| 29.9999 | 0.002 | 539.0 | M + H | 0.98 | A |
| 29.99991 | 0.129 | 569.0 | M + H | 0.92 | A |
| 29.99992 | 0.002 | 611.1 | M + H | 0.95 | A |
| 29.99993 | 0.003 | 583.1 | M + H | 0.93 | A |
| 29.99994 | 0.007 | 551.8 | M + H | 1.43 | A |
| 29.99995 | 0.032 | 600.0 | M + H | 0.93 | A |
| 29.99996 | 0.037 | 514.0 | M + H | 0.96 | A |
| 29.99997 | 0.004 | 661.3 | M + H | 1.73 | A |
| 29.99998 | 0.002 | 661.3 | M + H | 1.58 | A |
| 29.99999 | 0.021 | 585.0 | M + H | 1.00 | A |
| 29.999991 | 0.020 | 599.2 | M + H | 0.92 | A |
| 29.999992 | 0.007 | 653.2 | M + H | 1.10 | A |
| 29.999993 | 0.022 | 597.1 | M + H | 1.49 | A |
| 29.999994 | 0.003 | 544.0 | M + H | 0.96 | A |
| 29.999995 | 0.003 | 539.0 | M + H | 0.96 | A |
| 29.999996 | 0.012 | 588.0 | M + H | 1.07 | A |
| 29.999997 | 0.048 | 503.9 | M + H | 0.89 | A |
| 29.999998 | 0.004 | 514.0 | M + H | 1.00 | A |
| 29.999999 | 0.002 | 532.0 | M + H | 1.30 | A |
| 30 | 0.062 | 432.3 | M + H | 1.23 | A |
| 31 | 0.035 | 448.1 | M + H | 1.28 | A |
| 32 | 0.651 | 448.1 | M + H | 1.33 | A |
| 33 | 0.170 | 448.0 | M + H | 1.22 | A |
| 34 | 0.009 | 448.0 | M + H | 1.24 | A |
| 35 | 6.028 | 564.0 | M + H | 1.74 | A |
| 36 | 0.050 | 432.0 | M + H | 1.45 | A |
| 36.1 | 0.046 | 432.1 | M + H | 1.39 | A |
| 36.2 | 0.035 | 434.0 | M + H | 1.34 | A |
| 36.3 | 0.070 | 446.3 | M + H | 1.52 | A |
| 36.4 | 0.005 | 446.3 | M + H | 1.56 | A |
| 36.5 | 0.474 | 553.3 | M + H | 1.36 | A |
| 36.6 | 0.231 | 418.1 | M + H | 1.24 | A |
| 37 | 0.048 | 460.1 | M + H | 1.13 | A |
| 38 | 0.509 | 476.3 | M + H | 1.34 | A |
| 39 | 0.161 | 418.0 | M + H | 1.41 | A |
| 40 | | 525.2 | M + H | 1.36 | A |
| 41 | 0.003 | 544.0 | M + H | 1.14 | A |
| 41.1 | 0.002 | 558.0 | M + H | 1.23 | A |
| 42 | 0.002 | 586.2 | M + H | 1.52 | A |
| 42.1 | 0.003 | 572.1 | M + H | 1.45 | A |
| 43 | 0.002 | 572.1 | M + H | 1.47 | A |
| 43.1 | 0.002 | 558.1 | M + H | 1.52 | A |
| 44 | 0.020 | 543.6 | M + H | 1.09 | A |
| 44.1 | 0.005 | 540.0 | M + H | 1.44 | A |
| 45 | 0.008 | 548 | M + H | 1.01 | A |
| 46 | 0.003 | 592.7 | M + H | 1.27 | A |
| 46.1 | 0.003 | 556.1 | M + H | 1.28 | A |
| 47 | 0.002 | 514.1 | M + H | 1.37 | A |
| 47.1 | 0.668 | 647.3 | M + H | 1.64 | A |
| 47.2 | 0.058 | 647.3 | M + H | 1.65 | A |
| 47.3 | 0.003 | 514.1 | M + H | 1.36 | A |
| 47.4 | 0.003 | 572.2 | M + H | 1.36 | A |
| 47.5 | 0.003 | 558.2 | M + H | 1.32 | A |
| 47.6 | 0.005 | 691.3 | M + H | 1.55 | A |
| 47.7 | 0.002 | 544.1 | M + H | 1.50 | A |
| 47.71 | 0.026 | 789.3 | M + H | 1.72 | A |
| 47.72 | 0.006 | 703.3 | M + H | 1.69 | A |
| 48 | 0.008 | 584.0 | M + H | 1.05 | A |
| 49 | 0.002 | 624.0 | M + H | 0.92 | A |
| 49.1 | 0.006 | 804.4 | M + H | 1.26 | A |
| 50 | 0.003 | 558.1 | M + H | 1/33 | A |

What is claimed is:

1. A compound of formula I:

or a salt thereof, wherein

R is $C_1$-$C_6$alkyl, or halo$C_1$-$C_4$alkyl;

$R^1$ is $C_1$-$C_{12}$alkyl, $C_2$-$C_{12}$alkenyl, $C_2$-$C_{12}$alkynyl or $C_1$-$C_6$alkoxy$C_1$-$C_{12}$alkyl, each of which is unsubstituted or substituted with 1, 2, or 3 substituents independently selected from the group consisting of hydroxy, halogen, cyano, $CO_2H$, $C(O)N(R^{1D})_2$, $N(R^{1A})S(O)_2R^{1B}$, $N(R^{1A})C(O)R^{1B}$, $S(O)_2R^{1C}$, $S(O)R^{1C}$, $N(R^{1A})S(O)_2N(R^{1D})_2$, $N(R^{1A})C(O)N(R^{1D})_2$, $OC(O)N(R^{1D})_2$, $N(R^{1A})C(O)_2R^{1B}$, $C(O)R^{1B}$, $P(O)(R^{1E})_2$, $C(O)R^{1F}$, $C_1$-$C_6$alkoxy, amino, mono- and di-$C_1$-$C_4$alkylamino, $C_3$-$C_6$cycloalkyl, phenyl, phenoxy, heteroaryl, heteroaryloxy, and heterocycle, which heterocycle is saturated or partially unsaturated, has one or two rings and 1 or 2 ring heteroatoms selected from N, O or S, and wherein each phenyl, phenoxy, heteroaryl and heteroaryloxy is unsubstituted or substituted with one to four groups independently selected from the group consisting of $C_1$-$C_4$alkyl, $CO_2H$, $C(O)C_1$-$C_4$alkyl, $C(O)_2C_1$-$C_4$alkyl and halogen, and wherein the heterocycle and cycloalkyl substituents are unsubstituted or substituted with one to four groups independently selected from the group consisting of $C_1$-$C_4$alkyl, $CO_2H$, $C(O)C_1$-$C_4$alkyl, $C(O)_2C_1$-$C_4$alkyl, oxo and halogen;

$R^{1A}$ is independently selected at each occurrence from the group consisting of hydrogen, $C_1$-$C_6$alkyl and $C_2$-$C_6$alkenyl;

$R^{1B}$ is independently selected at each occurrence from $C_1$-$C_6$alkyl, $CF_3$ or phenyl, which phenyl is unsubstituted or substituted with one, two or three groups independently selected from $C_1$-$C_4$alkyl, halogen, $C_1$-$C_4$alkoxy, halo$C_1$-$C_4$alkyl or halo$C_1$-$C_4$alkoxy, wherein $R^{1A}$ and $R^{1B}$ may be taken together to form a cycle;

$R^{1C}$ is independently selected at each occurrence from the group consisting of $C_1$-$C_6$alkyl, hydroxy$C_1$-$C_6$alkyl, halo$C_1$-$C_4$alkyl, mono- and di-$C_1$-$C_4$alkylamino, or phenyl, which phenyl is unsubstituted or substituted with 1 or 2 $C_1$-$C_4$alkyl, $C_1$-$C_4$alkoxy, halo$C_1$-$C_4$alkyl, cyano, halogen morpholino, piperadino, piperazino, and pyrrolidino wherein each morpholino, piperadino, piperazino and pyrrolidino residue is unsubstituted or substituted with 1 or 2 groups independently selected from $C_1$-$C_4$alkyl, $C_1$-$C_4$alkoxy, halo$C_1$-$C_4$alkyl, hydroxy, or halogen;

$R^{1D}$ is independently selected at each occurrence from hydrogen or $C_1$-$C_6$alkyl, wherein each alkyl is substituted with 0, 1 or 2 substituents independently selected from the group consisting hydroxy, phenyl, $CO_2H$ or $C(O)_2C_1$-$C_4$alkyl; or $N(R^{1D})_2$, taken in combination, forms a five or six member heterocycle having 0, 1, or 2 additional ring heteroatoms selected from N or O and which is unsubstituted or substituted with one or two groups independently selected form $C_1$-$C_4$alkyl, benzyl, oxo or hydroxy;

$R^{1E}$ is independently selected at each occurrence from the group consisting of hydroxy, $C_1$-$C_4$alkyl, $C_1$-$C_4$alkoxy and benzyl wherein at least one occurrence of $R^{1E}$ is not $C_1$-$C_4$alkyl;

$R^{1F}$ is selected at each occurrence from the group consisting of $C_1$-$C_6$alkyl and $C_1$-$C_6$alkoxy each of which is optionally substituted with $OP(O)(R^{1E})_2$;

$R^2$ is halogen, or $R^2$ is $C_3$-$C_6$cycloalkyl, or $C_1$-$C_{10}$alkyl, which is unsubstituted or substituted with 1, 2, or 3 groups independently selected from the group consisting of hydroxy, halogen;

$R^3$ is phenyl, which is substituted with 0, 1, 2 or 3 groups independently selected from the group consisting of $C_1$-$C_6$alkyl, halogen, $C_1$-$C_6$alkoxy, halo$C_1$-$C_6$alkyl, and halo$C_1$-$C_6$alkoxy, and the phenyl is further substituted with 0 or 1 groups selected from $C_3$-$C_6$cycloalkyl, benzyl, phenoxy, pyridyloxy, phenylamino, and pyridylamino, wherein each benzyl, phenoxy, pyridyloxy, phenylamino and pyridylamino is para to the point of attachment of the $R^3$ group to the furyl ring and each benzyl, phenoxy, pyridyloxy, phenylamino and pyridylamino is unsubstituted or substituted with one to three groups independently selected from $C_1$-$C_4$alkyl, halo$C_1$-$C_4$alkyl, $C_1$-$C_4$alkoxy, cyano, fluoro, or chloro; and $R^4$ is H or $C_1$-$C_4$alkyl.

2. The compound of claim 1, or a salt thereof, wherein R is methyl, $CF_3$ or ethyl.

3. The compound of claim 1, or a salt thereof, wherein $R^1$ is $C_1$-$C_{10}$alkyl substituted with 1 or 2 substituents.

4. The compound of claim 1, or a salt thereof, wherein
$R^1$ is $C_1$-$C_6$alkyl which is unsubstituted or substituted with 1 or 2 substituents selected from the group consisting of hydroxy, halogen, cyano, $CO_2H$, $C(O)_2C_1$-$C_6$alkyl, $N(R^{1A})S(O)_2R^{1B}$, $S(O)_2R^{1C}$;

$R^{1A}$ is independently selected at each occurrence from the group consisting of hydrogen $C_1$-$C_6$alkyl and $C_2$-$C_6$alkenyl;

$R^{1B}$ is independently selected at each occurrence from $C_1$-$C_6$alkyl or phenyl, which phenyl is unsubstituted or substituted with one or two groups independently selected from $C_1$-$C_4$alkyl, halogen, or $C_1$-$C_4$alkoxy; wherein $R^{1A}$ and $R^{1B}$ may be taken together to form a cycle; and $R^{1C}$ is independently selected at each occurrence from $C_1$-$C_6$alkyl and phenyl, which phenyl is unsubstituted or substituted with methyl, methoxy, fluoro, or chloro.

5. The compound of claim 1, or a salt thereof, wherein $R^2$ is cyclopropyl.

6. The compound of claim 1, or a salt thereof, wherein $R^3$ is phenyl substituted with 1 or 2 groups independently selected from fluoro, chloro, methyl, or ethyl or phenyl is para-substituted with cyclopropyl, benzyl or phenoxy.

7. The compound of claim 1, or a salt thereof, wherein
R is methyl;
$R^1$ is $C_1$-$C_6$alkyl which is unsubstituted or substituted with 1 or 2 substituents selected from the group consisting of hydroxy, halogen, cyano, $CO_2H$, $C(O)_2C_1$-$C_6$alkyl, $N(R^{1A})S(O)_2R^{1B}$, $S(O)_2R^{1C}$;
$R^{1A}$ is independently selected at each occurrence from the group consisting of hydrogen and $C_1$-$C_6$alkyl;
$R^{1B}$ is independently selected at each occurrence from $C_1$-$C_6$alkyl or phenyl, which phenyl is unsubstituted or substituted with one or two groups independently selected from $C_1$-$C_4$alkyl, halogen, or $C_1$-$C_4$alkoxy;
$R^{1C}$ is independently selected at each occurrence from $C_1$-$C_6$alkyl and phenyl, which phenyl is unsubstituted or substituted with methyl, methoxy, fluoro, or chloro;
$R^2$ is cyclopropyl; and
$R^3$ is phenyl substituted with 1 or 2 groups independently selected from fluoro, chloro, methyl, or phenoxy.

8. The compound of claim 1, represented by the formula:

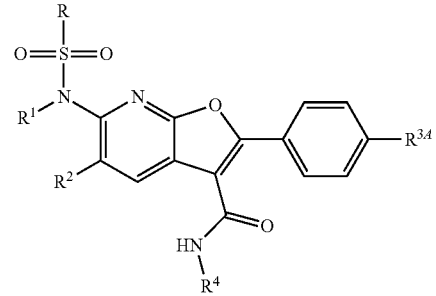

R is methyl;

R¹ is $C_1$-$C_6$alkyl which is unsubstituted or substituted with 1 or 2 substituents selected from the group consisting of hydroxy, halogen, cyano, $CO_2H$, $C(O)_2C_1$-$C_6$alkyl, $N(R^{1A})S(O)_2R^{1B}$, $S(O)_2R^{1C}$;

$R^{1A}$ is independently selected at each occurrence from the group consisting of hydrogen and $C_1$-$C_6$alkyl;

$R^{1B}$ is independently selected at each occurrence from $C_1$-$C_6$alkyl or phenyl, which phenyl is unsubstituted or substituted with one or two groups independently selected from $C_1$-$C_4$alkyl, halogen, or $C_1$-$C_4$alkoxy;

$R^{1C}$ is independently selected at each occurrence from $C_1$-$C_6$alkyl and phenyl, which phenyl is unsubstituted or substituted with methyl, methoxy, fluoro, or chloro;

$R^2$ is cyclopropyl, $C_1$-$C_4$alkyl, or halo$C_1$-$C_4$alkyl;

$R^{3A}$ is fluoro, chloro, methyl, or phenoxy; and $R^4$ is methyl or ethyl.

9. A compound selected from the group consisting of 2-(4-fluorophenyl)-N-methyl-6-(N-methylmethylsulfonamido)-5-vinylfuro[2,3-b]pyridine-3-carboxamide;

5-cyclopropyl-2-(4-fluorophenyl)-N-methyl-6-(N-methylmethylsulfonamido)furo[2,3-b]pyridine-3-carboxamide;

5-ethyl-2-(4-fluorophenyl)-N-methyl-6-(N-methylmethylsulfonamido)furo[2,3-b]pyridine-3-carboxamide;

2-(4-fluorophenyl)-N-methyl-6-(N-methylmethylsulfonamido)-5-(1,1,1-trifluoropropan-2-yl)furo[2,3-b]pyridine-3-carboxamide;

5-cyclopropyl-2-(4-fluorophenyl)-6-(N-(2-hydroxyethyl)methylsulfonamido)-N-methylfuro[2,3-b]pyridine-3-carboxamide;

2-(4-fluorophenyl)-5-isopropyl-N-methyl-6-(N-methylmethylsulfonamido)furo[2,3-b]pyridine-3-carboxamide;

5-ethynyl-2-(4-fluorophenyl)-N-methyl-6-(N-methylmethylsulfonamido)furo[2,3-b]pyridine-3-carboxamide;

6-(N-(but-3-enyl)methylsulfonamido)-2-(4-fluorophenyl)-5-iodo-N-methylfuro[2,3-b]pyridine-3-carboxamide;

5-(1,1-difluoroethyl)-2-(4-fluorophenyl)-N-methyl-6-(N-methylmethylsulfonamido)furo[2,3-b]pyridine-3-carboxamide;

5-allyl-2-(4-fluorophenyl)-N-methyl-6-(N-methylmethylsulfonamido)furo[2,3-b]pyridine-3-carboxamide;

2-(4-fluorophenyl)-N-methyl-6-(N-methylmethylsulfonamido)-5-(prop-1-en-2-yl)furo[2,3-b]pyridine-3-carboxamide;

5-(2-cyanoethyl)-2-(4-fluorophenyl)-N-methyl-6-(N-methylmethylsulfonamido)furo[2,3-b]pyridine-3-carboxamide;

2-(4-fluorophenyl)-5-iodo-N-methyl-6-(N-methylmethylsulfonamido)furo[2,3-b]pyridine-3-carboxamide;

(E)-5-(2-cyanovinyl)-2-(4-fluorophenyl)-N-methyl-6-(N-methylmethylsulfonamido)furo[2,3-b]pyridine-3-carboxamide;

2-(4-fluorophenyl)-6-(N-(2-hydroxyethyl)methylsulfonamido)-5-iodo-N-methylfuro[2,3-b]pyridine-3-carboxamide;

5-acetyl-2-(4-fluorophenyl)-N-methyl-6-(N-methylmethylsulfonamido)furo[2,3-b]pyridine-3-carboxamide;

5-(3-aminopropyl)-2-(4-fluorophenyl)-N-methyl-6-(N-methylmethylsulfonamido)furo[2,3-b]pyridine-3-carboxamide;

2-(4-fluorophenyl)-N-methyl-6-(N-methylmethylsulfonamido)-5-(3,3,3-trifluoroprop-1-en-2-yl)furo[2,3-b]pyridine-3-carboxamide;

2-(4-fluorophenyl)-N-methyl-6-(N-methylmethylsulfonamido)-5-(oxiran-2-ylmethyl)furo[2,3-b]pyridine-3-carboxamide;

5-(1,2-dihydroxypropan-2-yl)-2-(4-fluorophenyl)-N-methyl-6-(N-methylmethylsulfonamido)furo[2,3-b]pyridine-3-carboxamide;

2-(4-fluorophenyl)-5-(1-hydroxyethyl)-N-methyl-6-(N-methylmethylsulfonamido)furo[2,3-b]pyridine-3-carboxamide;

2-(4-fluorophenyl)-N,5-dimethyl-8-(methylsulfonyl)-5,6,7,8-tetrahydrofuro[2,3-b][1,8]naphthyridine-3-carboxamide;

5-(N-(2-(4-fluorophenyl)-5-iodo-3-(methylcarbamoyl)furo[2,3-b]pyridin-6-yl)methylsulfonamido)pentanoic acid;

6-(N-(3-cyanopropyl)methylsulfonamido)-2-(4-fluorophenyl)-5-iodo-N-methylfuro[2,3-b]pyridine-3-carboxamide;

4-(N-(2-(4-fluorophenyl)-5-iodo-3-(methylcarbamoyl)furo[2,3-b]pyridin-6-yl)methylsulfonamido)butanoic acid;

methyl 5-(N-(2-(4-fluorophenyl)-5-iodo-3-(methylcarbamoyl)furo[2,3-b]pyridin-6-yl)methylsulfonamido)pentanoate;

2-(4-fluorophenyl)-5-iodo-N-methyl-6-(N-(2-morpholinoethyl)methylsulfonamido)furo[2,3-b]pyridine-3-carboxamide;

6-(N-(4-aminobutyl)methylsulfonamido)-2-(4-fluorophenyl)-5-iodo-N-methylfuro[2,3-b]pyridine-3-carboxamide;

2-(4-fluorophenyl)-5-iodo-N-methyl-6-(N-(4-(methylsulfonamido)-4-oxobutyl)methylsulfonamido)furo[2,3-b]pyridine-3-carboxamide;

ethyl 5-(2-(4-fluorophenyl)-3-(methylcarbamoyl)-6-(N-methylmethylsulfonamido)furo[2,3-b]pyridin-5-yl)pentanoate;

5-(2-(4-fluorophenyl)-3-(methylcarbamoyl)-6-(N-methylmethylsulfonamido)furo[2,3-b]pyridin-5-yl)pentanoic acid;

(S)-methyl 1-(4-(2-(4-fluorophenyl)-3-(methylcarbamoyl)-6-(N-methylmethylsulfonamido)furo[2,3-b]pyridin-5-yl)butanoyl)pyrrolidine-2-carboxylate;

5-(4-amino-4-oxobutyl)-2-(4-fluorophenyl)-N-methyl-6-(N-methylmethylsulfonamido)furo[2,3-b]pyridine-3-carboxamide;

(S)-5-(4-(2-carbamoylpyrrolidin-1-yl)-4-oxobutyl)-2-(4-fluorophenyl)-N-methyl-6-(N-methylmethylsulfonamido)furo[2,3-b]pyridine-3-carboxamide;

5-(2-(4-fluorophenyl)-3-(methylcarbamoyl)-6-(N-methylmethylsulfonamido)furo[2,3-b]pyridin-5-yl)pent-4-ynoic acid;

5-cyclopropyl-2-(4-fluorophenyl)-6-(N-methylmethylsulfonamido)furo[2,3-b]pyridine-3-carboxamide;

5-cyclopropyl-N-ethyl-2-(4-fluorophenyl)-6-(N-methylmethylsulfonamido)furo[2,3-b]pyridine-3-carboxamide;

2-(4-Fluoro-phenyl)-9-methanesulfonyl-5-methyl-6,7,8,9-tetrahydro-5H-1-oxa-9,10-diaza-cyclohepta[f]indene-3-carboxylic acid methylamide;

2-(4-fluorophenyl)-N-methyl-6-(N-methylmethylsulfonamido)-5-(4-(methylsulfonamido)-4-oxobutyl)furo[2,3-b]pyridine-3-carboxamide;

2-(4-fluorophenyl)-5-iodo-N-methyl-6-(N-(pent-4-enyl)methylsulfonamido)furo[2,3-b]pyridine-3-carboxamide;

2-(4-fluorophenyl)-5-iodo-6-(N-(2-methoxyphenethyl) methylsulfonamido)-N-methylfuro[2,3-b]pyridine-3-carboxamide;

methyl 4-(N-(2-(4-fluorophenyl)-5-iodo-3-(methylcarbamoyl)furo[2,3-b]pyridin-6-yl)methylsulfonamido) butanoate;

6-(N-(3-carbamoylbenzyl)methylsulfonamido)-2-(4-fluorophenyl)-5-iodo-N-methylfuro[2,3-b]pyridine-3-carboxamide;

(S)-methyl 1-(5-(2-(4-fluorophenyl)-3-(methylcarbamoyl)-6-(N-methylmethylsulfonamido)furo[2,3-b]pyridin-5-yl)pentanoyl)pyrrolidine-2-carboxylate;

(S)-1-(5-(2-(4-fluorophenyl)-3-(methylcarbamoyl)-6-(N-methylmethylsulfonamido)furo[2,3-b]pyridin-5-yl) pentanoyl)pyrrolidine-2-carboxylic acid;

6-(N-(4-cyanobutyl)methylsulfonamido)-2-(4-fluorophenyl)-5-iodo-N-methylfuro[2,3-b]pyridine-3-carboxamide;

6-(N-(4,5-dihydroxypentyl)methylsulfonamido)-2-(4-fluorophenyl)-5-iodo-N-methylfuro[2,3-b]pyridine-3-carboxamide;

(S)-5-(5-(2-carbamoylpyrrolidin-1-yl)-5-oxopentyl)-2-(4-fluorophenyl)-N-methyl-6-(N-methylmethylsulfonamido)furo[2,3-b]pyridine-3-carboxamide;

6-(N-(3,4-dihydroxybutyl)methylsulfonamido)-2-(4-fluorophenyl)-5-iodo-N-methylfuro[2,3-b]pyridine-3-carboxamide;

2-(4-fluorophenyl)-5-iodo-N-methyl-6-(N-(3-(2-oxoimidazolidin-1-yl)propyl)methylsulfonamido)furo[2,3-b]pyridine-3-carboxamide;

5-(5-amino-5-oxopentyl)-2-(4-fluorophenyl)-N-methyl-6-(N-methylmethylsulfonamido)furo[2,3-b]pyridine-3-carboxamide;

5-cyclopropyl-N-methyl-6-(N-methylmethylsulfonamido)-2-phenylfuro[2,3-b]pyridine-3-carboxamide;

5-(5,6-dihydroxy-5,6-dimethylheptyl)-2-(4-fluorophenyl)-N-methyl-6-(N-methylmethylsulfonamido)furo[2,3-b]pyridine-3-carboxamide;

5-iodo-N-methyl-6-(N-methylmethylsulfonamido)-2-(pyridin-2-yl)furo[2,3-b]pyridine-3-carboxamide;

3-(4-(2-(4-fluorophenyl)-3-(methylcarbamoyl)-6-(N-methylmethylsulfonamido)furo[2,3-b]pyridin-5-yl)butylsulfonyl)propanoic acid;

2-(4-fluorophenyl)-N-methyl-6-(N-methylmethylsulfonamido)-5-propylfuro[2,3-b]pyridine-3-carboxamide;

tert-butyl 3-((N-(2-(4-fluorophenyl)-5-iodo-3-(methylcarbamoyl)furo[2,3-b]pyridin-6-yl)methylsulfonamido) methyl)piperidine-1-carboxylate;

5-(4,5-dihydroxypentyl)-2-(4-fluorophenyl)-N-methyl-6-(N-methylmethylsulfonamido)furo[2,3-b]pyridine-3-carboxamide;

2-(4-fluorophenyl)-5-(4-hydroxypentyl)-N-methyl-6-(N-methylmethylsulfonamido)furo[2,3-b]pyridine-3-carboxamide;

2-(4-fluorophenyl)-N-methyl-6-(N-methylmethylsulfonamido)-5-(3-(methylsulfonyl)propyl)furo[2,3-b]pyridine-3-carboxamide;

methyl 5-(N-(5-ethyl-2-(4-fluorophenyl)-3-(methylcarbamoyl)furo[2,3-b]pyridin-6-yl)methylsulfonamido) pentanoate;

methyl 4-(N-(5-ethyl-2-(4-fluorophenyl)-3-(methylcarbamoyl)furo[2,3-b]pyridin-6-yl)methylsulfonamido) butanoate;

5-(N-(2-(4-fluorophenyl)-3-(methylcarbamoyl)-5-vinylfuro[2,3-b]pyridin-6-yl)methylsulfonamido)pentanoic acid;

methyl 4-(N-(2-(4-fluorophenyl)-3-(methylcarbamoyl)-5-vinylfuro[2,3-b]pyridin-6-yl)methylsulfonamido)butanoate;

methyl 5-(N-(2-(4-fluorophenyl)-3-(methylcarbamoyl)-5-vinylfuro[2,3-b]pyridin-6-yl)methylsulfonamido)pentanoate;

5-(N-(5-ethyl-2-(4-fluorophenyl)-3-(methylcarbamoyl)furo[2,3-b]pyridin-6-yl)methylsulfonamido)pentanoic acid;

2-(4-fluorophenyl)-N,5-dimethyl-6-(N-methylmethylsulfonamido)furo[2,3-b]pyridine-3-carboxamide;

2-(4-Fluoro-phenyl)-6-hydroxy-9-methanesulfonyl-5-methyl-6,7,8,9-tetrahydro-5H-1-oxa-9,10-diaza-cyclohepta[f]indene-3-carboxylic acid methylamide;

2-(4-Fluoro-phenyl)-5-hydroxy-9-methanesulfonyl-5-methyl-6,7,8,9-tetrahydro-5H-1-oxa-9,10-diaza-cyclohepta[f]indene-3-carboxylic acid methylamide;

2-(4-Fluoro-phenyl)-10-methanesulfonyl-5,6,7,8,9,10-hexahydro-1-oxa-10,11-diaza-cycloocta[f]indene-3-carboxylic acid methylamide;

2-(4-Fluoro-phenyl)-9-methanesulfonyl-5-methylene-5,7,8,9-tetrahydro-1,6-dioxa-9,10-diaza-cyclohepta[f]indene-3-carboxylic acid methylamide;

2-(4-Fluoro-phenyl)-9-methanesulfonyl-5-methyl-5,7,8,9-tetrahydro-1,6-dioxa-9,10-diaza-cyclohepta[f]indene-3-carboxylic acid methylamide;

2-(4-Fluoro-phenyl)-9-methanesulfonyl-6,7,8,9-tetrahydro-5H-1-oxa-9,10-diaza-cyclohepta[f]indene-3-carboxylic acid methylamide;

2-(4-Fluoro-phenyl)-10-methanesulfonyl-5-methyl-5,6,7,8,9,10-hexahydro-1-oxa-10,11-diaza-cycloocta[f]indene-3-carboxylic acid methylamide;

2-(4-Fluoro-phenyl)-11-methanesulfonyl-6,7,8,9,10,11-hexahydro-5H-1-oxa-11,12-diaza-cyclonona[f]indene-3-carboxylic acid methylamide;

isobutyl 5-(N-(5-ethyl-2-(4-fluorophenyl)-3-(methylcarbamoyl)furo[2,3-b]pyridin-6-yl)methylsulfonamido)-2,2-dimethylpentanoate;

5-(N-(5-ethyl-2-(4-fluorophenyl)-3-(methylcarbamoyl)furo[2,3-b]pyridin-6-yl)methylsulfonamido)-2,2-dimethylpentanoic acid;

6-(N-(3-(N-(but-3-enyl)methylsulfonamido)propyl)methylsulfonamido)-2-(4-fluorophenyl)-5-iodo-N-methylfuro[2,3-b]pyridine-3-carboxamide;

6-{[3-(1,1-Dioxo-isothiazolidin-2-yl)-propyl]-methanesulfonyl-amino}-5-ethyl-2-(4-fluoro-phenyl)-furo[2,3-b]pyridine-3-carboxylic acid methylamide;

2-(4-Fluoro-phenyl)-9,13-bis-methanesulfonyl-6,7,8,9,10,11,12,13-octahydro-5H-1-oxa-9,13,14-triaza-cycloundeca[f]indene-3-carboxylic acid methylamide;

6-(N-(3-(2-cyanophenoxy)propyl)methylsulfonamido)-5-ethyl-2-(4-fluorophenyl)-N-methylfuro[2,3-b]pyridine-3-carboxamide;

(S)-5-ethyl-2-(4-fluorophenyl)-6-(N-(3-(6-methoxypyridin-3-yl)-2-methylpropyl)methylsulfonamido)-N-methylfuro[2,3-b]pyridine-3-carboxamide;

(R)-5-ethyl-2-(4-fluorophenyl)-6-(N-(3-(6-methoxypyridin-3-yl)-2-methylpropyl)methylsulfonamido)-N-methylfuro[2,3-b]pyridine-3-carboxamide;

5-ethyl-2-(4-fluorophenyl)-6-(N-(2-(2-methoxyethoxy) ethyl)methylsulfonamido)-N-methylfuro[2,3-b]pyridine-3-carboxamide;

5-ethyl-2-(4-fluorophenyl)-6-(N-(3-methoxyphenethyl) methylsulfonamido)-N-methylfuro[2,3-b]pyridine-3-carboxamide;

5-ethyl-2-(4-fluorophenyl)-6-(N-(2-(2-methoxyphenoxy)ethyl)methylsulfonamido)-N-methylfuro[2,3-b]pyridine-3-carboxamide;
5-ethyl-2-(4-fluorophenyl)-6-(N-(3-(2-methoxyphenoxy)propyl)methylsulfonamido)-N-methylfuro[2,3-b]pyridine-3-carboxamide;
5-ethyl-2-(4-fluorophenyl)-N-methyl-6-(N-(3-morpholinopropyl)methylsulfonamido)furo[2,3-b]pyridine-3-carboxamide;
5-ethyl-2-(4-fluorophenyl)-N-methyl-6-(N-(3-(3-methyl-2-oxoimidazolidin-1-yl)propyl)methylsulfonamido)furo[2,3-b]pyridine-3-carboxamide;
6-(N-(2-(2-cyanophenoxy)ethyl)methylsulfonamido)-5-ethyl-2-(4-fluorophenyl)-N-methylfuro[2,3-b]pyridine-3-carboxamide;
6-(N-(4-(2-cyanophenoxy)butyl)methylsulfonamido)-5-ethyl-2-(4-fluorophenyl)-N-methylfuro[2,3-b]pyridine-3-carboxamide;
5-ethyl-2-(4-fluorophenyl)-N-methyl-6-(N-(3-(phenylsulfonyl)propyl)methylsulfonamido)furo[2,3-b]pyridine-3-carboxamide;
5-ethyl-2-(4-fluorophenyl)-N-methyl-6-(N-(3-(morpholinosulfonyl)propyl)methylsulfonamido)furo[2,3-b]pyridine-3-carboxamide;
6-(N-(3-cyanobenzyl)methylsulfonamido)-5-ethyl-2-(4-fluorophenyl)-N-methylfuro[2,3-b]pyridine-3-carboxamide;
6-(N-(3-cyanopropyl)methylsulfonamido)-5-ethyl-2-(4-fluorophenyl)-N-methylfuro[2,3-b]pyridine-3-carboxamide;
2-(4-fluorophenyl)-5-iodo-N-methyl-6-(N-(3-(2-nitrophenylsulfonamido)propyl)methylsulfonamido)furo[2,3-b]pyridine-3-carboxamide;
5-ethyl-2-(4-fluorophenyl)-N-methyl-6-(N-(3-(methylsulfonyl)propyl)methylsulfonamido)furo[2,3-b]pyridine-3-carboxamide;
5-ethyl-2-(4-fluorophenyl)-6-(N-(3-hydroxypropyl)methylsulfonamido)-N-methylfuro[2,3-b]pyridine-3-carboxamide;
5-ethyl-2-(4-fluorophenyl)-N-methyl-6-(N-(3-(N-methylmethylsulfonamido)propyl)methylsulfonamido)furo[2,3-b]pyridine-3-carboxamide;
5-ethyl-2-(4-fluorophenyl)-N-methyl-6-(N-(3-(methylsulfonamido)propyl)methylsulfonamido)furo[2,3-b]pyridine-3-carboxamide;
6-(N-(3-(1H-imidazol-1-yl)propyl)methylsulfonamido)-2-(4-fluorophenyl)-5-iodo-N-methylfuro[2,3-b]pyridine-3-carboxamide;
5-ethyl-2-(4-fluorophenyl)-6-(N-(4-methoxyphenethyl)methylsulfonamido)-N-methylfuro[2,3-b]pyridine-3-carboxamide;
5-ethyl-2-(4-fluorophenyl)-N-methyl-6-(N-((tetrahydro-2H-pyran-4-yl)methyl)methylsulfonamido)furo[2,3-b]pyridine-3-carboxamide;
tert-butyl 4-(2-(N-(5-ethyl-2-(4-fluorophenyl)-3-(methylcarbamoyl)furo[2,3-b]pyridin-6-yl)methylsulfonamido)ethyl)piperidine-1-carboxylate;
5-ethyl-2-(4-fluorophenyl)-N-methyl-6-(N-(2-(pyridin-4-yl)ethyl)methylsulfonamido)furo[2,3-b]pyridine-3-carboxamide;
tert-butyl 4-((N-(5-ethyl-2-(4-fluorophenyl)-3-(methylcarbamoyl)furo[2,3-b]pyridin-6-yl)methylsulfonamido)methyl)piperidine-1-carboxylate;
tert-butyl 4-(2-(N-(5-ethyl-2-(4-fluorophenyl)-3-(methylcarbamoyl)furo[2,3-b]pyridin-6-yl)methylsulfonamido)ethyl)piperazine-1-carboxylate;
tert-butyl 4-(3-(N-(5-ethyl-2-(4-fluorophenyl)-3-(methylcarbamoyl)furo[2,3-b]pyridin-6-yl)methylsulfonamido)propyl)piperazine-1-carboxylate;
5-ethyl-2-(4-fluorophenyl)-N-methyl-6-(N-(2-(4-methylthiazol-5-yl)ethyl)methylsulfonamido)furo[2,3-b]pyridine-3-carboxamide;
5-ethyl-2-(4-fluorophenyl)-6-(N-(4-(2-methoxyphenoxy)butyl)methylsulfonamido)-N-methylfuro[2,3-b]pyridine-3-carboxamide;
6-(N-(3,4-dimethoxyphenethyl)methylsulfonamido)-5-ethyl-2-(4-fluorophenyl)-N-methylfuro[2,3-b]pyridine-3-carboxamide;
5-ethyl-2-(4-fluorophenyl)-N-methyl-6-(N-(2-thiomorpholinoethyl)methylsulfonamido)furo[2,3-b]pyridine-3-carboxamide;
6-(N-(2-(2-(4,4-dimethyl-2,5-dioxoimidazolidin-1-yl)ethoxy)ethyl)methylsulfonamido)-5-ethyl-2-(4-fluorophenyl)-N-methylfuro[2,3-b]pyridine-3-carboxamide;
methyl 2-(2-(N-(5-ethyl-2-(4-fluorophenyl)-3-(methylcarbamoyl)furo[2,3-b]pyridin-6-yl)methylsulfonamido)ethoxy)benzoate;
methyl 3-(2-(N-(5-ethyl-2-(4-fluorophenyl)-3-(methylcarbamoyl)furo[2,3-b]pyridin-6-yl)methylsulfonamido)ethoxy)benzoate;
methyl 4-(2-(N-(5-ethyl-2-(4-fluorophenyl)-3-(methylcarbamoyl)furo[2,3-b]pyridin-6-yl)methylsulfonamido)ethoxy)benzoate;
5-ethyl-2-(4-fluorophenyl)-N-methyl-6-(N-(2-(quinolin-7-yloxy)ethyl)methylsulfonamido)furo[2,3-b]pyridine-3-carboxamide;
(R)-5-ethyl-2-(4-fluorophenyl)-6-(N-(2-(7-methoxy-2,3-dihydrobenzofuran-3-yl)ethyl)methylsulfonamido)-N-methylfuro[2,3-b]pyridine-3-carboxamide;
5-ethyl-2-(4-fluorophenyl)-N-methyl-6-(N-(3-(pyrrolidin-1-ylsulfonyl)propyl)methylsulfonamido)furo[2,3-b]pyridine-3-carboxamide;
5-cyclopropyl-N-methyl-6-(N-methylmethylsulfonamido)-2-p-tolylfuro[2,3-b]pyridine-3-carboxamide;
6-(N-(2-(1H-imidazol-1-yl)ethyl)methylsulfonamido)-2-(4-fluorophenyl)-5-iodo-N-methylfuro[2,3-b]pyridine-3-carboxamide;
2-(4-Fluoro-phenyl)-7,10-bis-methanesulfonyl-5-methyl-5,6,7,8,9,10-hexahydro-1-oxa-7,10,11-triaza-cycloocta[f]indene-3-carboxylic acid methylamide;
6-{[3-(1,1-Dioxo-1,3-dihydro-benzo[d]isothiazol-2-yl)-propyl]-methanesulfonyl-amino}-5-ethyl-2-(4-fluoro-phenyl)-furo[2,3-b]pyridine-3-carboxylic acid methylamide;
5-ethyl-2-(4-fluorophenyl)-N-methyl-6-(N-(3-(phenylsulfonamido)propyl)methylsulfonamido)furo[2,3-b]pyridine-3-carboxamide;
6-{[3-(1,1-Dioxo-[1,2]thiazinan-2-yl)-propyl]-methanesulfonyl-amino}-5-ethyl-2-(4-fluoro-phenyl)-furo[2,3-b]pyridine-3-carboxylic acid methylamide;
2-(4-fluorophenyl)-5-iodo-N-methyl-6-(N-(2-(N-methylmethylsulfonamido)ethyl)methylsulfonamido)furo[2,3-b]pyridine-3-carboxamide;
6-{[2-(1,1-Dioxo-1,3-dihydrobenzo[d]isothiazol-2-yl)-ethyl]-methanesulfonyl-amino}-5-ethyl-2-(4-fluorophenyl)-furo[2,3-b]pyridine-3-carboxylic acid methylamide;
5-ethyl-2-(4-fluorophenyl)-N-methyl-6-(N-(3-(2-oxopyrrolidin-1-yl)propyl)methylsulfonamido)furo[2,3-b]pyridine-3-carboxamide;

5-ethyl-2-(4-fluorophenyl)-N-methyl-6-(N-(2-(N-methylphenylsulfonamido)ethyl)methylsulfonamido)furo[2,3-b]pyridine-3-carboxamide;

5-cyclopropyl-N-methyl-6-(N-methylmethylsulfonamido)-2-(4-phenoxyphenyl)furo[2,3-b]pyridine-3-carboxamide;

5-ethyl-2-(4-fluorophenyl)-N-methyl-6-(N-(4-(methylsulfonyl)butyl)methylsulfonamido)furo[2,3-b]pyridine-3-carboxamide;

5-ethyl-2-(4-fluorophenyl)-N-methyl-6-(N-(4-(phenylsulfonyl)butyl)methylsulfonamido)furo[2,3-b]pyridine-3-carboxamide;

5-ethyl-2-(4-fluorophenyl)-N-methyl-6-(N-(3-(N-methylphenylsulfonamido)propyl)methylsulfonamido)furo[2,3-b]pyridine-3-carboxamide;

2-(4-fluorophenyl)-6-(N-(4-hydroxyhex-5-enyl)methylsulfonamido)-5-iodo-N-methylfuro[2,3-b]pyridine-3-carboxamide;

5-iodo-N-methyl-6-(N-methylmethylsulfonamido)-2-p-tolylfuro[2,3-b]pyridine-3-carboxamide;

5-ethyl-N-methyl-6-(N-methylmethylsulfonamido)-2-(4-phenoxyphenyl)furo[2,3-b]pyridine-3-carboxamide;

5-ethyl-2-(4-fluorophenyl)-6-(N-(3-(isopropylsulfonyl)propyl)methylsulfonamido)-N-methylfuro[2,3-b]pyridine-3-carboxamide;

5-ethyl-2-(4-fluorophenyl)-6-(N-(4-(isopropylsulfonyl)butyl)methylsulfonamido)-N-methylfuro[2,3-b]pyridine-3-carboxamide;

2-(4-Fluoro-phenyl)-11-methanesulfonyl-5-methyl-6,7,8,9,10,11-hexahydro-5H-1-oxa-11,12-diaza-cyclonona[f]indene-3-carboxylic acid methylamide;

2-(4-Fluoro-phenyl)-6-hydroxy-11-methanesulfonyl-5-methyl-6,7,8,9,10,11-hexahydro-5H-1-oxa-11,12-diaza-cyclonona[f]indene-3-carboxylic acid methylamide;

5-ethyl-2-(4-fluorophenyl)-N-methyl-6-(N-(5-oxohexyl)methylsulfonamido)furo[2,3-b]pyridine-3-carboxamide;

5-(5-aminopentyl)-2-(4-fluorophenyl)-N-methyl-6-(N-methylmethylsulfonamido)furo[2,3-b]pyridine-3-carboxamide;

5-iodo-N-methyl-6-(N-methylmethylsulfonamido)-2-(4-(trifluoromethyl)phenyl)furo[2,3-b]pyridine-3-carboxamide;

6-(N-(3-(tert-butylsulfonyl)propyl)methylsulfonamido)-5-ethyl-2-(4-fluorophenyl)-N-methylfuro[2,3-b]pyridine-3-carboxamide;

5-ethyl-2-(4-fluorophenyl)-6-(N-(5-hydroxy-5-methylhexyl)methylsulfonamido)-N-methylfuro[2,3-b]pyridine-3-carboxamide;

5-ethyl-2-(4-fluorophenyl)-N-methyl-6-(N-(3-(N-methylacetamido)propyl)methylsulfonamido)furo[2,3-b]pyridine-3-carboxamide;

5-ethyl-2-(4-fluorophenyl)-N-methyl-6-(N-(3-(N-methylbenzamido)propyl)methylsulfonamido)furo[2,3-b]pyridine-3-carboxamide;

5-ethyl-2-(4-fluorophenyl)-6-(N-(5-hydroxyhexyl)methylsulfonamido)-N-methylfuro[2,3-b]pyridine-3-carboxamide;

5-ethyl-2-(4-fluorophenyl)-6-(N-(4-hydroxy-4-methylpentyl)methylsulfonamido)-N-methylfuro[2,3-b]pyridine-3-carboxamide;

5-ethyl-2-(4-fluorophenyl)-N-methyl-6-(N-(4-oxopentyl)methylsulfonamido)furo[2,3-b]pyridine-3-carboxamide;

6-(N-(4-(dimethylamino)-4-oxobutyl)methylsulfonamido)-5-ethyl-2-(4-fluorophenyl)-N-methylfuro[2,3-b]pyridine-3-carboxamide;

tert-butyl 5-(2-(4-fluorophenyl)-3-(methylcarbamoyl)-6-(N-methylmethylsulfonamido)furo[2,3-b]pyridin-5-yl)pentylcarbamate;

6-{[3-(1,1-Dioxo-tetrahydro-1lambdathiophen-2-yl)-propyl]-methanesulfonyl-amino}-5-ethyl-2-(4-fluoro-phenyl)-furo[2,3-b]pyridine-3-carboxylic acid methylamide;

6-(N-(5-(dimethylamino)-5-oxopentypmethylsulfonamido)-5-ethyl-2-(4-fluorophenyl)-N-methylfuro[2,3-b]pyridine-3-carboxamide;

(S)-6-(N-(2-(benzyloxy)but-3-enyl)methylsulfonamido)-2-(4-fluorophenyl)-N-methyl-5-(prop-1-en-2-yl)furo[2,3-b]pyridine-3-carboxamide;

5-ethyl-2-(4-fluorophenyl)-6-(N-(4-(2-hydroxy-5-oxocyclopent-1-enyl)butyl)methylsulfonamido)-N-methylfuro[2,3-b]pyridine-3-carboxamide;

5-ethyl-2-(4-fluorophenyl)-6-(N-(3-(2-hydroxy-5-oxocyclopent-1-enyl)propyl)methylsulfonamido)-N-methylfuro[2,3-b]pyridine-3-carboxamide;

5-ethyl-2-(4-fluorophenyl)-N-methyl-6-(N-(3-(methylsulfinyl)propyl)methylsulfonamido)furo[2,3-b]pyridine-3-carboxamide;

5-ethyl-2-(4-fluorophenyl)-N-methyl-6-(N-(3-(trifluoromethylsulfonyl)propyl)methylsulfonamido)furo[2,3-b]pyridine-3-carboxamide;

5-ethyl-2-(4-fluorophenyl)-N-methyl-6-(N-(4-(trifluoromethylsulfonyl)butyl)methylsulfonamido)furo[2,3-b]pyridine-3-carboxamide;

2-(4-chlorophenyl)-5-cyclopropyl-N-methyl-6-(N-methylmethylsulfonamido)furo[2,3-b]pyridine-3-carboxamide;

(S)-1-(4-(N-(5-ethyl-2-(4-fluorophenyl)-3-(methylcarbamoyl)furo[2,3-b]pyridin-6-yl)methylsulfonamido)butyl)pyrrolidine-2-carboxylic acid;

6-(N-(3-chloropropyl)methylsulfonamido)-5-ethyl-2-(4-fluorophenyl)-N-methylfuro[2,3-b]pyridine-3-carboxamide;

6-{[3-(1,1-Dioxo-tetrahydrothiophen-2-yl)-propyl]-methanesulfonyl-amino}-2-(4-fluoro-phenyl)-5-iodo-furo[2,3-b]pyridine-3-carboxylic acid methylamide;

5-Cyclopropyl-6-{[3-(1,1-dioxo-tetrahydrothiophen-2-yl)-propyl]-methanesulfonyl-amino}-2-(4-fluoro-phenyl)-furo[2,3-b]pyridine-3-carboxylic acid methylamide;

(5S,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide;

(5R,7S)-2-(4-Fluoro-phenyl)-7-hydroxy-9-methanesulfonyl-5-methyl-6,7,8,9-tetrahydro-5H-1-oxa-9,10-diaza-cyclohepta[f]indene-3-carboxylic acid methylamide;

5-Cyclopropyl-6-{[3-(1,1-dioxo-tetrahydrothiophen-2-yl)-propyl]-methanesulfonyl-amino}-2-(4-fluoro-phenyl)-furo[2,3-b]pyridine-3-carboxylic acid methylamide;

5-Cyclopropyl-6-{[3-(1,1-dioxo-tetrahydrothiophen-2-yl)-propyl]-methanesulfonyl-amino}-2-(4-fluoro-phenyl)-furo[2,3-b]pyridine-3-carboxylic acid methylamide;

6-{[3-(1,1-Dioxo-tetrahydro-1lambdathiophen-2-yl)-propyl]-methanesulfonyl-amino}-5-ethyl-2-(4-fluoro-phenyl)-furo[2,3-b]pyridine-3-carboxylic acid methylamide;

6-{[3-(1,1-Dioxo-tetrahydro-1lambdathiophen-2-yl)-propyl]-methanesulfonyl-amino}-5-ethyl-2-(4-fluoro-phenyl)-furo[2,3-b]pyridine-3-carboxylic acid methylamide;

5-cyclopropyl-2-(4-ethylphenyl)-N-methyl-6-(N-methylmethylsulfonamido)furo[2,3-b]pyridine-3-carboxamide;

5-ethyl-2-(4-fluorophenyl)-6-(N-isopropylmethylsulfonamido)-N-methylfuro[2,3-b]pyridine-3-carboxamide;

5-cyclopropyl-2-(4-fluorophenyl)-N-methyl-6-(N-(3-(methylsulfonyl)propyl)methylsulfonamido)furo[2,3-b]pyridine-3-carboxamide;

5-Ethyl-2-(4-fluoro-phenyl)-6-{methanesulfonyl-[3-(1,1,3-trioxo-tetrahydrothiophen-2-yl)-propyl]-amino}-furo[2,3-b]pyridine-3-carboxylic acid methylamide;

6-(N-(3-(cyclopropylsulfonyl)propyl)methylsulfonamido)-5-ethyl-2-(4-fluorophenyl)-N-methylfuro[2,3-b]pyridine-3-carboxamide;

5-ethyl-6-(N-(3-(ethylsulfonyl)propyl)methylsulfonamido)-2-(4-fluorophenyl)-N-methylfuro[2,3-b]pyridine-3-carboxamide;

2-(4-Chloro-phenyl)-6-{[3-(1,1-dioxo-tetrahydrothiophen-2-yl)-propyl]-methanesulfonyl-amino}-5-iodo-furo[2,3-b]pyridine-3-carboxylic acid methylamide;

2-(4-chloro-2-fluorophenyl)-5-iodo-N-methyl-6-(N-methylmethylsulfonamido)furo[2,3-b]pyridine-3-carboxamide;

6-{[3-(1,1-Dioxo-tetrahydrothiophen-2-yl)-propyl]-methanesulfonyl-amino}-5-iodo-2-p-tolyl-furo[2,3-b]pyridine-3-carboxylic acid methylamide;

2-(4-chlorophenyl)-5-iodo-N-methyl-6-(N-(3-(methylsulfonyl)propyl)methylsulfonamido)furo[2,3-b]pyridine-3-carboxamide;

5-Cyclopropyl-6-{[3-((R)-1,1-dioxo-tetrahydrothiophen-2-yl)-propyl]-methanesulfonyl-amino}-2-p-tolyl-furo[2,3-b]pyridine-3-carboxylic acid methylamide;

2-(4-Chloro-phenyl)-5-cyclopropyl-6-{[3-((R)-1,1-dioxo-tetrahydrothiophen-2-yl)-propyl]-methanesulfonyl-amino}-furo[2,3-b]pyridine-3-carboxylic acid methylamide;

5-cyclopropyl-2-(4-cyclopropylphenyl)-N-methyl-6-(N-(3-(methylsulfonyl)propyl)methylsulfonamido)furo[2,3-b]pyridine-3-carboxamide;

2-(4-fluorophenyl)-5-iodo-6-(N-(3-(2-methoxyethoxy)propyl)methylsulfonamido)-N-methylfuro[2,3-b]pyridine-3-carboxamide;

2-(4-fluorophenyl)-5-iodo-N-methyl-6-(N-(3-(methylsulfonyl)propyl)methylsulfonamido)furo[2,3-b]pyridine-3-carboxamide;

5-cyclopropyl-2-(4-fluorophenyl)-6-(N-(3-(2-methoxyethoxy)propyl)methylsulfonamido)-N-methylfuro[2,3-b]pyridine-3-carboxamide;

5-(N-(5-cyclopropyl-3-(methylcarbamoyl)-2-p-tolylfuro[2,3-b]pyridin-6-yl)methylsulfonamido)pentanoic acid;

methyl 5-(N-(5-cyclopropyl-3-(methylcarbamoyl)-2-p-tolylfuro[2,3-b]pyridin-6-yl)methylsulfonamido)pentanoate;

5-cyclopropyl-N-methyl-6-(N-(3-(methylsulfonyl)propyl)methylsulfonamido)-2-p-tolylfuro[2,3-b]pyridine-3-carboxamide;

5-Cyclopropyl-2-(4-cyclopropyl-phenyl)-6-{[3-(1,1-dioxo-tetrahydro-thiophen-2-yl)-propyl]-methanesulfonyl-amino}-furo[2,3-b]pyridine-3-carboxylic acid methylamide;

2-(4-chlorophenyl)-5-cyclopropyl-N-methyl-6-(N-(3-(methylsulfonyl)propyl)methylsulfonamido)furo[2,3-b]pyridine-3-carboxamide;

5-iodo-N-methyl-6-(N-(3-(methylsulfonyl)propyl)methylsulfonamido)-2-p-tolylfuro[2,3-b]pyridine-3-carboxamide;

2-(4-chlorophenyl)-5-iodo-N-methyl-6-(N-(4-(methylsulfonyl)butyl)methylsulfonamido)furo[2,3-b]pyridine-3-carboxamide;

5-iodo-N-methyl-6-(N-(4-(methylsulfonyl)butyl)methylsulfonamido)-2-p-tolylfuro[2,3-b]pyridine-3-carboxamide;

2-(4-fluorophenyl)-5-iodo-N-methyl-6-(N-(4-(methylsulfonyl)butyl)methylsulfonamido)furo[2,3-b]pyridine-3-carboxamide;

5-cyclopropyl-N-methyl-6-(N-(4-(methylsulfonyl)butyl)methylsulfonamido)-2-p-tolylfuro[2,3-b]pyridine-3-carboxamide;

5-cyclopropyl-2-(4-fluorophenyl)-N-methyl-6-(N-(4-(methylsulfonyl)butyl)methylsulfonamido)furo[2,3-b]pyridine-3-carboxamide;

2-(4-chlorophenyl)-5-cyclopropyl-N-methyl-6-(N-(4-(methylsulfonyl)butyl)methylsulfonamido)furo[2,3-b]pyridine-3-carboxamide;

5-(N-(5-cyclopropyl-2-(4-fluorophenyl)-3-(methylcarbamoyl)furo[2,3-b]pyridin-6-yl)methylsulfonamido)pentanoic acid;

methyl 5-(N-(5-cyclopropyl-2-(4-fluorophenyl)-3-(methylcarbamoyl)furo[2,3-b]pyridin-6-yl)methylsulfonamido)pentanoate;

5-cyclopropyl-2-(4-cyclopropylphenyl)-N-methyl-6-(N-(4-(methylsulfonyl)butyl)methylsulfonamido)furo[2,3-b]pyridine-3-carboxamide;

2-(4-chloro-2-fluorophenyl)-5-cyclopropyl-N-methyl-6-(N-methylmethylsulfonamido)furo[2,3-b]pyridine-3-carboxamide;

5-cyclopropyl-2-(4-cyclopropyl-2-fluorophenyl)-N-methyl-6-(N-methylmethylsulfonamido)furo[2,3-b]pyridine-3-carboxamide;

5-Cyclopropyl-6-{[2-(1,1-dioxo-tetrahydro-thiophen-3-yl)-ethyl]-methanesulfonyl-amino}-2-(4-fluoro-phenyl)-furo[2,3-b]pyridine-3-carboxylic acid methylamide;

4-(N-(5-cyclopropyl-3-(methylcarbamoyl)-2-p-tolylfuro[2,3-b]pyridin-6-yl)methylsulfonamido)butanoic acid;

5-(N-(5-cyclopropyl-3-(methylcarbamoyl)-2-(4-phenoxyphenyl)furo[2,3-b]pyridin-6-yl)methylsulfonamido)pentanoic acid;

isobutyl 5-(N-(5-cyclopropyl-2-(4-fluorophenyl)-3-(methylcarbamoyl)furo[2,3-b]pyridin-6-yl)methylsulfonamido)-2,2-dimethylpentanoate;

5-(N-(5-cyclopropyl-2-(4-fluorophenyl)-3-(methylcarbamoyl)furo[2,3-b]pyridin-6-yl)methylsulfonamido)-2,2-dimethylpentanoic acid;

5-Cyclopropyl-6-{[2-(1,1-dioxo-tetrahydro-thiophen-3-yl)-ethyl]-methanesulfonyl-amino}-2-p-tolyl-furo[2,3-b]pyridine-3-carboxylic acid methylamide;

2-(4-fluorophenyl)-6-(N-(4-hydroxypentyl)methylsulfonamido)-5-iodo-N-methylfuro[2,3-b]pyridine-3-carboxamide;

5-(N-(5-cyclopropyl-2-(4-(4-fluorophenoxy)phenyl)-3-(methylcarbamoyl)furo[2,3-b]pyridin-6-yl)methylsulfonamido)pentanoic acid;

5-(N-(5-cyclopropyl-2-(4-(2-fluorophenoxy)phenyl)-3-(methylcarbamoyl)furo[2,3-b]pyridin-6-yl)methylsulfonamido)pentanoic acid;

5-cyclopropyl-2-(4-fluorophenyl)-N-methyl-6-(N-(5-(methylsulfonyl)pentyl)methylsulfonamido)furo[2,3-b]pyridine-3-carboxamide;

5-(N-(5-cyclopropyl-3-(methylcarbamoyl)-2-(4-phenoxyphenyl)furo[2,3-b]pyridin-6-yl)methylsulfonamido)-2,2-dimethylpentanoic acid;

5-(N-(5-cyclopropyl-3-(methylcarbamoyl)-2-p-tolylfuro[2,3-b]pyridin-6-yl)methylsulfonamido)-2,2-dimethylpentanoic acid;

5-(N-(2-(4-chlorophenyl)-5-cyclopropyl-3-(methylcarbamoyl)furo[2,3-b]pyridin-6-yl)methylsulfonamido)pentanoic acid;

ethyl 5-(N-(2-(4-chlorophenyl)-5-cyclopropyl-3-(methylcarbamoyl)furo[2,3-b]pyridin-6-yl)methylsulfonamido)pentanoate;

5-cyclopropyl-2-(4-fluorophenyl)-6-(N-(4-hydroxypentyl)methylsulfonamido)-N-methylfuro[2,3-b]pyridine-3-carboxamide;

5-cyclopropyl-2-(4-fluorophenyl)-6-(N-(3-hydroxybutyl)methylsulfonamido)-N-methylfuro[2,3-b]pyridine-3-carboxamide;

5-cyclopropyl-2-(4-fluorophenyl)-N-methyl-6-(N-(3-(methylsulfonyl)butyl)methylsulfonamido)furo[2,3-b]pyridine-3-carboxamide;

5-(N-(2-(4-benzylphenyl)-5-cyclopropyl-3-(methylcarbamoyl)furo[2,3-b]pyridin-6-yl)methylsulfonamido)pentanoic acid;

5-(N-(5-cyclopropyl-2-(4-cyclopropylphenyl)-3-(methylcarbamoyl)furo[2,3-b]pyridin-6-yl)methylsulfonamido)pentanoic acid;

5-(N-(5-cyclopropyl-2-(4-ethylphenyl)-3-(methylcarbamoyl)furo[2,3-b]pyridin-6-yl)methylsulfonamido)pentanoic acid;

6-(N-(5-cyclopropyl-3-(methylcarbamoyl)-2-p-tolylfuro[2,3-b]pyridin-6-yl)methylsulfonamido)hexanoic acid;

1-(3-(N-(5-cyclopropyl-3-(methylcarbamoyl)-2-p-tolylfuro[2,3-b]pyridin-6-yl)methylsulfonamido)propyl)cyclopentanecarboxylic acid;

(1R,2S)-2-(2-(N-(5-cyclopropyl-3-(methylcarbamoyl)-2-p-tolylfuro[2,3-b]pyridin-6-yl)methylsulfonamido)ethyl)cyclopropanecarboxylic acid;

(1S,2R)-2-(2-(N-(5-cyclopropyl-3-(methylcarbamoyl)-2-p-tolylfuro[2,3-b]pyridin-6-yl)methylsulfonamido)ethyl)cyclopropanecarboxylic acid;

5-(N-(2-(4-chlorophenyl)-5-cyclopropyl-3-(methylcarbamoyl)furo[2,3-b]pyridin-6-yl)methylsulfonamido)-2,2-dimethylpentanoic acid;

4-(3-(N-(5-cyclopropyl-3-(methylcarbamoyl)-2-p-tolylfuro[2,3-b]pyridin-6-yl)methylsulfonamido)propyl)tetrahydro-2H-pyran-4-carboxylic acid;

5-(N-(5-cyclopropyl-3-(methylcarbamoyl)-2-p-tolylfuro[2,3-b]pyridin-6-yl)methylsulfonamido)-2-phenylpentanoic acid;

5-cyclopropyl-2-(4-methoxyphenyl)-N-methyl-6-(N-(3-(methylsulfonyl)propyl)methylsulfonamido)furo[2,3-b]pyridine-3-carboxamide;

5-cyclopropyl-6-(N-(3-hydroxybutyl)methylsulfonamido)-N-methyl-2-p-tolylfuro[2,3-b]pyridine-3-carboxamide;

6-(N-(5-cyclopropyl-3-(methylcarbamoyl)-2-p-tolylfuro[2,3-b]pyridin-6-yl)methylsulfonamido)-2,2-dimethylhexanoic acid;

2-(2-(N-(5-iodo-3-(methylcarbamoyl)-2-p-tolylfuro[2,3-b]pyridin-6-yl)methylsulfonamido)ethyl)cyclopentanecarboxylic acid;

2-(3-(N-(5-iodo-3-(methylcarbamoyl)-2-p-tolylfuro[2,3-b]pyridin-6-yl)methylsulfonamido)propyl)cyclopentanecarboxylic acid;

2-(2-(N-(5-cyclopropyl-3-(methylcarbamoyl)-2-p-tolylfuro[2,3-b]pyridin-6-yl)methylsulfonamido)ethyl)cyclopentanecarboxylic acid;

6-(N-(3-cyanopropyl)methylsulfonamido)-5-cyclopropyl-N-methyl-2-p-tolylfuro[2,3-b]pyridine-3-carboxamide;

6-(N-(4-cyanobutyl)methylsulfonamido)-5-cyclopropyl-N-methyl-2-p-tolylfuro[2,3-b]pyridine-3-carboxamide;

2-(3-(N-(5-cyclopropyl-3-(methylcarbamoyl)-2-p-tolylfuro[2,3-b]pyridin-6-yl)methylsulfonamido)propyl)cyclopentanecarboxylic acid;

1-(3-(N-(5-cyclopropyl-3-(methylcarbamoyl)-2-p-tolylfuro[2,3-b]pyridin-6-yl)methylsulfonamido)propyl)cyclopropanecarboxylic acid;

6-(N-(5-cyclopropyl-2-(4-ethylphenyl)-3-(methylcarbamoyl)furo[2,3-b]pyridin-6-yl)methylsulfonamido)hexanoic acid;

1-(3-(N-(5-cyclopropyl-2-(4-ethylphenyl)-3-(methylcarbamoyl)furo[2,3-b]pyridin-6-yl)methylsulfonamido)propyl)cyclobutanecarboxylic acid;

4-(3-(N-(5-cyclopropyl-2-(4-ethylphenyl)-3-(methylcarbamoyl)furo[2,3-b]pyridin-6-yl)methylsulfonamido)propyl)tetrahydro-2H-pyran-4-carboxylic acid;

6-(N-(3-(2H-tetrazol-5-yl)propyl)methylsulfonamido)-5-cyclopropyl-N-methyl-2-p-tolylfuro[2,3-b]pyridine-3-carboxamide;

6-(N-(4-(2H-tetrazol-5-yl)butyl)methylsulfonamido)-5-cyclopropyl-N-methyl-2-p-tolylfuro[2,3-b]pyridine-3-carboxamide;

4-(4-(N-(5-cyclopropyl-2-(4-ethylphenyl)-3-(methylcarbamoyl)furo[2,3-b]pyridin-6-yl)methylsulfonamido)butyl)tetrahydro-2H-pyran-4-carboxylic acid;

4-(4-(N-(5-cyclopropyl-3-(methylcarbamoyl)-2-p-tolylfuro[2,3-b]pyridin-6-yl)methylsulfonamido)butyl)tetrahydro-2H-pyran-4-carboxylic acid;

2-(2-(N-(5-cyclopropyl-3-(methylcarbamoyl)-2-p-tolylfuro[2,3-b]pyridin-6-yl)methylsulfonamido)ethyl)benzoic acid;

3-(2-(N-(5-cyclopropyl-3-(methylcarbamoyl)-2-p-tolylfuro[2,3-b]pyridin-6-yl)methylsulfonamido)ethoxy)-2,2-dimethylpropanoic acid;

3-(2-(N-(5-cyclopropyl-2-(4-ethylphenyl)-3-(methylcarbamoyl)furo[2,3-b]pyridin-6-yl)methylsulfonamido)ethoxy)-2,2-dimethylpropanoic acid;

5-(N-(5-cyclopropyl-2-(4-ethylphenyl)-3-(methylcarbamoyl)furo[2,3-b]pyridin-6-yl)methylsulfonamido)-2-(methoxymethyl)-2-methylpentanoic acid;

5-(N-(5-cyclopropyl-2-(4-ethylphenyl)-3-(methylcarbamoyl)furo[2,3-b]pyridin-6-yl)methylsulfonamido)-2-(2-methoxyethyl)-2-methylpentanoic acid;

5-(N-(5-cyclopropyl-3-(methylcarbamoyl)-2-p-tolylfuro[2,3-b]pyridin-6-yl)methylsulfonamido)-2-(methoxymethyl)-2-methylpentanoic acid;

5-(N-(5-cyclopropyl-3-(methylcarbamoyl)-2-p-tolylfuro[2,3-b]pyridin-6-yl)methylsulfonamido)-2-(2-methoxyethyl)-2-methylpentanoic acid;

5-(N-(5-cyclopropyl-2-(4-ethylphenyl)-3-(methylcarbamoyl)furo[2,3-b]pyridin-6-yl)methylsulfonamido)-2-methoxy-2-methylpentanoic acid;

5-(N-(5-cyclopropyl-3-(methylcarbamoyl)-2-p-tolylfuro[2,3-b]pyridin-6-yl)methylsulfonamido)-2-methoxy-2-methylpentanoic acid;

1-(3-(N-(5-cyclopropyl-2-(4-ethylphenyl)-3-(methylcarbamoyl)furo[2,3-b]pyridin-6-yl)methylsulfonamido)propyl)cyclopropanecarboxylic acid;

6-(N-(5-cyclopropyl-3-(methylcarbamoyl)-2-p-tolylfuro[2,3-b]pyridin-6-yl)methylsulfonamido)-2-(methylsulfonyl)hexanoic acid;

6-(N-(5-cyclopropyl-3-(methylcarbamoyl)-2-p-tolylfuro[2,3-b]pyridin-6-yl)methylsulfonamido)-3-hydroxy-2,2-dimethylhexanoic acid;

(Z)-6-(N-(5-cyclopropyl-3-(methylcarbamoyl)-2-p-tolylfuro[2,3-b]pyridin-6-yl)methylsulfonamido)-2-(1-hydroxyethylidene)hexanoic acid;

5-(N-(5-cyclopropyl-3-(methylcarbamoyl)-2-p-tolylfuro[2,3-b]pyridin-6-yl)methylsulfonamido)-2-methylpentanoic acid;

5-(N-(5-cyclopropyl-2-(4-ethylphenyl)-3-(methylcarbamoyl)furo[2,3-b]pyridin-6-yl)methylsulfonamido)-2-methylpentanoic acid;

(S)-5-(N-(5-cyclopropyl-3-(methylcarbamoyl)-2-p-tolylfuro[2,3-b]pyridin-6-yl)methylsulfonamido)-2-methylpentanoic acid;

(R)-5-(N-(5-cyclopropyl-3-(methylcarbamoyl)-2-p-tolylfuro[2,3-b]pyridin-6-yl)methylsulfonamido)-2-methylpentanoic acid;

(S)-6-(N-(5-cyclopropyl-2-(4-ethylphenyl)-3-(methylcarbamoyl)furo[2,3-b]pyridin-6-yl)methylsulfonamido)-2-(methoxymethyl)hexanoic acid;

(R)-6-(N-(5-cyclopropyl-3-(methylcarbamoyl)-2-p-tolylfuro[2,3-b]pyridin-6-yl)methylsulfonamido)-2-(methoxymethyl)hexanoic acid;

5-cyclopropyl-6-(N—((R)-6-((S)-1-hydroxy-3-phenylpropan-2-ylamino)-5-(methoxymethyl)-6-oxohexyl)methylsulfonamido)-N-methyl-2-p-tolylfuro[2,3-b]pyridine-3-carboxamide;

(S)-methyl 2-((R)-5-(N-(5-cyclopropyl-3-(methylcarbamoyl)-2-p-tolylfuro[2,3-b]pyridin-6-yl)methylsulfonamido)-2-methylpentanamido)-2-phenylacetate;

(R)-methyl 2-((R)-5-(N-(5-cyclopropyl-3-(methylcarbamoyl)-2-p-tolylfuro[2,3-b]pyridin-6-yl)methylsulfonamido)-2-methylpentanamido)-2-phenylacetate;

5-cyclopropyl-6-(N—((R)-5-((R)-1-hydroxy-3-phenylpropan-2-ylamino)-4-methyl-5-oxopentyl)methylsulfonamido)-N-methyl-2-p-tolylfuro[2,3-b]pyridine-3-carboxamide;

5-cyclopropyl-6-(N-((S)-5-((R)-1-hydroxy-3-phenylpropan-2-ylamino)-4-methyl-5-oxopentyl)methylsulfonamido)-N-methyl-2-p-tolylfuro[2,3-b]pyridine-3-carboxamide;

6-(N—((R)-5-((S)-4-benzyl-2-oxooxazolidin-3-yl)-4-(methoxymethyl)-5-oxopentyl)methylsulfonamido)-5-iodo-N-methyl-2-p-tolylfuro[2,3-b]pyridine-3-carboxamide;

6-(N—((R)-5-((S)-4-benzyl-2-oxooxazolidin-3-yl)-4-(methoxymethyl)-5-oxopentyl)methylsulfonamido)-5-cyclopropyl-N-methyl-2-p-tolylfuro[2,3-b]pyridine-3-carboxamide;

(R)-5-(N-(5-cyclopropyl-3-(methylcarbamoyl)-2-p-tolylfuro[2,3-b]pyridin-6-yl)methylsulfonamido)-2-(methoxymethyl)pentanoic acid;

ethyl 4-(N-(2-(4-ethylphenyl)-5-iodo-3-(methylcarbamoyl)furo[2,3-b]pyridin-6-yl)methylsulfonamido)butyl(methyl)phosphinate;

ethyl 5-(N-(2-(4-ethylphenyl)-5-iodo-3-(methylcarbamoyl)furo[2,3-b]pyridin-6-yl)methylsulfonamido)pentyl(methyl)phosphinate;

2-(4-ethylphenyl)-6-(N-(5-hydroxypentyl)methylsulfonamido)-5-iodo-N-methylfuro[2,3-b]pyridine-3-carboxamide;

ethyl 5-(N-(5-iodo-3-(methylcarbamoyl)-2-p-tolylfuro[2,3-b]pyridin-6-yl)methylsulfonamido)pentyl(methyl)phosphinate;

ethyl 4-(N-(5-iodo-3-(methylcarbamoyl)-2-p-tolylfuro[2,3-b]pyridin-6-yl)methylsulfonamido)butyl(methyl)phosphinate;

6-(N-(4-hydroxybutyl)methylsulfonamido)-5-iodo-N-methyl-2-p-tolylfuro[2,3-b]pyridine-3-carboxamide;

5-(N-(2-(4-ethylphenyl)-5-iodo-3-(methylcarbamoyl)furo[2,3-b]pyridin-6-yl)methylsulfonamido)pentyl(methyl)phosphinic acid;

5-(N-(5-iodo-3-(methylcarbamoyl)-2-p-tolylfuro[2,3-b]pyridin-6-yl)methylsulfonamido)pentyl(methyl)phosphinic acid;

4-(N-(5-iodo-3-(methylcarbamoyl)-2-p-tolylfuro[2,3-b]pyridin-6-yl)methylsulfonamido)butyl(methyl)phosphinic acid;

6-(N-(5-hydroxypentyl)methylsulfonamido)-5-iodo-N-methyl-2-p-tolylfuro[2,3-b]pyridine-3-carboxamide;

6-(N-(4-bromobutyl)methylsulfonamido)-5-cyclopropyl-N-methyl-2-p-tolylfuro[2,3-b]pyridine-3-carboxamide;

6-(N-(5-bromopentyl)methylsulfonamido)-5-cyclopropyl-N-methyl-2-p-tolylfuro[2,3-b]pyridine-3-carboxamide;

6-(N-(3-bromopropyl)methylsulfonamido)-5-cyclopropyl-N-methyl-2-p-tolylfuro[2,3-b]pyridine-3-carboxamide;

ethyl 3-(N-(5-cyclopropyl-3-(methylcarbamoyl)-2-p-tolylfuro[2,3-b]pyridin-6-yl)methylsulfonamido)propyl(methyl)phosphinate;

ethyl 4-(N-(5-cyclopropyl-3-(methylcarbamoyl)-2-p-tolylfuro[2,3-b]pyridin-6-yl)methylsulfonamido)butyl(methyl)phosphinate;

5-cyclopropyl-6-(N-(4-hydroxybutyl)methylsulfonamido)-N-methyl-2-p-tolylfuro[2,3-b]pyridine-3-carboxamide;

ethyl 5-(N-(5-cyclopropyl-3-(methylcarbamoyl)-2-p-tolylfuro[2,3-b]pyridin-6-yl)methylsulfonamido)pentyl(methyl)phosphinate;

5-cyclopropyl-6-(N-(5-hydroxypentyl)methylsulfonamido)-N-methyl-2-p-tolylfuro[2,3-b]pyridine-3-carboxamide;

(S)-(bis(benzyloxy)phosphoryloxy)methyl 5-(N-(5-cyclopropyl-3-(methylcarbamoyl)-2-p-tolylfuro[2,3-b]pyridin-6-yl)methylsulfonamido)-2-methylpentanoate;

5-cyclopropyl-6-(N-(3-hydroxypropyl)methylsulfonamido)-N-methyl-2-p-tolylfuro[2,3-b]pyridine-3-carboxamide;

3-(N-(5-cyclopropyl-3-(methylcarbamoyl)-2-p-tolylfuro[2,3-b]pyridin-6-yl)methylsulfonamido)propyl(methyl)phosphinic acid;

4-(N-(5-cyclopropyl-3-(methylcarbamoyl)-2-p-tolylfuro[2,3-b]pyridin-6-yl)methylsulfonamido)butyl(methyl)phosphinic acid;

5-(N-(5-cyclopropyl-3-(methylcarbamoyl)-2-p-tolylfuro[2,3-b]pyridin-6-yl)methylsulfonamido)pentyl(methyl)phosphinic acid;

(S)-phosphonooxymethyl 5-(N-(5-cyclopropyl-3-(methylcarbamoyl)-2-p-tolylfuro[2,3-b]pyridin-6-yl)methylsulfonamido)-2-methylpentanoate;

5-cyclopropyl-N-methyl-2-p-tolyl-6-(N-(3-(trifluoromethylsulfonamido)propyl)methylsulfonamido)furo[2,3-b]pyridine-3-carboxamide;

5-(N-(5-cyclopropyl-3-(methylcarbamoyl)-2-p-tolylfuro
[2,3-b]pyridin-6-yl)methylsulfonamido)-3-(dimethylamino)pentanoic acid;
1-(tert-butoxycarbonyl)-4-(3-(N-(5-cyclopropyl-3-(methylcarbamoyl)-2-p-tolylfuro[2,3-b]pyridin-6-yl)methylsulfonamido)propyl)piperidine-4-carboxylic acid;
3-(3-(N-(5-cyclopropyl-3-(methylcarbamoyl)-2-p-tolylfuro[2,3-b]pyridin-6-yl)methylsulfonamido)propyl)oxetane-3-carboxylic acid;
2-(4-(3-(N-(5-cyclopropyl-3-(methylcarbamoyl)-2-p-tolylfuro[2,3-b]pyridin-6-yl)methylsulfonamido)propyl)tetrahydro-2H-pyran-4-yl)acetic acid;
7-(N-(5-cyclopropyl-3-(methylcarbamoyl)-2-p-tolylfuro[2,3-b]pyridin-6-yl)methylsulfonamido)heptanoic acid;
5-(N-(5-(2-hydroxyethyl)-3-(methylcarbamoyl)-2-p-tolylfuro[2,3-b]pyridin-6-yl)methylsulfonamido)pentanoic acid;
4-(3-(N-(5-cyclopropyl-3-(methylcarbamoyl)-2-p-tolylfuro[2,3-b]pyridin-6-yl)methylsulfonamido)propyl)piperidine-4-carboxylic acid;
methyl 5-(N-(5-cyclopropyl-3-(methylcarbamoyl)-2-p-tolylfuro[2,3-b]pyridin-6-yl)methylsulfonamido)-2-methylenepentanoate;
6-(N-allylmethylsulfonamido)-5-cyclopropyl-N-methyl-2-p-tolylfuro[2,3-b]pyridine-3-carboxamide;
6-(N-(but-3-enyl)methylsulfonamido)-5-cyclopropyl-N-methyl-2-p-tolylfuro[2,3-b]pyridine-3-carboxamide;
5-cyclopropyl-N-methyl-6-(N-(pent-4-enyl)methylsulfonamido)-2-p-tolylfuro[2,3-b]pyridine-3-carboxamide;
5-cyclopropyl-N-methyl-6-(N-((5-oxotetrahydrofuran-2-yl)methyl)methylsulfonamido)-2-p-tolylfuro[2,3-b]pyridine-3-carboxamide;
5-(N-(5-cyclopropyl-3-(methylcarbamoyl)-2-p-tolylfuro[2,3-b]pyridin-6-yl)methylsulfonamido)-4-hydroxypentanoic acid;
9-(N-(5-cyclopropyl-3-(methylcarbamoyl)-2-p-tolylfuro[2,3-b]pyridin-6-yl)methylsulfonamido)nonanoic acid;
8-(N-(5-cyclopropyl-3-(methylcarbamoyl)-2-p-tolylfuro[2,3-b]pyridin-6-yl)methylsulfonamido)octanoic acid;
ethyl 4-(3-(N-(5-cyclopropyl-3-(methylcarbamoyl)-2-p-tolylfuro[2,3-b]pyridin-6-yl)methylsulfonamido)propyl)piperidine-4-carboxylate;
1-acetyl-4-(3-(N-(5-cyclopropyl-3-(methylcarbamoyl)-2-p-tolylfuro[2,3-b]pyridin-6-yl)methylsulfonamido)propyl)piperidine-4-carboxylic acid;
4-(3-(N-(5-cyclopropyl-3-(methylcarbamoyl)-2-p-tolylfuro[2,3-b]pyridin-6-yl)methylsulfonamido)propyl)-1-methylpiperidine-4-carboxylic acid;
10-(N-(5-cyclopropyl-3-(methylcarbamoyl)-2-p-tolylfuro[2,3-b]pyridin-6-yl)methylsulfonamido)decanoic acid;
2-(cyanomethyl)-5-(N-(5-cyclopropyl-3-(methylcarbamoyl)-2-p-tolylfuro[2,3-b]pyridin-6-yl)methylsulfonamido)pentanoic acid;
6-(N-(5-cyclopropyl-3-(methylcarbamoyl)-2-p-tolylfuro[2,3-b]pyridin-6-yl)methylsulfonamido)-3-methoxyhexanoic acid;
3-cyano-6-(N-(5-cyclopropyl-3-(methylcarbamoyl)-2-p-tolylfuro[2,3-b]pyridin-6-yl)methylsulfonamido)hexanoic acid;
6-(N-(2-(2-bromoethoxy)ethyl)methylsulfonamido)-5-cyclopropyl-N-methyl-2-p-tolylfuro[2,3-b]pyridine-3-carboxamide;
methyl 2-(cyanomethyl)-5-(N-(5-cyclopropyl-3-(methylcarbamoyl)-2-p-tolylfuro[2,3-b]pyridin-6-yl)methylsulfonamido)pentanoate;
(E)-ethyl 6-(N-(5-cyclopropyl-3-(methylcarbamoyl)-2-p-tolylfuro[2,3-b]pyridin-6-yl)methylsulfonamido)hex-2-enoate;
4-(3-(N-(5-cyclopropyl-3-(methylcarbamoyl)-2-p-tolylfuro[2,3-b]pyridin-6-yl)methylsulfonamido)propyl)-1-pivaloylpiperidine-4-carboxylic acid;
4-(2-(2-(N-(5-cyclopropyl-3-(methylcarbamoyl)-2-p-tolylfuro[2,3-b]pyridin-6-yl)methylsulfonamido)ethoxy)ethyl)tetrahydro-2H-pyran-4-carboxylic acid;
6-(N-(5-cyclopropyl-3-(methylcarbamoyl)-2-p-tolylfuro[2,3-b]pyridin-6-yl)methylsulfonamido)-3-(2-methoxyethoxy)hexanoic acid;
4-(2-(N-(5-cyclopropyl-3-(methylcarbamoyl)-2-p-tolylfuro[2,3-b]pyridin-6-yl)methylsulfonamido)ethoxy)butanoic acid;
4-{2-[(5-Cyclopropyl-3-methylcarbamoyl-2-p-tolyl-furo[2,3-b]pyridin-6-yl)-methanesulfonyl-amino]-ethoxy}-2-(2-methoxy-ethyl)-butyric acid;
4-{2-[(5-Cyclopropyl-3-methylcarbamoyl-2-p-tolyl-furo[2,3-b]pyridin-6-yl)-methanesulfonyl-amino]-ethoxy}-2-(2-methoxy-ethyl)-butyric acid;
6-(N-(4-aminobutyl)methylsulfonamido)-5-cyclopropyl-N-methyl-2-p-tolylfuro[2,3-b]pyridine-3-carboxamide;
6-(N-(5-aminopentyl)methylsulfonamido)-5-cyclopropyl-N-methyl-2-p-tolylfuro[2,3-b]pyridine-3-carboxamide;
4-(3-(N-(5-cyclopropyl-3-(methylcarbamoyl)-2-p-tolylfuro[2,3-b]pyridin-6-yl)methylsulfonamido)propylamino)butanoic acid;
5-cyclopropyl-N-methyl-6-(N-(3-(2-oxopyrrolidin-1-yl)propyl)methylsulfonamido)-2-p-tolylfuro[2,3-b]pyridine-3-carboxamide;
5-(3-hydroxypropyl)-N-methyl-6-(N-methylmethylsulfonamido)-2-p-tolylfuro[2,3-b]pyridine-3-carboxamide;
5-(2,3-dihydroxypropyl)-N-methyl-6-(N-methylmethylsulfonamido)-2-p-tolylfuro[2,3-b]pyridine-3-carboxamide;
6-(N-(3-aminopropyl)methylsulfonamido)-5-cyclopropyl-N-methyl-2-p-tolylfuro[2,3-b]pyridine-3-carboxamide;
5-cyclopropyl-2-(2,4-dimethylphenyl)-N-methyl-6-(N-methylmethylsulfonamido)furo[2,3-b]pyridine-3-carboxamide;
5-(N-(5-cyclopropyl-2-(2,4-dimethylphenyl)-3-(methylcarbamoyl)furo[2,3-b]pyridin-6-yl)methylsulfonamido)pentanoic acid;
4-(5-(N-(5-cyclopropyl-3-(methylcarbamoyl)-2-p-tolylfuro[2,3-b]pyridin-6-yl)methylsulfonamido)pentanamido)butanoic acid;
5-(N-(5-cyclopropyl-2-(3,4-dimethylphenyl)-3-(methylcarbamoyl)furo[2,3-b]pyridin-6-yl)methylsulfonamido)pentanoic acid;
5-(N-(5-cyclopropyl-2-(3-fluoro-4-methylphenyl)-3-(methylcarbamoyl)furo[2,3-b]pyridin-6-yl)methylsulfonamido)pentanoic acid;
(S)-4-(5-(N-(5-cyclopropyl-3-(methylcarbamoyl)-2-p-tolylfuro[2,3-b]pyridin-6-yl)methylsulfonamido)-2-methylpentanamido)butanoic acid, and salts thereof.

10. A pharmaceutical composition comprising a therapeutically effective amount of a compound according to claim 1 and one or more pharmaceutically acceptable carriers.

* * * * *